(12) United States Patent
Breslin et al.

(10) Patent No.: US 12,344,595 B2
(45) Date of Patent: Jul. 1, 2025

(54) 2-AMINO-N-PHENYL-NICOTINAMIDES AS NAV1.8 INHIBITORS

(71) Applicant: Merck Sharp & Dohme LLC, Rahway, NJ (US)

(72) Inventors: Michael J. Breslin, Drexel Hill, PA (US); Christopher James Bungard, Lansdale, PA (US); Harry R. Chobanian, Westfield, NJ (US); Kristen L. G. Jones, Oreland, PA (US); Mark E. Layton, Harleysville, PA (US); Jian Liu, Edison, NJ (US); James J. Perkins, Churchville, PA (US); Jeffrey William Schubert, North Wales, PA (US); Shawn J. Stachel, Perkasie, PA (US); Linda M. Suen-Lai, Philadelphia, PA (US); Zhe Wu, Blue Bell, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 1034 days.

(21) Appl. No.: 17/289,152

(22) PCT Filed: Oct. 28, 2019

(86) PCT No.: PCT/US2019/058251
§ 371 (c)(1),
(2) Date: Apr. 27, 2021

(87) PCT Pub. No.: WO2020/092187
PCT Pub. Date: May 7, 2020

(65) Prior Publication Data
US 2022/0119363 A1    Apr. 21, 2022

Related U.S. Application Data

(60) Provisional application No. 62/754,852, filed on Nov. 2, 2018.

(51) Int. Cl.
*C07D 401/04* (2006.01)
*C07D 213/82* (2006.01)
(Continued)

(52) U.S. Cl.
CPC ......... *C07D 401/04* (2013.01); *C07D 213/82* (2013.01); *C07D 401/14* (2013.01); *C07D 403/04* (2013.01); *C07D 405/14* (2013.01); *C07D 409/14* (2013.01); *C07D 413/04* (2013.01); *C07D 417/04* (2013.01); *C07D 417/14* (2013.01); *C07D 451/02* (2013.01); *C07D 487/08* (2013.01); *C07D 487/18* (2013.01); *C07D 491/048* (2013.01); *C07D 491/107* (2013.01); *C07D 498/04* (2013.01); *C07D 498/08* (2013.01); *C07D 513/04* (2013.01)

(58) Field of Classification Search
CPC .. C07D 401/04; C07D 213/82; C07D 401/14; C07D 403/04; C07D 405/14; C07D 409/14; C07D 413/04; C07D 417/04; C07D 417/14; C07D 451/02; C07D 487/08; C07D 487/18; C07D 491/048; C07D 491/107; C07D 498/04; C07D 498/08; C07D 513/04
See application file for complete search history.

(56) References Cited

U.S. PATENT DOCUMENTS

| | | |
|---|---|---|
| 8,519,137 B2 | 8/2013 | Joshi et al. |
| 9,051,270 B2 | 6/2015 | Hadida-Ruah et al. |

(Continued)

FOREIGN PATENT DOCUMENTS

| | | |
|---|---|---|
| EP | 3470404 A1 | 4/2019 |
| WO | 2006050476 A2 | 5/2006 |

(Continued)

OTHER PUBLICATIONS

CAS Registry No. 1147812-98-3, which entered STN on May 20, 2009 (Year: 2009).*

(Continued)

*Primary Examiner* — Joseph K McKane
*Assistant Examiner* — Quincy McKoy
(74) *Attorney, Agent, or Firm* — Baerbel R. Brown; Catherine D. Fitch

(57) ABSTRACT

Novel compounds of the structural formula (I), and the pharmaceutically acceptable salts thereof, are inhibitors of $Na_v1.8$ channel activity and may be useful in the treatment, prevention, management, amelioration, control and suppression of diseases mediated by $Na_v1.8$ channel activity. The compounds of the present invention may be useful in the treatment, prevention or management of pain disorders, cough disorders, acute itch disorders, and chronic itch disorders.

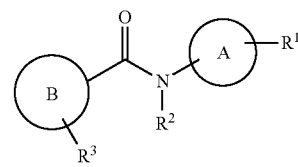

15 Claims, No Drawings

(51) Int. Cl.
| | | |
|---|---|---|
| C07D 401/14 | (2006.01) | |
| C07D 403/04 | (2006.01) | |
| C07D 405/14 | (2006.01) | |
| C07D 409/14 | (2006.01) | |
| C07D 413/04 | (2006.01) | |
| C07D 417/04 | (2006.01) | |
| C07D 417/14 | (2006.01) | |
| C07D 451/02 | (2006.01) | |
| C07D 487/08 | (2006.01) | |
| C07D 487/18 | (2006.01) | |
| C07D 491/048 | (2006.01) | |
| C07D 491/107 | (2006.01) | |
| C07D 498/04 | (2006.01) | |
| C07D 498/08 | (2006.01) | |
| C07D 513/04 | (2006.01) | |

(56) References Cited

U.S. PATENT DOCUMENTS

| | | |
|---|---|---|
| 9,108,903 B2 | 8/2015 | Hadida-Ruah et al. |
| 9,163,042 B2 | 10/2015 | Anderson et al. |
| 9,783,501 B2 | 10/2017 | Hadida-Ruah et al. |
| 2009/0099233 A1 | 4/2009 | Joshi et al. |
| 2013/0231370 A1 | 9/2013 | Chen et al. |
| 2016/0152561 A1 | 6/2016 | Hadida-ruah et al. |

FOREIGN PATENT DOCUMENTS

| | | |
|---|---|---|
| WO | 2009049180 A2 | 4/2009 |
| WO | 2009049181 A1 | 4/2009 |
| WO | 2009049183 A1 | 4/2009 |
| WO | 2009100406 A2 | 8/2009 |
| WO | 2013033037 A2 | 3/2013 |
| WO | 2013171640 A1 | 11/2013 |
| WO | 2014120808 A1 | 8/2014 |
| WO | 2014120815 A1 | 8/2014 |
| WO | 2014120820 A1 | 8/2014 |
| WO | 2015010065 A1 | 1/2015 |
| WO | 2015089361 A1 | 6/2015 |
| WO | 2015157127 A1 | 10/2015 |
| WO | 2017209322 A1 | 12/2017 |

OTHER PUBLICATIONS

CAS Registry No. 1031190-62-1, which entered STN on Jun. 27, 2008 (Year: 2008).*
CAS Registry No. 1007741-67-4, which entered STN on Mar. 13, 2008 (Year: 2008).*
CAS Registry No. 1324464-77-8, which entered STN on Aug. 27, 2011. (Year: 2011).*
Bagal, Sharan K. et al., Discovery and Optimization of Selective Nav1.8 Modulator Series That Demonstrate Efficacy in Preclinical Models of Pain, ACS Med. Chem. Lett., 2015, 650-654, 6.
Belkouch, Mounir et al., Functional up-regulation of Nav1.8 sodium channel in Aβ afferent fibers subjected to chronic peripheral inflammation, Journal of Neuroinflammation, 2014, 1-17, 11:45.
Bennett, David L. et al., Painful and painless channelopathies, Lancet Neurol., 2014, 587-599, 13(6).
Black, Joel A. Et A., Multiple Sodium Channel Isoforms and Mitogen-Activated Protein Kinases Are Present in Painful Human Neuromas, Ann Neurol, 2008, 644-653, 64(6).
Carter et al., Advances in the Management of Neuropathic Pain, Physical Medicine and Rehabilitation Clinics of North America, 2001, 447-459, 12(2).
Catterall, William A. et al., The chemical basis for electrical signaling, Nature Chemical Biology, 2017, 455-463, 13(5).
Coward, K et al., Immunolocalizationof SNS/PN3 and NaN/SNS2 sodium channels in human pain states, Pain, 2000, 41-50, 85.
Emery, Edward C. et al., Novel SCN9A Mutations Underlying Extreme Pain Phenotypes: Unexpected Electrophysiological and Clinical Phenotype Correlations, Journal of Neuroscience, 2015, 7674-7681, 35(20).
Flaxman et al., Years Lived with Disability (YLDs) for 1160 Sequelae of 289 Diseases and Injuries 1990-2010: A Systematic Analysis for the Global Burden of Disease Study 2010, Lancet, 2012, 2163-2196, 380.
Goldin et al., Nomenclature of Voltage-Gated Sodium Channels, Neuron, 2000, 365-368, 28.
Goldin, Diveristy of Mammalian Voltage-Gated Sodium Channels, Ann NY Acad Sci., 1999, 38-50, 30, 868.
Han, Chongyang et al., The G1662S NaV1.8 mutation in small fibre neuropathy: impaired inactivation underlying DRG neuron hyperexcitability, J Neurol Neurosurg Psychiatry, 2014, 499-505, 85(5).
Han, Chongyang, et al., Sodium channel Nav1.8, Emerging links to human disease, Neurology, 2016, 473-483, 86.
Huang, Jianying et al., Small-Fiber Neuropathy Nav1.8 Mutation Shifts Activation to Hyperpolarized Potentials and Increases Excitability of Dorsal Root Ganglion Neurons, Journal of Neuroscience, 2013, 14087-14097, 33(35).
Jarvis, Michael F. et al., A-803467, a potent and selective Nav1.8 sodium channel blocker, attenuates neuropathic and inflammatory pain in the rat, PNAS, 2007, 8520-8525, 104.
Kist, Andreas M. et al., SCN10A Mutation in a Patient with Erythromelalgia Enhances C-Fiber Activity Dependent Slowing, PLOS One, 2016, pp. 1-19, 11(9):e0161789.
Kort, Michael E. et al., Discovery and Biological Evaluation of 5-Aryl-2-furfuramides, Potent and Selective Blockers of the Nav1.8 Sodium Channel with Efficacy in Models of Neuropathic and Inflammatory Pain, J. Med. Chem., 2008, 407-416, 51.
Liu, Yang et al., VGLUT2-Dependent Glutamate Release from Nociceptors Is Required to Sense Pain and Suppress Itch, Neuron, 2010, 543-556, 68(3).
McGaraughty, Steve et al., A Selective Nav1.8 Sodium Channel Blocker, A-803467 [5-(4-Chlorophenyl-N-(3,5-dimethoxyphenyl)furan-2-carboxamide], Attenuates Spinal Neuronal Activity in Neuropathic Rats, JPET, 2008, 1204-1211, 324.
Notification of Transmittal of the International Search Report and the Written Opinion of the International Searching Authority, or the Declaration, date of mailing Feb. 11, 2020 (23 pages).
Payne, Claire Elizabeth et al., A novel selective and orally bioavailable NAv1.8 channel blocker, PF-01247324, attenuates nociception and sensory neuron excitability, British Journal of Pharmacology, 2015, 2654-2670, 172.
Schreiber, Anne K. et al., Diabetic neuropathic pain: Physiopathology and treatment, World Journal of Diabetes, 2015, 432-444, 6(3).
Yiangou, Y. et al., SNS/PN3 and SNS2/NaN sodium channel-like immunoreactivity in human adult and neonate injured sensory nerves, FEBS Letters, 2000, 249-252, 467.
Yu et al., Overview of the Voltage-Gated Sodium Channel Family, Genome Biology, 2003, 207, 4.
Zeng, Chao et al., Relative efficacy and safety of topical non-steroidal anti-inflammatory drugs for osteoarthritis: a systematic review and network meta-analysis of randomised controlled trials and observational studies, Br J Sports Med, 2018, 642-650, 52.
Zhang, Xu-Feng et al., A-887826 is a structurally novel, potent and voltage-dependent Nav1.8 sodium channel blocker that attenuates neuropathic tactile allodynia in rats, Neuropharmacology, 2010, 201-207, 59.

* cited by examiner

2-AMINO-N-PHENYL-NICOTINAMIDES AS NAV1.8 INHIBITORS

CROSS-REFERENCE TO RELATED APPLICATIONS

This application is a U.S. National Phase application under 35 U.S.C. § 371 of PCT Application No. PCT/US2019/058251, filed Oct. 28, 2019, which claims priority from and the benefit of U.S. Provisional Application No. 62/754,852, filed Nov. 2, 2018.

BACKGROUND OF THE INVENTION

Voltage-gated sodium channels (VGSC) mediate the selective influx of sodium ions in excitable cells and play a central role in initiating and propagating action potentials (Yu et al., Genome Biology 4:207 (2003)). Voltage-gated sodium channels are ubiquitous in the central and peripheral nervous system where they play a central role in the initiation and propagation of action potentials, and also in skeletal and cardiac muscle where the action potential triggers cellular contraction (Goldin et al., Ann N Y Acad Sci. 1999 Apr. 30; 868:38-50). Alterations in VGSC function or their expression can profoundly affect normal cell excitability (Huang et al., J Neurosci. 2013 Aug. 28; 33 (35):14087-97; Emery et al., J Neurosci. 2015 May 20; 35(20):7674-81; Kist et al., PLoS One. 2016 Sep. 6; 11(9):e0161789; and Schreiber et al., World J Diabetes. 2015 Apr. 15; 6(3):432-44).

Voltage-gated sodium channels are multimeric complexes characterized by one α-subunit, which forms an ion-conducting aqueous pore, and at least one β-subunit that modifies the kinetics and voltage-dependence of the channel gating. Nine different α-subunits have been identified and characterized in mammalian voltage-gated sodium channels, including $Na_v1.8$, also known as SNS, PN3 or $Na_v1.8$ (Goldin et al., Neuron. 2000 November; 28 (2):365-8).

Expression of sodium channels can be tissue specific. $Na_v1.8$ voltage-gated sodium ion channels are expressed primarily in sensory neurons, which are responsible for conveying information from the periphery (e.g. skin, muscle and joints) to the central nervous system via the spinal cord. Sodium channels are integral to this process as sodium channel activity is required for initiation and propagation of action potentials triggered by noxious stimuli (thermal, mechanical and chemical) activating peripheral nociceptors (Catterall et al., Nat Chem Biol. 2017 Apr. 13; 13(5):455-463). An increase in VGSC protein level at the cell surface or an alteration in activity of the VGSC channels can result in disease states such as migraine, neurodegeneration following ischemia, epilepsies, and chronic neuropathic and inflammatory pain states. Gain of function mutations in Nav1.7, Nav1.8, and Nav1.9 manifest in a variety of pain syndromes where patients experience spontaneous pain without an external stimulus (Bennett et al., Lancet Neurol. 2014 June; 13(6):587-99; Huang et al., J Neurosci. 2013 Aug. 28; 33(35):14087-97; Kist et al., PLoS One. 2016 Sep. 6; 11(9):e0161789; Emery et al., J Neurosci. 2015 May 20; 35(20):7674-81; and Schreiber et al., World J Diabetes. 2015 Apr. 15; 6(3):432-44).

$Na_v1.8$ voltage-gated sodium ion channels are believed to play a role in various maladies, including neuropathic pain, chronic itch, and inflammatory pain perception (Belkouch et al., J Neuroinflammation. 2014 Mar. 7; 11:45; Coward et al., Pain. 2000 March; 85(1-2):41-50; Yiangou et al., FEBS Lett. 2000 Feb. 11; 467(2-3):249-52; Black et al., Ann Neurol. 2008 December; 64(6):644-53; Bird et al., Br J Pharmacol. 2015 May; 172(10):2654-70; Liu et al., Neuron. 2010 Nov. 4; 68(3):543-56; and Zhao et al., J Clin Invest. 2013).

Large portions of the voltage gated sodium ion channels are conserved among the various subtypes, therefore there is a potential for producing serious side effects when utilizing therapeutic agents that do not demonstrate subtype selectivity. Therefore, therapeutic agents suitable for use in addressing nociception, cough, or itch disorders, require specificity in their action, for example, discriminating between action upon $Na_v1.5$ sodium ion channels, thought to be important in regulation of cardiac function, and action upon $Na_v1.8$ sodium ion channels, thought to be central in inflammatory nociception, or itch and disorders arising from dysfunctional and/or upregulated $Na_v1.8$ sodium ion channels.

Accordingly, it is believed that inhibitors of $Na_v1.8$ voltage-gated sodium ion channel activity may useful to treat or prevent diseases, disorders and conditions involving $Na_v1.8$ receptors and/or stemming specifically from dysfunction of $Na_v1.8$ voltage-gated sodium ion channels (Han et al., J Neurol Neurosurg Psychiatry 2014 May; 85(5):499-505), including but not limited to, migraine, neurodegeneration following ischemia, epilepsy, inflammatory pain, spontaneous pain, acute pain, preoperative pain, perioperative pain, post-operative pain, neuropathic pain, chronic itch, and itch disorders.

There remains a need for potent $Na_v1.8$ sodium ion channel activity inhibitors with selective activity for $Na_v1.8$ sodium ion channels. As a result, the compounds of the present invention are useful for the treatment and prevention of diseases, disorders and conditions involving $Na_v1.8$ receptors and $Na_v1.8$ voltage-gated sodium ion channels.

The role of Nav1.8 sodium ion channels is discussed in: Bennett et al., Physical Medicine and Rehabilitation Clinics of North America, 2001, 12(2):447-459; Meissner et al., Br J Sports Med. 2018 May; 52(10):642-650; Legroux-Crespel et al., Neurology. 2016 Feb. 2; 86(5):473-83; and Flaxman et al., Lancet, 380:2163-2196 (2012).

Compounds useful to treat $Na_v1.8$ sodium ion channel related conditions are disclosed in: ACS Med. Chem. Lett. 2015, 6, 650; BJP 2015, 172, 2654; PNAS 2007, 104, 8520; J. Med. Chem. 2008, 51, 407; JPET 2008, 324, 1204; and Neuropharmacology 2010, 59, 201.

$Na_v1.8$ compounds are also disclosed in: WO 2009/049180, WO 2009/049181, WO 2009/049183, WO 2014/120808; WO 2014/120815; WO 2014/120820; WO 2015/010065; and WO 2015/089361; WO 2017/209322; U.S. Pat. Nos. 8,519,137; 9,051,270; 9,108,903; 9,163,042; and 9,783,501.

SUMMARY OF THE INVENTION

The present invention relates to novel compounds of structural formula I:

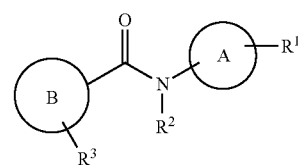

and pharmaceutically acceptable salts thereof. The compounds of structural formula I, and embodiments thereof, are inhibitors of Na$_v$1.8 sodium ion channel activity (or Na$_v$1.8 inhibitors) and may be useful in the treatment and prevention of diseases, disorders and conditions mediated by Na$_v$1.8 sodium ion channel activity, such as nociception, osteoarthritis, peripheral neuropathy, inherited erythromelalgia, multiple sclerosis, asthma, itch, atopy, allergic or contact dermatitis, renal failure, cholestasis, pruritus, acute itch, chronic itch, migraine, neurodegeneration following ischemia, epilepsy, pain, inflammatory pain, spontaneous pain, acute pain, acute pain due to fractures, musculoskeletal damage, pancreatitis and renal colic, pen-operative pain, post-operative pain, neuropathic pain, postherpetic neuralgia, trigeminal neuralgia, diabetic neuropathy, chronic lower back pain, phantom limb pain, sciatica, pain caused by 2° or 3° burn injury, optic neuritis, pain resulting from cancer and chemotherapy, chronic pelvic pain, pain syndromes, and complex regional pain syndromes. In one embodiment of the present invention, the condition, disease or disorder is a pain disorder, an acute pain disorder or chronic pain disorder. In another embodiment of the present invention, the condition, disease or disorder is an acute pain disorder.

The present invention also relates to pharmaceutical compositions comprising the compounds of the present invention and a pharmaceutically acceptable carrier.

The present invention also relates to methods for the treatment, management, prevention, alleviation, amelioration, suppression or control of disorders, diseases, and conditions that may be responsive to inhibition of Na$_v$1.8 sodium ion channel activity in a subject in need thereof by administering the compounds and pharmaceutical compositions of the present invention.

The present invention also relates to the use of compounds of the present invention for manufacture of a medicament useful in treating diseases, disorders and conditions that may be responsive to the inhibition of Na$_v$1.8 sodium ion channel activity.

The present invention is also concerned with treatment or prevention of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

The present invention is concerned with novel compounds of structural Formula I:

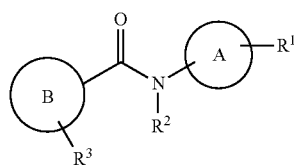

I or a pharmaceutically acceptable salt thereof, wherein
A is phenyl or phenyl fused to a saturated or unsaturated 5- or 6-membered ring containing 0-3 heteroatoms independently selected from O, S and N(R$^h$)$_q$, wherein each phenyl, 5-membered ring and 6-membered ring is unsubstituted or substituted with one to five substituents selected from R$^a$;

B is heteroaryl, wherein heteroaryl is unsubstituted or substituted with one to three substituents selected from R$^b$;
R$^1$ is selected from the group consisting of:
(1) hydrogen,
(2) —SO$_3$H,
(3) —SO$_2$NH$_2$,
(4) —SO$_2$NR$^e$C$_{1-6}$alkyl,
(5) —SO$_2$NR$^e$C(O)C$_{1-6}$alkyl,
(6) —SO$_2$NR$^e$C$_{2-6}$alkenyl,
(7) —SO$_2$NR$^e$C$_{3-6}$cycloalkyl,
(8) —SO$_2$NR$^e$C(O)C$_{3-6}$cloalkyl,
(9) —SO$_2$NR$^e$C$_{2-6}$cycloheteroalkyl,
(10) —SO$_2$NR$^e$C(O)C$_{2-6}$cloheteroalkyl,
(11) —SO$_2$NR$^e$-aryl,
(12) —SO$_2$NR$^e$-heteroaryl,
(13) —SO$_2$C$_{1-6}$alkyl,
(14) —SO$_2$C$_{1-6}$alkenyl,
(15) —SO$_2$C$_{3-6}$cycloalkyl,
(16) —SO$_2$C$_{2-6}$cycloheteroalkyl,
(17) —SO$_2$aryl,
(18) —SO$_2$heteroaryl,
(19) —S(O)Rj,
(20) —SRj,
(21) —C(O)NH$_2$,
(22) —C(O)NR$^e$Rj,
(23) —CO$_2$H,
(24) —CO$_2$Rj,
(25) —C(O)Rj,
(26) —CN,
(27) CF$_3$,
(28) halogen,
(29) —OH,
(30) —OC$_{1-6}$alkyl,
(31) —OC$_{2-6}$alkenyl,
(32) —OC$_{3-6}$cycloalkyl,
(33) —OC$_{2-6}$cycloheteroalkyl,
(34) —O-aryl,
(35) —O-heteroaryl,
(36) —OC(O)Rj,
(37) —OC(O)NR$^e$Rj,
(38) —OC(O)N(Rj)$_2$,
(39) —C$_{1-6}$alkyl,
(40) —C$_{2-6}$alkenyl,
(41) —C$_{1-6}$cycloalkyl,
(42) —C$_{2-6}$cycloheteroalkyl,
(43) aryl,
(44) heteroaryl,
(45) —(CH$_2$)nNR$^e$C(O)Rj,
(46) —(CH$_2$)nNR$^e$C(O)ORj,
(47) —(CH$_2$)nNR$^e$C(O)N(Re)$_2$,
(48) —(CH$_2$)nNR$^e$C(O)NR$^e$Rj,
(49) —(CH$_2$)nNR$^e$C(O)N(Rj)$_2$,
(50) —(CH$_2$)nNReS(O)Rj,
(51) —(CH$_2$)nNReS(O)mN(Re)$_2$,
(52) —(CH$_2$)nNReS(O)mNR$^e$Rj,
(53) —(CH$_2$)nNReS(O)mN(Rl)$_2$, and
(54) —(CH$_2$)nNR$^e$Rj,
wherein each CH$_2$, alkyl, alkenyl, cycloalkyl, cycloheteroalkyl, aryl and heteroaryl is unsubstituted or substituted with one to four substituents selected from R$^d$;
R$^2$ is selected from the group consisting of:
(1) hydrogen, and
(2) —C$_{1-6}$alkyl;
R$^3$ is selected from the group consisting of:
(1) a monocyclic, bicyclic or spirocyclic C$_{3-12}$cycloalkyl ring, and (2) a monocyclic, bicyclic or spirocyclic $C_{2-12}$cycloheteroalkyl ring,
wherein the cycloheteroalkyl contains 1-4 heteroatoms independently selected from $N(R^m)_r$, O, and S, wherein each cycloalkyl ring and each cycloheteroalkyl ring may be fused to an aryl or heteroaryl, and wherein each cycloalkyl, cycloheteroalkyl, aryl and heteroaryl is unsubstituted or substituted with one to eight substitutents selected from $R^c$;
each $R^a$ is selected from the group consisting of:
(1) —$C_{1-6}$alkyl
(2) —$OC_{1-6}$alkyl
(3) halogen
(4) —OH,
(5) oxo
(6) —CN,
(7) —$C_{3-6}$cycloalkyl, and
(8) —$C_{2-5}$cycloheteroalkyl,
wherein each alkyl, cycloalkyl and cycloheteroalkyl is unsubstituted or substituted with one to six substituents selected from halogen, OH, $NH_2$, $NH(C_{1-6}alkyl)$ and $N(C_{1-6}alkyl)_2$;
each $R^b$ is independently selected from the group consisting of:
(1) —$CF_3$,
(2) —$CF_2CF_3$,
(3) —$CHF_2$,
(4) —$OCHF_2$,
(5) —$OCH_2CF_3$,
(6) —$OCF_3$,
(7) CN,
(8) halogen,
(9) —$Si(C_{1-6}alkyl)_3$,
(10) —$C_{1-6}$alkyl-O-Rj,
(11) —$C_{1-6}$alkyl,
(12) —$C_{2-6}$alkenyl,
(13) —$C_{2-6}$alkynyl,
(14) —$C_{3-6}$cycloalkyl,
(15) —$C_{2-6}$cycloheteroalkyl,
(16) aryl,
(17) heteroaryl,
(18) —$C_{1-6}$alkyl-$C_{3-6}$cycloalkyl,
(19) —$C_{1-6}$alkyl-$C_{2-6}$cycloheteroalkyl,
(20) —$C_{1-6}$alkyl-aryl,
(21) —$C_{1-6}$alkyl-heteroaryl,
(22) —$C_{2-6}$alkenyl-$C_{3-6}$cycloalkyl,
(23) —$C_{2-6}$alkenyl-$C_{2-6}$cycloheteroalkyl,
(24) —$C_{2-6}$alkenyl-aryl,
(25) —$C_{2-6}$alkenyl-heteroaryl,
(26) —$C_{2-6}$alkynyl-$C_{3-6}$cycloalkyl,
(27) —$C_{2-6}$alkynyl cycloheteroalkyl,
(28) —$C_{2-6}$alkynyl-aryl,
(29) —$C_{2-6}$alkynyl-heteroaryl,
(30) $NO_2$,
(31) —OH,
(32) —$(CH_2)_p$-$OC_{1-6}$alkyl,
(33) —$(CH_2l)_p$-$OC_{2-6}$alkenyl,
(34) —$(CH_2l)_p$-$OC_{2-6}$alkynyl,
(35) —$(CH_2l)_p$-$OC_{3-6}$cycloalkyl,
(36) —$(CH_2l)_p$-$OC_{2-6}$heterocycloalkyl,
(37) —$(CH_2l)_p$-O-aryl,
(38) —$(CH_2l)_p$-O-heteroaryl,
(39) —$OC_{1-6}$alkyl-$C_{3-6}$cycloalkyl,
(40) —$OC_{1-6}$alkyl-$C_{2-6}$heterocycloalkyl,
(41) —$OC_{1-6}$alkyl-aryl,
(42) —$OC_{1-6}$alkyl-heteroaryl,
(55) —$S(O)_mR^k$,
(43) —$C_{1-6}$alkyl-$S(O)_mR^k$,
(44) —$C(O)R^k$,
(45) —$N(R^i)_2$, and
(46) —$NR^iR^k$,
wherein each $R^b$ is unsubstituted or substituted with one to five substituents selected from $R^f$;
each $R^c$ is independently selected from the group consisting of:
(1) —$CF_3$,
(2) —$CH_2CF_3$,
(3) —$CHF_2$,
(4) —$OCHF_2$,
(5) —$OCF_3$,
(6) CN,
(7) oxo,
(8) —OH,
(9) halogen,
(10) —$C_{1-6}$alkyl,
(11) —$C_{2-6}$alkenyl,
(12) —$C_{2-6}$alkynyl,
(13) —$C_{3-6}$cycloalkyl,
(14) —$C_{2-6}$cycloheteroalkyl,
(15) —$C_{1-6}$alkyl-$C_{3-6}$cycloalkyl,
(16) —$C_{1-6}$alkyl-$C_{2-6}$cycloheteroalkyl,
(17) —$C_{1-6}$alkyl-aryl,
(18) —$C_{1-6}$alkyl-heteroaryl,
(19) —$C_{1-6}$alkenyl-$C_{3-6}$cycloalkyl,
(20) —$C_{1-6}$alkenyl-aryl,
(21) —$C_{1-6}$alkenyl heteroaryl,
(22) —$C_{1-6}$alkenyl-$C_{2-6}$cycloheteroalkyl,
(23) —$C_{2-6}$alkynyl-$C_{3-6}$cycloalkyl,
(24) —$C_{2-6}$alkynyl-$C_{2-6}$cycloheteroalkyl,
(25) —$C_{2-6}$alkynyl-aryl,
(26) —$C_{2-6}$alkynyl heteroaryl,
(27) —$OC_{1-6}$alkyl,
(28) —$OC_{2-6}$alkenyl,
(29) —$OC_{2-6}$alkynyl,
(30) -$OC_{3-6}$cycloalkyl,
(31) —$OC_{2-6}$heterocycloalkyl,
(32) —O-aryl,
(33) —O-heteroaryl,
(34) —$OC_{1-6}$alkyl-cycloalkyl,
(35) —$OC_{1-6}$alkyl-cycloheteroalkyl,
(36) —$OC_{1-6}$alkyl-aryl,
(37) —$OC_{1-6}$alkyl-heteroaryl,
(38) —$S(O)_mR^L$,
(39) —$S(O)R^L$,
(40) —S—$R^L$,
(41) —$C_{1-6}$alkyl-$S(O)_mR^L$,
(42) —$C(O)R^L$,
(43) —$C(O)C_{1-6}$alkyl-$R^L$,
(44) —$OC(O)R^L$,
(45) —$CO_2R^L$,
(46) aryl, and
(47) heteroaryl,
wherein each $R^c$ is unsubstituted or substituted with one to five substituents selected from $R^g$;
$R^d$ is independently selected from the group consisting of:
(1) hydrogen,
(2) halogen,
(3OH,
(4) oxo,
(5) —$C_{1-6}$alkyl,
(6) —$OC_{1-6}$alkyl,
(7) $NH_2$,
(8) $NH(C_{1-6}alkyl)$, and
(9) $N(C_{1-6}alkyl)_2$, each $R^e$ is independently selected from the group consisting of:
(1) hydrogen,
(2) —$C_{1-6}$alkyl, and
(3) $C_{2-6}$alkenyl, each $R^f$ is selected from the group consisting of:
(1) halogen,
(2) —$C_{1-6}$alkyl,
(3) —OH,
(4) —$OC_{1-6}$alkyl,
(5) —$OC_{3-6}$cycloalkyl,
(6) —$OC_{2-6}$cycloheteroalkyl,
(7) CN,
(8) —$NH_2$,
(9) —NH($C_{1-6}$alkyl),
(10) —NH($C_{3-6}$cycloalkyl),
(11) —NH($C_{2-6}$cycloheteroalkyl),
(12) —N($C_{1-6}$alkyl)$_2$,
(13) —N($C_{3-6}$cycloalkyl)$_2$, and
(14) —N($C_{2-6}$cycloheteroalkyl)$_2$, wherein each alkyl, cycloalkyl, and cycloheteroalkyl is unsubstituted or substituted with one to three substituents independently selected from: —OH, halogen, cyano, and —$S(O)_2CH_3$;

each $R^g$ is selected from the group consisting of:
(1) halogen,
(2) $C_{1-6}$alkyl,
(3) —OH,
(4) —$OC_{1-6}$alkyl,
(5) —$S(O)_m$-$C_{1-6}$alkyl,
(6) —CN,
(7) —$CF_3$,
(8) —$OCHF_2$, and
(9) —$OCF_3$, wherein each alkyl is unsubstituted or substituted with one to three substituents independently selected from: —OH, halogen, cyano, and —$S(O)_2CH_3$;

each $R^h$ is independently selected from the group consisting of:
(1) hydrogen, and
(2) —$C_{1-6}$alkyl;

each $R^i$ is independently selected from the group consisting of:
(1) hytdrogen, and
(2) —$C_{1-6}$alkyl;

each $R^j$ is selected from the group consisting of:
(1) —$C_{1-6}$alkyl,
(2) —$C_{2-6}$alkenyl,
(3) —$C_{3-6}$cycloalkyl,
(4) —$C_{2-6}$cycloheteroalkyl,
(5) aryl, and
(6) heteroaryl, wherein each alkyl, alkenyl, cycloalkyl, cycloheteroalkyl, aryl and heteroaryl is unsubstituted or substituted with one to three substituents independently selected from: —$C_{1-6}$alkyl, —$C_{3-6}$cycloalkyl, —OH, —$OC_{1-6}$alkyl, —$OC_{3-6}$cycloalkyl, halogen, cyano, and —$S(O)_2CH_3$;

each $R^k$ is selected from the group consisting of:
(1) —$C_{1-6}$alkyl,
(2) —$C_{2-6}$alkenyl,
(3) —$C_{3-6}$cycloalkyl,
(4) —$C_{3-6}$cycloalkyl,
(5) —$C_{2-6}$cycloheteroalkyl,
(6) aryl, and
(7) heteroaryl, wherein each alkyl, alkenyl, cycloalkyl, cycloheteroalkyl, aryl and heteroaryl is unsubstituted or substituted with one to three substituents independently selected from: —$C_{1-6}$alkyl, —$C_{3-6}$cycloalkyl, —OH, —$OC_{1-6}$alkyl, —$OC_{3-6}$ cycloalkyl, halogen, cyano, and —$S(O)_2CH_3$;

each $R^L$ is selected from the group consisting of:
(1) —$C_{1-6}$alkyl,
(2) —$C_{2-6}$alkenyl,
(3) —$C_{3-6}$cycloalkyl,
(4) —$C_{2-6}$cycloheteroalkyl,
(5) aryl, and
(6) heteroaryl, wherein each alkyl, alkenyl, cycloalkyl, cycloheteroalkyl, aryl and heteroaryl is unsubstituted or substituted with one to three substituents independently selected from: —$C_{1-6}$ alkyl, —$C_{3-6}$cycloalkyl, —OH, —$OC_{1-6}$alkyl, —$OC_{3-6}$cycloalkyl, halogen, cyano, and —$S(O)_2CH_3$; each $R^m$ is independently selected from the group consisting of:
(1) hydrogen, and
(2) —$C_{1-6}$alkyl, each n is independently 0, 1, 2, 3 or 4;
each m is independently 0, 1 or 2;
each p is independently 0, 1, 2, 3 or 4;
each q is independently 0 or 1; and
each r is independently 0 or 1.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In one embodiment of the present invention, A is phenyl or phenyl fused to a saturated or unsaturated 5- or 6-membered ring containing 0-3 heteroatoms independently selected from O, S and $N(R^h)_q$, wherein each phenyl, 5-membered ring and 6-membered ring is unsubstituted or substituted with one to five substituents selected from $R^a$. In a class of this embodiment, A is unsubstituted or substituted with one to four substituents selected from $R^a$. In another class of this embodiment, A is unsubstituted or substituted with one to three substituents selected from $R^a$. In another class of this embodiment, A is unsubstituted or substituted with one to two substituents selected from $R^a$. In another class of this embodiment, A is unsubstituted or substituted with one substituent selected from $R^a$. In another class of this embodiment A is not substituted with a substituent selected from $R^a$. In another class of this embodiment A is unsubstituted.

In another embodiment, A is phenyl or phenyl fused to a saturated or unsaturated 5- or 6-membered ring containing 0-3 heteroatoms independently selected from O, S and $N(R^h)_q$, wherein each phenyl, 5-membered ring and 6-membered ring is unsubstituted or substituted with one to four substituents selected from $R^a$. In another class of this embodiment, A is unsubstituted or substituted with one to three substituents selected from $R^a$. In another class of this embodiment, A is unsubstituted or substituted with one to two substituents selected from $R^a$. In another class of this embodiment, A is unsubstituted or substituted with one substituent selected from $R^a$. In another class of this embodiment A is not substituted with a substituent selected from $R^a$. In another class of this embodiment A is unsubstituted.

In another embodiment of the present invention, A is selected from the group consisting of phenyl, dihydrobenzothiazole, dihydrobenzoisothiazole, and benzothiophene, wherein A is unsubstituted or substituted with one to five substituents selected from $R^a$. In a class of this embodiment, A is unsubstituted or substituted with one to four substituents selected from $R^a$. In another class of this embodiment, A is unsubstituted or substituted with one to three substituents selected from $R^a$. In another class of this embodiment, A is unsubstituted or substituted with one to two substituents selected from $R^a$. In another class of this embodiment, A is unsubstituted or substituted with one substituent selected from $R^a$. In another class of this embodiment A is not substituted with a substituent selected from $R^a$. In another class of this embodiment A is unsubstituted.

In another embodiment, A is selected from the group consisting of: phenyl, dihydro-benzothiazole, dihydrobenzoisothiazole, and benzothiophene, wherein A is unsubstituted or substituted with one to four substituents selected from $R^a$. In a class of this embodiment, A is unsubstituted or substituted with one to three substituents selected from $R^a$. In another class of this embodiment, A is unsubstituted or substituted with one to two substituents selected from $R^a$. In another class of this embodiment A is not substituted with a substituent selected from $R^a$. In another class of this embodiment A is unsubstituted.

In another embodiment, A is selected from the group consisting of: phenyl, 2,3-dihydro-1,2-benzothiazole, 2,3-dihydrobenzo[d]isothiaole, and benzothiophene, wherein A is unsubstituted or substituted with one to four substituents selected from $R^a$. In a class of this embodiment, A is unsubstituted or substituted with one to three substituents selected from $R^a$. In another class of this embodiment, A is unsubstituted or substituted with one to two substituents selected from $R^a$. In another class of this embodiment, A is unsubstituted or substituted with one substituent selected from $R^a$. In another class of this embodiment A is not substituted with a substituent selected from $R^a$. In another class of this embodiment A is unsubstituted.

In another embodiment, A is selected from the group consisting of: phenyl, dihydrobenzothiazole, and benzothiophene, wherein A is unsubstituted or substituted with one to five substituents selected from $R^a$. In a class of this embodiment, A is selected from the group consisting of phenyl, 2,3-dihydro-1,2-benzothiazole, and benzothiophene, wherein A is unsubstituted or substituted with one to five substituents selected from $R^a$. In another class of this embodiment, A is unsubstituted or substituted with one to four substituents selected from $R^a$. In another class of this embodiment, A is unsubstituted or substituted with one to three substituents selected from $R^a$. In another class of this embodiment, A is unsubstituted or substituted with one to two substituents selected from $R^a$. In another class of this embodiment, A is unsubstituted or substituted with one substituent selected from $R^a$. In another class of this embodiment A is not substituted with a substituent selected from $R^a$. In another class of this embodiment A is unsubstituted.

In another embodiment, A is phenyl, wherein phenyl is unsubstituted or substituted with one to three substituents selected from $R^a$. In another class of this embodiment, A is unsubstituted or substituted with one to two substituents selected from $R^a$. In another class of this embodiment, A is unsubstituted or substituted with one substituent selected from $R^a$. In another class of this embodiment A is not substituted with a substituent selected from $R^a$. In another class of this embodiment A is unsubstituted.

In another embodiment, A is

In another embodiment, A is

In another embodiment of the present invention, B is heteroaryl, wherein heteroaryl is unsubstituted or substituted with one to three substituents selected from $R^b$. In a class of this embodiment, B is unsubstituted or substituted with one to two substituents selected from $R^b$.

In another class of this embodiment, B is unsubstituted or substituted with one substituent selected from $R^b$. In another class of this embodiment, B is not substituted with a substituent selected from $R^b$. In another class of this embodiment B is unsubstituted.

In another embodiment, B is selected from the group consisting of pyridine, pyrimidine and pyridazine, wherein each pyridine, pyrimidine and pyridazine is unsubstituted or substituted with one to three substituents selected from $R^b$. In another embodiment, B is selected from the group consisting of pyridine, pyrimidine and pyridazine, wherein each pyridine, pyrimidine and pyridazine is unsubstituted or substituted with one or two substituents selected from $R^b$. In another class of this embodiment, B is selected from the group consisting of pyridine, pyrimidine and pyridazine, wherein each pyridine, pyrimidine and pyridazine is unsubstituted or substituted with one substituent selected from $R^b$. In another class of this embodiment, B is selected from the group consisting of pyridine, pyrimidine and pyridazine, wherein each pyridine, pyrimidine and pyridazine is not substituted with a substituent selected from $R^b$. In another class of this embodiment, B is selected from the group consisting of pyridine, pyrimidine and pyridazine, wherein each pyridine, pyrimidine and pyridazine is unsubstituted.

In another embodiment, B is pyridine, wherein pyridine is unsubstituted or substituted with one to three substituents selected from $R^b$. In another embodiment, B is pyridine, wherein pyridine is unsubstituted or substituted with one or two substituents selected from $R^b$. In another class of this embodiment, B is pyridine, wherein pyridine is unsubstituted or substituted with one substituent selected from $R^b$. In another class of this embodiment, B is pyridine, wherein pyridine is not substituted with a substituent selected from $R^b$. In another class of this embodiment, B is pyridine, wherein pyridine is unsubstituted.

In another embodiment, B is pyrimidine, wherein pyrimidine is unsubstituted or substituted with one or two substituents selected from $R^b$. In another class of this embodiment, B is pyrimidine, wherein pyrimidine is unsubstituted or substituted with one substituent selected from $R^b$. In another class of this embodiment, B is pyrimidine, wherein pyrimidine is not substituted with a substituent selected from $R^b$. In another class of this embodiment, B is pyrimidine, wherein pyrimidine is unsubstituted.

In another embodiment, B is pyridazine, wherein pyridazine is unsubstituted or substituted with one or two substituents selected from $R^b$. In another class of this embodiment, B is pyridazine, wherein pyridazine is unsubstituted or substituted with one substituent selected from $R^b$. In another class of this embodiment, B is pyridazine, wherein pyridazine is not substituted with a substituent selected from $R^b$. In another class of this embodiment, B is pyridazine, wherein pyridazine is unsubstituted.

In another embodiment of the present invention, $R^1$ is selected from the group consisting of: hydrogen, —$SO_3H$, —$SO_2NH_2$, —$SO_2NR^eC_{1-6}$alkyl, —$SO_2NR^eC(O)C_{1-6}$alkyl, —$SO_2NR^eC_{2-6}$alkenyl, —$SO_2NR^eC_{3-6}$cycloalkyl, —$SO_2NR^eC(O)C_{3-6}$cycloalkyl, —$SO_2NR^eC_{2-6}$cycloheteroalkyl, —$SO_2NR^eC(O)C_{2-6}$cycloheteroalkyl, —$SO_2NR^e$-aryl, —$SO_2NR^e$-heteroaryl, —$SO_2C_{1-6}$alkyl, —$SO_2C_{1-6}$alkenyl, —$SO_2C_{3-6}$cycloalkyl, —$SO_2C_{2-6}$cycloheteroalkyl, —$SO_2$aryl, —$SO_2$heteroaryl, —$S(O)R^j$, —$SR^j$, —$C(O)NH_2$, —$C(O)NR^eR^j$, —$CO_2H$, —$CO_2R^j$, —$C(O)R^j$, —CN, $CF_3$, halogen, —OH, —$OC_{1-6}$alkyl, —$OC_{2-6}$alkenyl, —$OC_{3-6}$cycloalkyl, —$OC_{2-6}$cycloheteroalkyl, —O-aryl, —O-heteroaryl, —$OC(O)R^j$, —$OC(O)NR^eR^j$, —$OC(O)N(R^j)_2$, —$C_{1-6}$alkyl, —$C_{2-6}$alkenyl, —$C_{1-6}$cycloalkyl, —$C_{2-6}$cycloheteroalkyl, aryl, heteroaryl, —$(CH_2)_nNR^eC(O)R^j$, —$(CH_2)_nNR^eC(O)OR^j$, —$(CH_2)_nNR^eC(O)N(R^e)_2$, —$(CH_2)_n$ $NR^eC(O)NR^eR^j$, —$(CH_2)_nNR^eC(O)N(R^j)_2$, —$(CH_2)_nNR^eS(O)_mR^j$, —$(CH_2)_nNR^eS(O)_mN(R^e)_2$, —$(CH_2)_nNR^eS(O)_mNR^eR^j$, —$(CH_2)_nNR^eS(O)_mN(R^j)_2$, and —$(CH_2)_nNR^eR^j$, wherein each $CH_2$, alkyl, alkenyl, cycloalkyl, cycloheteroalkyl, aryl and heteroaryl is unsubstituted or substituted with one to four substituents selected from $R^d$. In a class of this embodiment, each alkyl, alkenyl, cycloalkyl, cycloheteroalkyl, aryl and heteroaryl is unsubstituted or substituted with one to three substituents selected from $R^d$. In another class of this embodiment, each alkyl, alkenyl, cycloalkyl, cycloheteroalkyl, aryl and heteroaryl is unsubstituted or substituted with one to two substituents selected from $R^d$.

In another embodiment, $R^1$ is selected from the group consisting of: hydrogen, —$SO_2NH_2$, —$SO_2NH$-heteroaryl, —$SO_2C_{1-6}$alkyl, —$SO_2C_{3-6}$cycloalkyl, —$SO_2C_{3-6}$cycloheteroalkyl, —$C(O)NH_2$, —CN, —$SO_2NR^eC(O)C_{1-6}$alkyl, —$SO_2NR^eC(O)C_{3-6}$cycloalkyl, and —$SO_2NR^eC(O)C_{2-6}$cycloheteroalkyl, wherein each alkyl, cycloalkyl, cycloheteroalkyl and heteroaryl is unsubstituted or substituted with one to four substituents selected from $R^d$. In a class of this embodiment, each alkyl, cycloalkyl, cycloheteroalkyl and heteroaryl is unsubstituted or substituted with one to three substituents selected from $R^d$. In another class of this embodiment, each alkyl, cycloalkyl, cycloheteroalkyl and heteroaryl is unsubstituted or substituted with one to two substituents selected from $R^d$.

In another embodiment, $R^1$ is selected from the group consisting of: hydrogen, —$SO_2NH_2$, —$SO_2NH$-heteroaryl, —$SO_2C_{1-6}$alkyl, —$SO_2C_{3-6}$cycloalkyl, —$SO_2C_{3-6}$cycloheteroalkyl, —$C(O)NH_2$, and —CN, wherein each alkyl, cycloalkyl, cycloheteroalkyl and heteroaryl is unsubstituted or substituted with one to four substituents selected from $R^d$. In a class of this embodiment, each alkyl, cycloalkyl, cycloheteroalkyl and heteroaryl is unsubstituted or substituted with one to three substituents selected from $R^d$. In another class of this embodiment, each alkyl, cycloalkyl, cycloheteroalkyl and heteroaryl is unsubstituted or substituted with one to two substituents selected from $R^d$.

In another embodiment, $R^1$ is selected from the group consisting of: —$SO_2NH_2$, —$SO_2NH$-heteroaryl, —$SO_2C_{1-6}$alkyl, —$SO_2C_{3-6}$cycloalkyl, —$SO_2C_{3-6}$cycloheteroalkyl, —$C(O)NH_2$, —CN, —$SO_2NR^eC(O)C_{1-6}$alkyl, —$SO_2NR^eC(O)C_{3-6}$cycloalkyl, and —$SO_2NR^eC(O)C_{2-6}$cycloheteroalkyl, wherein each alkyl, cycloalkyl, cycloheteroalkyl and heteroaryl is unsubstituted or substituted with one to four substituents selected from $R^d$. In a class of this embodiment, each alkyl, cycloalkyl, cycloheteroalkyl and heteroaryl is unsubstituted or substituted with one to three substituents selected from $R^d$. In another class of this embodiment, each alkyl, cycloalkyl, cycloheteroalkyl and heteroaryl is unsubstituted or substituted with one to two substituents selected from $R^d$.

In another embodiment, $R^1$ is selected from the group consisting of: —$SO_2NR^eC(O)C_{1-6}$alkyl, —$SO_2NR^eC(O)C_{3-6}$ cycloalkyl, and —$SO_2NR^eC(O)C_{2-6}$cycloheteroalkyl, wherein each alkyl, cycloalkyl, and cycloheteroalkyl is unsubstituted or substituted with one to four substituents selected from $R^d$. In a class of this embodiment, each alkyl, cycloalkyl, cycloheteroalkyl and heteroaryl is unsubstituted or substituted with one to three substituents selected from $R^d$. In another class of this embodiment, each alkyl, cycloalkyl, cycloheteroalkyl and heteroaryl is unsubstituted or substituted with one to two substituents selected from $R^d$.

In another embodiment, $R^1$ is selected from the group consisting of: —$SO_2NH_2$, —$SO_2NH$-heteroaryl, —$SO_2C_{1-6}$alkyl, —$SO_2C_{3-6}$cycloalkyl, —$SO_2C_{3-6}$cycloheteroalkyl, —$C(O)NH_2$, and —CN, wherein each alkyl, cycloalkyl, cycloheteroalkyl and heteroaryl is unsubstituted or substituted with one to four substituents selected from $R^d$. In a class of this embodiment, each alkyl, cycloalkyl, cycloheteroalkyl and heteroaryl is unsubstituted or substituted with one to three substituents selected from $R^d$. In another class of this embodiment, each alkyl, cycloalkyl, cycloheteroalkyl and heteroaryl is unsubstituted or substituted with one to two substituents selected from $R^d$.

In another embodiment, $R^1$ is selected from the group consisting of: —$SO_2NH_2$, —$SO_2NH$-pyrimidine, —$SO_2CH_3$, —$SO_2CH(CH_3)_2$, —$SO_2CH_2CH(CH_3)_2$, —$SO_2$-cyclopentyl, —$SO_2$-pyrollidine, —$C(O)NH_2$, and —CN, wherein each alkyl, cycloalkyl, cycloheteroalkyl and heteroaryl is unsubstituted or substituted with one to four substituents selected from $R^d$. In a class of this embodiment, each alkyl, cycloalkyl, cycloheteroalkyl and heteroaryl is unsubstituted or substituted with one to three substituents selected from $R^d$. In another class of this embodiment, each alkyl, cycloalkyl, cycloheteroalkyl and heteroaryl is unsubstituted or substituted with one to two substituents selected from $R^d$.

In another embodiment, $R^1$ is selected from the group consisting of: —$SO_2NH_2$, —$SO_2C_{1-6}$alkyl, and —$C(O)NH_2$, wherein each alkyl is unsubstituted or substituted with one to four substituents selected from $R^d$. In a class of this embodiment, each alkyl is unsubstituted or substituted with one to three substituents selected from $R^d$. In another class of this embodiment, each alkyl is unsubstituted or substituted with one to two substituents selected from $R^d$.

In another embodiment, $R^1$ is selected from the group consisting of: —$SO_2NH_2$, —$SO_2CH_3$, —$SO_2CH(CH_3)_2$, —$SO_2CH_2CH(CH_3)_2$, and —$C(O)NH_2$, wherein each alkyl is unsubstituted or substituted with one to four substituents selected from $R^d$. In a class of this embodiment, each alkyl is unsubstituted or substituted with one to three substituents selected from $R^d$. In another class of this embodiment, each alkyl is unsubstituted or substituted with one to two substituents selected from $R^d$.

In another embodiment, $R^1$ is selected from the group consisting of: —$SO_2NH_2$, —$SO_2CH_3$, and —$C(O)NH_2$, wherein each alkyl is unsubstituted or substituted with one to four substituents selected from $R^d$. In a class of this embodiment, each alkyl is unsubstituted or substituted with one to three substituents selected from $R^d$. In another class of this embodiment, each alkyl is unsubstituted or substituted with one to two substituents selected from $R^d$.

In another embodiment of the present invention, $R^2$ is selected from the group consisting of: hydrogen, and —$C_{1-6}$alkyl. In another embodiment, $R^2$ is —$C_{1-6}$alkyl. In another embodiment, $R^2$ is hydrogen.

In another embodiment of the present invention, $R^3$ is selected from the group consisting of: 1) a monocyclic, bicyclic or spirocyclic $C_{3-12}$cycloalkyl ring, and 2) a monocyclic, bicyclic or spirocyclic $C_{2-12}$cycloheteroalkyl ring, wherein the cycloheteroalkyl contains 1-4 heteroatoms independently selected from $N(R^m)_r$, O, and S, wherein each cycloalkyl ring and each cycloheteroalkyl ring may be fused to an aryl or heteroaryl, and wherein each cycloalkyl, cycloheteroalkyl, aryl and heteroaryl is unsubstituted or substituted with one to eight substitutents selected from $R^c$. In a class of this embodiment, $R^3$ is selected from the group consisting of: 1) a monocyclic, bicyclic or spirocyclic $C_{3-12}$cycloalkyl ring, and 2) a monocyclic, bicyclic or spirocyclic $C_{2-12}$cycloheteroalkyl ring, wherein the cycloheteroalkyl contains 1-4 heteroatoms independently selected from NH, O, and S, wherein each cycloalkyl ring and each cycloheteroalkyl ring may be fused to an aryl or heteroaryl, and wherein each cycloalkyl, cycloheteroalkyl, aryl and heteroaryl is unsubstituted or substituted with one to eight substitutents selected from $R^c$. In another class of this embodiment, $R^3$ is selected from the group consisting of: 1) a monocyclic, bicyclic or spirocyclic $C_{3-8}$cycloalkyl ring, and 2) a monocyclic, bicyclic or spirocyclic $C_{2-10}$cycloheteroalkyl ring, wherein the cycloheteroalkyl contains 1-4 heteroatoms independently selected from $N(R^m)_r$, O, and S, wherein each cycloalkyl ring and each cycloheteroalkyl ring may be fused to an aryl or heteroaryl, and wherein each cycloalkyl, cycloheteroalkyl, aryl and heteroaryl is unsubstituted or substituted with one to eight substitutents selected from $R^c$. In another class of this embodiment, each cycloalkyl and cycloheteroalkyl may be fused to phenyl or thiene. In another class of this embodiment, each cycloalkyl and cycloheteroalkyl may be fused to phenyl. In another class of this embodiment, each cycloalkyl and cycloheteroalkyl ring may be fused to thiene. In another class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment and subclass of these classes, the cycloheteroalkyl contains nitrogen and is attached to the B ring via a bond to the nitrogen.

In another embodiment of the present invention, $R^3$ is selected from the group consisting of: a monocyclic, bicyclic or spirocyclic $C_{3-12}$cycloalkyl ring, and a monocyclic, bicyclic or spirocyclic $C_{2-12}$cycloheteroalkyl ring, wherein the cycloheteroalkyl contains 1-4 heteroatoms independently selected from NH, O, and S, wherein each cycloalkyl and cycloheteroalkyl may be fused to an aryl or heteroaryl, and wherein each cycloalkyl, cycloheteroalkyl, aryl and heteroaryl is unsubstituted or substituted with one to eight substitutents selected from $R^c$. In a class of this embodiment, $R^3$ is selected from the group consisting of: a monocyclic, bicyclic or spirocyclic $C_{3-8}$cycloalkyl ring, and a monocyclic, bicyclic or spirocyclic $C_{2-12}$cycloheteroalkyl ring, wherein the cycloheteroalkyl contains 1-4 heteroatoms independently selected from NH, O, and S, wherein each cycloalkyl and cycloheteroalkyl may be fused to an aryl or heteroaryl, and wherein each cycloalkyl, cycloheteroalkyl, aryl and heteroaryl is unsubstituted or substituted with one to eight substitutents selected from $R^c$. In another class of this embodiment, each cycloalkyl and cycloheteroalkyl may be fused to phenyl or thiene. In another embodiment, each cycloalkyl and cycloheteroalkyl ring may be fused to thiene. In another class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment and subclass of these classes, the cycloheteroalkyl contains nitrogen and is attached to the B ring via a bond to the nitrogen.

In another embodiment of the present invention, $R^3$ is a monocyclic, bicyclic or spirocyclic $C_{3-12}$cycloalkyl ring, wherein each cycloalkyl may be fused to an aryl or heteroaryl, and wherein each cycloalkyl, aryl and heteroaryl is unsubstituted or substituted with one to eight substitutents selected from $R^c$. In a class of this embodiment, $R^3$ is a monocyclic, bicyclic or spirocyclic $C_{3-8}$cycloalkyl ring, wherein each cycloalkyl may be fused to an aryl or heteroaryl, and wherein each cycloalkyl, aryl and heteroaryl is unsubstituted or substituted with one to eight substitutents selected from $R^c$. In another class of this embodiment, each cycloalkyl and cycloheteroalkyl may be fused to phenyl or thiene. In another embodiment, each cycloalkyl and cycloheteroalkyl may be fused to phenyl. In another embodiment, each cycloalkyl and cycloheteroalkyl ring may be fused to thiene. In another class of this embodiment, $R^3$ is unsubstituted or substituted with one to six substituents selected from $R^c$. In another class of this embodiment, $R^3$ is unsubstituted or substituted with one to four substituents selected from $R^c$.

In another embodiment of the present invention, $R^3$ is a monocyclic, bicyclic or spirocyclic $C_{2-12}$cycloheteroalkyl ring, wherein the cycloheteroalkyl contains 1-4 heteroatoms independently selected from $N(R^m)_r$, O, and S, wherein each cycloheteroalkyl may be fused to an aryl or heteroaryl, and wherein each cycloheteroalkyl, aryl and heteroaryl is unsubstituted or substituted with one to eight substitutents selected from $R^c$. In a class of this embodiment, $R^3$ is a monocyclic, bicyclic or spirocyclic $C_{2-10}$cycloheteroalkyl ring, wherein the cycloheteroalkyl contains 1-4 heteroatoms independently selected from $N(R^m)_r$, O, and S, wherein each cycloheteroalkyl may be fused to an aryl or heteroaryl, and wherein each cycloheteroalkyl, aryl and heteroaryl is unsubstituted or substituted with one to eight substitutents selected from $R^c$. In another class of this embodiment, each cycloheteroalkyl may be fused to phenyl or thiene. In another embodiment, each cyclohetero-alkyl may be fused to phenyl. In another embodiment, each cycloheteroalkyl ring may be fused to thiene. In another class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment and subclass of these classes, the cycloheteroalkyl contains nitrogen and is attached to the B ring via a bond to the nitrogen.

In another embodiment of the present invention, $R^3$ is selected from the group consisting of: a monocyclic, bicyclic or spirocyclic $C_{3-12}$cycloalkyl ring, and a monocyclic, bicyclic or spirocyclic $C_{2-12}$cycloheteroalkyl ring, wherein the cycloheteroalkyl contains a nitrogen and 0-3 heteroatoms independently selected from $N(R^m)_r$, O, and S, wherein each cycloalkyl and cycloheteroalkyl may be fused to an aryl or heteroaryl, and wherein each cycloalkyl, cycloheteroalkyl, aryl and heteroaryl is unsubstituted or substituted with one to eight substitutents selected from $R^c$. In a class of this embodiment, $R^3$ is selected from the group consisting of: a monocyclic, bicyclic or spirocyclic $C_{3-8}$cycloalkyl ring, and a monocyclic, bicyclic or spirocyclic $C_{2-12}$cycloheteroalkyl ring, wherein the cycloheteroalkyl contains a nitrogen and 0-3 heteroatoms independently selected from $N(R^m)_r$, O, and S, wherein each cycloalkyl and cycloheteroalkyl may be fused to an aryl or heteroaryl, and wherein each cycloalkyl, cycloheteroalkyl, aryl and heteroaryl is unsubstituted or substituted with one to eight substituents selected from $R^c$. In another class of this embodiment, each cycloalkyl and cycloheteroalkyl may be fused to phenyl or thiene. In another embodiment, each cycloalkyl and cycloheteroalkyl may be fused to phenyl. In another class of this embodiment, each cycloalkyl and cycloheteroalkyl ring may be fused to thiene. In another class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment and subclass of these classes, the cycloheteroalkyl contains nitrogen and is attached to the B ring via a bond to the nitrogen.

In another embodiment of the present invention, $R^3$ is a monocyclic, bicyclic or spirocyclic $C_{3-12}$cycloalkyl ring, wherein each cycloalkyl may be fused to an aryl or heteroaryl, and wherein each cycloalkyl, aryl and heteroaryl is unsubstituted or substituted with one to eight substituents selected from $R^c$. In a class of this embodiment, $R^3$ is a monocyclic, bicyclic or spirocyclic $C_{3-8}$cycloalkyl ring, wherein each cycloalkyl may be fused to an aryl or heteroaryl, and wherein each cycloalkyl, aryl and heteroaryl is unsubstituted or substituted with one to eight substituents selected from $R^c$. In another class of this embodiment, each cycloalkyl and cycloheteroalkyl may be fused to phenyl or thiene. In another class of this embodiment, each cycloalkyl and cycloheteroalkyl may be fused to phenyl. In another embodiment, each cycloalkyl and cycloheteroalkyl ring may be fused to thiene. In another class of this embodiment, $R^3$ is unsubstituted or substituted with one to six substituents selected from $R^c$. In another class of this embodiment, $R^3$ is unsubstituted or substituted with one to four substituents selected from $R^c$.

In another embodiment of the present invention, $R^3$ is a monocyclic, bicyclic or spirocyclic $C_{2-12}$cycloheteroalkyl ring, wherein the cycloheteroalkyl contains a nitrogen and 0-3 heteroatoms independently selected from $N(R^m)_r$, O, and S, wherein each cycloheteroalkyl may be fused to an aryl or heteroaryl, and wherein each cycloheteroalkyl, aryl and heteroaryl is unsubstituted or substituted with one to eight substituents selected from $R^c$. In a class of this embodiment, the cycloheteroalkyl contains a nitrogen and 0-2 heteroatoms independently selected from NH, O, and S. In a class of this embodiment, each cycloheteroalkyl may be fused to phenyl or thiene. In another embodiment, each cycloheteroalkyl may be fused to phenyl. In another embodiment, each cycloheteroalkyl ring may be fused to thiene. In another class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment and subclass of these classes, the cycloheteroalkyl contains nitrogen and is attached to the B ring via a bond to the nitrogen.

In another embodiment of the present invention, $R^3$ is selected from the group consisting of: a monocyclic, bicyclic or spirocyclic $C_{3-12}$cycloalkyl ring, and a monocyclic, bicyclic or spirocyclic $C_{2-12}$cycloheteroalkyl ring, wherein the cycloheteroalkyl contains 1-4 heteroatoms independently selected from $N(R^m)_r$, O, and S, and wherein each cycloalkyl and cycloheteroalkyl is unsubstituted or substituted with one to four substituents selected from $R^c$. In a class of this embodiment of the present invention, $R^3$ is selected from the group consisting of: a monocyclic, bicyclic or spirocyclic $C_{3-8}$cycloalkyl ring, and a monocyclic, bicyclic or spirocyclic $C_{2-12}$cycloheteroalkyl ring, wherein the cycloheteroalkyl contains 1-4 heteroatoms independently selected from $N(R^m)_r$, O, and S, and wherein each cycloalkyl and cycloheteroalkyl is unsubstituted or substituted with one to four substituents selected from $R^c$. In another class of this embodiment, $R^3$ is unsubstituted or substituted with one to three substituents selected from $R^c$. In another class of this embodiment, $R^3$ is unsubstituted or substituted with one to two substituents selected from $R^c$. In another class of this embodiment and subclass of these classes, the cycloheteroalkyl contains nitrogen and is attached to the B ring via a bond to the nitrogen.

In another embodiment of the present invention, $R^3$ is a monocyclic, bicyclic or spirocyclic $C_{3-12}$cycloalkyl ring, wherein each cycloalkyl is unsubstituted or substituted with one to four substituents selected from $R^c$. In a class of this embodiment, $R^3$ is a monocyclic, bicyclic or spirocyclic $C_{3-8}$cycloalkyl ring, wherein each cycloalkyl is unsubstituted or substituted with one to four substituents selected from $R^c$. In another class of this embodiment, $R^3$ is unsubstituted or substituted with one to three substituents selected from $R^c$. In a class of this embodiment, $R^3$ is unsubstituted or substituted with one to three substituents selected from $R^c$.

In another embodiment of the present invention, $R^3$ is a monocyclic, bicyclic or spirocyclic $C_{2-12}$cycloheteroalkyl ring, wherein the cycloheteroalkyl contains 1-4 heteroatoms independently selected from $N(R^m)_r$, O, and S, and wherein each cycloheteroalkyl is unsubstituted or substituted with one to four substituents selected from $R^c$. In a class of this embodiment, $R^3$ is a monocyclic, bicyclic or spirocyclic $C_{2-10}$cycloheteroalkyl ring, wherein the cycloheteroalkyl contains 1-4 heteroatoms independently selected from $N(R^m)_r$, O, and S, and wherein each cycloheteroalkyl is unsubstituted or substituted with one to four substituents selected from $R^c$. In another class of this embodiment, $R^3$ is unsubstituted or substituted with one to three substituents selected from $R^c$. In another class of this embodiment, $R^3$ is unsubstituted or substituted with one to two substituents selected from $R^c$. In another class of this embodiment, the cycloheteroalkyl contains nitrogen and is attached to the B ring via a bond to the nitrogen.

In another embodiment of the present invention, $R^3$ is selected from the group consisting of: a monocyclic, bicyclic or spirocyclic $C_{3-12}$cycloalkyl ring, and a monocyclic, bicyclic or spirocyclic $C_{2-12}$cycloheteroalkyl ring, wherein the cycloheteroalkyl contains a nitrogen and 0-3 heteroatoms independently selected from $N(R^m)_r$, O, and S, and wherein each cycloalkyl and cycloheteroalkyl is unsubstituted or substituted with one to four substituents selected from $R^c$.

In a class of this embodiment, $R^3$ is selected from the group consisting of: a monocyclic, bicyclic or spirocyclic $C_{3-8}$cycloalkyl ring, and a monocyclic, bicyclic or spirocyclic $C_{2-12}$cycloheteroalkyl ring, wherein the cycloheteroalkyl contains a nitrogen and 0-3 heteroatoms independently selected from $N(R^m)_r$, O, and S, and wherein each cycloalkyl and cycloheteroalkyl is unsubstituted or substituted with one to four substituents selected from $R^c$. In another class of this embodiment, the cycloheteroalkyl contains a nitrogen and 0-2 heteroatoms independently selected from NH, O, and S. In another class of this embodiment, $R^3$ is unsubstituted or substituted with one to three substituents selected from $R^c$. In another class of this embodiment, $R^3$ is unsubstituted or substituted with one to two substituents selected from $R^c$. In another class of this embodiment and subclass of these classes, the cycloheteroalkyl contains nitrogen and is attached to the B ring via a bond to the nitrogen.

In another embodiment of the present invention, $R^3$ is a monocyclic, bicyclic or spirocyclic $C_{3-12}$cycloalkyl ring, and wherein each cycloalkyl is unsubstituted or substituted with one to three substitutents selected from $R^c$. In a class of this embodiment, $R^3$ is a monocyclic, bicyclic or spirocyclic $C_{3-8}$cycloalkyl ring, and wherein each cycloalkyl is unsubstituted or substituted with one to three substituents selected from $R^c$. In another class of this embodiment, $R^3$ is a monocyclic, bicyclic or spirocyclic $C_{3-8}$cycloalkyl ring, and wherein each cycloalkyl is unsubstituted or substituted with one to three substituents selected from $R^c$.

In another embodiment of the present invention, $R^3$ is a monocyclic, bicyclic or spirocyclic $C_{2-12}$cycloheteroalkyl ring, wherein the cycloheteroalkyl contains a nitrogen and 0-3 heteroatoms independently selected from $N(R^m)_r$, O, and S, and wherein each cycloheteroalkyl is unsubstituted or substituted with one to four substituents selected from $R^c$. In a class of this embodiment, $R^3$ is a monocyclic, bicyclic or spirocyclic $C_{2-10}$cycloheteroalkyl ring, wherein the cycloheteroalkyl contains a nitrogen and 0-3 heteroatoms independently selected from $N(R^m)_r$, O, and S, and wherein each cycloheteroalkyl is unsubstituted or substituted with one to four substitutents selected from $R^c$. In another class of this embodiment, the cycloheteroalkyl contains a nitrogen and 0-2 heteroatoms independently selected from NH, O, and S. In another class of this embodiment, $R^3$ is unsubstituted or substituted with one to three substituents selected from $R^c$. In another class of this embodiment, $R^3$ is unsubstituted or substituted with one to two substituents selected from $R^c$. In another class of this embodiment and subclass of these classes, the cycloheteroalkyl contains nitrogen and is attached to the B ring via a bond to the nitrogen.

In another embodiment, $R^3$ is selected from the group consisting of: pyrrolidine, azetidine, piperidine, piperazine, azepane, azocane, morpholine, thiomorpholine, thiomorpholine dione, oxazepane, 1,4-thiazepane, isoindoline, dihydroisoquinoline, tetrahydroisoquinoline, octahydro-isoindole, azabicyclo[2.2.1]heptane, oxa-azabicyclo[2.2.1]heptane, azabicyclo[3.1.1]-heptane, azabicyclo[4.1.0]heptane, azabicyclo[3.2.1]octane, diazabicyclo[3.2.1]octane, oxa-azabicyclo-[3.2.1]octane, azabicyclo[3.2.0]heptane, oxa-azabicyclo[3.2.0]heptane, azaspiro[2.5]-octane, azaspiro[2.6]nonane, azaspiro[3.5]nonane, oxa-azaspiro[3.5]nonane, oxa-azaspiro[4.5]-decane, dihydrothieno[3,2-c]pyridine, dihydrothiazolo[4,5-c]pyridine, dihydrooxazolo[4,5-c]pyridine, dihydroimidazo[1,2-a]pyrazine, hexahydrofuro[3,2-b]pyrrole, hexahydrocyclopenta-[c]pyrrole, octahydrocyclpenta[c]pyrrole, and azatricyclo[4.3.1.13,8]undecane, wherein $R^3$ is unsubstituted or substituted with one to eight substituents selected from $R^c$. In a class of this embodiment, $R^3$ is unsubstituted or substituted with one to six substituents selected from $R^c$. In another class of this embodiment, $R^3$ is unsubstituted or substituted with one to four substituents selected from $R^c$. In a class of this embodiment and subclass of these classes, $R^3$ contains nitrogen and is attached to the B ring via a bond to the nitrogen.

In another embodiment of the present invention, $R^3$ is selected from the group consisting of pyrrolidine, azetidine, piperidine, piperazine, azepane, azocane, morpholine, thiomorpholine, oxazepane, isoindoline, dihydroisoquinoline, octahydroisoindole, azabicyclo[2.2.1]heptane, azabicyclo[3.1.1]heptane, azabicyclo[4.1.0]heptane, azabicyclo[3.2.1]octane, diazabicyclo-[3.2.1]octane, azabicyclo[3.2.0]heptane, oxa-azabicyclo[3.2.1]octane, azaspiro[2.5]octane, azaspiro[2.6]nonane, azaspiro[3.5]nonane, oxa-azaspiro[3.5}nonane, oxa-azaspiro[4.5]decane, dihydrothieno[3,2-c]pyridine, dihydrothiazolo[4,5-c]pyridine, dihydrooxazolo[4,5-c]pyridine, dihydroimidazo[1,2-a]pyrazine, hexahydrofuro[3,2-b]pyrrole, hexahydrocyclopenta[c]pyrrole, and azatricyclo[4.3.1.13,8]undecane, wherein $R^3$ is unsubstituted or substituted with one to eight substituents selected from $R^c$. In a class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In a class of this embodiment and subclass of these classes, $R^3$ contains nitrogen and is attached to the B ring via a bond to the nitrogen.

In another embodiment of the present invention, $R^3$ is selected from the group consisting of: pyrrolidine, azetidine, piperidine, piperazine, azepane, azocane, morpholine, thiomorpholine, oxazepane, 1,4-oxazepane, isoindoline, 2-isoindoline, dihydroisoquinoline, octahydroisoindole, azabicyclo[2.2.1]heptane, azabicyclo[3.1.1]heptane, azabicyclo[4.1.0]heptane, azabicyclo[3.2.1]-octane, diazabicyclo[3.2.1]octane, azabicyclo[3.2.0]heptane, oxa-azabicyclo[3.2.1]octane, azaspiro[2.5]octane, azaspiro[2.6]nonane, azaspiro[3.5]nonane, oxa-azaspiro[3.5]nonane, oxa-azaspiro[4.5]decane, dihydrothieno[3,2-c]pyridine, dihydrothiazolo[4,5-c]pyridine, dihydrooxazolo[4,5-c]pyridine, dihydroimidazo[1,2-a]pyrazine, hexahydrofuro[3,2-b]pyrrole, hexahydrocyclopenta[c]pyrrole, and azatricyclo[4.3.1.13,8]undecane, wherein $R^3$ is unsubstituted or substituted with one to eight substituents selected from $R^c$. In a class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In another class of this embodiment and subclass of these classes, $R^3$ contains nitrogen and is attached to the B ring via a bond to the nitrogen.

In another embodiment of the present invention, $R^3$ is selected from the group consisting of: pyrrolidine, azetidine, piperidine, piperazine, azepane, azocane, morpholine, thiomorpholine, oxazepane, isoindoline, dihydroisoquinoline, octahydroisoindole, azabicyclo[2.2.1]heptane, azabicyclo[3.1.1]heptane, azabicyclo[4.1.0]heptane, azabicyclo[3.2.1]octane, diazabicyclo[3.2.1]octane, azabicyclo[3.2.0]heptane, oxa-azabicyclo[3.2.1]octane, azaspiro[2.5]octane, azaspiro[2.6]nonane, oxa-azaspiro[3.5}nonane, oxa-azaspiro[4.5]decane, dihydrothiazolo[4,5-c]pyridine, dihydrooxazolo[4,5-c]pyridine, hexahydrofuro[3,2-b]pyrrole, hexahydrocyclopenta[c]pyrrole, and azatricyclo[4.3.1.13,8]undecane, wherein $R^3$ is unsubstituted or substituted with one to eight substituents selected from $R^c$. In a class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In another class of this embodiment and subclass of these classes, $R^3$ contains nitrogen and is attached to the B ring via a bond to the nitrogen.

In another embodiment of the present invention, $R^3$ is selected from the group consisting of: pyrrolidine, azetidine, piperidine, piperazine, azepane, azocane, morpholine, thiomorpholine, 1,4-oxazepane, 2-isoindoline, 3,4-dihydroisoquinoline, 1,3,3a,4,5,6,7,7a-octahydroisoindole, 2-azabicyclo[2.2.1]heptane, 7-azabicyclo[2.2.1]heptane, 3-azabicyclo[3.1.1]heptane, 3-azabicyclo[4.1.0]heptane; 3-azabicyclo[3.2.1]octane, 3,8-diazabicyclo[3.2.1]octane, 3-azabicyclo[3.2.0]heptane, 6-azabicyclo[3.2.0]heptane, 8-oxa-3-azabicyclo[3.2.1]octane, 6-oxa-3-azabicyclo[3.2.1]octane, 6-azaspiro[2.5]octane, 5-azaspiro[2.5]octane, 6-azaspiro[2.6]nonane, 2-oxa-7-azaspiro[3.5]nonane, 7-oxa-2-azaspiro[3.5]nonane, 1-oxa-8-azaspiro[4.5]decane, 6,7-dihydrothiazolo[4,5-c]pyridine, 6,7-dihydrooxazolo[4,5-c]pyridine, 2,3,3a,5,6,6a-hexahydrofuro[3,2-b]pyrrole, 1,3,3a,5,6,6a-hexahydrocyclopenta[c]pyrrole, and azatricyclo[4.3.1.13,8]undecane, wherein $R^3$ is unsubstituted or substituted with one to eight substituents selected from $R^c$. In a class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In another class of this embodiment and subclass of these classes, $R^3$ contains nitrogen and is attached to the B ring via a bond to the nitrogen.

In another embodiment of the present invention, $R^3$ is selected from the group consisting of piperidine, azepane, morpholine, and azaspiro[2.5]octane, wherein $R^3$ is unsubstituted or substituted with one to eight substituents selected from $R^c$. In a class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In another class of this embodiment and subclass of these classes, $R^3$ contains nitrogen and is attached to the B ring via a bond to the nitrogen.

In another embodiment of the present invention, $R^3$ is selected from the group consisting of piperidine, azepane, morpholine, 6-azaspiro[2.5]octane, and 5-azaspiro[2.5]octane, wherein $R^3$ is unsubstituted or substituted with one to eight substituents selected from $R^c$. In a class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In another class of this embodiment and subclass of these classes, $R^3$ contains nitrogen and is attached to the B ring via a bond to the nitrogen.

In another embodiment of the present invention, $R^3$ is selected from the group consisting of piperidine, azepane, morpholine, and 6-azaspiro[2.5]octane, wherein $R^3$ is unsubstituted or substituted with one to eight substituents selected from $R^c$. In a class of this embodiment, $R^3$ is unsubstituted or substituted with one to six substituents selected from $R^c$. In another class of this embodiment, $R^3$ is unsubstituted or substituted with one to four substituents selected from $R^c$. In another class of this embodiment, $R^3$ is unsubstituted or substituted with one to three substituents selected from $R^c$. In another class of this embodiment and subclass of these classes, $R^3$ contains nitrogen and is attached to the B ring via a bond to the nitrogen.

In another embodiment of the present invention, each $R^a$ is selected from the group consisting of: —$C_{1-6}$alkyl, —$OC_{1-6}$alkyl, halogen, —OH, oxo, —CN, —$C_{3-6}$cycloalkyl, and —$C_{2-5}$cycloheteroalkyl, wherein each alkyl, cycloalkyl and cycloheteroalkyl is unsubstituted or substituted with one to six substituents selected from halogen, OH, $NH_2$, $NH(C_{1-6}alkyl)$ and $N(C_{1-6}alkyl)_2$. In a class of this embodiment, $R^a$ is substituted with a halogen is selected from: F, Br, and Cl. In a subclass of this class, the halogen is F or Cl. In another subclass of this class, the halogen is Cl. In another subclass of this class, the halogen is F.

In another embodiment, each $R^a$ is selected from the group consisting of: —$C_{1-6}$alkyl, —$OC_{1-6}$alkyl, halogen, —OH, oxo, —CN, and —$C_{3-6}$cycloalkyl, wherein each alkyl and cycloalkyl is unsubstituted or substituted with one to six substituents selected from halogen, OH, $NH_2$, $NH(C_{1-6}$ alkyl) and $N(C_{1-6}alkyl)_2$. In a class of this embodiment, $R^a$ is substituted with a halogen is selected from: F, Br, and Cl. In a subclass of this class, the halogen is F or Cl. In another subclass of this class, the halogen is Cl. In another subclass of this class, the halogen is F.

In another embodiment, each $R^a$ is selected from the group consisting of: —$C_{1-6}$alkyl, —$OC_{1-6}$alkyl, halogen, —OH, oxo, and —CN, wherein each alkyl is unsubstituted or substituted with one to six substituents selected from halogen, OH, $NH_2$, $NH(C_{1-6}alkyl)$ and $N(C_{1-6}alkyl)_2$. In a class of this embodiment, $R^a$ is substituted with a halogen is selected from: F, Br, and Cl. In a subclass of this class, the halogen is F or Cl. In another subclass of this class, the halogen is Cl. In another subclass of this class, the halogen is F.

In another embodiment, each $R^a$ is selected from the group consisting of: —$C_{1-6}$alkyl, halogen, —OH, oxo, and —CN, wherein each alkyl is unsubstituted or substituted with one to six substituents selected from halogen, OH, $NH_2$, $NH(C_{1-6}alkyl)$ and $N(C_{1-6}alkyl)_2$. In a class of this embodiment, $R^a$ is substituted with a halogen is selected from: F, Br, and Cl. In a subclass of this class, the halogen is F or Cl. In another subclass of this class, the halogen is Cl. In another subclass of this class, the halogen is F.

In another embodiment, each $R^a$ is selected from the group consisting of: —$C_{1-6}$alkyl, halogen, —OH, and oxo, wherein each alkyl is unsubstituted or substituted with one to six substituents selected from halogen, OH, $NH_2$, $NH(C_{1-6}$ alkyl) and $N(C_{1-6}alkyl)_2$. In a class of this embodiment, $R^a$ is substituted with a halogen is selected from: F, Br, and Cl. In a subclass of this class, the halogen is F or Cl. In another subclass of this class, the halogen is Cl. In another subclass of this class, the halogen is F.

In another embodiment, each $R^a$ is selected from the group consisting of: —$C_{1-6}$alkyl, halogen, —OH, and oxo. In another class of this embodiment, each $R^a$ is selected from the group consisting of: $CH_3$, F, —OH, and oxo.

In another embodiment, each $R^a$ is selected from the group consisting of: —$C_{1-6}$alkyl and halogen. In another embodiment, each $R^a$ is selected from the group consisting of: $CH_3$ and halogen. In another embodiment, each $R^a$ is halogen. In a class of this embodiment, $R^a$ is F. In another embodiment, $R^a$ is —$C_{1-6}$alkyl. In a class of this embodiment, $R^a$ is $CH_3$.

In another embodiment of the present invention, each $R^b$ is independently selected from the group consisting of: —$CF_3$, —$CF_2CF_3$, —$CHF_2$, —$OCHF_2$, —$OCH_2CF_3$, —$OCF_3$, CN, halogen, —$Si(C_{1-6}alkyl)_3$, —$C_{1-6}alkyl$-O—

$R^k$, —$C_{1-6}$alkyl, —$C_{2-6}$alkenyl, —$C_{2-6}$alkynyl, —$C_{3-6}$cycloalkyl, —$C_{2-6}$cycloheteroalkyl, aryl, heteroaryl, —$C_{1-6}$alkyl-$C_{3-6}$cycloalkyl, —$C_{1-6}$alkyl-$C_{2-6}$cycloheteroalkyl, —$C_{1-6}$alkyl-aryl, —$C_{1-6}$alkyl-heteroaryl, —$C_{2-6}$alkenyl-$C_{3-6}$ cycloalkyl, —$C_{2-6}$alkenyl-$C_{2-6}$cycloheteroalkyl, —$C_{2-6}$ alkenyl-aryl, —$C_{2-6}$alkenyl-heteroaryl, —$C_{2-6}$alkynyl-$C_{3-6}$cycloalkyl, —$C_{2-6}$alkynyl cycloheteroalkyl, —$C_{2-6}$ alkynyl-aryl, —$C_{2-6}$alkynyl-heteroaryl, NO$_2$, —OH, —(CH$_2$)$_p$—OC$_{1-6}$alkyl, —(CH$_2$)$_p$—OC$_{2-6}$alkenyl, —(CH$_2$)$_p$ —OC$_{2-6}$alkynyl, —(CH$_2$)$_p$—OC$_{3-6}$cycloalkyl, —(CH$_2$)$_p$—OC$_{2-6}$heterocycloalkyl, —(CH$_2$)$_p$—O-aryl, —(CH$_2$)$_p$—O-heteroaryl, —OC$_{1-6}$alkyl-$C_{3-6}$cycloalkyl, —OC$_{1-6}$alkyl-$C_{2-6}$heterocycloalkyl, —OC$_{1-6}$alkyl-aryl, —OC$_{1-6}$alkyl-heteroaryl, —S(O)$_m$R$^k$, —$C_{1-6}$alkyl-S(O)$_m$ R$^k$, —C(O)R$^k$, —N(R$^i$)$_2$, and —NR$^i$R$^k$, wherein each R$^b$ is unsubstituted or substituted with one to five substituents selected from R$^f$.

In another embodiment of the present invention, each R$^b$ is independently selected from the group consisting of: —CF$_3$, —CF$_2$CF$_3$, —CHF$_2$, —OCHF$_2$, —OCH$_2$CF$_3$, —OCF$_3$, CN, halogen, —Si(C$_{1-6}$alkyl)$_3$, —C$_{1-6}$alkyl, —C$_{1-6}$ alkyl-O—R$^k$, —C$_{2-6}$alkenyl, —C$_{2-6}$alkynyl, —C$_{3-6}$ cycloalkyl, —C$_{2-6}$cycloheteroalkyl, aryl, heteroaryl, —C$_{1-6}$ alkyl-C$_{3-6}$cycloalkyl, —C$_{1-6}$alkyl-C$_{2-6}$cycloheteroalkyl, —C$_{1-6}$alkyl-aryl, —C$_{1-6}$alkyl-heteroaryl, NO$_2$, —OH, —(CH$_2$)$_p$—OC$_{1-6}$alkyl, —(CH$_2$)$_p$—OC$_{2-6}$alkenyl, —(CH$_2$)$_p$ —OC$_{2-6}$alkynyl, —(CH$_2$)$_p$—OC$_{3-6}$cycloalkyl, —(CH$_2$)$_p$—OC$_{2-6}$heterocycloalkyl, —(CH$_2$)$_p$—O-aryl, and —(CH$_2$)$_p$—O-heteroaryl, wherein each R$^b$ is unsubstituted or substituted with one to five substituents selected from R$^f$.

In another embodiment of the present invention, each R$^b$ is independently selected from the group consisting of: —CF$_3$, —CF$_2$CF$_3$; —CHF$_2$, —OCHF$_2$, —OCH$_2$CF$_3$, —OCF$_3$, CN, halogen, —Si(C$_{1-6}$alkyl)$_3$, —C$_{1-6}$alkyl-O—R$^k$, —C$_{1-6}$alkyl, —C$_{3-6}$cycloalkyl, —C$_{2-6}$cycloheteroalkyl, aryl, heteroaryl, NO$_2$, —OH, —(CH$_2$)$_p$—OC$_{1-6}$alkyl, wherein each R$^b$ is unsubstituted or substituted with one to five substituents selected from R$^f$.

In another embodiment, each R$^b$ is independently selected from the group consisting of: —CF$_3$, —CHF$_2$, —OCHF$_2$, —CF$_2$CF$_3$, —OCF$_3$, CN, halogen, —Si(CH$_3$)$_3$, —C$_{1-6}$alkyl, —C$_{2-6}$alkenyl, —OC$_{1-6}$alkyl, —C$_{3-6}$cycloalkyl, —C$_{2-6}$cycloheteroalkyl, aryl, and heteroaryl, wherein each R$^b$ is unsubstituted or substituted with one to five substituents selected from R$^f$ In a class of this embodiment, each R$^b$ is independently selected from the group consisting of: —CF$_3$, —CHF$_2$, —OCHF$_2$, —CF$_2$CF$_3$, —OCF$_3$, CN, Br, Cl, F, —Si(CH$_3$)$_3$, —CH$_3$, —CH(CH$_3$)$_2$, —CH$_2$CH(CH$_3$)$_2$, —C(CH$_3$)$_3$, —(CH$_2$)$_2$CH=CH$_2$, —OCH$_3$, cyclopropyl, cyclobutyl, cyclopentyl, oxetane, phenyl, and pyridine, wherein each R$^b$ is unsubstituted or substituted with one to five substituents selected from R$^f$.

In another embodiment, each R$^b$ is independently selected from the group consisting of: —CF$_3$, —CHF$_2$, —OCHF$_2$, —CF$_2$CF$_3$, —OCF$_3$, CN, halogen, —Si(CH$_3$)$_3$, —C$_{1-6}$alkyl, —C$_{2-6}$alkenyl, —OC$_{1-6}$alkyl, and —C$_{3-6}$cycloalkyl, wherein each R$^b$ is unsubstituted or substituted with one to five substituents selected from R$^f$. In a class of this embodiment, each R$^b$ is independently selected from the group consisting of: —CF$_3$, —CHF$_2$, —OCHF$_2$, —CF$_2$CF$_3$, —OCF$_3$, CN, Br, Cl, F, —Si(CH$_3$)$_3$, —CH$_3$, —CH(CH$_3$)$_2$, —CH$_2$CH(CH$_3$)$_2$, —C(CH$_3$)$_3$, —(CH$_2$)$_2$CH=CH$_2$, —OCH$_3$, and cyclopropyl, wherein each R$^b$ is unsubstituted or substituted with one to five substituents selected from R$^f$.

In another embodiment, each R$^b$ is independently selected from the group consisting of: —CF$_3$, CN, halogen, —C$_{1-6}$ alkyl, and —C$_{3-6}$cycloalkyl, wherein each R$^b$ is unsubstituted or substituted with one to five substituents selected from R$^f$. In a class of this embodiment, each R$^b$ is independently selected from the group consisting of: —CF$_3$, CN, Br, Cl, F, —CH$_3$, —CH(CH$_3$)$_2$, —CH$_2$CH(CH$_3$)$_2$, —C(CH$_3$)$_3$, and cyclopropyl, wherein each R$^b$ is unsubstituted or substituted with one to five substituents selected from R$^f$.

In another embodiment, each R$^b$ is independently selected from the group consisting of: —CF$_3$, CN, halogen, —C$_{1-6}$ alkyl, and —C$_{3-6}$cycloalkyl, wherein each R$^b$ is unsubstituted or substituted with one to five substituents selected from R$^f$. In a class of this embodiment, each R$^b$ is independently selected from the group consisting of —CF$_3$, CN, Cl, —CH$_3$, and cyclopropyl, wherein each R$^b$ is unsubstituted or substituted with one to five substituents selected from R$^f$.

In another embodiment, each R$^b$ is independently selected from the group consisting of: —CF$_3$, —CHF$_2$, —OCHF$_2$, —CF$_2$CF$_3$, —OCF$_3$, CN, halogen, —Si(CH$_3$)$_3$, —C$_{1-6}$alkyl, —C$_{2-6}$alkenyl, and —OC$_{1-6}$alkyl, wherein each R$^b$ is unsubstituted or substituted with one to five substituents selected from R$^f$. In a class of this embodiment, each R$^b$ is independently selected from the group consisting of: —CF$_3$, —CHF$_2$, —OCHF$_2$, —CF$_2$CF$_3$, —OCF$_3$, CN, Br, Cl, F, —Si(CH$_3$)$_3$, —CH$_3$, —CH(CH$_3$)$_2$, —CH$_2$CH(CH$_3$)$_2$, —C(CH$_3$)$_3$, —(CH$_2$)$_2$CH=CH$_2$, and —OCH$_3$, wherein each R$^b$ is unsubstituted or substituted with one to five substituents selected from R$^f$.

In another embodiment, each R$^b$ is independently selected from the group consisting of: —C$_{3-6}$cycloalkyl, —C$_{2-6}$cycloheteroalkyl, aryl, and heteroaryl, wherein each R$^b$ is unsubstituted or substituted with one to five substituents selected from R$^f$. In a class of this embodiment, each R$^b$ is independently selected from the group consisting of cyclopropyl, cyclobutyl, cyclopentyl, oxetane, phenyl, and pyridine, wherein each R$^b$ is unsubstituted or substituted with one to five substituents selected from R$^f$.

In another embodiment, each R$^b$ is independently selected from the group consisting of: —CF$_3$, —OCHF$_2$, —CF$_2$CF$_3$, —OCF$_3$, CN, halogen, —Si(CH$_3$)$_3$, —C$_{1-6}$alkyl, —C$_{2-6}$alkenyl, —OC$_1$-6alkyl, —C$_{3-6}$cycloalkyl, —C$_{2-6}$cycloheteroalkyl, aryl, and heteroaryl, wherein each R$^b$ is unsubstituted or substituted with one to five substituents selected from R$^f$. In a class of this embodiment, each R$^b$ is independently selected from the group consisting of: —CF$_3$, —OCHF$_2$, —CF$_2$CF$_3$, —OCF$_3$, CN, Br, Cl, F, —Si(CH$_3$)$_3$, —CH$_3$, —CH(CH$_3$)$_2$, —CH$_2$CH(CH$_3$)$_2$, —C(CH$_3$)$_3$, —(CH$_2$)$_2$CH=CH$_2$, —OCH$_3$, cyclopropyl, cyclobutyl, cyclopentyl, oxetane, phenyl, and pyridine, wherein each R$^b$ is unsubstituted or substituted with one to five substituents selected from R$^f$.

In another embodiment, each R$^b$ is independently selected from the group consisting of: —CF$_3$, CN, halogen, and —C$_{1-6}$alkyl, wherein each R$^b$ is unsubstituted or substituted with one to five substituents selected from R$^f$. In a class of this embodiment, each R$^b$ is independently selected from the group consisting of: —CF$_3$, CN, Br, Cl, F, —CH$_3$, —CH(CH$_3$)$_2$, —CH$_2$CH(CH$_3$)$_2$, and —C(CH$_3$)$_3$, wherein each R$^b$ is unsubstituted or substituted with one to five substituents selected from R$^f$.

In another embodiment, each R$^b$ is independently selected from the group consisting of: —CF$_3$, CN, halogen, and —C$_{1-6}$alkyl, wherein each R$^b$ is unsubstituted or substituted with one to five substituents selected from R$^f$. In a class of this embodiment, each R$^b$ is independently selected from the group consisting of: —CF$_3$, CN, Cl, and —CH$_3$, wherein each R$^b$ is unsubstituted or substituted with one to five substituents selected from R$^f$.

In another embodiment of the present invention, each R$^c$ is independently selected from the group consisting of:

—CF$_3$, —CH$_2$CF$_3$, —CHF$_2$, —OCHF$_2$, —OCF$_3$, CN, oxo, —OH, halogen, —C$_{1-6}$alkyl, —C$_{2-6}$alkenyl, —C$_{2-6}$alkynyl, —C$_{3-6}$cycloalkyl, —C$_{2-6}$cycloheteroalkyl, —C$_{1-6}$alkyl-C$_{3-6}$cycloalkyl, —C$_{1-6}$alkyl-C$_{2-6}$cycloheteroalkyl, —C$_{1-6}$alkyl-aryl, —C$_{1-6}$alkyl-heteroaryl, —C$_{1-6}$alkenyl-C$_{3-6}$cycloalkyl, —C$_{1-6}$alkenyl-aryl, —C$_{1-6}$alkenyl heteroaryl, —C$_{1-6}$alkenyl-C$_{2-6}$cycloheteroalkyl, —C$_{2-6}$alkynyl-C$_{3-6}$cycloalkyl, —C$_{2-6}$alkynyl-C$_{2-6}$cycloheteroalkyl, —C$_{2-6}$alkynyl-aryl, —C$_{2-6}$alkynyl heteroaryl, —OC$_{1-6}$alkyl, —OC$_{2-6}$ alkenyl, —OC$_{2-6}$ alkynyl, —OC$_{3-6}$ cycloalkyl, —OC$_{2-6}$ heterocycloalkyl, —O-aryl, —O-heteroaryl, —OC$_{1-6}$alkyl-cycloalkyl, —OC$_1$-6alkyl-cycloheteroalkyl, —OC$_{1-6}$alkyl-aryl, —OC$_{1-6}$ alkyl-heteroaryl, —S(O)$_m$R$^L$, —S(O)R$^L$, —S—R$^L$, —C$_{1-6}$alkyl-S(O)$_m$R$^L$, —C(O)R$^L$, —C(O)C$_{1-6}$alkyl-R$^L$, —OC(O)R$^L$, —CO$_2$R$^L$, aryl, and heteroaryl, wherein each R$^c$ is unsubstituted or substituted with one to five substituents selected from R$^g$; In another embodiment of the present invention, each R$^c$ is independently selected from the group consisting of: —CF$_3$, —CH$_2$CF$_3$, —CHF$_2$, —OCHF$_2$, —OCF$_3$, CN, oxo, —OH, halogen, —C$_{1-6}$alkyl, —OC$_{1-6}$ alkyl, —C$_{3-6}$cycloalkyl, —C$_{2-6}$cycloheteroalkyl, —NR$^c$S(O)$_m$R$^e$, —S(O)$_m$R$^e$, —S(O)$_m$NR$^h$R$^h$, —NR$^h$R$^h$, —C(O)R$^e$, —OC(O)R$^e$, —CO$_2$R$^e$, —CN, —C(O)NR$^h$R$^h$, —NR$^h$C(O)R$^e$, —NR$^h$C(O)OR$^e$, —NR$^h$C(O)NR$^h$R$^h$, —OCF$_3$, —OCHF$_2$, aryl, and heteroaryl, wherein each R$^c$ is unsubstituted or substituted with one to five substituents selected from R$^g$.

In another embodiment of the present invention, each R$^c$ is independently selected from the group consisting of: —CF$_3$, —CH$_2$CF$_3$, —CHF$_2$, —OCHF$_2$, —OCF$_3$, CN, oxo, —OH, halogen, —C$_{1-6}$alkyl, —OC$_{1-6}$alkyl, —C$_{3-6}$cycloalkyl, —C$_{2-6}$cycloheteroalkyl, —NR$^c$S(O)$_m$R$^e$, —S(O)$_m$R$^e$, —S(O)$_m$NR$^h$R$^h$, —NR$^h$R$^h$, —C(O)R$^e$, —OC(O)R$^e$, —CO$_2$R$^e$, —CN, —OCF$_3$, —OCHF$_2$, aryl, heteroaryl, wherein each R$^c$ is unsubstituted or substituted with one to five substituents selected from R$^g$.

In another embodiment, each R$^c$ is independently selected from the group consisting of: —CF$_3$, —CHF$_2$, halogen, —C$_{1-6}$alkyl, —OC$_{1-6}$alkyl, oxo, —OH, —CO$_2$R$^e$, and aryl, wherein each R$^c$ is unsubstituted or substituted with one to five substituents selected from R$^g$. In a class of this embodiment, each R$^c$ is independently selected from the group consisting of: —CF$_3$, —CHF$_2$, F, —CH$_3$, —CH$_2$CH(CH$_3$)$_2$, —OCH$_3$, oxo, —OH, —CO$_2$CH$_3$, and phenyl, wherein each R$^c$ is unsubstituted or substituted with one to five substituents selected from R$^g$.

In another embodiment, each R$^c$ is independently selected from the group consisting of: —CF$_3$, halogen, and —C$_{1-6}$alkyl, wherein each R$^c$ is unsubstituted or substituted with one to five substituents selected from R$^g$. In a class of this embodiment, each R$^c$ is independently selected from the group consisting of: —CF$_3$, F, —CH$_3$, and —CH$_2$CH(CH$_3$)$_2$. In another class of this embodiment, each R$^c$ is independently selected from the group consisting of: —CF$_3$, F, and —CH$_3$.

In another embodiment, each R$^c$ is —CF$_3$.

In another embodiment, each R$^c$ is halogen. In a class of this embodiment, R$^c$ is F.

In another embodiment, each R$^c$ is —C$_{1-6}$alkyl, wherein —C$_{1-6}$alkyl is unsubstituted or substituted with one to five substituents selected from R$^g$. In a class of this embodiment, each R$^c$ is independently selected from: —CH$_3$, and —CH$_2$CH(CH$_3$). In another class of this embodiment, each R$^c$ is —CH$_2$CH(CH$_3$). In another class of this embodiment, each R$^c$ is —CH$_3$.

In another embodiment of the present invention, R$^d$ is independently selected from the group consisting of: hydrogen, halogen, OH, oxo, —C$_{1-6}$alkyl, —OC$_{1-6}$alkyl, and NH$_2$. In another embodiment of the present invention, R$^d$ is independently selected from the group consisting of: halogen, OH, oxo, —C$_{1-6}$alkyl, —OC$_{1-6}$alkyl, and NH$_2$.

In another embodiment, R$^d$ is independently selected from the group consisting of: hydrogen, halogen, —OH, N(R$^g$)$_2$, and C$_{1-6}$alkyl. In a class of this embodiment, R$^d$ is independently selected from the group consisting of: hydrogen, F, —OH, NH$_2$, and CH$_3$.

In another embodiment, R$^d$ is independently selected from the group consisting of: hydrogen, halogen, —OH, oxo, N(R$^9$)$_2$, and C$_{1-6}$alkyl. In a class of this embodiment, R$^d$ is independently selected from the group consisting of: hydrogen, F, —OH, NH$_2$, and CH$_3$. In another embodiment, R$^d$ is independently selected from the group consisting of: halogen, —OH, oxo, N(R$^g$)$_2$, and C$_{1-6}$alkyl. In a class of this embodiment, R$^d$ is independently selected from the group consisting of: F, —OH, NH$_2$, and CH$_3$.

In another embodiment, R$^d$ is independently selected from the group consisting of: halogen, —OH, N(R$^9$)$_2$, and C$_{1-6}$alkyl. In a class of this embodiment, R$^d$ is independently selected from the group consisting of: F, —OH, NH$_2$, and CH$_3$.

In another embodiment, R$^d$ is independently selected from the group consisting of: hydrogen, halogen, and C$_{1-6}$alkyl. In a class of this embodiment, R$^d$ is independently selected from the group consisting of: hydrogen, F and CH$_3$. In another embodiment, R$^d$ is independently selected from the group consisting of: halogen, and C$_{1-6}$alkyl. In a class of this embodiment, R$^d$ is independently selected from the group consisting of: F and CH$_3$.

In another embodiment of the present invention, each R$^e$ is independently selected from the group consisting of: hydrogen, —C$_{1-6}$alkyl, and —C$_{2-6}$alkenyl. In another embodiment, R$^d$ is independently selected from the group consisting of: —OH, and N(R$^9$)$_2$. In a class of this embodiment, R$^d$ is independently selected from the group consisting of: —OH, and NH$_2$. In another class of this embodiment, R$^d$ is —OH. In another class of this embodiment, R$^d$ is NH$_2$.

In another embodiment of the present invention, each R$^e$ is independently selected from the group consisting of: hydrogen, and —C$_{1-6}$alkyl. In a class of this embodiment, R$^e$ is hydrogen. In another class of this embodiment, R$^e$ is —C$_{1-6}$alkyl.

In another embodiment of the present invention, each R$^f$ is selected from the group consisting of: halogen, —C$_{1-6}$alkyl, —OH, —OC$_{1-6}$alkyl, —OC$_{3-6}$cycloalkyl, —OC$_{2-6}$cycloheteroalkyl, CN, —NH$_2$, —NH(C$_{1-6}$alkyl), —NH(C$_{3-6}$cycloalkyl), —NH(C$_{2-6}$cycloheteroalkyl), —N(C$_{1-6}$alkyl)$_2$, —N(C$_{3-6}$cycloalkyl)$_2$, and —N(C$_{2-6}$cycloheteroalkyl)$_2$, wherein each alkyl, cycloalkyl, and cycloheteroalkyl is unsubstituted or substituted with one to three substituents independently selected from: —OH, halogen, cyano, and —S(O)$_2$CH$_3$.

In another embodiment of the present invention, each R$^f$ is selected from the group consisting of: halogen, —C$_{1-6}$alkyl, —OH, —OC$_{1-6}$alkyl, —OC$_{3-6}$cycloalkyl, —OC$_{2-6}$cycloheteroalkyl, CN, —NH$_2$, —NH(C$_{1-6}$alkyl), and —N(C$_{1-6}$alkyl)$_2$, wherein each alkyl, cycloalkyl, and cycloheteroalkyl is unsubstituted or substituted with one to three substituents independently selected from: —OH, halogen, cyano, and —S(O)$_2$CH$_3$.

In another embodiment of the present invention, each R$^f$ is selected from the group consisting of: halogen, —C$_{1-6}$alkyl, —OH, —OC$_{1-6}$alkyl, CN, —NH$_2$, —NH(C$_{1-6}$alkyl), and —N(C$_{1-6}$alkyl)$_2$, wherein each alkyl is unsubstituted or substituted with one to three substituents independently selected from: —OH, halogen, cyano, and —S(O)$_2$CH$_3$.

In another embodiment of the present invention, each R$^f$ is selected from the group consisting of: halogen, —C$_{1-6}$alkyl, —OH, —OC$_{1-6}$alkyl, and CN, wherein each alkyl is unsubstituted or substituted with one to three substituents independently selected from: —OH, halogen, cyano, and —S(O)$_2$CH$_3$.

In another embodiment of the present invention, each R$^f$ is selected from the group consisting of: halogen, —C$_{1-6}$alkyl, and —OH, wherein each alkyl is unsubstituted or substituted with one to three substituents independently selected from: —OH, halogen, cyano, and —S(O)$_2$CH$_3$. In a class of this embodiment, each R$^f$ is selected from the group consisting of: F, —CH$_3$, and —OH.

In another embodiment of the present invention, each R$^f$ is halogen. In a class of this embodiment, R$^f$ is F.

In another embodiment of the present invention, each R$^f$ is —C$_{1-6}$alkyl, wherein each alkyl is unsubstituted or substituted with one to three substituents independently selected from: —OH, halogen, cyano, and —S(O)$_2$CH$_3$. In a class of this embodiment, each R$^f$ is —C$_{1-6}$alkyl. In a subclass of this class, R$^f$ is —CH$_3$.

In another embodiment of the present invention, each R$^f$ is —OH.

In another embodiment of the present invention, each R$^g$ is selected from the group consisting of: halogen, C$_{1-6}$alkyl, —OH, —OC$_{1-6}$alkyl, —S(O)$_m$—C$_{1-6}$alkyl, —CN, —CF$_3$, —OCHF$_2$, and —OCF$_3$, wherein each alkyl is unsubstituted or substituted with one to three substituents independently selected from: —OH, halogen, cyano, and —S(O)$_2$CH$_3$.

In another embodiment of the present invention, each R$^g$ is selected from the group consisting of: halogen, C$_{1-6}$alkyl, —OH, —OC$_{1-6}$alkyl, —CN, —CF$_3$, —OCHF$_2$, and —OCF$_3$, wherein each alkyl is unsubstituted or substituted with one to three substituents independently selected from: —OH, halogen, cyano, and —S(O)$_2$CH$_3$.

In another embodiment of the present invention, each R$^g$ is selected from the group consisting of: halogen, C$_{1-6}$alkyl, —OH, —CN, —CF$_3$, wherein each alkyl is unsubstituted or substituted with one to three substituents independently selected from: —OH, halogen, cyano, and —S(O)$_2$CH$_3$.

In another embodiment of the present invention, each R$^g$ is selected from the group consisting of: halogen, —OH, —CN, and —CF$_3$. In a class of this embodiment, each R$^g$ is selected from the group consisting of: F, —OH, —CN, and —CF$_3$.

In another embodiment of the present invention, each R$^h$ is independently selected from the group consisting of: hydrogen, and —C$_{1-6}$alkyl. In a class of this embodiment, R$^h$ is hydrogen. In another class of this embodiment, R$^h$ is —C$_{1-6}$alkyl.

In another embodiment of the present invention, each R$^i$ is independently selected from the group consisting of: hydrogen, and —C$_{1-6}$alkyl. In a class of this embodiment, R$^i$ is hydrogen. In another class of this embodiment, R$^i$ is —C$_{1-6}$alkyl.

In another embodiment of the present invention, R$^g$ is halogen. In a class of this embodiment, R$^g$ is F.

In another embodiment of the present invention, each R$^j$ is selected from the group consisting of: —C$_{1-6}$alkyl, —C$_{2-6}$alkenyl, —C$_{3-6}$cycloalkyl, —C$_{2-6}$cycloheteroalkyl, aryl, and heteroaryl, wherein each alkyl, alkenyl, cycloalkyl, cycloheteroalkyl, aryl and heteroaryl is unsubstituted or substituted with one to three substituents independently selected from: —C$_{1-6}$alkyl, —C$_{3-6}$cycloalkyl, —OH, —OC$_{1-6}$alkyl, —OC$_{3-6}$cycloalkyl, halogen, cyano, and —S(O)$_2$CH$_3$.

In another embodiment of the present invention, each R$^j$ is selected from the group consisting of: —C$_{1-6}$alkyl, —C$_{2-6}$alkenyl, —C$_{3-6}$cycloalkyl, and —C$_{2-6}$cycloheteroalkyl, wherein each alkyl, alkenyl, cycloalkyl, and cycloheteroalkyl is unsubstituted or substituted with one to three substituents independently selected from: —C$_{1-6}$alkyl, —C$_{3-6}$cycloalkyl, —OH, —OC$_{1-6}$alkyl, —OC$_{3-6}$cycloalkyl, halogen, cyano, and —S(O)$_2$CH$_3$.

In another embodiment of the present invention, each R$^j$ is selected from the group consisting of: —C$_{1-6}$alkyl, —C$_{3-6}$cycloalkyl, and —C$_{2-6}$cycloheteroalkyl, wherein each alkyl, cycloalkyl, and cycloheteroalkyl is unsubstituted or substituted with one to three substituents independently selected from: —C$_{1-6}$alkyl, —C$_{3-6}$cycloalkyl, —OH, —OC$_{1-6}$alkyl, —OC$_{3-6}$cycloalkyl, halogen, cyano, and —S(O)$_2$CH$_3$. In another embodiment of the present invention, each R$^j$ is selected from the group consisting of: —C$_{1-6}$alkyl, —C$_{3-6}$cycloalkyl, and —C$_{2-6}$cycloheteroalkyl, wherein each alkyl, cycloalkyl, and cycloheteroalkyl.

In another embodiment of the present invention, each R$^j$ is —C$_{1-6}$alkyl, wherein each alkyl, is unsubstituted or substituted with one to three substituents independently selected from: —C$_{1-6}$alkyl, —C$_{3-6}$cycloalkyl, —OH, —OC$_{1-6}$alkyl, —OC$_{3-6}$cycloalkyl, halogen, cyano, and —S(O)$_2$CH$_3$.

In a class of this embodiment, each R$^j$ is —C$_{1-6}$alkyl.

In another embodiment of the present invention, each R$^k$ is selected from the group consisting of: —C$_{1-6}$alkyl, —C$_{2-6}$alkenyl, —C$_{3-6}$cycloalkyl, —C$_{3-6}$cycloalkyl, —C$_{2-6}$cycloheteroalkyl, aryl, and heteroaryl, wherein each alkyl, alkenyl, cycloalkyl, cycloheteroalkyl, aryl and heteroaryl is unsubstituted or substituted with one to three substituents independently selected from: —C$_{1-6}$alkyl, —C$_{3-6}$cycloalkyl, —OH, —OC$_{1-6}$alkyl, —OC$_{3-6}$cycloalkyl, halogen, cyano, and —S(O)$_2$CH$_3$.

In another embodiment of the present invention, each R$^k$ is selected from the group consisting of: —C$_{1-6}$alkyl, —C$_{2-6}$alkenyl, —C$_{3-6}$cycloalkyl, and —C$_{2-6}$cycloheteroalkyl, wherein each alkyl, alkenyl, cycloalkyl, and cycloheteroalkyl is unsubstituted or substituted with one to three substituents independently selected from: —C$_{1-6}$alkyl, —C$_{3-6}$cycloalkyl, —OH, —OC$_{1-6}$alkyl, —OC$_{3-6}$cycloalkyl, halogen, cyano, and —S(O)$_2$CH$_3$.

In another embodiment of the present invention, each R$^k$ is selected from the group consisting of: —C$_{1-6}$alkyl, —C$_{3-6}$cycloalkyl, and —C$_{2-6}$cycloheteroalkyl, wherein each alkyl, cycloalkyl, and cycloheteroalkyl is unsubstituted or substituted with one to three substituents independently selected from: —C$_{1-6}$alkyl, —C$_{3-6}$cycloalkyl, —OH, —OC$_{1-6}$alkyl, —OC$_{3-6}$cycloalkyl, halogen, cyano, and —S(O)$_2$CH$_3$.

In another embodiment of the present invention, each R$^k$ is —C$_{1-6}$alkyl, wherein each alkyl, is unsubstituted or substituted with one to three substituents independently selected from: —C$_{1-6}$alkyl, —C$_{3-6}$cycloalkyl, —OH, —OC$_{1-6}$alkyl, —OC$_{3-6}$cycloalkyl, halogen, cyano, and —S(O)$_2$CH$_3$. In a class of this embodiment, each R$^k$ is —C$_{1-6}$alkyl.

In another embodiment of the present invention, each R$^L$ is selected from the group consisting of: —C$_{1-6}$alkyl, —C$_{2-6}$alkenyl, —C$_{3-6}$cycloalkyl, —C$_{2-6}$cycloheteroalkyl, aryl, and heteroaryl, wherein each alkyl, alkenyl, cycloalkyl, cycloheteroalkyl, aryl and heteroaryl is unsubstituted or substituted with one to three substituents independently selected from: —$C_{1-6}$alkyl, —$C_{3-6}$cycloalkyl, —OH, —$OC_{1-6}$alkyl, —$OC_{3-6}$cycloalkyl, halogen, cyano, and —$S(O)_2CH_3$.

In another embodiment of the present invention, each $R^L$ is selected from the group consisting of: —$C_{1-6}$alkyl, —$C_{2-6}$alkenyl, —$C_{3-6}$cycloalkyl, and —$C_{2-6}$cycloheteroalkyl, wherein each alkyl, alkenyl, cycloalkyl, and cycloheteroalkyl is unsubstituted or substituted with one to three substituents independently selected from: —$C_{1-6}$alkyl, —$C_{3-6}$cycloalkyl, —OH, —$OC_{1-6}$alkyl, —$OC_{3-6}$cycloalkyl, halogen, cyano, and —$S(O)_2CH_3$.

In another embodiment of the present invention, each $R^L$ is selected from the group consisting of: —$C_{1-6}$alkyl, —$C_{3-6}$cycloalkyl, and —$C_{2-6}$cycloheteroalkyl, wherein each alkyl, cycloalkyl, and cycloheteroalkyl is unsubstituted or substituted with one to three substituents independently selected from: —$C_{1-6}$alkyl, —$C_{3-6}$cycloalkyl, —OH, —$OC_{1-6}$alkyl, —$OC_{3-6}$cycloalkyl, halogen, cyano, and —$S(O)_2CH_3$.

In another embodiment of the present invention, each $R^L$ is —$C_{1-6}$alkyl, wherein each alkyl, is unsubstituted or substituted with one to three substituents independently selected from: —$C_{1-6}$alkyl, —$C_{3-6}$cycloalkyl, —OH, —$OC_{1-6}$alkyl, —$OC_{3-6}$cycloalkyl, halogen, cyano, and —$S(O)_2CH_3$. In a class of this embodiment, each $R^L$ is —$C_{1-6}$alkyl.

In another embodiment of the present invention, each $R^m$ is independently selected from the group consisting of: hydrogen, and —$C_{1-6}$alkyl. In a class of this embodiment, $R^m$ is hydrogen. In another class of this embodiment, $R^m$ is —$C_{1-6}$alkyl.

In another embodiment of the present invention, n is 0, 1, 2, 3 or 4. In a class of this embodiment, n is 0, 1, 2 or 3. In another class of this embodiment, n is 0, 1 or 2. In a class of this embodiment, n is 0 or 1. In a class of this embodiment, n is 1, 2, 3 or 4. In another class of this embodiment, n is 1, 2 or 3. In another class of this embodiment, n is 1 or 2. In another class of this embodiment, n is 0. In another class of this embodiment, n is 1. In another class of this embodiment, n is 2. In another class of this embodiment, n is 3. In another class of this embodiment, n is 4.

In another embodiment of the present invention, m is 0, 1 or 2. In a class of this embodiment, m is 0 or 1. In another class of this embodiment, m is 1 or 2. In another class of this embodiment, m is 0. In another class of this embodiment, m is 1. In another class of this embodiment, m is 2.

In another embodiment of the present invention, p is 0, 1, 2, 3 or 4. In a class of this embodiment, p is 0, 1, 2 or 3. In another class of this embodiment, p is 0, 1 or 2. In a class of this embodiment, p is 0 or 1. In a class of this embodiment, p is 1, 2, 3 or 4. In another class of this embodiment, p is 1, 2 or 3. In another class of this embodiment, p is 1 or 2. In another class of this embodiment, p is 0. In another class of this embodiment, p is 1. In another class of this embodiment, p is 2. In another class of this embodiment, p is 3. In another class of this embodiment, p is 4.

In another embodiment of the present invention, q is 0 or 1. In another class of this embodiment, q is 0. In another class of this embodiment, q is 1.

In another embodiment of the present invention, r is 0 or 1. In another class of this embodiment, r is 0. In another class of this embodiment, r is 1.

In another embodiment of the present invention, the invention relates to compounds of structural formula Ia:

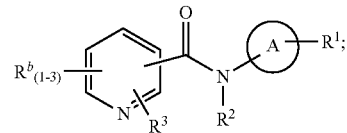

Ia or a pharmaceutically acceptable salt thereof. In a class of this embodiment, A is

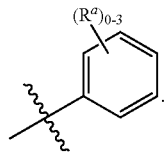

In another embodiment of the present invention, the invention relates to compounds of structural formula Ib:

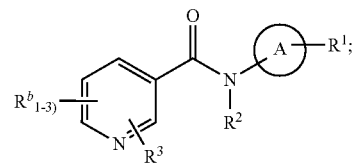

Ib or a pharmaceutically acceptable salt thereof. In a class of this embodiment, A is

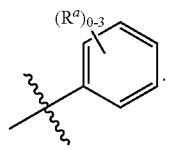

In another embodiment of the present invention, the invention relates to compounds of structural formula Ic:

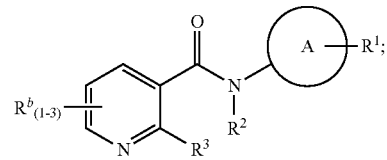

Ic or a pharmaceutically acceptable salt thereof. In a class of this embodiment, A is

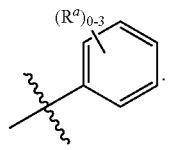

The compound of structural formula I, includes the compounds of structural formulas Ia, Ib, and Ic, and pharmaceutically acceptable salts, hydrates and solvates thereof.

Another embodiment of the present invention relates to compounds of structural formula I wherein:

A is selected from the group consisting of:
(1) phenyl,
(2) dihydrobenzothiazole,
(3) dihydrobenzoisothiazole, and
(4) benzothiophene wherein A is unsubstituted or substituted with one to five substituents selected from $R^a$;

B is selected from the group consisting of:
(1) pyridine,
(2) pyrimidine, and
(3) pyridazine, wherein pyridine, pyrimidine and pyridazine is unsubstituted or substituted with one to three substituents selected from $R^b$;

$R^1$ is selected from the group consisting of:
(1) —$SO_2NH_2$,
(2) —$SO_2NH$-heteroaryl,
(3) —$SO_2C_{1-6}$alkyl,
(4) —$SO_2C_{3-6}$cycloalkyl,
(5) —$SO_2C_{3-6}$cycloheteroalkyl,
(6) —$C(O)NH_2$, and
(7) —CN, wherein each alkyl, cycloalkyl, cycloheteroalkyl and heteroaryl is unsubstituted or substituted with one to four substituents selected from $R^d$;

$R^2$ is hydrogen;

$R^3$ is selected from the group consisting of:
(1) pyrrolidine,
(2) azetidine,
(3) piperidine,
(4) piperazine,
(5) azepane,
(6) azocane,
(7) morpholine,
(8) thiomorpholine,
(9) oxazepane,
(10) isoindoline,
(11) dihydroisoquinoline,
(12) octahydroisoindole,
(13) azabicyclo[2.2.1]heptane,
(14) azabicyclo[3.1.1]heptane,
(15) azabicyclo[4.1.0]heptane,
(16) azabicyclo[3.2.1]octane,
(17) diazabicyclo[3.2.1]octane,
(18) azabicyclo[3.2.0]heptane,
(19) oxa-azabicyclo[3.2.1]octane,
(20) azaspiro[2.5]octane,
(21) azaspiro[2.6]nonane,
(22) oxa-azaspiro[3.5}nonane,
(23) oxaroazaspnro[4.5]decane,
(24) dihydrothiazolo[4,5-c]pyridine,
(25) dihydrooxazolo[4,5-c]pyridine:,
(26) hexahydrofuro[3,2-b]pyrrole,
(27) hexahydrocyclopenta[c]pyrrole, and
(28) azatricyclo[4.3.1.13,8]undecane, wherein $R^3$ is unsubstituted or substituted with one to eight substituents selected from $R^c$; or a pharmaceutically acceptable salt thereof.

Another embodiment of the present invention relates to compounds of structural formula I wherein:

A is selected from the group consisting of:
(1) phenyl,
(2) dihydrobenzothiazole,
(3) dihydrobenzoisothiazole, and
(4) benzothiophene wherein A is unsubstituted or substituted with one to five substituents selected from $R^a$; B is pyridine, wherein pyridine is unsubstituted or substituted with one to three substituents selected from $R^b$;

$R^1$ is selected from the group consisting of:
(1) —$SO_2NH_2$,
(2) —$SO_2NH$-heteroaryl,
(3) —$SO_2C_{1-6}$alkyl,
(4) —$SO_2C_{3-6}$cycloalkyl,
(5) —$SO_2C_{3-6}$cycloheteroalkyl,
(6) —$C(O)NH_2$,and
(7) —CN, wherein each alkyl, cycloalkyl, cycloheteroalkyl and heteroaryl is unsubstituted or substituted with one to four substituents selected from $R^d$;

$R^2$ is hydrogen;

$R^3$ is selected from the group consisting of:
(1) pyrrolidine,
(2) azetidine,
(3) piperidine,
(4) piperazine,
(5) azepane,
(6) azocane,
(7) morpholine,
(8) thiomorpholine,
(9) oxazepane,
(10) isoindoline,
(11) dihydroisoquinoline,
(12) octahydroisoindole,
(13) azabicyclo[2.2.1]heptane,
(14) azabicyclo[3.1.1]heptane,
(15) azabicyclo[4.1.0]heptane,
(16) azabicyclo[3.2.1]octane,
(17) diazabicyclo[3.2.1]octane,
(18) azabicyclo[3.2.0]heptane,
(19) oxa-azabicyclo[3.2.1]octane,
(20) azaspiro[2.5]octane,
(21) azaspiro[2.6]nonane,
(22) oxa-azaspiro[3,5}nonane,
(23) oxa-oazaspiro[4,5]decane,
(24) dihydrothiazolo[4,5-c]pyridine,
(25) dihydrooxazolo[4,5-c]pyridine,
(26) hexahydrofuro[3,2-b]pyrrole,
(27) hexahydrocyclopenta[c]pyrrole, and
(28) azatricyclo[4.3.1.13,8]undecane, wherein $R^3$ is unsubstituted or substituted with one to eight substituents selected from $R^c$; or a pharmaceutically acceptable salt thereof.

Another embodiment of the present invention relates to compounds of structural formula I wherein:

$R^2$ is hydrogen;

A is phenyl, wherein phenyl is unsubstituted or substituted with one to three substituents selected from $R^a$;

B is pyridine, wherein pyridine is unsubstituted or substituted with one to three substituents selected from $R^b$;

$R^1$ is selected from the group consisting of
(1) —$SO_2NH_2$,
(2) —$SO_2C_{1-6}$alkyl, and
(3) —$C(O)NH_2$, wherein each alkyl is unsubstituted or substituted with one to four substituents selected from $R^d$;

$R^2$ is hydrogen;

$R^3$ is selected from the group consisting of
(1) piperidine,
(2) azepane,
(3) morpholine, and
(4) azaspiro[2.5]octane, wherein $R^3$ is unsubstituted or substituted with one to eight substituents selected from $R^c$; or a pharmaceutically acceptable salt thereof.

Illustrative, but non-limiting, examples of the compounds of the present invention that are useful as inhibitors of $Na_v1.8$ channel activity are the following compounds:

(1) 2-(4,4-difluoropiperidin-1-yl)-N-(3-sulfamoylphenyl)-5-(trifuoromethyl)-nicotinamide;
(2) 2-(azepan-1-yl)-5-chloro-4,6-dimethyl-N-(3-sulfamoylphenyl)nicotinamide;
(3) 2-(azepan-1-yl)-6-chloro-5-fuoro-4-methyl-N-(3-sulfamoylphenyl)pyridine-3-carboxamide;
(4) 2-(azepan-1-yl)-4,6-dimethyl-N-(3-sulfamoylphenyl)pyridine-3-carboxamide;
(5) 5-chloro-2-(3,3-difuoropyrrolidin-1-yl)-4,6-dimethyl-N-(3-sulfamoylphenyl)pyridine-3-carboxamide;
(6) 5-fuoro-2-(1-piperidyl)-N-(3-sulfamoylphenyl)pyridine-3-carboxamide;
(7) 2-(azepan-1-yl)-5-chloro-4,6-dimethyl-N-(3-methylsulfonylphenyl)pyridine-3-carboxamide;
(8) 6-chloro-2-(4,4-difuoroazepan-1-yl)-4-methyl-N-(3-methylsulfonylphenyl)pyridine-3-carboxamide;
(9) 6-chloro-2-(4,4-difuoroazepan-1-yl)-N-(3-methylsulfonylphenyl)pyridine-3-carboxamide;
(10) 2-(4,4-difuoroazepan-1-yl)-6-methyl-N-(3-methylsulfonylphenyl)pyridine-3-carboxamide;
(11) 2-(4,4-difuoroazepan-1-yl)-6-methoxy-N-(3-methylsulfonylphenyl)pyridine-3-carboxamide;
(12) 5-chloro-4,6-dimethyl-N-(3-methylsulfonylphenyl)-2-(1-pipeidyl)pyridine-3-carboxamide;
(13) 2-(6-azaspiro [2.5]octan-6-yl)-N-(3-carbamoylphenyl)-5-chloro-4,6-dimethyl-pyridine-3-carboxamide;
(14) N-(3-carbamoylphenyl)-6-chloro-2-(4,4-difuoroazepan-1-yl)pyridine-3-carboxamide;
(15) N-(3-carbamoylphenyl)-5-chloro-2-(4,4-difuoroazepan-1-yl)pyridine-3-carboxamide;
(16) N-(3-carbamoylphenyl)-5-chloro-2-(4,4-difluoro-1-piperidyl)-4,6-dimethyl-pyridine-3-carboxamide;
(17) N-(3-carbam0ylphenyl)-6-ch1oro-2-(4,4-difuoroazepan-1-yl)-4-methyl-pyridine-3-carboxamide;
(18) N-(3-carbamoylphenyl)-2-(4,4-difuoroazepan-1-yl)-6-methoxy-pyridine-3-carboxamide;
(19) N-(3-carbamoylphenyl)-5-chloro-4,6-dimethyl-2-(1-piperidyl)pyridine-3-carboxamide;
(20) 5-chloro-N-(3-cyanophenyl)-2-(4,4-difluoro-1-piperidyl)-4,6-dimethyl-pyidine-3-carboxamide;
(21) 2-(azepan-1-yl)-N-(3-cyanophenyl)-5-(trifuoromethyl)pyridine-3-carboxamide;
(22) 2-(azepan-1-yl)-N-(4-cyanophenyl)-5-(trifuoromethyl)pyridine-3-carboxamide;
(23) 2-(azepan-1-yl)-5-methyl-N-(3-sulfamoylphenyl)nicotinamide;
(24) 2-(azepan-1-yl)-N-(3-pyrrolidin-1-ylsu1fonylphenyl)-5-(triuoromethyl)pynidine-3-carboxamide;
(25) 2-(azepan-1-yl)-N-(2-hydroxy-5-su1famoyl-phenyl)-5-(trifuoromethyl)pyridine-3-carboxamide;
(26) 2-(azepan-1-yl)-5-chloro-6-methyl-N-(3-sulfamoylphenyl)nicotinamide;
(27) 2-(piperidin-1-yl)-N-(3-sulfamoylphenyl)-5-(p-tolyl)nicotinamide;
(28) N-(2,4-difuoro-3-sulfamoylphenyl)-2-(4,4-difuoropiperidin-1-yl)-5-(trifuoromethyl)nicotinamide;
(29) 2-(azepan-1-yl)-6-chloro-4-methyl-N-(3-sulfamoylphenyl)nicotinamide;
(30) 2-(azepan-1-yl)-5,6-dimethyl-N-(3-su1fam0ylphenyl)pyridine-3-carboxamide;
(31) 2-(azepan-1-yl)-5-chloro-N-(3-su1famoylphenyl)pyridine-3-carboxamide;
(32) 2-(azepan-1-yl)-5-bromo-N-(3-su1famoylphenyl)pyridine-3-carboxamide;
(33) 2-(azepan-1-yl)-4-bromo-N-(3-sulfamoylphenyl)pyridine-3-carboxamide;
(34) 2-(azepan-1-yl)-5-(3-pyridyl)-N-(3-sulfamoylphenyl)pyridine-3-carboxamide;
(35) 2-(azepan-1-yl)-5-brom0-N-(3-methylsulfonylphenyl)pyridine-3-carboxamide;
(36) 2-(azepan-1-yl)-5,6-dimethyl-N-(3-methylsulfonylphenyl)pyridine-3-carboxamide;
(37) 2-(azepan-1-yl)-N-(3-carbamoylphenyl)-5,6-dimethyl-pyridine-3-carboxamide;
(38) 2-(azepan-1-yl)-5-bromo-N-(3-carbamoylphenyl)pyridine-3-carboxamide;
(39) 2-(4,4-difuoroazepan-1-yl)-N-(3-sulfamoylphenyl)-5-(trifluoromethoxy)nicotinamide;
(40) 6-(tert-butyl)-5-chloro-2-(piperidin-1-yl)-N-(3-sulfamoylphenyl)nicotinamide;
(41) 6-tert-butyl-N-(3-methylsulfonylphenyl)-2-(1-piperidyl)pyridine-3-carboxamide;
(42) 6-(tert-butyl)-2-(piperidin-1-yl)-N-(3-sulfamoylphenyl)nicotinamide;
(43) 2-(6-azaspiro [2.5]octan-6-yl)-N-(3-sulfamoylphenyl)-5-(trifuoromethyl)nicotinamide;
(44) 2-(azepan-1-yl)-N-(3-sulfamoylphenyl)-5-(trifuoromethyl)pyridine-3-carboxamide;
(45) 2-[rac-3-azabicyclo[3.2.1]0ctan-3-yl]-N-(3-sulfamoylphenyl)-5-(trifuoromethyl)pyridine-3-carboxamide;
(46) N-(3-sulfamoylphenyl)-2-(4-azatricyc10-[4.3.1.13,8]undecan-4-yl)-5-(trifuoromethyl)-nicotinamide;
(47) N-(3-sulfamoylphenyl)-5-(trifuoromethyl)-2-(3,3,5-trimethylazepan-1-yl)pyridine-3-carboxamide;
(48) methyl 1-[3-[(3 -sulfamoylphenyl)carbamoyl]-5-(trifuoromethyl)-2-pyridyl]azepane-4-carboxylate;
(49) 2-(4-methoxyazepan-1-yl)-N-(3-sulfamoylphenyl)-5-(trifuoromethyl)pyridine-3-carboxamide;
(50) 2-[4-(difuoromethyl)-1-piperidyl]-N-(3-sulfamoylphenyl)-5-(trifuoromethyl)pyridine-3-carboxamide;
(51) 2-(3,3-difuoro-1-piperidyl)-N-(3-sulfamoylphenyl)-5-(trifuoromethyl)pyridine-3-carboxamide;
(52) 2-(8-oxa-3-azabicyclo[3.2.1]octan-3-yl)-N-(3-sulfamoylphenyl)-5-(trifuoromethyl)pyridine-3-carboxarnide;
(53) 2-(4-hydroxy-4-methyl-azepan-1-yl)-N-(3-sulfamoylphenyl)-5-(trifuoromethyl)pyridine-3-carboxamide;
(54) 2-[(3S)-3-fluoroazepan-1-yl]-N-(3-sulfamoylphenyl)-5-(trifuoromethyl)pyridine-3-carboxamide;
(55) 2-(6,7-dihydro-4H-thiazolo[4,5-c]pyridin-S-yl)-N-(3-sulfamoylphenyl)-5-(trifuoromethyl)-pyridine-3-carboxamide;
(56) 2-(1,4-oxazepan-4-yl)-N-(3-sulfamoylphenyl)-5-(trifuoromethyl)pyridine-3-carboxamide;

(57) 2-(8-oxa-3-azabicyclo[3.2.1]octan-3-yl)-N-(3-sulfamoylphenyl)-5-(trifuoromethyl)pyridine-3-carboxamide;

(58) N-(3-sulfamoylphenyl)5-(trifuoromethyl)-2-[3-(trifluoromethyl)azetidin-1-yl]pyridine-3-carboxamide;

(59) 2-(6-azabicyclo[3.2.0]heptan-6-yl)-N-(3-sulfamoylphenyl)-5-(trifuoromethyl)pyridine-3-carboxamide;

(60) 2-(3,3-difuoropyrrolidin-1-yl)-N-(3-sulfamoylphenyl)-5-(trifuoromethyl)pyridine-3-carboxamide;

(61) methyl 1-[3-[(3-sulfamoylphenyl)carbamoyl]-5-(trifluoromethyl)-2-pyridyl]piperidine-4-carboxylate;

(62) 2-(3-fluoropyrrolidin-1-yl)-N-(3-sulfamoylphenyl)-5-(trifuoromethyl)pyridine-3-carboxamide;

(63) 2-pyrrolidin-1-yl-N-(3-sulfamoylphenyl)-5-(trifuoromethyl)pyridine-3-carboxamide;

(64) 2-(6-oxa-3-azabicyclo[3.2.1]octan-3-yl)-N-(3-sulfamoylphenyl)-5-(trifuoromethyl)pyridine-3-carboxamide;

(65) 2-(4-hydroxyazepan-1-yl)-N-(3-sulfamoylphenyl)-5-(triuoromethyl)pyridine-3-carboxamide;

(66) 2-(4-meth0xy-1-piperidyl)-N-(3-sulfamoylphenyl)-5-(trifuoromethyl)pyridine-3-carboxamide;

(67) methyl 1-[3-[(3-sulfamoylphenyl)carbamoyl]-5-(trifluoromethyl)-2-pylidyl]azepane-3-carboxylate;

(68) 2-(2-isobutylazepan-1-yl)-N-(3-sulfamoylphenyl)-5-(trifuoromethyl)pyridine-3-carboxamide;

(69) 2-morpholino-N-(3-sulfamoylphenyl)-5-(trifuoromethyl)pyridine-3-carboxamide;

(70) 2-(1,1-dioxo-1,4-thiazman-4-yl)-N-(3-sulfamoylphenyl)-5-(trifuoromethyl)pyridine-3-carboxamide;

(71) 2-[rac-(1S,5R and 1R, 5S)-8-methyl-3,8-diazabicyclo[3.2.1]octan-3-yl]-N-(3-sulfamoylphenyl)-5-(trifuoromethyl)pyridine-3-carboxamide;

(72) 2-(1-oxa-8-azaspiro [4.5]decan-8-yl)-N-(3-sulfamoylphenyl)-5-(trifuoromethyl)pyridine-3-carboxamide;

(73) 2-(2-methyl-6,7-dihydro-4H-oxazolo[4,5-c]pyridin-5-yl)-N-(3-sulfamoylphenyl)-5-(trifuoromethyl)pyridine-3-carboxamide;

(74) methyl 4-[3-[(3-sulfamoylphenyl)carbamoyl]-5-(triuoromethyl)-2-pylidyl]piperazine-1-carboxylate;

(75) N-(3-carbamoylphenyl)-2-(4,4-difuoroazepan-1-yl)-6-methylnicotmamide;

(76) 2-(6-azaspiro[2.5]octan-6-yl)-5-chloro-4,6-dimethyl-N-(3-sulfamoylphenyl)pyridine-3-carboxamide;

(77) 2-(1-piperidyl)-N-(3-sulfamoylphenyl)-6-(trifuoromethyl)pyridine-3-carboxamide;

(78) 2-(4,4-difuoroazepan-1-yl)-N-(3-sulfamoylphenyl)-5-(trifluoromethyl)nicotinamide;

(79) 2-(6-azaspiro [2.6]nonan-6-yl)-N-(3-sulfamoylphenyl)-5-(triuoromethyl)nicotinamide;

(80) 2-(4,4-dimethylazepan-1-yl)-N-(3-sulfamoylphenyl)-5-(triuoromethyl)nicotinamide;

(81) 2-(7-oxa-2-azaspiro[3.5]n0nan-2-yl)-N-(3-sulfamoylphenyl)-5-(trifuoromethyl)nicotinamide;

(82) 2-(azepan-1-yl)-N-(3-(methylsulfonyl)phenyl)-6-(triuoromethyl)nicotinamide;

(83) N-(3-carbamoylphenyl)-2-(6-azaspiro[2.5]octan-6-yl)-6-(trifuoromethyl)nicotinamide;

(84) 2-(piperidin-1-yl)-N-(3-sulfamoylphenyl)-6-(trifuorometh0xy)nicotinamide;

(85) 2-(azepan-1-yl)-N-(3-sulfamoylphenyl)-6-(triuoromethoxy)-5-(trimethylsilyl)nicotinamide;

(86) 2-(azepan-1-yl)-N-(3-sulfamoylphenyl)-5-(trimethylsilyl)nicotinamide;

(87) 2-(2-oxa-7-azaspiro[3.5]n0nan-7-yl)-N-(3-sulfamoylphenyl)-5-(trimethylsilyl)nicotinamide;

(88) 2-(azocan-1-yl)-N-(3-sulfamoylphenyl)-5-(trifuoromethyl)pyridine-3-carboxamide;

(89) 2-(azepan-1-yl)-6-chloro-N-(3-sulfamoylphenyl) pyridine-3-carboxamide;

(90) 2-(azepan-1-yl)-6-methyl-N-(3-sulfamoylphenyl) pyridine-3-carboxamide;

(91) 2-(azepan-1-yl)-6-methoxy-N-(3-sulfamoylphenyl) pyridine-3-carboxamide;

(92) 2-(azepan-1-yl)-6-chloro-5-fluoro-N-(3-sulfamoylphenyl)pyridine-3-carboxamide;

(93) 2-(azepan-1-yl)-6-fluoro-N-(3-sulfamoylphenyl) pyridine-3-carboxamide;

(94) 2-(4,4-difuoroazepan-1-yl)-N-(3-methylsulf0nylphenyl)-5-(trifuoromethyl)pyridine-3-carboxamide;

(95) 2-(azocan-1-yl)-N-(3-methylsulfonylphenyl)-5-(trifluoromethyl)pyridine-3-carboxamide;

(96) 2-(4,4-difuoro-1,3,3a,5,6,6a-hexahydrocyclopenta[c]pyrrol-2-yl)-N-(3-methylsulfonylphenyl)-5-(trifuoromethyl)pyridine-3-carboxamide;

(97) 2-[(3aS,7aR)-1,3,3a,4,5,6,7,7a-octahydroisoindol-Z-yl]-N-(3-methylsulf0nylphenyl)-5-(trifuoromethyl) pyridine-3-carboxamide;

(98) 2-(3,4-dihydro-1H-isoquinolin-Z-yl)-N-(3-methylsulfinylphenyl)-5-(triuoromethyl)pyridine-3-carboxamide;

(99) 2-(6-azaspiro[2.5]octan-6-yl)-N-(3-methylsulfonylphenyl)-5-(trifuoromethyl)pyridine-3-carboxamide;

(100) 2-(4-fluoro-1-piperidyl)-N-(3-methylsulfonylphenyl)-5-(trifuoromethyl)pyridine-3-carboxamide;

(101) 2-(8,8-difuoro-6-azaspiro[2.5]octan-6-yl)-N-(3-methylsulfonylphenyl)-5-(trifuoromethyl)pyridine-3-carboxamide;

(102) 2-(3,3-difuoro-1-piperidyl)-N-(3-methylsulfonylphenyl)-5-(trifuoromethyl)pyridine-3-carboxamide;

(103) 2-isoindolin-2-yl-N-(3-methylsulfonylphenyl)-5-(trifuoromethyl)pyridine-3-carboxamide;

(104) 2-(2,3,3a,5,6,6a-hexahydrofuro[3,2-b]pyrrol-4-yl)-N-(3-methylsulfonylphenyl)-5-(trifuoromethyl) pyridine-3-carboxamide;

(105) N-(3-methylsulfonylphenyl)-2-(4-phenyl-1-piperidyl)-5-(triuoromethyl)pyridine-3-carboxamide;

(106) N-(3-carbamoylphenyl)-2-(4,4-difuoroazepan-1-yl)-5-(trifuoromethyl)pyridine-3-carboxamide;

(107) 2-(azocan-1-yl)-N-(3-carbamoylphenyl)-5-(trifluoromethyl)pyridine-3-carboxamide;

(108) N-(3-carbamoylphenyl)-2-(4,4-difuoro-1,3,3a,5,6,6a-hexahydrocyclopenta[c]pyrro1-2-yl)-5-(trifuoromethyl)pyridine-3-carboxamide;

(109) N-(3-carbamoylphenyl)-2-(8,8-difuoro-6-azaspiro[2.5]ictan-6-yl)-5-(trifuoromethyl)pyridine-3-carboxamide;

(110) N-(3-carbamoylphenyl)-2-(3,3-difuoro-1-piperidyl)-5-(triuoromethyl)pyridine-3-carboxamide;

(111) 2-[(3S,5R)-4,4-difuoro-3,S-dimethyl-1-piperidyl]-N-(1,1-dioxo-2,3-dihydro-1,2-benzothiazol-6-yl)-5-(trifuoromethyl) pyridine-3-carboxamide;

(112) 2-[(3R)-4,4-difuoro-3-methyl-1-piperidyl]-N-(1,1-dioxo-2,3-dihydro-1,2-benzothiazol-6-yl)-5-(trifuoromethyl)pyridine-3-carboxamide;

(113) 2-[(3S)-4,4-difuoro-3-methyl-1-piperidyl]-N-(1,1-dioxo-2,3-dihydro-1,2-benzothiazol-6-yl)-5-(trifuoromethyl)pyridine-3-carboxamide;

(114) N-(3-fluoro-5-sulfamoyl-phenyl)-2-(1-piperidyl)-5-(trifuoromethyl)pyridine-3-carboxamide;

(115) N-(4-fluoro-3-sulfamoyl-phenyl)-2-(1-piperidyl)-5-(trifluoromethyl)pyridine-3-carboxamide;
(116) N-(2-fluoro-5-sulfamoyl-phenyl)-2-(1-piperidyl)-5-(trifluoromethyl)pyridine-3-carboxamide;
(117) 2-(azepan-1-yl)-N-(3-1sopropylsulfonylphenyl)-5-(trufluoromethyl)pyridine-3-carboxamide;
(118) 2-(azepan-1-yl)-N-(1,1-dioxobenzothiophen-6-yl)-5-(trifluoromethyl)pyr1dine-3-carboxamide;
(119) 2-(azepan-1-yl)-N-(3-1sobutylsulfonylphenyl)-5-(trifluoromethyl)pyr1dine-3-carboxamide;
(120) 2-(azepan-1-yl)-N-(3-cyclopentylsulfonylphenyl)-5-(trifluoromethyl)pyrid1ne-3-carboxamide;
(121) 2-(azepan-1-yl)-N-(1,1-dioxo-2,3-dihydro-1,2-benzothiazol-6-yl)-5-(trufluoromethylpyridine-3-carboxarnide;
(122) 2-(azepan-1-yl)-3-((2-methyl-1,1-dioxido-2,3-d1hydrobenzo[d]isothiazol-6-yl)carbamoyl)-5-(trifuoromethyl)pyridine;
(123) (R)-2-(4,4-Difluuoro-3-methylpiperidin-1-yl)-N-(3-sulfamoylphenyl)-5-(trifluoromethyl)nicotinamide;
(124) (S)-2-(4,4-difuoro-3-methylpiperidin-1-yl)-N-(3-sulfamoylphenyl)-5-(trifluoromethyl)nicotinamide;
(125) 2-[(3 S,5R)-4,4-difluoro-3,5-d1methyl-1-p1per1dyl]-N-(3-sulfamoylphenyl)-5-(truifluoromethyl)pyridine-3-carboxamide;
(126) 2-[(3S)-2,2-difluoro-5-azaspiro[2.5]ctan-5-yl]-N-(3-sulfamoylphenyl)-5-(trifluoromethyl)pyridine-3-carboxamide;
(127) 2-[(3R)-2,2-difuoro-5-azaspiro[2.5]octan-5-yl]-N-(3-sulfamoylphenyl)-5-(trifluoromethyl)pyridine-3-carboxamide;
(128) 2-[(1R,6R)-7,7-difluoro-6-methyl-3-azab1cyc10[4.1.0]heptan-3-yl]-N-(3-sulfamoylphenyl)-5-(trifluoromethyl)pyrodine-3-carboxamide;
(129) 2-[(1S,6S)-7,7-difluoro-6-methyl-3-azab1cyc10[4.1.0]heptan-3-yl]-N-(3-sulfamoylphenyl)-5-(trifluoromethyl)pyl1dine-3-arboxamide;
(130) N-(3-sulfamoylphenyl)-5-(trifluoromethyl)-2-[(1R,5R)-1-(trifluoromethyl)-3-azabicyclo-[3.2.0]heptan-3-yl]pyridine-3-carboxamide;
(131) N-(3-sulfamoylphenyl)-5-(trifluoromethyl)-2-[(1 8,5 S)-1-(trifluoromethyl)-3-azabicyclo-[3.2.0]heptan-3-yl]pyridine-3-carboxamide;
(132) 2-[(1R,5S)-6,6-difuoro-3-azab1cyclo[3.1.1]heptan-3-yl]-N-(3-sulfamoylphenyl)-5-(trifluoromethyl)pyridine-3-carboxamide;
(133) N-(3-sulfamoylphenyl)-2-[(1R,5S)-6,6,7,7-tetrafluoro-3-azab1cyclo[3.2.0]heptan-3-yl]-5-(trifluoromethyl)pyridine-3-carboxamide;
(134) 2-[(1R,5S)-3-azab1cyclo[3.2.0]heptan-3-yl]-N-(3-sulfamoylphenyl)-5-(trifluoromethyl)pyridine-3-carboxarnide;
(135) 2-[(1S,5R)-6,6-difluoro-3-azab1cyclo[3.2.0]heptan-3-yl]-N-(3-sulfamoylphenyl)-5-(trifluoromethyl)pyridine-3-carboxamide;
(136) 2-[(1R,5S)-6,6-difuoro-3-azab1cyclo[3.2.0]heptan-3-yl]-N-(3-sulfamoylphenyl)-5-(trifluoromethyl)pyridine-3-carboxamide;
(137) 2-[(1S,4S)-5,5-difluoro-2-azab1cyclo[2.2.1]heptan-2-yl]-N-(3-sulfamoylphenyl)-5-(trifluoromethyl)pyridine-3-carboxamide;
(138) 2-[(1R,4R)-5,5-difluoro-2-azab1cyclo[2.2.1]heptan-2-yl]-N-(3-sulfamoylphenyl)-5-(trifluoromethyl)pyridine-3-carboxamide;
(139) 2-(7-azab1cyclo[2.2.1]heptan-7-yl)-N-(3-sulfamoylphenyl)-5-(trifluoromethyl)pyridine-3-carboxamide;
(140) N-(3-sulfamoylphenyl)-5-(trifluoromethyl)-2-[(28)-2-(trifluoromethyl)morpholin-4-yl]pyridine-3-carboxamide;
(141) N-(3-sulfamoylphenyl)-5-(trifluoromethyl)-2-[(2R)-2-(trifluoromethyl)morpholin-4-yl]pyridine-3-carboxamide;
(142) 2-[(2R,6R)-2-methyl-6-(trifluoromethyl)morpholin-4-yl]-N-(3-sulfamoylphenyl)-5-(trifluoromethyl)pyridine-3-carboxamide;
(143) N-(3-sulfamoylphenyl)-5-(trifluoromethyl)-2-[3-(trifluoromethyl)piperazin-1-yl]pyridine-3-carboxamide;
(144) (R)-N-(3-sulfamoylphenyl)-5-(trifluoromethyl)-2-(2-(trifluoromethyl)-1,4-oxazepan-4-yl)-nicotinamide;
(145) 2-[(28,6R)-2-methyl-6-(trifluoromethyl)morpholin-4-yl]-N-(3-sulfamoylphenyl)-5-(trifluoromethyl)pyridine-3-carboxamide;
(146) 2-[(2R,6S)-2-methyl-6-(trifluoromethyl)morph011n-4-yl]-N-(3-sulfamoylphenyl)-5-(trifluoromethyl)pyridine-3-carboxamide;
(147) N-(3-sulfamoylphenyl)-5-(trifluoromethyl)-2-[(28)-2-(trifluoromethyl)-1,4-oxazepan-4-yl]pyridine-3-carboxamide;
(148) 2-[(2S,6S)-2-methyl-6-(trifluoromethyl)morpholin-4-yl]-N-(3-sulfamoylphenyl)-5-(trifluoromethyl)pyridine-3-carboxamide;
(149) 2-[(2R,6S or 2S,6R)-2,6-d1methylmorpholin-4-yl]-N-(3-sulfamoylphenyl)-5-(trifluoromethyl)pyridine-3-carboxamide;
(150) 2-[(2S,6S or 2R,6R)-2,6-d1methylmorpholin-4-yl]-N-(3-sulfamoylphenyl)-5-(trifluoromethyl)pyridine-3-carboxamide;
(151) 2-(azepan-1-yl)-3-((3-(N-(pyrimid1n-4-yl)sulfamoyl)phenyl)carbamoyl)-5-(trifluoromethyl)pyridin-1-ium;
(152) 2-(4,4-difluoropiperidin-1-yl)-N-(3-(methylsulfonyl)phenyl)-5-(trifluoromethyl)nicotinamide;
(153) 5-isobutyl-2-(piperidin-1-yl)-N-(3-sulfamoylphenyl)nicotinamide;
(154) 5-cyclopentyl-2-(piperidin-1-yl)-N-(3-sulfamoylphenyl)nicotinamide;
(155) 2-(azepan-1-yl)-6-methoxy-5-methyl-N-(3-sulfamoylphenyl)nicotinamide;
(156) 2-(azepan-1-yl)-5-bromo-6-methoxy-N-(3-sulfamoylphenyl)nicotinamide;
(157) 2-(azepan-1-yl)-5-cyano-6-methyl-N-(3-sulfamoylphenyl)pyridine-3-carboxamide;
(158) 2-(azepan-1-yl)-4-chloro-6-methyl-N-(3-sulfamoylphenyl)pyridine-3-carboxamide;
(159) 5-cyclobutyl-2-(4,4-difuoroazepan-1-yl)-N-(3-sulfamoylphenyl)nicotinamide;
(160) 2-(4,4-difluoroazepan-1-yl)-5-(oxetan-3-yl)-N-(3-sulfamoylphenyl)nicotinamide;
(161) 5-(but-3-en-1-yl)-2-(4,4-difluoroazepan-1-yl)-N-(3-sulfamoylphenyl)nicotinamide;
(162) 2-(4,4-difuoroazepan-1-yl)-5-isoropyl-N-(3-sulfamoylphenyl)nicotinamide;
(163) 5-cyclopropyl-2-(4,4-difluoroazepan-1-yl)-N-(3-sulfamoylphenyl)nicotinamide;
(164) 2-(azepan-1-yl)-5-(perfluoroethyl)-N-(3-sulfamoylphenyl)nicotinamide
(165) 6-(1,1,2,2,2-pentafluoroethyl)-2-(1-piperidyl)-N-(3-sulfamoylphenyl)pyridine-3-carboxamide;
(166) 2-(azepan-1-yl)-N-(3-methylsulfonylphenyl)-5-(1,1,2,2,2-pentafluoroethyl)pyl1dine-3-carboxamide;
(167) 2-(azepan-1-yl)-N-(3-carbamoylphenyl)-5-(1,1,2,2,2-pentafluoroethyl)pyridine-3-carboxamide;

(168) 2-(azepan-1-yl)-6-methyl-N-(3-sulfamoylphenyl)-5-(trifuoromethyl)nicotinamide;
(169) 2-(azepan-1-yl)-6-meth0xy-N-(3-sulfamoylphenyl)-5-(trifluoromethyl)nicotinamide;
(170) 2-(4,4-difuoropiperidin-1-yl)-N-(2-fluoro-3-sulfamoylphenyl)-5-(trifluoromethyl)nicotinamide;
(171) N-(3,4-difluoro-5-sulfamoylphenyl)-2-(4,4-difluorop1peridin-1-yl)-5-(trifluoromethyl)nicotinamide;
(172) 2-(4,4-difluoroazepan-1-yl)-5-(difluoromethoxy)-N-(3-sulfamoylphenyl)nicotinamide;
(173) 5-chioro-2-(4,4-difuoroazepan-1-yl)-N-(3-(methylsulfonyl)phenyl)nicotinamide;
(174) 2-(azepan-1-yl)-6-chloro-4,5-d1methyl-N-(3-sulfamoylphenyl)pyridine-3-carboxamide;
(175) 2-(azepan-1-yl)-4-methyl-N-(3-sulfamoylphenyl)pyridine-3-carboxamide;
(176) 5-cyano-2-(4,4-difluoroazepan-1-yl)-6-methyl-N-(3-methylsulfonylphenyl)pyridine-3-carboxamide;
(177) N-(3-carbamoylphenyl)-5-cyano-2-(4,4-difuoroazepan-1-yl)-6-methyl-pyridine-3-carboxamide,
(178) 2-(azepan-1-yl)-N-(3-carbamoylphenyl)-5-cyano-6-methyl-pyridine-3-carboxamide,
(179) 5-chloro-2-(4,4-difuoroazepan-1-yl)-N,4,6-trimethyl-N-(3-sulfamoylphenyl)nicotinamide,
(180) 2-cyclopropyl-4-(4,4-difuoroazepan-1-yl)-N-(3-sulfamoylphenyl)pyrimidine-5-carboxamide, and
(181) 3-(4,4-difuoroazepan-1-yl)-N-(3-sulfamoylphenyl)-6-(trifuoromethyl)pyridazine-4-carboxamide,
and pharmaceutically acceptable salts thereof.

Although the specific stereochemistries described above are preferred, other stereoisomers, including diastereoisomers, enantiomers, epimers, and mixtures of these may also have utility in treating $Na_v1.8$ mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

Definitions

"Ac" is acetyl, which is $CH_3C(=O)-$.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like.

"Cycloalkyl" means a saturated monocyclic, bicyclic, spirocyclic or bridged carbocyclic ring, having a specified number of carbon atoms. Examples of cycloalkyl include cyclopropyl, cyclobutyl, cyclopentyl, cyclohexyl, cycloheptyl, and the like.

"Cycloheteroalkyl" means a saturated or partly unsaturated non-aromatic monocyclic, bicyclic, spirocyclic or bridged ring or ring system having a specified number of carbon atoms and containing at least one ring heteroatom selected from N, NH, S (including SO and $SO_2$) and O. The cycloheteroalkyl ring may be substituted on the ring carbons and/or the ring nitrogen or sulfur. Examples of cycloheteroalkyl include tetrahydrofuran, pyrrolidine, tetrahydrothiophene, azetidine, piperazine, piperidine, morpholine, oxetane and tetrahydropyran. In one embodiment of the present invention, cycloheteroalkyl is selected from: pyrrolidine, azetidine, piperidine, piperazine, azepane, azocane, morpholine, thiomorpholine, thiomorpholine dione, oxazepane, 1,4-thiazepane, isoindoline, dihydroisoquinoline, tetrahydroisoquinoline, octahydro-isoindole, azabicyclo[2.2.1]heptane, oxa-azabicyclo[2.2.1]heptane, azabicyclo[3.1.1]-heptane, azabicyclo[4.1.0]heptane, azabicyclo[3.2.1]octane, diazabicyclo[3.2.1]octane, oxa-azabicyclo-[3.2.1]octane, azabicyclo[3.2.0]heptane, oxa-azabicyclo[3.2.0]heptane, azaspiro[2.5]-octane, azaspiro[2.6]nonane, azaspiro[3.5]nonane, oxa-azaspiro[3.5]nonane, oxa-azaspiro[4.5]-decane, dihydrothieno[3,2-c]pyridine, dihydrothiazolo[4,5-c]pyridine, dihydrooxazolo[4,5-c]pyridine, dihydroimidazo[1,2-a]pyrazine, hexahydrofuro[3,2-b]pyrrole, hexahydrocyclopenta[c]pyrrole, octahydrocyclpenta[c]pyrrole, and azatricyclo[4.3.1.13,8]undecane. In another embodiment of the present invention, cycloheteroalkyl is selected from: pyrrolidine, azetidine, piperidine, piperazine, azepane, azocane, morpholine, thiomorpholine, oxazepane, isoindoline, dihydroisoquinoline, octahydroisoindole, azabicyclo[2.2.1]heptane, azabicyclo[3.1.1]heptane, azabicyclo[4.1.0]heptane, azabicyclo[3.2.1]octane, diazabicyclo[3.2.1]octane, azabicyclo[3.2.0]-heptane, oxa-azabicyclo[3.2.1]octane, azaspiro[2.5]octane, azaspiro[2.6]nonane, oxa-azaspiro-[3.5]nonane, oxa-azaspiro[4.5]decane, dihydrothiazolo[4,5-c]pyridine, dihydrooxazolo[4,5-c]pyridine, hexahydrofuro[3,2-b]pyrrole, hexahydrocyclopenta[c]pyrrole, and azatricyclo[4.3.1.13,8]undecane. In another embodiment, cycloheteroalkyl is selected from: piperidine, azepane, morpholine, 6-azaspiro[2.5]octane, and 5-azaspiro[2.5]octane. In another embodiment, cycloheteroalkyl is selected from: piperidine, azepane, morpholine, and 6-azaspiro[2.5]octane.

"Aryl" means a monocyclic, bicyclic or tricyclic carbocyclic aromatic ring or ring system containing 6-14 carbon atoms, wherein at least one of the rings is aromatic. Examples of aryl include phenyl and naphthyl. In one embodiment of the present invention, aryl is phenyl.

"Heteroaryl" means a monocyclic, bicyclic or tricyclic ring or ring system containing 5-14 ring atoms and containing at least one ring heteroatom selected from N, NH, S (including SO and $SO_2$) and O, wherein at least one of the heteroatom containing rings is aromatic. Examples of heteroaryl include: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl, quinolyl, indolyl, isoquinolyl, quinazolinyl, dibenzofuranyl, and the like. In one embodiment of the present invention, heteroaryl is a 5 or 6 membered heteroaryl ring. In another embodiment, heteroaryl is pyridine.

"Halogen" includes fluorine, chlorine, bromine and iodine. In one embodiment, halogen is fluorine, chorine or bromine. In another embodiment, halogen is fluorine or chlorine. In another embodiment, halogen is fluorine or bromine. In another embodiment, halogen is fluorine. In another embodiment, halogen is chlorine. In another embodiment, halogen is bromine.

"Me" represents methyl.

"Oxo" represents =O.

"Saturated" means containing only single bonds.

"Unsaturated" means containing at least one double or triple bond. In one embodiment, unsaturated means containing at least one double bond. In another embodiment, unsaturated means containing at least one triple bond.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

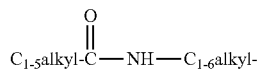

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

Compounds of Formula I may contain one or more asymmetric centers and can thus occur as racemates and racemic mixtures, single enantiomers, diastereomeric mixtures and individual diastereomers. The present invention is meant to encompass all such isomeric forms of the compounds of Formula I.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration or sufficient heavy atoms to make an absolute assignment.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I. For example, the compounds of formula I include the following tautomers:

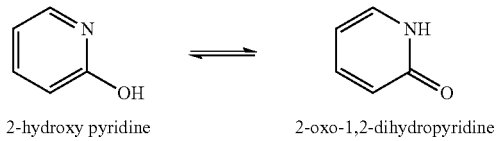 [SMILES: Oc1ccccn1 ; O=c1cccc[nH]1]

2-hydroxy pyridine ⇌ 2-oxo-1,2-dihydropyridine

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H), deuterium ($^2$H), and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts

It will be understood that, as used herein, references to the compounds of the present invention are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

The term "prodrug" means compounds that are rapidly transformed, for example, by hydrolysis in blood, in vivo to the parent compound, e.g., conversion of a prodrug of Formula A to a compound of Formula A, or to a salt thereof, a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. The scope of this invention includes prodrugs of the novel compounds of this invention.

Solvates, and in particular, the hydrates of the compounds of the present invention are included in the present invention as well.

Utilities

The compound of the present invention are selective inhibitors of $Na_v1.8$ sodium ion channel activity or have selective activity as $Na_v1.8$ sodium ion channel blockers. In one embodiment, the compounds of the present invention exhibit at least 10-fold selectivity for $Na_v1.8$ sodium channels over $Na_v1.5$ sodium channels, and in some embodiments exhibit at least 100-fold selectivity for $Na_v1.8$ sodium channels over $Na_v1.5$ sodium channels based on functional potency ($IC_{50}$ values) for each channel in Qube® assay system.

The compounds of the present invention are potent inhibitors of $Na_v1.8$ channel activity. The compounds, and pharmaceutically acceptable salts thereof, may be efficacious in the treatment of diseases, disorders and conditions that are mediated by the inhibition of $Na_v1.8$ sodium ion channel activity and/or $Na_v1.8$ receptors.

Diseases, disorders or conditions mediated by $Na_v1.8$ sodium ion channel activity and/or $Na_v1.8$ receptors, include but are not limited to nociception, osteoarthritis, peripheral neuropathy, inherited erythromelalgia, multiple sclerosis, asthma, pruritus, acute itch, chronic itch, migraine, neurodegeneration following ischemia, epilepsy, inflammatory pain, spontaneous pain, acute pain, pen-operative pain, post-operative pain, neuropathic pain, postherpetic neuralgia, trigeminal neuralgia, diabetic neuropathy, chronic lower back pain, phantom limb pain, pain resulting from cancer and chemotherapy, chronic pelvic pain, pain syndromes, and complex regional pain syndromes.

One or more of these conditions or diseases may be treated, managed, prevented, reduced, alleviated, ameliorated or controlled by the administration of a therapeutically effective amount of a compound of the present invention, or a pharmaceutically acceptable salt thereof, to a patient in need of treatment. Also, the compounds of the present invention may be used for the manufacture of a medicament which may be useful for treating, preventing, managing, alleviating, ameliorating or controlling one or more of these conditions, diseases or disorders: nociception, osteoarthritis, peripheral neuropathy, inherited erythromelalgia, multiple sclerosis, asthma, pruritus, acute itch, chronic itch, migraine, neurodegeneration following ischemia, epilepsy, inflammatory pain, spontaneous pain, acute pain, peri-operative pain, post-operative pain, neuropathic pain, postherpetic neuralgia, trigeminal neuralgia, diabetic neuropathy, chronic lower back pain, phantom limb pain, pain resulting from cancer and chemotherapy, chronic pelvic pain, pain syndromes, and complex regional pain syndromes.

Preferred uses of the compounds may be for the treatment of one or more of the following diseases by administering a therapeutically effective amount to a patient in need of treatment. The compounds may be used for manufacturing a medicament for the treatment of one or more of these diseases:

(1) pain conditions,
(2) pruritic conditions, and
(3) cough conditions.

In one embodiment of the present invention, the pain condition is an acute pain or chronic pain disorder. In another embodiment of the present invention, the the pain condition is an acute pain disorder.

The compounds of the present invention may be effective in treating nociception. Nociception or pain is essential for survival and often serves a protective function. However, the pain associated with surgical procedures and current therapies to relieve that pain, can delay recovery after surgery and increase the length of hospital stays. As many as 80% of surgical patients experience post-operative pain due to tissue damage, and damage to peripheral nerves and subsequent inflammation. Approximately 10-50% of surgical patients will develop chronic pain after surgery often because the nerve damage results in lasting neuropathic pain once the wound has healed.

The compounds of the present invention may be effective in treating osteoarthritis. Osteoarthritis is type of arthritis caused by inflammation, breakdown, and eventual loss of cartilage in the joints. The standards of care for pain associated with osteoarthritis are non-steroidal anti-inflammatory drugs (NSAIDs), for example celecoxib and diclofenac (reviewed in Zeng et al., 2018). Patients that do not respond to NSAID therapies are typically treated with low dose opiates, such as hydrocodone. Patients that are refractory to the above therapies will usually opt for total joint replacement.

The compounds of the present invention may be effective in treating peripheral neuropathy. Peripheral neuropathy is nerve damage caused by chronically high blood sugar and diabetes. It leads to numbness, loss of sensation, and sometimes pain in distal limbs such as feet, legs, or hands. It is the most common complication of diabetes. The standards of care for the treatment of painful diabetic neuropathy are gabapentinoids, for example gabapentin and pregabalin. Some patients will respond well to tricyclic antidepressants such as amitriptyline, while other patients get significant relief using SRI/NRI drugs such as duloxetine (Schreiber et al., World J Diabetes. 2015 Apr. 15; 6(3):432-44). Many options are available, however side-effects are common (e.g. dizziness, nausea) which limit their full potential.

The compounds of the present invention may be effective in treating inherited erythromelalgia. Inherited erythromelalgia (IEM) is a chronic pain syndrome which has been linked to mutations in several voltage-gated sodium channels, including Nav1.8 (Kist et al., PLoS One. 2016 Sep. 6; 11(9):e0161789). Patients present with the classic "gloves and stocking" flare pattern on distal regions such as hands and feet, typically brought on with warm temperatures and exercise. Some patients find relief from the burning pain associated with flares by cold water immersion. Although medications that affect voltage-gated sodium channels (eg, lidocaine and mexiletine) show promise, there is no current standard of care to treat IEM.

The compounds of the present invention may be effective in treating neuropathic pain. Neuropathic pain is pain caused by damage or disease affecting the somatosensory nervous system. It has been demonstrated in human patients, as well as in animal models of neuropathic pain, that damage to primary afferent sensory neurons can lead to neuroma formation and spontaneous activity, as well as evoked activity in response to normally innocuous stimuli. (Colloca et al., Nat Rev Dis Primers. 2017 Feb. 16; 3:17002; Coward et al., Pain. 2000 March; 85(1-2):41-50; Yiangou et al., FEBS Lett. 2000 Feb. 11; 467(2-3):249-52; Carter et al., Phys Med Rehabil Clin N Am. 2001 May; 12(2):447-59). Some nerve injuries result in an increase in Nav1.8 expression, which is believed to be an underlying mechanism for pathological pain. (Black et al., Ann Neurol. 2008 December; 64(6):644-53; Bird et al., Br J Pharmacol. 2015 May; 172(10):2654-70). Injuries of the peripheral nervous system often result in neuropathic pain persisting long after an initial injury resolves. Examples of neuropathic pain include, but are not limited to, post herpetic neuralgia, trigeminal neuralgia, diabetic neuropathy, chronic lower back pain, lumbar radiculopathy, phantom limb pain, pain resulting from cancer and chemotherapy, chronic pelvic pain, complex regional pain syndrome and related neuralgias, and painful conditions that arise due to gain-of-function mutations in Nav1.8 (Huang et al., J Neurosci. 2013 Aug. 28; 33(35): 14087-97; Kist et al., PLoS One. 2016 Sep. 6; 11(9): e0161789; Emery et al., J Neurosci. 2015 May 20; 35(20): 7674-81; and Schreiber et al., World J Diabetes. 2015 Apr. 15; 6(3):432-44.

The ectopic activity of normally silent sensory neurons is thought to contribute to the generation and maintenance of neuropathic pain, which is generally assumed to be associated with an increase in sodium channel activity in the injured nerve. (Wood et al., Curr Opin Pharmacol. 2001 February; 1(1):17-21; Baker et al., TRENDS in Pharmacological Sciences, 2001, 22(1): 27-31). Standards of care for neuropathic pain vary considerably depending on the particular condition, but first line therapies are typically pregabalin, gabapentin, tricyclic antidepressants (e.g. amitriptyline), and SRI/NRI drugs (e.g. duloxetine). Patients refractory to these therapies are usually prescribed low dose opiates (e.g. hydrocodone).

The compounds of the present invention may be effective in treating multiple sclerosis. Recent evidence points to a potential role for Nav1.8 in multiple sclerosis. Nav1.8 expression in cerebellum has been identified in tissues taken from animal models of multiple sclerosis (EAE model) and in postmortem brains from patients suffering from multiple sclerosis (MS) (Shields et al., Ann Neurol. 2012 February; 71(2):186-94; Black et al., Proc Natl Acad Sci USA. 2000 Oct. 10; 97(21):11598-602). Also, two SCN10A polymorphisms showed significant association with MS (Roostaei et al., Neurology. 2016 Feb. 2; 86 (5):410-7). When Nav1.8 is overexpressed in cerebellum, mice develop ataxic-related motor deficits which are ameliorated with oral delivery of a selective small molecule Nav1.8 antagonist (Shields et al., PLoS One. 2015 Mar. 6; 10(3)). These studies suggest that a Nav1.8 antagonist may be a useful therapy to treat symptoms related to multiple sclerosis.

The compounds of the present invention may be effective in treating asthma. Asthma is caused by airway inflammation in which a person's airways become hyper-responsive, narrow and swollen, which makes it difficult to breathe. These symptoms are typically triggered through an allergic reaction (Nair P et al., J Allergy Clin Immunol Pract. 2017 May-June; 5(3):649-659).

In a preclinical model of asthma, deletion of Nav1.8-containing neurons, or inhibition of nerve fibers via small molecules reduces airway inflammation and immune cell infiltration (Talbot et al., Neuron. 2015 Jul. 15; 87(2):341-54). Selective Nav1.8 antagonists may be a useful therapy to prevent airway hypersensitivity caused by immune cell infiltration.

The compounds of the present invention may be effective in treating pruritus. Pruritus, also commonly known as itch, affects approximately 4% of the global population is an unpleasant sensation that elicits the desire or reflex to scratch, and is regarded as closely related to pain (Luo et al., Cell Mol Life Sci. 2015 September; 72 (17): 3201-23). Theories on the origin of itch implicate the subtle, low-frequency activation of nociceptors (pain-sensing neurons); however, it has been described that some afferents preferentially respond to histamine, which induces itch (Schmelz et al., J Neurosci. 1997 Oct. 15; 17(20):8003-8). At the same time, it has been found that histamine-responding neurons also respond to capsaicin which produces pain (McMahon et al., Trends in Neuroscience 1992, 15:497-501). Members of the transient receptor potential (TRP) family, and nerve growth factor (NGF) are both known to play a role in itch and pain, and clinically, both maladies are treated with therapeutic agents such as gabapentin and antidepressants. Therefore, it continues to be accepted that the underlying mechanisms of pain and itch are highly interwoven and complex, and distinguishing pan-selective or itch-selective pathways remains ambiguous (Ikoma et al., Nat Rev Neurosci. 2006 July; 7(7):535-47). A role for Nav1.8 in pruritis was studied using a mouse transgenically expressing a constitutively active form of the serine/threonine kinase BRAF was expressed in Nav1.8-expressing neurons. This resulted in enhanced pruriceptor excitability, and heightened evoked and spontaneous scratching behavior (Zhao et al., 2013). In skin, pruritogens are released from keratinocytes, lymphocytes, mast cells, and eosinophils during inflammation. These molecules act directly on free nerve endings which express Nav1.8 to induce itch (Riol-Blanco et al., Nature. 2014 Jun. 5; 510 (7503):157-61). Chronic and acute itch can arise from many different insults, diseases and disorders, and may be classified as dermal or pruriceptive, neurogenic, neuropathic, or psychogenic: itch can arise from both systemic disorders, skin disorders, as well as physical or chemical insult to the dermis. Pathologically, conditions such as dry skin, eczema, psoriasis, varicella zoster, urticaria, scabies, renal failure, cirrhosis, lymphoma, iron deficiency, diabetes, menopause, polycythemia, uremia, and hyperthyroidism can cause itch, as can diseases of the nervous system such as tumors, multiple sclerosis, peripheral neuropathy, nerve compression, and delusions related to obsessive-compulsive disorders. Medicines such as opioids and chloroquine can also trigger itch (Ikoma et al., Nat Rev Neurosci. 2006 July; 7(7):535-47). Itching following burn is also an extremely serious clinical problem as it hampers the healing process, resulting in permanent scaring, and negatively impacting quality of life (Van Loey et al., Br J Dermatol. 2008 January; 158(1):95-100).

The invention also includes pharmaceutically acceptable salts of the compounds, and pharmaceutical compositions comprising the compounds and a pharmaceutically acceptable carrier.

The compounds, or pharmaceutically acceptable salts thereof, may be useful in treating pain conditions, pruritic conditions, and cough conditions.

A compound of the present invention, or a pharmaceutically acceptable salt thereof, may be used in the manufacture of a medicament for the treatment of pain conditions, pruritic conditions, and cough conditions in a human or other mammalian patient.

A method of treating a pain conditions comprises the administration of a therapeutically effective amount of a compound of the present invention, or a pharmaceutically acceptable salt thereof, or a pharmaceutical composition comprising the compound, to a patient in need of treatment. A method of treating a pruritic condition comprises the administration of a therapeutically effective amount of a compound of the present invention, or a pharmaceutically acceptable salt thereof, or a pharmaceutical composition comprising the compound, to a patient in need of treatment. A method of treating a cough condition comprises the administration of a therapeutically effective amount of a compound of the present invention, or a pharmaceutically acceptable salt thereof, or a pharmaceutical composition comprising the compound, to a patient in need of treatment. Other medical uses of the compounds of the present invention are described herein.

The term "pain condition" as used herein includes, but are not limited to, acute pain, peri-operative pain, pre-operative pain, post-operative pain, neuropathic pain, post herpetic neuralgia, trigeminal neuralgia, diabetic neuropathy, chronic lower back pain, phantom limb pain, chronic pelvic pain, vulvodynia, complex regional pain syndrome and related neuralgias, pain associated with cancer and chemotherapy, pain associated with HIV, and HIV treatment-induced neuropathy, nerve injury, root avulsions, painful traumatic mononeuropathy, painful polyneuropathy, erythromyelalgia, paroxysmal extreme pain disorder, small fiber neuropathy, burning mouth syndrome, central pain syndromes (potentially caused by virtually any lesion at any level of the nervous system), postsurgical pain syndromes (e.g., post mastectomy syndrome, post thoracotomy syndrome, stump pain)), bone and joint pain (osteoarthritis), repetitive motion pain, dental pain, myofascial pain (muscular injury, fibromyalgia), perioperative pain (general surgery, gynecological), chronic pain, dysmennorhea, pain associated with angina, inflammatory pain of varied origins (e.g. osteoarthritis, rheumatoid arthritis, rheumatic disease, teno-synovitis and gout), shoulder tendonitis or bursitis, gouty arthritis, and aolymyalgia rheumatica, primary hyperalgesia, secondary hyperalgesia, primary allodynia, secondary allodynia, or other pain caused by central sensitization, complex regional pain syndrome, chronic arthritic pain and related neuralgias acute pain, migraine, migraine headache, headache pain, cluster headache, non-vascular headache, traumatic nerve injury, nerve compression or entrapment, and neuroma pain, The term "pruritic condition" or "pruritic disorder" as used herein includes, but is not limited to, conditions with an unpleasant sensation that provokes the desire to scratch, such as chronic itch.

The term "cough condition" or "cough disorder" as used herein includes, but is not limited to, chronic cough, neuropathic cough or cough due to neurological conditions.

Treatment of a disease, disorder or condition mediated by $Na_v1.8$ sodium ion channel activity or $Na_v1.8$ receptors refers to the administration of the compounds of the present invention to a subject with the disease, disorder or condition. One outcome of treatment may be reducing the disease, disorder or condition mediated by $Na_v1.8$ sodium ion channel activity or $Na_v1.8$ receptors. Another outcome of treatment may be alleviating the disease, disorder or condition mediated by $Na_v1.8$ sodium ion channel activity or $Na_v1.8$ receptors. Another outcome of treatment may be ameliorating the disease, disorder or condition mediated by $Na_v1.8$ sodium ion channel activity or $Na_v1.8$ receptors. Another outcome of treatment may be suppressing the disease, disorder or condition mediated by $Na_v1.8$ sodium ion channel activity or $Na_v1.8$ receptors. Another outcome of treatment may be managing the disease, disorder or condition mediated by $Na_v1.8$ sodium ion channel activity or $Na_v1.8$ receptors.

Another outcome of treatment may be preventing the disease, disorder or condition mediated by $Na_v1.8$ sodium ion channel activity or $Na_v1.8$ receptors.

Prevention of the disease, disorder or condition mediated by $Na_v1.8$ sodium ion channel activity or $Na_v1.8$ receptors refers to the administration of the compounds of the present invention to a subject at risk of the disease, disorder or condition. One outcome of prevention may be reducing the disease, disorder or condition mediated by $Na_v1.8$ sodium ion channel activity or $Na_v1.8$ receptors in a subject at risk of the disease, disorder or condition. Another outcome of prevention may be suppressing the disease, disorder or condition mediated by $Na_v1.8$ sodium ion channel activity or $Na_v1.8$ receptors in a subject at risk of the disease, disorder or condition. Another outcome of prevention may be ameliorating the disease, disorder or condition mediated by $Na_v1.8$ sodium ion channel activity or $Na_v1.8$ receptors in a subject at risk of the disease, disorder or condition. Another outcome of prevention may be alleviating the disease, disorder or condition mediated by $Na_v1.8$ sodium ion channel activity or $Na_v1.8$ receptors in a subject at risk of the disease, disorder or condition. Another outcome of prevention may be managing the disease, disorder or condition mediated by $Na_v1.8$ sodium ion channel activity or $Na_v1.8$ receptors in a subject at risk of the disease, disorder or condition.

One outcome of treatment may be reducing the amount of pain experienced by a subject relative to that subject's pain immediately before the administration of the compounds of the present invention. Another outcome of treatment may be alleviating the amount of pain experienced by a subject relative to that subject's pain immediately before the administration of the compounds of the present invention. Another outcome of treatment may be ameliorating the amount of pain experienced by a subject relative to that subject's pain immediately before the administration of the compounds of the present invention. Another outcome of treatment may be suppressing the amount of pain experienced by a subject relative to that subject's pain immediately before the administration of the compounds of the present invention. Another outcome of treatment may be managing the amount of pain experienced by a subject relative to that subject's pain immediately before the administration of the compounds of the present invention. Another outcome of treatment may be ameliorating the amount of pain experienced by a subject relative to that subject's pain immediately before the administration of the compounds of the present invention.

Another outcome of treatment may be preventing further pain experienced by a subject after the administration of the compounds of the present invention.

Prevention of pain refers to the administration of the compounds of the present invention to reduce the pain of a subject at risk of pain. Prevention includes, but is not limited to, the administration to a subject prior to surgery or other expected painful event. One outcome of prevention may be reducing pain in a subject at risk of pain. Another outcome of prevention may be suppressing pain in a subject at risk of pain. Another outcome of prevention may be ameliorating pain in a subject at risk of pain. Another outcome of prevention may be alleviating pain in a subject at risk of pain. Another outcome of prevention may be managing pain in a subject at risk of pain.

The terms "administration of" and or "administering a" compound should be understood to mean providing a compound of the invention or a prodrug of a compound of the invention to the individual or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with an effective dose of a compound of the present invention. For example, oral, intravenous, infusion, subcutaneous, transcutaneous, intramuscular, intradermal, transmucosal, intramucosal, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of disorders, diseases and/or conditions which require inhibition of $Na_v1.8$ sodium ion channel activity, a suitable dosage level will generally be about 0.0001 to 500 mg per kg patient body weight per day which can be administered in single or multiple doses. In one embodiment, a suitable dosage level may be about 0.001 to 500 mg per kg patient body weight per day. In another embodiment, a suitable dosage level may be about 0.001 to about 250 mg/kg per day. In another embodiment, a suitable dosage level may be about 0.01 to about 250 mg/kg per day. In another embodiment, a suitable dosage level may be about 0.1 to about 100 mg/kg per day. In another embodiment, a suitable dosage level may be about 0.05 to 100 mg/kg per day. In another embodiment, a suitable dosage level may be about 0.1 to 50 mg/kg per day. In another embodiment, a suitable dosage level may be about 0.05 to 0.5 mg/kg per day. In another embodiment, a suitable dosage level may be about 0.5 to 5 mg/kg per day. In another embodiment, a suitable dosage level may be about 5 to 50 mg/kg per day. For oral administration, the compositions are preferably provided in the form of tablets containing 0.01 to 1000 mg of the active ingredient, particularly 0.01, 0.025, 0.05, 0.075, 0.1, 0.25, 0.5, 0.75, 1.0, 2.5, 5.0, 7.5, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 8 times per day; preferably, 1 to 4 times a day; more preferably once or twice per day. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Compounds of the present invention may be used in combination with other drugs that may also be useful in the treatment or amelioration of the diseases or conditions for which compounds of the present invention are useful. Such other drugs may be administered, by a route and in an amount commonly used therefor, contemporaneously or sequentially with a compound of the present invention. In the treatment of patients who have pain conditions, pruritic conditions and cough conditions, more than one drug is commonly administered. The compounds of this invention may generally be administered to a patient who is already taking one or more other drugs for these conditions. Often the compounds will be administered to a patient who is already being treated with one or more anti-pain compounds when the patient's pain is not adequately responding to treatment.

The combination therapy also includes therapies in which the compound of the present invention and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the present invention.

Examples of other active ingredients that may be administered in combination with a compound of the present invention, and either administered separately or in the same pharmaceutical composition, include but are not limited to:
  (i) an opioid agonist;
  (ii) an opioid antagonist;
  (iii) a calcium channel antagonist;
  (iv) a NMDA receptor agonist;
  (v) a NMDA receptor antagonist;
  (vi) a COX-2 selective inhibitor;
  (vii) a NSAID (non-steroidal anti-inflammatory drug); and
  (viii) an analgesic;
  (ix) a sodium channel inhibitor;
  (x) an anti-NGF antibody;
  (xi) a $Na_v1.7$ inhibitor;
  (xii) a HCN inhibitor;
  (xiii) a TRPV1 antagonist;
  (xiv) a $Na_v1.7$ biological; and
  (xv) a $Na_v1.8$ biological; and
pharmaceutically acceptable salts thereof.

In another embodiment of the present invention, the pharmaceutical composition comprises:
(1) a compound of Claim 1 or a pharmaceutically acceptable salt thereof;
(2) one or more compounds, or pharmaceutically acceptable salts thereof, selected from the group consisting of:
  (i) an opioid agonist;
  (ii) an opioid antagonist;
  (iii) a calcium channel antagonist;
  (iv) a NMDA receptor agonist;
  (v) a NMDA receptor antagonist;
  (vi) a COX-2 selective inhibitor;
  (vii) a NSAID (non-steroidal anti-inflammatory drug); and
  (viii) an analgesic;
  (ix) a sodium channel inhibitor;
  (x) an anti-NGF antibody;
  (xi) a $Na_v1.7$ inhibitor;
  (xii) a HCN inhibitor;
  (xiii) a TRPV1 antagonist;
  (xiv) a $Na_v1.7$ biological; and
  (xv) a $Na_v1.8$ biological; and
pharmaceutically acceptable salts thereof; and
(3) a pharmaceutically acceptable carrier.

A Nav 1.7 biological means a protein, including, but not limited to, antibodies, nanobodies and peptides, that inhibits the function of the Nav1.7 channel. A Nav 1.8 biological means a protein, including, but not limited to, antibodies, nanobodies and peptides, that inhibits the function of the Nav1.8 channel.

Specific compounds of use in combination with a compound of the present invention include: sodium channel inhibitors, including but not limited to, lidocaine, including the lidocaine patch; tricyclic antidepressants including, but not limited to, amitriptyline; and SRI/NRI drugs, including but not limited to, duloxetine.

Suitable opioid agonists include, but are not limited to, codeine, fentanyl, hydrocodone, hydromorphone, levorphanol, meperidine, methadone, morphine, oxycodone, oxymorphone, buprenorphine, butorphanol, dezocine, nalbuphine, pentazocine, and tramadol.

Suitable opioid antagonists include, but are not limited to, naltrexone and naloxone.

Suitable calcium channel antagonists include, but are not limited to, Amlodipine, Diltiazern, Felodipine, gabapentin, Isradipine, Nicardipine, Nifedipine, Nisoldipine, pregabalin, Verapanil, and ziconitide.

Suitable NMDA receptor antagonists include, but are not limited to, ketanine, methadone, memantine, amantadine, and dextromethorphan.

Suitable COX-2 inhibitors include, but are not limited to, celecoxib, etoricoxib and parecoxib.

Suitable NSAIDs or non-steroidal anti-inflammatory drugs include, but are not limited to, aspirin, diclofenac, diflunisal, etodolac, fenoprofin, flurbiprofen, ibuprofen, indomethacin, ketoprofen, meclofenamic acid, mefenamic acid, meloxicam, naproxen, naproxen sodium, oxaprozin, piroxicam, sulindac, and tolmetin.

Suitable analgesics include, but are not limited to, acetaminophen and duloxetine.

The above combinations include combinations of a compound of the present invention not only with one other active compound, but also with two or more other active compounds.

Non-limiting examples include combinations of compounds with two or more active compounds selected from: opioid agonists; opioid antagonists; calcium channel antagonists; NMDA receptor agonists; NMDA receptor antagonists; COX-2 selective inhibitors; NSAIDs (non-steroidal anti-inflammatory drugs); and an analgesic.

The compounds of the present invention, or a pharmaceutically acceptable salt thereof, may also be used in combination with spinal cord stimulation therapy and cutaneous stimulation therapy.

The present invention also provides a method for the treatment or prevention of a $Na_v1.8$ sodium ion channel activity mediated disease, disorder or condition, which method comprises administration to a patient in need of such treatment or at risk of developing a $Na_v1.8$ sodium ion channel activity mediated disease with a therapeutically effective amount of a $Na_v1.8$ sodium ion channel activity inhibitor and an amount of one or more active ingredients, such that together they give effective relief.

In a further aspect of the present invention, there is provided a pharmaceutical composition comprising a $Na_v1.8$ sodium ion channel activity inhibitor and one or more active ingredients, together with at least one pharmaceutically acceptable carrier or excipient.

Thus, according to a further aspect of the present invention there is provided the use of a $Na_v1.8$ sodium ion channel activity inhibitor and one or more active ingredients for the manufacture of a medicament for the treatment or prevention of a $Na_v1.8$ sodium ion channel activity mediated disease, disorder or condition. In a further or alternative aspect of the present invention, there is therefore provided a product comprising a $Na_v1.8$ sodium ion channel activity inhibitor and one or more active ingredients as a combined preparation for simultaneous, separate or sequential use in the treatment or prevention of a $Na_v1.8$ sodium ion channel activity mediated disease, disorder or condition. Such a combined preparation may be, for example, in the form of a twin pack.

It will be appreciated that for the treatment or prevention of pain conditions, pruritic conditions and cough conditions, a compound of the present invention may be used in conjunction with another pharmaceutical agent effective to treat that disease, disorder or condition.

The present invention also provides a method for the treatment or prevention of pain conditions, pruritic conditions and cough conditions, which method comprises administration to a patient in need of such treatment an amount of a compound of the present invention and an amount of another pharmaceutical agent effective to threat that disorder, disease or condition, such that together they give effective relief.

The present invention also provides a method for the treatment or prevention of pain conditions, pruritic conditions and cough conditions, which method comprises administration to a patient in need of such treatment an amount of a compound of the present invention and an amount of another pharmaceutical agent useful in treating that particular condition, disorder or disease, such that together they give effective relief.

The term "therapeutically effective amount" means the amount the compound of structural formula I that will elicit the biological or medical response of a cell, tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a COX-2 inhibitor the weight ratio of the compound of the Formula I to the COX-2 inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Methods of Synthesis of the Compounds of the Present Invention:

The following reaction schemes and Examples illustrate methods which may be employed for the synthesis of the compounds of structural formula I described in this invention. These reaction schemes and Examples are provided to illustrate the invention and are not to be construed as limiting the invention in any manner. All substituents are as defined above unless indicated otherwise. Several strategies based upon synthetic transformations known in the literature of organic synthesis may be employed for the preparation of the compounds of structural formula I. The scope of the invention is defined by the appended claims.

The compounds of the present invention can be prepared according to the procedures of the following Examples, using appropriate materials. The compounds illustrated in the examples are not, however, to be construed as forming the only genus that is considered as the invention. The Examples further illustrate details for the preparation of the compounds of the present invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI).

Instrumentation

Reverse phase chromatography was carried out on a Gilson GX-281 equipped with a column selected from the following: Phenomenexd Synergi C18 (150 mm×30 mm×4 micron), YMC-Actus Pro C18 (150 mm×30 mm×5 micron), Xtimate C18 (150 mm×25 mm×5 micron), Boston Green ODS (150 mm×30 mm×5 micron), XSELECT C18 (150 mm×30 mm×5 micron), and Waters XSELECT C18 (150 mm×30 mm×5 micron). Conditions included either high pH (0-100% acetonitrile/water eluent comprising 0.1% v/v 10 mM NH$_4$CO$_3$ or 0.05% NH$_4$OH) or low pH (0-95% acetonitrile/water eluent comprising 0.1% v/v TFA) and are noted for some examples.

SFC chiral resolution was carried out on a Sepiate Prep SFC 100, Multigram II (MG II), THAR80 prep SFC, or a Waters SFC (80, 200, or 350) using the following conditions: Chiral Method A: AD-H column, 15% ethanol/CO$_2$; Chiral Method B: AD-H column, 20% IPA/CO$_2$; Chiral Method C: AS-H column, 20% MeOH/CO$_2$; Chiral Method D: AD-H column, 20% ethanol/CO$_2$; Chiral Method E: Lux Cellulose-4 column, 30% ethanol/CO$_2$; Chiral Method F: IA column, 15% ethanol/CO$_2$; Chiral Method G: IA column, 40% methanol/CO$_2$; Chiral Method H: AD-H column, 10% methanol/CO$_2$; Chiral Method I: AD-H column, 30% ethanol/CO$_2$; Chiral Method J: AD-H column, 40% ethanol/CO$_2$; and Chiral Method K: IG column, 12% methanol/CO$_2$.

LC/MS determinations were carried out on a Waters Classing Aquity system equipped with TUV and MS detectors and a Waters SQD mass spectrometer, a Shimadzu 20 UV 254 and 220 nM with Shimadzu 2010 or 2020 mass spectrometer, or an Agilent 1200 HPLC quipped with DAD/ELSD and G6110 MSD using one of the following conditions: 1) Ascentis Express C18 (3×50 mm) 2.7 µm column using mobile phase containing A: 0.05% Trifluoroacetic acid in water and B: 0.05% Trifluoroacetic acid in acetonitrile with a gradient from 90:10 (A:B) to 5:95 (A:B) over 6 min at a flow rate of 1.8 mL/min, UV detection at 210 nm; 2) Aquity BEH C18, (1.0×50 mm) 1.7 µm column using mobile phase containing A: 0.05% Trifluoroacetic acid in water and B: 0.05% Trifluoroacetic acid in acetonitrile with a gradient from 90:10 (A:B) to 5:95 (A:B) over 2 min at a flow rate of 0.3 mL/min, UV detection at 215 nm; 3) Agilent YMC J'Sphere H-80 (3×50 mm) 5 µm column using mobile phase containing A: 0.1% Trifluoroacetic acid in water and B: acetonitrile with a gradient from 95:5 (A:B) to 0:100 (A:B) over 3.6 min and 0:100 (A:B) for 0.4 min at a flow rate of 1.4 mL/min, UV detection at 254 and 220 nm and Agilent 1100 quadrupole mass spectrometer; 4) an Agilent TC-C18 (2.1×50 mm) 5 µm column using mobile phase containing A: 0.0375% Trifluoroacetic acid in water and B: 0.01875% Trifluoroacetic acid in acetonitrile with a gradient from 90:10 (A:B) for 0.4 min to 90:10 to 0:100 (A:B) over 3 min and 10:90 (A:B) for 0.6 min at a flow rate of 0.8 mL/min, UV detection at 254 and 220 nm and Agilent 6110 quadrupole mass spectrometer.

Proton or $^1$H NMR was acquired using a Varian Unity-Inova 400 MHz NMR spectrometer equipped with a Varian 400 ATB PFG 5 mm, Nalorac DBG 400-5 or a Nalorac IDG 400-5 probe, a Varian-400 MHz MR spectrometer equipped with an Auto X ID PFG Probe 5 mm, a Varian 400 MHz VNMRS spectrometer equipped with a PFG 4Nuc Probe 5 mm, or a Bruker AvanceIII 500 MHz spectrometer equipped with a PABBO Probe 5 mm in accordance with standard analytical techniques, unless specified otherwise, and results of spectral analysis are reported.

Abbreviations

Throughout the Examples section, the following abbreviations are used to indicate various reagents, substituents and solvents: AcCN is acetonitrile; ACE-Cl is 1-chloroethyl chloroformate; AcOH is acetic acid; Boc is tert-butoxycarbonyl; Brettphos-Pd-G3 is [(2-di-cyclohexylphosphino-3,6-dimethoxy-2',4',6'-triisopropyl-1,1'-biphenyl)-2-(2'-amino-1,1'-biphenyl)]palladium(II) methane-sulfonate; cal'd is calculated; DCE is dichloroethane; DCM is dichloromethane; DIPEA is diisopropylamine; DMA is dimethylacetamide; DMAP is 4-dimethylaminopyridine; DMB is 2,4-dimethoxybenzyl-; DMF is dimethylformamide; DMSO is dimethylsulfoxide; dppf is 1,1'-bis(diphenylphosphino)ferrocene; EDC is N-(3-dimethylaminopropyl)-N'-ethylcarbodiimide hydrochloride; Et20 is diethyl ether; EtOAc or EA is ethyl acetate; EtOH is ethanol; g is grams; HATU is 1-[bis(dimethyl-amino)-methylene]-1H-1,2,3-triazolo[4,5-b]pyridinium-3-oxide-hexafluorophosphate; h or hr(s) is hour(s); HPLC is high-performance liquid chromatography; IPA is isopropyl alcohol; L is liter; LAH is lithium aluminum hydride; LC/MS is liquid chromatography/mass spectrometry; LDA is lithium diisopropylamide; LG is leaving group; LHMDS is lithium bis(trimethylsilyl)amide; MeOH is methanol; LRMS is low resolution mass spectrometry; mg is milligrams; mL is milliliter; mmol is millimolar; M is molar; NCS is N-chlorosuccinimide; NMP is N-methylpyrrolidone; Pd/C is palladium on carbon; Pd$_2$(dba)$_3$ is tris(dibenzylideneacetone)dipalladium(0); PdCl$_2$(dppf) is [1,1'-bis(diphenylphosphino)-ferrocene]dichloropalladium(II); Pd(tBu$_3$P)$_2$ is bis(tri-tert-butylphosphine)palladium(0); PE or pet. ether is petroleum ether; PG is protecting group; POCl$_3$ is phosphorus(V)oxychloride; P(tBu)$_3$-Pd-G2 is chloro[(tri-tert-butylphosphine)-2-(2-aminobiphenyl)] palladium(II); r.t. or rt or RT is room temperature; SFC is Supercritical Fluid Chromatography; THF is tetrahydrofuran; TFA is trifluoroacetic acid; TMS-Cl is trimethylsilyl chloride; UV is ultraviolet; TEA is triethylamine; Xantphos is 4,5-Bis(diphenylphosphino)-9,9-dimethylxanthene; and Xantphos G2 or XantPhos Pd G2 or XantPhos-Pd-G2 is chloro[(4,5-bis(diphenylphosphino)-9,9-dimethyl-xanthene)-2-(2'-amino-1,1'-biphenyl)]-palladium(II).

Several methods for preparing the compounds of this invention are illustrated in the following Schemes and Examples. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products. The following examples are provided for the purpose of illustration only and are not to be construed as limitations on the disclosed invention.

As illustrated in Scheme A, in general, compounds of the invention can be prepared by coupling an appropriately functionalized carboxylic acid (A-1) with an arylamine (A-2), using amide coupling agents such as EDC or HATU or by forming the acid chloride from POCl$_3$ or oxalyl chloride, to afford intermediates of type A-3. Intermediates of type A-3 can undergo nucleophilic aromatic substitution reactions with secondary amines (A-4) by displacing a heteroaryl chloride in the presence of a base, such as K$_2$CO$_3$, DIPEA or TEA, to yield a compound of Formula A-5. Arylamines of type A-2 and amines of type A-4 are commercially available or may be synthesized from appropriate intermediates.

Scheme A

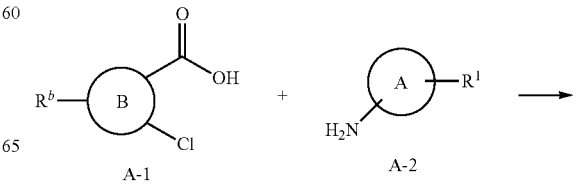

-continued

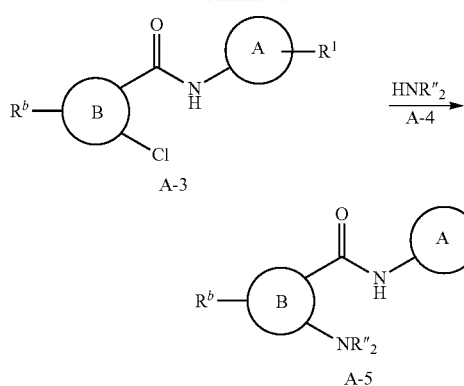

$R^3$ is HNR''$_2$ (A-4)

The nucleophilic aromatic substitution reaction with the amine (A-4) can be incorporated before the amide coupling to the carboxylic acid to give compounds of Formula A-5. The nucleophilic aromatic substitution can also occur in the presence of alternative functional groups that can be converted to the carboxylic acid, including an ester or cyano functional group, by hydrolyzing to a carboxylic acid before being coupled to an arylamine to provide compounds of Formula A-5.

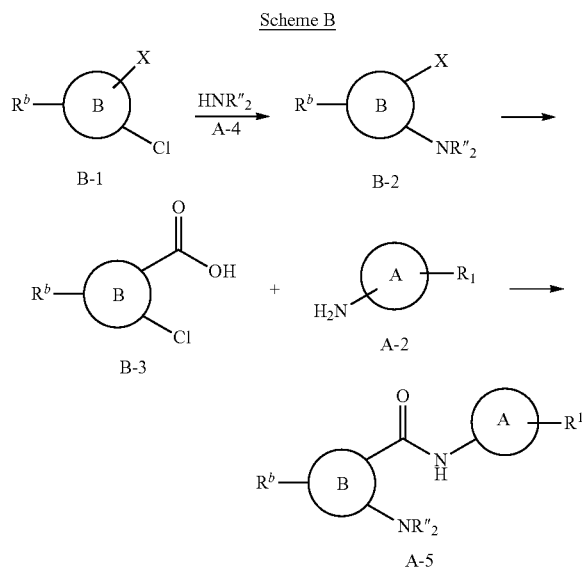

$R^3$ is HNR''$_2$ (A-4)

Alternatively, the compound of Formula A-5 may be prepared via reaction of heteroaryl chloride with an amine, followed by halogenation of the adjacent position of the heteroaryl ring. The heteroaryl halide, such as the heteroaryl bromide, can be converted to a carboxylic acid, which can be activated to the acid chloride and coupled to an arylamine. The heteroaryl halide can also be converted to a cyano group, which can be hydrolyzed to a primary amide, and the primary amide can be coupled to an appropriately functionalized aryl halide and deprotected as needed to provide compounds of Formula A-5.

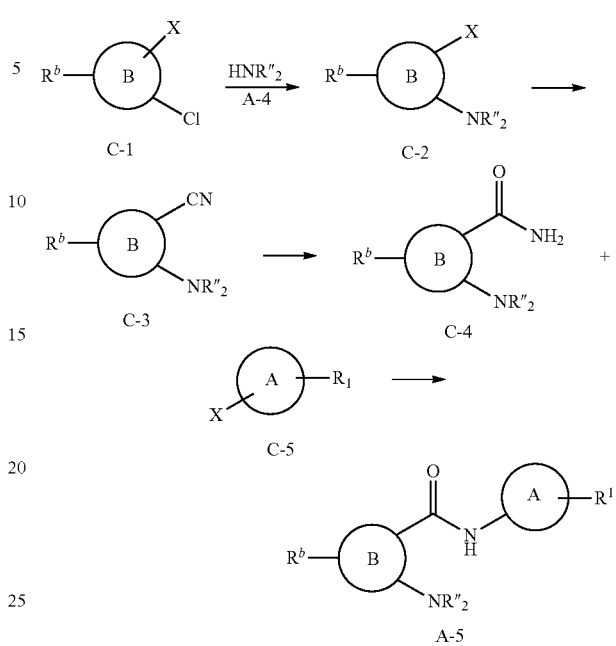

$R^3$ is HNR''$_2$ (A-4)

Other functional groups may additionally or alternatively be introduced into the compounds of the invention by utilizing other known functional group transformations to prepare useful pyridine reagents before the final coupling has been carried out.

Intermediate 1

3-amino-N,N-bis(2,4-dimethoxybenzyl)-2,6-difluorobenzenesulfonamide

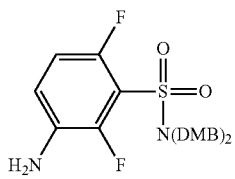

Step 1: 2,6-difluoro-3-nitrobenzenesulfonyl chloride To a stirred mixture of 2,6-difluorobenzenesulfonyl chloride (0.10 g, 0.47 mmol) in H$_2$SO$_4$ (2 mL) was added nitric acid (30 mg, 0.47 mmol). The mixture was stirred at 15° C. for 12 h. Then the mixture was added to water and extracted with ethyl acetate. The combined organic layers were dried over Na$_2$SO$_4$, filtered and concentrated under reduced pressure to give the title compound.

Step 2: N,N-bis(2,4-dimethoxybenzyl)-2,6-difluoro-3-nitrobenzenesulfonamide To a stirred mixture of bis(2,4-dimethoxybenzyl)amine (0.20 g, 0.62 mmol) and triethylamine (94 mg, 0.93 mmol) in DCM (3 mL) was added 2,6-difluoro-3-nitrobenzenesulfonyl chloride (80 mg crude). The mixture was stirred at 15° C. for 10 min. Then the mixture was added to water and extracted with ethyl acetate. The combined organic layers were dried over Na$_2$SO$_4$, filtered and concentrated under reduced pressure to give the title compound.

Step 3: 3-amino-N,N-bis(2,4-dimethoxybenzyl)-2,6-difluorobenzenesulfonamide To a stirred mixture of N,N-bis(2,4-dimethoxybenzyl)-2,6-difluoro-3-nitrobenzenesulfonamide (0.12 g 0.22 mmol) in EtOAc (3 mL) was added Pd/C (24 mg, 0.22 mmol). The mixture was stirred under hydrogen (15 psi) at 15° C. for 30 min. Then the mixture was filtered and concentrated under reduced pressure to give a residue that was purified by silica gel chromatography (50% petroleum ether/ethyl acetate) to give the title compound.

Intermediate 2

3-bromo-N,N-bis(2,4-dimethoxybenzyl)-2-fluorobenzenesulfonamide

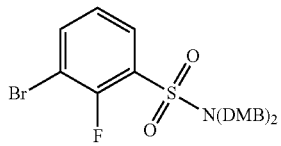

Step 1: 3-bromo-2-fluorobenzenesulfonyl chloride To a solution of 3-bromo-2-fluoroaniline (1.0 g, 5.3 mmol) in acetonitrile (15 mL) at 0° C. was added $HBF_4$ (0.69 g, 7.9 mmol) and tert-butyl nitrite (0.81 g, 7.9 mmol). The mixture was stirred at 0° C. for 1 hour. In a separate flask, a suspension of copper(I) chloride (0.78 g, 7.9 mmol) in acetonitrile (15 mL) at 0° C. was saturated with sulfur dioxide (excess) by bubbling the gas through the suspension with vigorous stirring for 15 minutes. After 1 hour, the solution was added dropwise to the suspension of copper (I) chloride at 0° C. The combined mixture was warmed to rt for 1 hour. Then the mixture was poured into ice-water and extracted with EtOAc. The organic layer was washed with water, brine, dried over $Na_2SO_4$, filtered and concentrated under reduced pressure to give the title compound.

Step 2: 3-bromo-N,N-bis(2,4-dimethoxybenzyl)-2-fluorobenzenesulfonamide To a solution of bis(2,4-dimethoxybenzyl)amine (1.0 g, 3.1 mmol) and Et3N (1.3 mL, 9.4 mmol) in DCM (15 mL) was added 3-bromo-2-fluorobenzenesulfonyl chloride (0.86 g crude). The mixture was stirred at 20° C. for 30 min, then diluted with water and extracted with DCM. The organic layers were dried over $Na_2SO_4$, filtered and concentrated under reduced pressure to give a residue that was purified by silica gel chromatography (PE:EtOAc=20:1 to 3:1) to give the title compound.

Intermediate 3

3-bromo-N,N-bis(2,4-dimethoxybenzyl)benzenesulfonamide

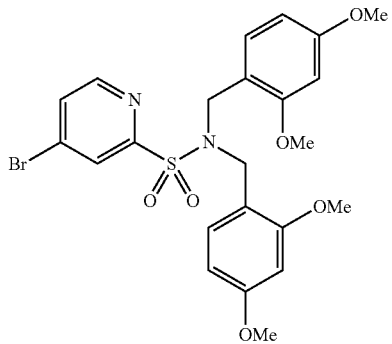 [SMILES: COc1ccc(CN(Cc2ccc(OC)cc2OC)S(=O)(=O)c2cc(Br)ccn2)c(OC)c1]

To a solution of 3-bromobenzene-1-sulfonyl chloride (80 g, 0.31 mol) in DCM (1.5 L) under an atmosphere of nitrogen was added Et3N (48 g, 0.47 mol) and bis(2,4-dimethoxybenzyl)amine (0.10 kg, 0.33 mol).

The mixture was stirred at 20° C. for 60 min, then diluted with water and extracted with DCM. The organic layers were washed with brine, dried over anhydrous magnesium sulfate, filtered and concentrated under reduced pressure to give a residue that was purified by silica gel chromatography (PE:EtOAc:DCM=1:0:0 to 1:1:1) to give the title compound.

Intermediate 4

(2R,6R)-2-methyl-6-(trifluoromethyl)morpholine hydrochloride

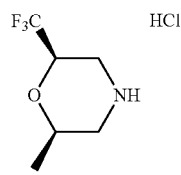

Step 1: (R)-3-(benzylamino)-1,1,1-trifluoropropan-2-ol To a solution of lithium trifluoromethanesulfonate (1.4 g, 9.2 mmol) in acetonitrile (23 mL) was added (R)-(+)-3,3,3-trifluoro-1,2-epoxypropane (5.5 g, 49 mmol) slowly at −10° C. After 5 minutes, benzylamine (5.1 mL, 47 mmol) was added slowly. The mixture was stirred at ambient temperature for 18 hours. Then the mixture was concentrated under reduced pressure to give a residue that was purified by silica gel chromatography (0-100% EtOAc/hexanes) to give the title compound.

Step 2: N-benzyl-2-bromo-N-((R)-3,3,3-trifluoro-2-hydroxypropyl)propanamide To a solution of (R)-3-(benzylamino)-1,1,1-trifluoropropan-2-ol (3.0 g, 14 mmol) in DCM (55 mL) was added TEA (2.5 mL, 18 mmol), then 2-bromopropionyl chloride (1.5 mL, 15 mmol) at 0° C. The mixture was stirred at 0° C. for 30 minutes, then warmed to ambient temperature for 4 hours. Then the mixture was concentrated under reduced pressure. The resulting residue was suspended in EtOAc, filtered through a pad of silica gel, washed with EtOAc, and concentrated under reduced pressure to give the title compound.

Step 3: (6R)-4-benzyl-2-methyl-6-(trifluoromethyl)morpholin-3-one To a stirred solution of N-benzyl-2-bromo-N-((R)-3,3,3-trifluoro-2-hydroxypropyl)propanamide (4.0 g, 11 mmol) in THF (45 mL) at 0° C. was added portionwise NaH (0.68 g, 17 mmol). The mixture was warmed to ambient temperature and stirred for 3 hours. Then the mixture was diluted with ½ saturated brine and extracted with DCM. The organic layers were filtered through a pad of Celite™, washing with dichloromethane, and concentrated to give a residue that was purified by silica gel chromatography (0-50% EtOAc/hexanes) to give the title compound.

Step 4: (2R,6R)-4-benzyl-2-methyl-6-(trifluoromethyl)morpholine To a solution of (6R)-4-benzyl-2-methyl-6-(trifluoromethyl)morpholin-3-one (3.0 g, 11 mmol) in THF (55 mL) at ambient temperature was added LAH (11 mL, 22 mmol) portionwise over 20 minutes. The mixture was heated to reflux for 1 hour. Then the mixture was cooled to rt, diluted with ether, cooled to 0°. The mixture was slowly treated with water (0.9 mL), followed by 15% aqueous sodium hydroxide (0.9 mL), and then water (2.7 mL). The mixture was warmed to ambient temperature and stirred for 15 minutes. Then the mixture was treated with anhydrous magnesium sulfate, stirred for 1 hour and filtered to remove solids. The filter cake was washed with Et20.

The filtrate was concentrated under reduced pressure to give a residue that was purified by silica gel chromatography (0-100% EtOAc/hexanes) to give the title compound Step 5: (2R,6R)-2-methyl-6-(trifluoromethyl)morpholine hydrochloride To a stirred solution of (2R,6R)-4-benzyl-2-methyl-6-(trifluoromethyl)morpholine (1.5 g, 5.8 mmol) in DCE (5.8 mL) was added ACE-Cl (1.9 mL, 17 mmol). The mixture was heated to reflux for 16 hours, then cooled to rt and concentrated under reduced pressure. The resulting residue was dissolved in MeOH (5.8 mL), and the mixture was heated to reflux for 4 hours. Then the mixture was cooled to ambient temperature and concentrated to give a residue that was triturated with $Et_2O$:hexanes (~1:3) to give a solid. The solid containing mixture was filtered and the solid was dried under reduced pressure to give the title compound.

Intermediate 5

(2S,6R)-2-methyl-6-(trifluoromethyl)morpholine hydrochloride

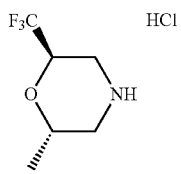

Step 1: (2S,6R)-4-benzyl-2-methyl-6-(trifluoromethyl) morpholine To a solution of (6R)-4-benzyl-2-methyl-6-(trifluoromethyl)morpholin-3-one (3.0 g, 11 mmol) in THF (55 mL) at ambient temperature was added LAH (11 mL, 22 mmol) portionwise over 20 minutes. The mixture was heated to reflux for 1 hour. Then the mixture was cooled to rt, diluted with ether, cooled to 0° C. and then slowly treated with water (0.9 mL), followed by 15% aqueous sodium hydroxide (0.9 mL), and then water (2.7 mL). The mixture was warmed to ambient temperature and stirred for 15 minutes. Then the mixture was treated with anhydrous magnesium sulfate and stirred for 1 hour. The mixture was filtered to remove solids and the filter cake was washed with $Et_2O$. The filtrate was concentrated under reduced pressure to give a residue that was purified by silica gel chromatography (0-100% EtOAc/hexanes) to give the title compound.

Step 2: (2S,6R)-2-methyl-6-(trifluoromethyl)morpholine hydrochloride To a stirred solution of (2S,6R)-4-benzyl-2-methyl-6-(trifluoromethyl)morpholine (0.30 g, 1.2 mmol) in DCE (1.2 mL) was added ACE-Cl (0.13 mL, 1.2 mmol). The mixture was heated to reflux for 16 hours, then the mixture was cooled to rt and concentrated under reduced pressure. The resulting residue was dissolved in MeOH (1.2 mL), and the mixture was heated to reflux for 4 hours. Then the mixture was cooled to ambient temperature and concentrated to give a residue that was triturated with $Et_2O$:hexanes (~1:3) to give a solid. The solid containing mixture was filtered, and the solid was dried under reduced pressure to give the title compound.

Intermediate 6

(R)-2-(trifluoromethyl)-1,4-oxazepane hydrobromide

Step 1: (R)-3-((3,3,3-trifluoro-2-hydroxypropyl)amino) propan-1-ol (R)-2-(trifluoromethyl)-oxirane (3.7 g, 33 mmol) was added to a stirred solution of 3-amino-1-propanol (2.5 g, 33 mmol) in THF (33 mL) at 0° C. The mixture was stirred at 0° C. for 1 hour then warmed to ambient temperature for 16 hours. Then the mixture was concentrated and azeotroped with THF to give the title compound.

Step 2: (R)—N-(3-hydroxypropyl)-4-methyl-N-(3,3,3-trifluoro-2-hydroxypropyl)benzene-sulfonamide Tosyl-Cl (6.7 g, 35 mmol) was added to a solution of (R)-3-((3,3,3-trifluoro-2-hydroxypropyl)amino)propan-1-ol (6.0 g, 32 mmol), and TEA (8.9 mL, 64 mmol) in dichloromethane (80 mL) at 0° C. The mixture was stirred at 0° C. for 1 hour, then warmed to ambient temperature for 16 hours. Then the mixture was diluted with EtOAc and the organic layer was washed with brine, dried over $MgSO_4$, filtered and concentrated under reduced pressure. The resulting residue was purified by silica gel chromatography (0-100% EtOAc/hexanes) to give the title compound.

Step 3: (R)-4-tosyl-2-(trifluoromethyl)-1,4-oxazepane To a stirred solution of (R)—N-(3-hydroxypropyl)-4-methyl-N-(3,3,3-trifluoro-2-hydroxypropyl)benzenesulfonamide (4.0 g, 12 mmol) in THF (120 mL) at 0° C. was added sodium hydride (1.2 g, 29 mmol). The mixture was stirred 5 minutes, then treated with 1-(p-toluenesulfonyl)imidazole (2.6 g, 12 mmol) at 0° C. The mixture was warmed to ambient temperature for 16 hours, then quenched with water and extracted with EtOAc. The organic layer was washed with brine, dried over $MgSO_4$, filtered and concentrated to give a residue that was purified by column chromatography (0-100% EtOAc/hexanes) to give the title compound.

Step 4: (R)-2-(trifluoromethyl)-1,4-oxazepane hydrobromide To a mixture of (R)-4-tosyl-2-(trifluoromethyl)-1,4-oxazepane (3.0 g, 9.3 mmol) and phenol (1.6 mL, 19 mmol) at rt was added HBr in AcOH (1.7 mL, 9.3 mmol). The mixture was heated to 80° C. for 6 hours. Then the mixture was cooled to ambient temperature, concentrated under reduced pressure and azeotroped with toluene. The resulting residue was triturated with $Et_2O$, collected by filtration, washed with Et20 and dried under reduced pressure to give the title compound.

Intermediate 7

5-bromo-2-(piperidin-1-yl)nicotinic acid

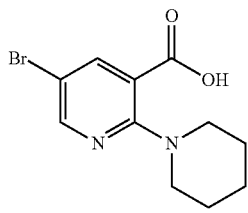 [SMILES: O=C(O)c1cc(Br)cnc1N1CCCCC1]

To a solution of methyl 5-bromo-2-chloronicotinate (2.0 g, 8.0 mmol) in DMA (20 mL) was added piperidine (1.4 g, 16 mmol) and DIPEA (2.1 g, 16 mmol). The mixture was stirred at 100° C. for 10 hours, then diluted with water and extracted with EtOAc. The organic layers were washed with brine, dried over anhydrous $Na_2SO_4$, filtered and concentrated to give a residue that was purified by silica gel chromatography (Petroleum Ether/ethyl acetate=10:1) to give the title compound.

Intermediate 8

2-(4,4-difluoropiperidin-1-yl)-5-(trifluoromethyl) nicotinic acid

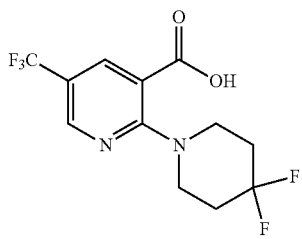 [SMILES: O=C(O)c1cc(C(F)(F)F)cnc1N1CCC(F)(F)CC1]

To a mixture of 4,4-difluoropiperidine hydrochloride (4.2 g, 27 mmol), 2-chloro-5-(trifluoromethyl)nicotinic acid (5.0 g, 22 mmol) was added DMF (110 mL) and $K_2CO_3$ (9.2 g, 66 mmol). The mixture was stirred at rt for 16 h. Then the mixture was diluted with water, the pH was adjusted to 4 with 1N HCl, and extracted with DCM. The organic layer was dried over $Na_2SO_4$ and concentrated to give the title compound.

Intermediate 9 methyl 2-(azepan-1-yl)-5-bromo-6-methoxynicotinate

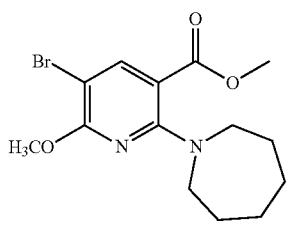 [SMILES: COC(=O)c1cc(Br)c(OC)nc1N1CCCCCC1]

Step 1: methyl 2-chloro-6-methoxynicotinate To a solution of 2-chloro-6-methoxynicotinic acid (1.0 g, 5.3 mmol) in MeOH (10 mL) and DCM (10 mL) was added (diazomethyl)trimethylsilane (8.0 mL, 16 mmol) at 23° C. under an atmosphere of nitrogen. The mixture was stirred at 23° C. for 12 hours, then concentrated under reduced pressure. The resulting residue was purified by silica gel chromatography (0-11% EtOAc/petroleum ether) to give the title compound.

Step 2: methyl 2-(azepan-1-yl)-6-methoxynicotinate To a solution of methyl 2-chloro-6-methoxynicotinate (0.90 g, 4.5 mmol) in DMA (15 mL) was added DIPEA (1.6 mL, 8.9 mmol) and azepane (0.66 g, 6.7 mmol) at 23° C. under an atmosphere of nitrogen. The mixture was stirred at 100° C. for 13 hours, then diluted with water and extracted with EtOAc. The organic layer was washed with brine, dried over $Na_2SO_4$, filtered and concentrated to give a residue that was purified by silica gel chromatography (0-11% EtOAc/Petroleum ether) to give the title compound.

Step 3: methyl 2-(azepan-1-yl)-5-bromo-6-methoxynicotinate To a solution of methyl 2-(azepan-1-yl)-6-methoxynicotinate (0.87 g, 3.3 mmol) in DMF (15 mL) was added 1-1-bromo-pyrrolidine-2,5-dione (0.64 g, 3.6 mmol). The mixture was stirred at 24° C. for 1 hour. Then the mixture was treated with saturated $Na_2SO_3$, diluted with water and extracted with EtOAc. The organic layer was washed with brine, dried over $Na_2SO_4$, filtered and concentrated to give a residue that was purified by silica gel chromatography (0-4% EtOAc/petroleum ether) to give the title compound.

Intermediate 10

5-bromo-2-(4,4-difluoroazepan-1-yl)-N-(3-sulfamoylphenyl)nicotinamide

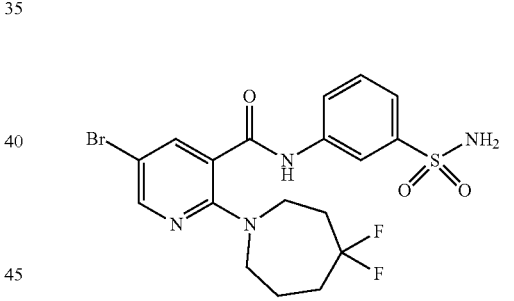

Step 1: methyl 5-bromo-2-(4,4-difluoroazepan-1-yl)nicotinate To a solution of methyl 5-bromo-2-chloronicotinate (1.0 g, 4.0 mmol) in DMA (20 mL) was added 4,4-difluoroazepane (1.1 g, 8.0 mmol) and DIPEA (1.0 g, 8.0 mmol). The mixture was stirred at 100° C. for 2 hours, then diluted with water and extracted with EtOAc. The organic layers were washed with brine, dried over anhydrous $Na_2SO_4$, filtered and concentrated. The resulting residue was purified by silica gel chromatography (30% EtOAc/hexane) to give the title compound.

Step 2: 5-bromo-2-(4,4-difluoroazepan-1-yl)nicotinic acid A mixture of methyl 5-bromo-2-(4,4-difluoroazepan-1-yl)nicotinate (1.0 g, 2.9 mmol) and LiOH $H_2O$ (0.36 g, 8.6 mmol) in MeOH (9 mL), water (3 mL) and THF (5 mL) was stirred at 40° C. for 4 h. Then the mixture was concentrated under reduced pressure. The resulting residue was dissolved in water, acidified with 1N HCl to pH~3 and extracted with EtOAc. The combined organic layers were washed with brine, dried over anhydrous $Na_2SO_4$, filtered and concentrated under reduced pressure to give the title compound.

Step 3: 5-bromo-2-(4,4-difluoroazepan-1-yl)-N-(3-sulfamoylphenyl)nicotinamide To a solution of 5-bromo-2-(4,4-difluoroazepan-1-yl)nicotinic acid (0.40 g, crude) in DCM (5 mL) was added oxalyl dichloride (0.16 mL, 1.8 mmol) and DMF (0.1 mL). The mixture was stirred at 20° C. for 0.5 h, then concentrated under reduced pressure. The resulting residue was dissolved in THF (2 mL) and added dropwise to a mixture of 3-aminobenzenesulfonamide (0.41 g, 2.4 mmol) and DMAP (0.15 g, 1.2 mmol) in THF (3 mL). The resulting mixture was stirred at 40° C. for 2 h, then washed with water and extracted with EtOAc. The combined organic layers were concentrated under reduced pressure to give a residue that was purified by silica gel chromatography (30% EtOAc/hexane) to give the title compound.

Intermediate 11

1-(6-chloro-5-(trifluoromethyl)pyridin-2-yl)azepane

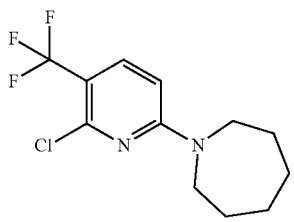 [SMILES: FC(F)(F)c1ccc(N2CCCCCC2)nc1Cl]

To a solution of 2,6-dichloro-3-(trifluoromethyl)pyridine (0.60 g, 2.8 mmol) in DMF (3 mL) was added DIPEA (0.97 mL, 5.6 mmol) and azepane (0.41 g, 4.2 mmol). The reaction mixture was stirred at 25° C. for 10, then diluted with water and extracted with EtOAc. The combined organic layers were washed with brine, dried over anhydrous $Na_2SO_4$, filtered and concentrated to give a residue that was purified by silica gel chromatography (5% EtOAc/petroleum ether) to give the title compound.

Intermediate 12

6-(tert-butyl)-2-(piperidin-1-yl)nicotinic acid

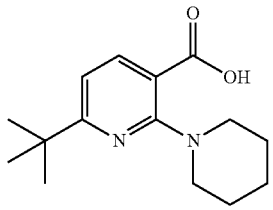 [SMILES: CC(C)(C)c1ccc(C(=O)O)c(N2CCCCC2)n1]

Step 1: 6-(tert-butyl)-2-chloronicotinonitrile To a solution of 2-chloronicotinonitrile (0.20 g, 1.4 mmol) in water (2 mL) was added pivalic acid (0.59 g, 5.8 mmol), sulfuric acid (2.0 mL, 1.4 mmol) and (nitrooxy)silver (59 mg, 0.35 mmol). The mixture was flushed with nitrogen, then a solution of $(NH_4)_2S_2O_8$ (0.66 g, 2.9 mmol) in water (3 mL) was added portionwise. The mixture was stirred at 18° C. for 1 hour, then diluted with water and extracted with EtOAc. The organic layer was washed with brine, dried over $Na_2SO_4$, filtered and concentrated to give a residue that was purified by silica gel chromatography (petroleum ether/EtOAc=5:1) to give the title compound.

Step 2: 6-(tert-butyl)-2-(piperidin-1-yl)nicotinonitrile To a solution of 6-(tert-butyl)-2-chloronicotinonitrile (0.10 g, 0.51 mmol) in DMA (3 mL) was added triethylamine (0.14 mL, 1.0 mmol) and piperidine (87 mg, 1.0 mmol). The mixture was stirred at 100° C. for 1 hour, then diluted with water and extracted with EtOAc. The organic layer was washed with brine, dried over $Na_2SO_4$, filtered and concentrated to give a residue that was purified by silica gel chromatography (petroleum ether/EtOAc=5:1) to give the title compound.

Step 3: 6-(tert-butyl)-2-(piperidin-1-yl)nicotinic acid To a solution of 6-(tert-butyl)-2-(piperidin-1-yl)nicotinonitrile (0.10 g, 0.41 mmol) in EtOH (10 mL) and water (5 mL) was added potassium hydroxide (0.46 g, 8.2 mmol). The mixture was stirred at 80° C. for 96 hours, then diluted with water and extracted with petroleum ether/EtOAc (2:1). The aqueous layer was acidified with aqueous HCl (2 N) and extracted with EtOAc. The organic layer was washed with brine, dried over $Na_2SO_4$, filtered and concentrated to give the title compound.

Intermediate 13

2-chloro-6-(trifluoromethoxy)-5-(trimethylsilyl)nicotinic acid

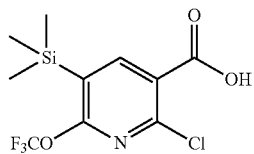 [SMILES: C[Si](C)(C)c1cc(C(=O)O)c(Cl)nc1OC(F)(F)F]

Step 1: 6-chloro-2-(trifluoromethoxy)-3-(trimethylsilyl)pyridine A LDA solution was prepared from butyllithium (1.3 mL, 3.3 mmol) in hexane and diisopropylamine (0.33 g, 3.3 mmol) in THF (20 mL) at 0° C. To the LDA solution at −78° C. was added dropwise over 10 minutes a solution of 2-chloro-6-(trifluoromethoxy)pyridine (0.50 g, 2.5 mmol) in THF (4 mL). The mixture was stirred at −78° C. for 2 hours, then chlorotrimethylsilane (0.36 g, 3.3 mmol) was added dropwise. The mixture was allowed to warm up to rt and stirred 1 hour. Then the mixture was quenched with water and extracted with diethyl ether. The organic layers were dried over sodium sulfate, filtered and concentrated under reduced pressure to give a residue that was purified by silica gel chromatography (petroleum ether:EtOAc=50:1) to give the title compound.

Step 2: 2-chloro-6-(trifluoromethoxy)-5-(trimethylsilyl)nicotinic acid A LiTMP solution was prepared from butyllithium (0.80 mL, 2.0 mmol) and 2,2,6,6-tetramethylpiperidine (0.31 g, 2.2 mmol) in THF (20 mL) at −78° C. To the LiTMP solution at −78° C., was added a solution of 6-chloro-2-(trifluoromethoxy)-3-(trimethylsilyl)pyridine (0.40 g, 1.5 mmol) in THF (4 mL) dropwise over 10 minutes. The mixture was stirred at −78° C. for 2 hours, then carbon dioxide (0.65 g, 15 mmol) was added. Then the mixture was warmed to rt for 1 hour, diluted in water and extracted with EtOAc. The organic layer was dried over sodium sulfate, filtered and concentrated under reduced pressure to a give the title compound.

Intermediate 14

2-Chloro-N-(3-sulfamoylphenyl)-5-(trifluoromethyl)nicotinamide

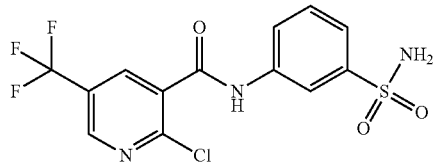 [SMILES: NS(=O)(=O)c1cccc(NC(=O)c2cc(C(F)(F)F)cnc2Cl)c1]

To 2-chloro-5-(trifluoromethyl)pyridine-3-carboxylic acid (3.0 g, 13 mmol) and 3-amino-benzenesulfonamide (2.3 g, 13 mmol) in ethyl acetate (67 mL) was added 1-propanephosphonic anhydride (16 mL, 27 mmol) and DIPEA (4.6 mL, 27 mmol). The mixture was stirred at ambient temperature for 4 hours. Then the mixture was quenched with aqueous potassium phosphate monobasic (saturated) and extracted with ethyl acetate. The combined organic layers were dried over MgSO$_4$, filtered and concentrated under reduced pressure to give a residue that was purified by silica gel chromatography (0-100% EtOAc/hexanes) to give the title compound.

Intermediate 15

2-(4,4-difluoropiperidin-1-yl)-5-(trifluoromethyl)nicotinamide

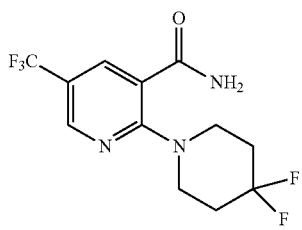 [SMILES: NC(=O)c1cc(C(F)(F)F)cnc1N1CCC(F)(F)CC1]

To a solution of 2-(4,4-difluoropiperidin-1-yl)-5-(trifluoromethyl)nicotinic acid (Intermediate 8, 0.5 g crude) in DMF (12 mL) was added TEA (0.23 g, 2.3 mmol), HATU (0.52 g, 1.4 mmol) and ammonia hydrochloride (91 mg, 1.7 mmol). The mixture was stirred at 30° C. for 13 hours. Then the mixture was diluted with water and extracted with EtOAc. The organic layer was washed with brine, dried over Na$_2$SO$_4$ and concentrated to give a residue that was purified by silica gel chromatography (0-27% PE/EtOAc) to give the title compound.

EXAMPLES

Example 1

2-(4,4-difluoropiperidin-1-yl)-N-(3-sulfamoylphenyl)-5-(trifluoromethyl)nicotinamide

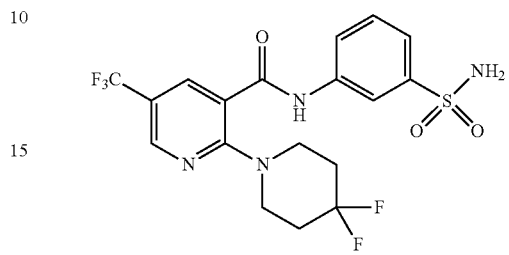

To a mixture of 2-(4,4-difluoropiperidin-1-yl)-5-(trifluoromethyl)nicotinic acid (Intermediate 8, 6.0 g, 19 mmol), 3-aminobenzenesulfonamide (5.0 g, 29 mmol) and EDC (4.1 g, 21 mmol) was added pyridine (200 mL). The mixture was stirred at rt for 16 h, then concentrated under reduced pressure and dissolved in DCM. The organic layer was washed with 1N HCl, dried over Na$_2$SO$_4$, filtered and concentrated to give a residue that was purified by reverse phase chromatography (5-95% MeCN in water with 0.1% NH$_4$OH, C18 column) to give the title compound. LRMS m/z (M+H): calculated 465.1, observed 465.2. $^1$H NMR δ (ppm) (600 MHz, DMSO-d6) δ 10.86 (s, 1H), 8.62 (s, 1H), 8.29 (s, 1H), 8.10 (d, J=2.1 Hz, 1H), 7.85-7.80 (m, 1H), 7.60-7.55 (m, 2H), 7.42 (s, 2H), 3.69-3.54 (m, 4H), 2.11-1.96 (m, 4H).

Example 2

2-(azepan-1-yl)-5-chloro-4,6-dimethyl-N-(3-sulfamoylphenyl)nicotinamide

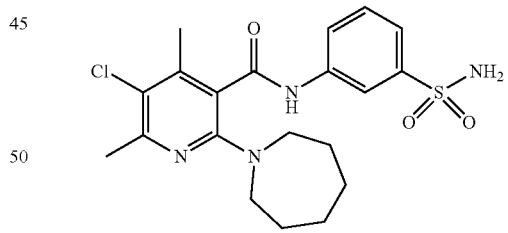

Step 1: 2-(azepan-1-yl)-5-chloro-4,6-dimethylnicotinic acid To a solution of 2,6-dichloro-4,6-dimethylnicotinic acid (0.50 g, 2.3 mmol) in DMF (5 mL) was added hexamethyleneimine (0.56 g, 5.7 mmol) and K$_2$CO$_3$ (1.0 g, 7.2 mmol). The mixture was heated at 85° C. for 3 days in a sealed tube, then additional hexamethyleneimine (0.50 g) and K$_2$CO$_3$ (1.0 g) were added. The mixture was heated at 140° C. in a sealed tube for 24 hours, then cooled to rt and diluted with EtOAc. The organic layer was washed with 5% aqueous AcOH, water, brine, and then dried over MgSO$_4$ and concentrated. The resulting residue was purified by silica gel chromatography (0-75% EtOAc/hexanes) to give the title compound.

Step 2: 2-(azepan-1-yl)-5-chloro-4,6-dimethyl-N-(3-sulfamoylphenyl)nicotinamide To a mixture of 2-(azepan-1-yl)-5-chloro-4,6-dimethylnicotinic acid (0.20 g, 0.71 mmol), 3-aminobenzene-sulfonamide (0.24 g, 1.4 mmol) and EDC (0.20 g, 1.1 mmol) was added pyridine (3 mL). The mixture was sonicated and heated at 50° C. for 17 hours, then cooled to r and diluted with EtOAc. The organic layer was washed with saturated aqueous $NaHCO_3$, water and brine, then dried over $MgSO_4$ and concentrated. The resulting residue that was purified by reverse phase chromatography (5-95% MeCN in water with 0.100 TFA, C18 column). The product containing fractions were partially concentrated to remove acetonitrile, then diluted with EtOAc and washed with saturated aqueous $NaHCO_3$, water and brine. The organic layer was dried over $MgSO_4$ and concentrated to give the title compound. LRMS m/z (M+H): calculated 437.1, observed 437.2. $^1$H NMR δ (ppm) (500 MHz, $CDCl_3$) □ 8.22 (s, 1H), 7.81 (m, 2H), 7.69 (d, 1H), 7.51 (t, 1H), 5.02 (s, 2H), 3.51 (t, 4H), 2.50 (s, 3H), 2.36 (s, 3H), 1.73 (m, 4H), 1.50 (m, 4H) ppm.

TABLE 1

The compounds of Examples 3-25 were prepared according to the procedure for Example 2 starting from the appropriate starting materials.

| Example | Compound | Name | Calc'd [M + H]⁺ | Observed [M + H]⁺ |
|---|---|---|---|---|
| 3 | | 2-(azepan-1-yl)-6-chloro-5-fluoro-4-methyl-N-(3-sulfamoyl-phenyl)pyridine-3-carboxamide | 441.1 | 441.2 |
| 4 | | 2-(azepan-1-yl)-4,6-dimethyl-N-(3-sulfamoyl-phenyl)pyridine-3-carboxamide | 403.1 | 403.2 |
| 5 | | 5-chloro-2-(3,3-difluoropyridin-1-yl)-4,6-dimethyl-N-(3-sulfamoylphenyl)-pyridine-3-carboxamide | 445.1 | 445.1 |
| 6 | | 5-fluoro-2-(1-piperidyl)-N-(3-sulfamoyl-phenyl)pyridine-3-carboxamide | 379.1 | 379.1 |
| 7 | | 2-(azepan-1-yl)-5-chloro-4,6-dimethyl-N-(3-methylsulfonyl-phenyl)pyridine-3-carboxamide | 436.1 | 436.2 |

TABLE 1-continued

The compounds of Examples 3-25 were prepared according to the procedure for Example 2 starting from the appropriate starting materials.

| Example | Compound | Name | Calc'd [M + H]+ | Observed [M + H]+ |
|---|---|---|---|---|
| 8 | | 6-chloro-2-(4,4-difluoroazepan-1-yl)-4-methyl-N-(3-methylsulfonylphenyl)pyridine-3-carboxamide | 458.1 | 458.1 |
| 9 | | 6-chloro-2-(4,4-difluoroazepan-1-yl)-N-(3-methylsulfonylphenyl)pyridine-3-carboxamide | 444.1 | 444.1 |
| 10 | | 2-(4,4-difluoroazepan-1-yl)-6-methyl-N-(3-methylsulfonylphenyl)pyridine-3-carboxamide | 424.1 | 424.1 |
| 11 | | 2-(4,4-difluoroazepan-1-yl)-6-methoxy-N-(3-methylsulfonylphenyl)pyridine-3-carboxamide | 440.1 | 440.1 |
| 12 | | 5-chloro-4,6-dimethyl-N-(3-methylsulfonyl-phenyl)-2-(1-piperidyl)pyridine-3-carboxamide | 422.1 | 422.2 |
| 13 | | 2-(6-azaspiro[2.5]-octan-6-yl)-N-(3-carbamoyl-phenyl)-5-chloro-4,6-dimethyl-pyridine-3-carboxamide | 413.2 | 413.2 |

TABLE 1-continued

The compounds of Examples 3-25 were prepared according to the procedure for Example 2 starting from the appropriate starting materials.

| Example | Compound | Name | Calc'd [M + H]+ | Observed [M + H]+ |
|---|---|---|---|---|
| 14 | | N-(3-carbamoyl-phenyl)-6-chloro-2-(4,4-difluoroazepan-1-yl)pyridine-3-carboxamide | 409.1 | 409.1 |
| 15 | | N-(3-carbamoyl-phenyl)-5-chloro-2-(4,4-difluoroazepan-1-yl)pyridine-3-carboxamide | 409.1 | 409.1 |
| 16 | | N-(3-carbamoyl-phenyl)-5-chloro-2-(4,4-difluoro-1-piperidyl)-4,6-dimethyl-pyridine-3-carboxamide | 423.1 | 423.1 |
| 17 | | N-(3-carbamoyl-phenyl)-6-chloro-2-(4,4-difluoroazepan-1-yl)-4-methyl-pyridine-3-carboxamide | 423.1 | 423.1 |
| 18 | | N-(3-carbamoyl-phenyl)-2-(4,4-difluoroazepan-1-yl)-6-methoxy-pyridine-3-carboxamide | 405.2 | 405.2 |
| 19 | | N-(3-carbamoyl-phenyl)-5-chloro-4,6-dimethyl-2-(1-piperidyl)pyridine-3-carboxamide | 387.2 | 387.2 |

TABLE 1-continued

The compounds of Examples 3-25 were prepared according to the procedure for Example 2 starting from the appropriate starting materials.

| Example | Compound | Name | Calc'd [M + H]⁺ | Observed [M + H]⁺ |
|---------|----------|------|-----------------|-------------------|
| 20 | | 5-chloro-N-(3-cyanophenyl)-2-(4,4-difluoro-1-piperidyl)-4,6-dimethyl-pyridine-3-carboxamide | 405.1 | 405.1 |
| 21 | | 2-(azepan-1-yl)-N-(3-cyanophenyl)-5-(trifluoromethyl)pyridine-3-carboxamide | 389.2 | 389.1 |
| 22 | | 2-(azepan-1-yl)-N-(4-cyanophenyl)-5-(trifluoromethyl)pyridine-3-carboxamide | 389.2 | 389.1 |
| 23 | | 2-(azepan-1-yl)-5-methyl-N-(3-sulfamoyl-phenyl)nicotinamide | 389.5 | 389.2 |
| 24 | | 2-(azepan-1-yl)-N-(3-pyrrolidin-1-yl-sulfonylphenyl)-5-(trifluoromethyl)-pyridine-3-carboxamide | 497.2 | 497.3 |
| 25 | | 2-(azepan-1-yl)-N-(2-hydroxy-5-sulfamoyl-phenyl)-5-(trifluoro-methyl)pyridine-3-carboxamide | 459.1 | 459.3 |

Example 26

2-(azepan-1-yl)-5-chloro-6-methyl-N-(3-sulfamoylphenyl)nicotinanmide

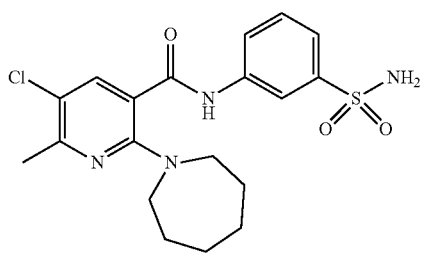 [SMILES: Cc1nc(N2CCCCCC2)c(C(=O)Nc2cccc(S(N)(=O)=O)c2)cc1Cl]

Step 1: 2-(azepan-1-yl)-6-methylnicotinic acid To a solution of 2-chloro-6-methylnlcotinic acid (0.15 g, 0.87 mmol) and DIPEA (0.23 mg, 1.7 mmol) in DMA (3 mL) was added azepane (0.17 g, 1.7 mmol). The mixture was stirred at 90° C. for 13 hours, then diluted with water and extracted with EtOAc. The organic layer was washed with brine, dried over $Na_2SO_4$, filtered and concentrated to give the title compound.

Step 2: 2-(azepan-1-yl)-5-chloro-6-methylnicotinic acid To a solution of 2-(azepan-1-yl)-6-methylnicotinic acid (0.12 g crude) in DMF (1 mL) and DCE (1 mL) was added NCS (0.10 g, 0.77 mmol). The mixture was stirred at 30° C. for 2 hours, then concentrated, diluted by water and extracted with EtOAc. The organic layer was washed with brine, dried over $Na_2SO_4$, filtered and concentrated under reduced pressure. The resulting residue was purified by silica gel chromatography (DCM: MeOH=10:1) to give the title compound.

Step 3: 2-(azepan-1-yl)-5-chloro-6-methylnicotinoyl chloride To a solution of 2-(azepan-1-yl)-5-chloro-6-methylnicotinic acid (30 mg, 0.11 mmol) in DCM (1.5 mL) was added $(COCl)_2$ (28 mg, 0.22 mmol). The mixture was stirred at 30° C. for 1 hour and then concentrated under reduced pressure to give the title compound.

Step 4: 2-(azepan-1-yl)-5-chloro-6-methyl-N-(3-sulfamoylphenyl)nicotinamide A solution of 2-(azepan-1-yl)-5-chloro-6-methylnicotinoyl chloride (18 mg crude) in pyridine (1.5 mL) was added 3-aminobenzenesulfonamide (30 mg, 0.10 mmol). The mixture was stirred at 30° C. for 1 hour, then concentrated to give a residue that was purified by reverse phase chromatography (42-100% MeCN in water with 0.1% TFA, C18 column) to give the title compound. LRMS m/z (M+H): calculated 423.1, observed 423.0. $^1$H NMR δ (ppm) (400 MHz, $CDCl_3$) δ 10.92 (s, 1H), 8.31 (s, 1H), 8.29 (s, 1H), 7.87 (d, J=8.0 Hz, 1H), 7.70 (d, J=8.0 Hz, 1H), 7.52 (t, J=8.0 Hz, 1H), 5.19 (s, 2H), 3.54-3.56 (m, 4H), 2.63 (s, 3H), 1.92 (br s, 4H), 1.74 (br s, 4H).

Example 27

2-(piperidin-1-yl)-N-(3-sulfamoylphenyl)-5-(p-tolyl)nicotinamide

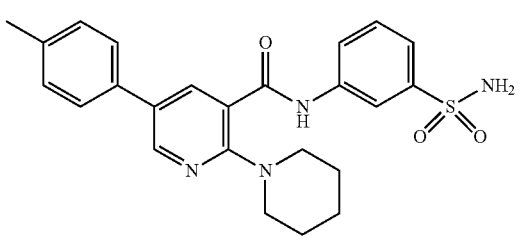 [SMILES: Cc1ccc(-c2cnc(N3CCCCC3)c(C(=O)Nc3cccc(S(N)(=O)=O)c3)c2)cc1]

Step 1: 2-(piperidin-1-yl)-5-(p-tolyl)nicotinic acid To a solution of 5-bromo-2-(piperidin-1-yl)nicotinic acid (Intermediate 7, 0.30 g, 1.1 mmol) in dioxane (3 mL) and water (1.5 mL) were added p-tolylboronic acid (0.29 g, 2.1 mmol), $K_2CO_3$ (0.29 g, 2.1 mmol) and $PdCl_2(dppf)$ (77 mg, 0.11 mmol). The mixture was stirred at 100° C. for 10 hours under nitrogen, then diluted with water and extracted with EtOAc. The organic layer was washed with brine, dried over $Na_2SO_4$, filtered and concentrated to give a residue that was purified by silica gel chromatography (10% MeOH/DCM) to give the title compound.

Step 2: 2-(piperidin-1-yl)-5-(p-tolyl)nicotinoyl chloride A solution of 2-(piperidin-1-yl)-5-(p-tolyl)nicotinic acid (0.10 g, 0.34 mmol) in sulfurous dichloride (2.0 mL, 0.34 mmol) was stirred at 80° C. for 2 hours. Then the mixture was concentrated under reduce pressure to give the title compound.

Step 3: 2-(piperidin-1-yl)-N-(3-sulfamoylphenyl)-5-(p-tolyl)nicotinamide To a solution of 2-(piperidin-1-yl)-5-(p-tolyl)nicotinoyl chloride (30 mg crude) in pyridine (2 mL) was added 3-aminobenzenesulfonamide (33 mg, 0.19 mmol). The mixture was stirred at 30° C. for 2 h. Then the mixture was diluted with DMF and purified by reverse phase chromatography (42-100% MeCN in water with 0.1% TFA, C18 column) to give the title compound. LRMS m/z (M+H): calculated 451.2, observed 451.1. $^1$H NMR δ (ppm) (400 MHz, $CD_3OD$): 8.51 (d, J=2.0 Hz, 1H), 8.41 (br d, J=2.0 Hz, 2H), 7.87 (d, J=7.6 Hz, 1H), 7.71 (d, J=8.4 Hz, 1H), 7.54-7.60 (m, 3H), 7.32 (d, J=7.6 Hz, 2H), 3.43-3.44 (m, 4H), 2.39 (s, 3H), 1.76 (br s, 4H), 1.68-1.69 (m, 2H).

Example 28

N-(2,4-difluoro-3-sulfamoylphenyl)-2-(4,4-difluoropiperidin-1-yl)-5-(trifluoromethyl)nicotinamide

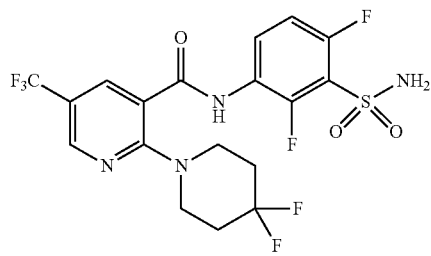 [SMILES: NS(=O)(=O)c1c(F)ccc(NC(=O)c2cc(C(F)(F)F)cnc2N2CCC(F)(F)CC2)c1F]

Step 1: N-(3-(N,N-bis(2,4-dimethoxybenzyl)sulfamoyl)-2,4-difluorophenyl)-2-(4,4-difluoro-piperidin-1-yl)-5-(trifluoromethyl)nicotinamide To a stirred mixture of 2-(4,4-difluoro-piperidin-1-yl)-5-(trifluoromethyl)nicotinic acid (Intermediate 8, 50 mg, 0.16 mmol) in pyridine (2 mL) was added phosphoryl trichloride (49 mg, 0.32 mmol). The mixture was stirred at 60° C. for 10 min, then 3-amino-N,N-bis(2,4-dimethoxybenzyl)-2,6-difluorobenzenesulfonamide (82 mg, 0.16 mmol) was added. The mixture was stirred at 60° C. for 10 min, then diluted in water and extracted with ethyl acetate. The organic layer was dried over $Na_2SO_4$, filtered and concentrated under reduced pressure to give a residue that was purified by silica gel chromatography (petroleum ether: ethyl acetate=1:1) to give the title compound.

Step 2: N-(2,4-difluoro-3-sulfamoylphenyl)-2-(4,4-difluoropiperidin-1-yl)-5-(trifluoromethyl)-nicotinamide To a stirred mixture of N-(3-(N,N-bis(2,4-dimethoxybenzyl)sulfamoyl)-2,4-difluorophenyl)-2-(4,4-difluoropiperidin-1-yl)-5-(trifluoromethyl)nicotinamide (60 mg, 0.075 mmol) in DCM (2 mL) was added TFA (1.0 mL, 13 mmol). The mixture was stirred at 20° C. for 1 h, then concentrated under reduced pressure. The resulting residue was purified by reverse phase reverse phase chromatography (45-100% MeCN in water with 0.1% TFA, C18 column) to give the title compound. LRMS m/z (M+H): calculated 501.1, observed 501.2. $^1$H NMR δ (ppm) (400 MHz, $CD_3OD$): 8.53-8.59 (m, 1H), 8.05-8.18 (m, 2H), 7.09-7.25 (m, 1H), 3.61-3.74 (m, 4H), 2.15-2.00 (m, 4H).

Example 29

2-(azepan-1-yl)-6-chloro-4-methyl-N-(3-sulfamoylphenyl)nicotinamide

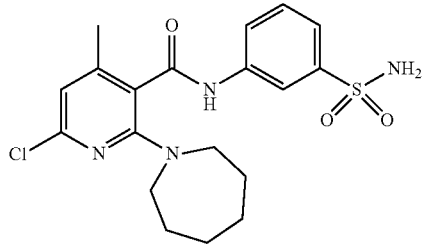 [SMILES: Cc1cc(Cl)nc(N2CCCCCC2)c1C(=O)Nc1cccc(S(N)(=O)=O)c1]

Step 1: 2-(azepan-1-yl)-6-chloro-4-methylnicotinic acid A solution of 2,6-dichloro-4-methyl-3-pyridinecarboxylic acid (0.20 g, 0.97 mmol) in THF (3 mL) was treated with hexamethyleneimine (0.19 g, 1.9 mmol) and DIPEA (0.85 mL, 4.8 mmol). The mixture was heated at 85° C. for 16 h, then additional hexamethyleneimine (0.30 mL) and DIPEA (0.30 mL) were added. The resulting mixture was heated at 100° C. in a sealed tube for 10 hours, then cooled to rt and diluted in EtOAc. The organic layer was washed with 5% aqueous AcOH, water, brine, dried over $MgSO_4$, filtered and concentrated under reduced pressure to give the title compound.

Step 2: 2-(azepan-1-yl)-6-chloro-4-methyl-N-(3-sulfamoylphenyl)nicotinamide To a mixture of 2-(azepan-1-yl)-6-chloro-4-methylnicotinic acid (25 mg, 0.093 mmol), 3-aminobenzene-sulfonamide (40 mg, 0.23 mmol) and EDC (36 mg, 0.19 mmol) in a vial was added pyridine (1 mL). The mixture was sonicated and heated at 75° C. for 3 hours. Then the mixture was concentrated under a stream of nitrogen while heating at 75° C. The resulting residue was purified by reverse phase reverse phase chromatography (35-100% MeCN in water with 0.1% TFA, C18 column) to give the title compound. LRMS m/z (M+H): calculated 423.1, observed 423.1. $^1$H NMR δ (ppm) (500 MHz, DMSO-$d_4$) ☐ 10.78 (s, 1H), 8.29 (s, 1H), 7.75 (m, 1H), 7.56 (m, 2H), 7.42 (s, 2H), 3.48 (m, 4H), 2.19 (s, 3H), 1.68 (m, 4H), 1.45 (m, 4H) ppm.

TABLE 2

The compounds of Examples 30-38 were prepared according to the procedure of Example 29 starting fromm the appropriate starting materials.

| Example | Compound | Name | Calc'd [M + H]+ | Observed [M + H]+ |
|---|---|---|---|---|
| 30 | | 2-(azepan-1-yl)-5,6-dimethyl-N-(3-sulfamoylphenyl)pyridine-3-carboxamide | 403.2 | 403.0 |

TABLE 2-continued

The compounds of Examples 30-38 were prepared according to the procedure of Example 29 starting fromm the appropriate starting materials.

| Example | Compound | Name | Calc'd [M + H]+ | Observed [M + H]+ |
|---|---|---|---|---|
| 31 | | 2-(azepan-1-yl)-5-chloro-N-(3-sulfamoyl-phenyl)pyridine-3-carboxamide | 409.1 | 408.9 |
| 32 | | 2-(azepan-1-yl)-5-bromo-N-(3-sulfamoyl-phenyl)pyridine-3-carboxamide | 453.1 | 453.1 |
| 33 | | 2-(azepan-1-yl)-4-bromo-N-(3-sulfamoyl-phenyl)pyridine-3-carboxamide | 453.1 | 453.0 |
| 34 | | 2-(azepan-1-yl)-5-(3-pyridyl)-N-(3-sulfamoyl-phenyl)pyridine-3-carboxamide | 452.2 | 452.1 |
| 35 | | 2-(azepan-1-yl)-5-bromo-N-(3-methylsulfonyl-phenyl)pyridine-3-carboxamide | 452.1 | 452.1 |

TABLE 2-continued

The compounds of Examples 30-38 were prepared according to the procedure of Example 29 starting fromm the appropriate starting materials.

| Example | Compound | Name | Calc'd [M + H]+ | Observed [M + H]+ |
|---|---|---|---|---|
| 36 | 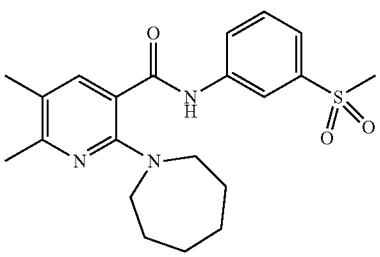 | 2-(azepan-1-yl)-5,6-dimethyl-N-(3-methyl-sulfonylphenyl)pyridine-3-carboxamide | 402.2 | 402.2 |
| 37 | 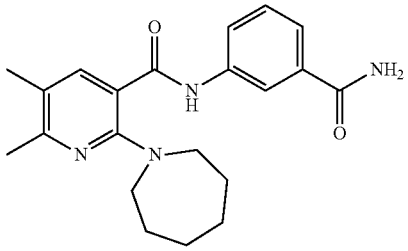 [SMILES: Cc1cc(C(=O)Nc2cccc(C(N)=O)c2)c(N2CCCCCC2)nc1C] | 2-(azepan-1-yl)-N-(3-carbamoylphenyl)-5,6-dimethyl-pyridine-3-carboxamide | 367.1 | 367.2 |
| 38 | 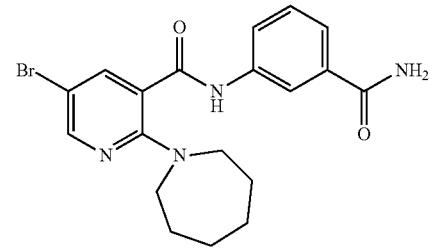 [SMILES: NC(=O)c1cccc(NC(=O)c2cc(Br)cnc2N2CCCCCC2)c1] | 2-(azepan-1-yl)-5-bromo-N-(3-carbamoyl-phenyl)pyridine-3-carboxamide | 417.1 | 417.0 |

Example 39

2-(4,4-difluoroazepan-1-yl)-N-(3-sulfamoylphenyl)-5-(trifluoromethoxy)nicotinamide

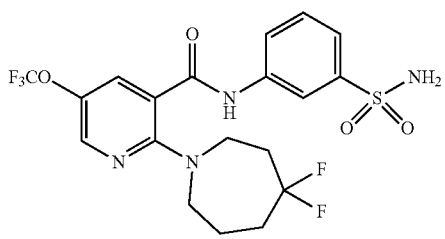 [SMILES: NS(=O)(=O)c1cccc(NC(=O)c2cc(OC(F)(F)F)cnc2N2CCCC(F)(F)CC2)c1]

Step 1: 4,4-difluoro-1-(5-(trifluoromethoxy)pyridin-2-yl)azepane To a solution of 2-bromo-5-(trifluoromethoxy)pyridine (0.30 g, 1.2 mmol) in THF (3 mL) were added 4,4-difluoroazepane (0.25 g, 1.9 mmol), sodium 2-methylpropan-2-olate (0.36 g, 3.7 mmol) and Brettphos-Pd-G3 (0.17 g, 1.2 mmol) dropwise with stirring at 25° C. under a nitrogen atmosphere. The mixture was stirred at 60° C. for 12 h, then extracted with EtOAc. The organic layer was washed with water, brine, dried over Na₂SO₄, filtered and concentrated under reduced pressure to give a residue that was purified by silica gel column chromatography (5-20% EtOAc/petroleum ether) to give the title compound.

Step 2: 1-(3-bromo-5-(trifluoromethoxy)pyridin-2-yl)-4,4-difluoroazepane To a solution of 4,4-difluoro-1-(5-(trifluoromethoxy)pyridin-2-yl)azepane (0.20 g, 0.68 mmol) in DCM (3 mL) was added NBS (0.12 g, 0.68 mmol) dropwise with stirring at 20° C. The mixture was stirred at 20° C. for 10 h, then extracted with EtOAc. The organic layer was washed with water, brine, dried over Na₂SO₄, filtered and concentrated under reduced pressure to give a residue that was purified by silica gel column chromatography (5-20% EtOAc/PE) to give the title compound.

Step 3: 2-(4,4-difluoroazepan-1-yl)-5-(trifluoromethoxy)nicotinonitrile To a solution of 1-(3-bromo-5-(trifluoromethoxy)pyridin-2-yl)-4,4-difluoroazepane (0.12 g, 0.32 mmol) in NMP (3 mL) was added Zn(CN)₂ (0.19 g, 1.6 mmol), Pd(tBu₃P)₂ (16 mg, 0.032 mmol) at 20° C. The mixture was degassed and backfilled with nitrogen three times, and then heated to 140° C. under microwave irradiation for 40 min. Then the mixture was dissolved in water and extracted with EtOAc. The combined organic layers were washed with brine, dried over anhydrous Na₂SO₄, filtered and concentrated to give a residue that was purified by silica gel column chromatography (10% EtOAc/petroleum ether) to give the title compound.

Step 4: 2-(4,4-difluoroazepan-1-yl)-5-(trifluoromethoxy)nicotinamide To a solution of 2-(4,4-difluoroazepan-1-yl)-5-(trifluoromethoxy)nicotinonitrile (80 mg, 0.25 mmol) in DMSO (3 mL) were added K₂CO₃ (0.10 g, 0.75 mmol) and hydrogen peroxide (0.5 mL, 0.25 mmol) dropwise with stirring at 20° C. The mixture was stirred at 20° C. for 2 h, then quenched with Na₂SO₃ and extracted with EtOAc. The combined organic layers were washed with water, brine, dried over Na₂SO₄, filtered and concentrated under reduced pressure to give a residue that was purified by silica gel column chromatography (50% EtOAc/PE) to give the title compound.

Step 5: N-(3-(N,N-bis(2,4-dimethoxybenzyl)sulfamoyl) phenyl)-2-(4,4-difluoroazepan-1-yl)-5-(trifluoromethoxy) nicotinamide To a solution of 2-(4,4-difluoroazepan-1-yl)-5-(trifluoro-methoxy)nicotinamide (20 mg, 0.059 mmol) in dioxane (2 mL) were added 3-bromo-N,N-bis(2,4-dimethoxybenzyl)benzenesulfonamide (35 mg, 0.065 mmol), cesium carbonate (58 mg, 0.18 mmol) and Brettphos-Pd-G3 (8.0 mg, 8.8 μmol). The mixture was stirred at 100° C. for 12 hours under nitrogen, then extracted with EtOAc. The organic layers were washed with water, brine, dried over Na₂SO₄, filtered and concentrated under reduced pressure. The resulting residue was purified by silica gel column chromatography (50% EtOAc/PE) to give the title compound.

Step 6: 2-(4,4-difluoroazepan-1-yl)-N-(3-sulfamoylphenyl)-5-(trifluoromethoxy)nicotinamide To a solution of N-(3-(N,N-bis(2,4-dimethoxybenzyl)sulfamoyl)phenyl)-2-(4,4-difluoroazepan-1-yl)-5-(trifluoromethoxy)nicotinamide (20 mg, 0.025 mmol) in DCM (2 mL) was added TFA (1 mL) dropwise with stirring. The mixture was stirred at 20° C. for 10 h, concentrated under reduced pressure and purified by reverse phase chromatography (5-95% MeCN in water with 0.1% TFA, C18 column) to give the title compound. LRMS m/z (M+H): calculated 495.1, observed 495.1. ¹H NMR δ (ppm) (400 MHz, CD₃OD): 8.31 (d, J=1.6 Hz, 1H), 8.21 (d, J=2.0 Hz, 1H), 7.81 (d, J=8.0 Hz, 1H), 7.72 (d, J=2.0 Hz, 1H), 7.67 (d, J=7.6 Hz, 1H), 7.49-7.56 (m, 1H), 3.69-3.75 (m, 2H), 3.50 (t, J=6.0 Hz, 2H), 2.26-2.37 (m, 2H), 1.97-2.03 (m, 2H), 1.91-1.96 (m, 2H).

Example 40

6-(tert-butyl)-5-chloro-2-(piperidin-1-yl)-N-(3-sulfamoylphenyl)nicotinamide

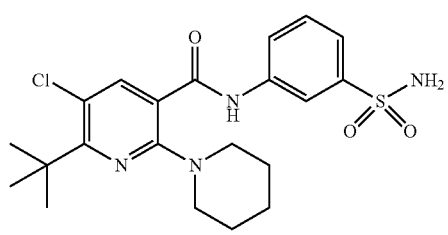 [SMILES: CC(C)(C)c1nc(N2CCCCC2)c(C(=O)Nc2cccc(S(N)(=O)=O)c2)cc1Cl]

A solution of 6-(tert-butyl)-2-(piperidin-1-yl)nicotinic acid (Intermediate 12, 50 mg crude) in sulfurous dichloride (2.0 mL, 0.19 mmol) was stirred at 80° C. for 2 hours. Then the mixture was concentrated to give a residue that was dissolved in pyridine and treated with 3-aminobenzenesulfonamide (23 mg, 0.13 mmol). The mixture was stirred at 17° C. for 1 hour, then diluted with water and extracted with EtOAc. The organic layer was dried over Na₂SO₄, filtered and concentrated to give a residue that was purified by reverse phase chromatography (47-100% MeCN in water with 0.1% TFA, C18 column) to give the title compound. LRMS m/z (M+H): calculated 451.1, observed 450.9. ¹H NMR δ (ppm) (400 MHz, CD₃OD): 8.40 (s, 1H), 8.05 (br s, 1H), 7.84 (d, J=8.0 Hz, 1H), 7.69 (d, J=8.0 Hz, 1H), 7.50-7.59 (m, 1H), 3.37 (br s, 4H), 1.75 (br s, 4H), 1.66 (br s, 2H), 1.51 (s, 9H).

Example 41

6-tert-butyl-N-(3-methylsulfonylphenyl)-2-(1-piperidyl)pyridine-3-carboxamide

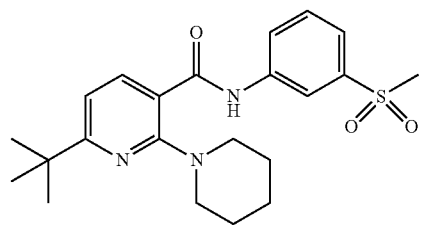 [SMILES: CC(C)(C)c1ccc(C(=O)Nc2cccc(S(C)(=O)=O)c2)c(N2CCCCC2)n1]

To a solution of 6-(tert-butyl)-2-(piperidin-1-yl)nicotinic acid (Intermediate 12, 50 mg, 0.19 mmol) in DMF (4 mL) were added HATU (72 mg, 0.19 mmol) and DIPEA (0.067 mL, 0.38 mmol). The mixture was stirred at rt for 30 minutes, then 3-aminophenylmethyl-sulfone (0.210 mmol) was added. The reaction mixture was stirred at 20° C. for 10 h, then diluted with water and extracted with EtOAc. The organic layers were washed with brine, dried over anhydrous Na₂SO₄, filtered and concentrated to give a residue that was purified by silica gel chromatography (petroleum ether/ethyl acetate=5:1) to give the title compound. LRMS m/z (M+H): calculated 416.4, observed 416.0. ¹H NMR δ (ppm) (400 MHz, CDCl₃) δ 11.84 (br s, 1H), 8.56 (d, J=8.0 Hz, 1H), 8.52 (s, 1H), 7.91 (d, J=8.0 Hz, 1H), 7.76 (d, J=7.6 Hz, 1H), 7.59 (t, J=8.0 Hz, 1H), 7.49 (d, J=8.0 Hz, 1H), 3.49 (br s, 4H), 3.11 (s, 3H), 2.00 (br s, 4H), 1.80 (br s, 2H), 1.39 (s, 9H).

Example 42

6-(tert-butyl)-2-(piperidin-1-yl)-N-(3-sulfamoylphenyl)nicotinamide

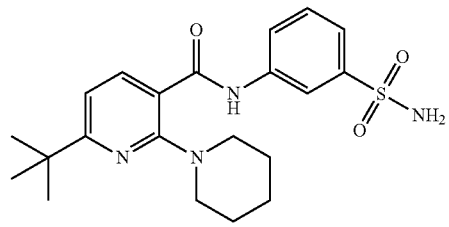 [SMILES: CC(C)(C)c1ccc(C(=O)Nc2cccc(S(N)(=O)=O)c2)c(N2CCCCC2)n1]

To a solution of 6-(tert-butyl)-2-(piperidin-1-yl)nicotinic acid (Intermediate 12, 50 mg, 0.19 mmol) in DCM (1 mL) was added oxalyl dichloride (24 mg, 0.19 mmol). The mixture was stirred at 40° C. for 2 hours, then concentrated under reduced pressure. The resulting residue was treated with a solution of 3-aminobenzenesulfonamide (34 mg, 0.20 mmol) in pyridine (1.5 mL). The reaction mixture was stirred at 19° C. for 2 hours, then concentrated to give a residue that was purified by reverse phase chromatography (40-100% MeCN in water with 0.1% TFA, C18 column) to give the title compound. LRMS m/z (M+H): calculated 417.2, observed 417.0. ¹H NMR δ (ppm) (400 MHz, DMSO-d₆): 10.75 (s, 1H), 8.43 (s, 1H), 7.73-7.83 (m, 2H), 7.53 (d, J=4.8 Hz, 2H), 7.40 (br s, 2H), 6.97 (d, J=8.0 Hz, 1H), 3.28 (br s, 4H), 1.54 (br s, 6H), 1.30 (s, 9H).

Example 43

2-(6-azaspiro[2.5]octan-6-yl)-N-(3-sulfamoylphenyl)-5-(trifluoromethyl)nicotinamide

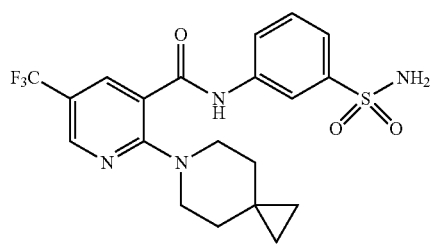 [SMILES: NS(=O)(=O)c1cccc(NC(=O)c2cc(C(F)(F)F)cnc2N2CCC3(CC2)CC3)c1]

Step 1: 2-((3H-[1,2,3]triazolo[4,5-b]pyridin-3-yl)oxy)-N-(3-sulfamoylphenyl)-5-(trifluoromethyl)nicotinamide To a solution of HATU (8.8 g, 23 mmol) in dimethylacetamide (110 mL) was added 2-chloro-5-(trifluoromethyl)nicotinic acid (5.0 g, 22 mmol). The resulting mixture was stirred at ambient temperature for 10 minutes, then 3-aminobenzenesulfonamide (5.7 g, 33 mmol) and DIPEA (12 mL, 66 mmol) were added. The mixture was stirred 72 hours at ambient temperature, then diluted in water and extracted with ethyl acetate. The combined organic layers were washed with water, brine, dried over magnesium sulfate, filtered and concentrated to give the title compound.

Step 2: 2-(6-azaspiro[2.5]octan-6-yl)-N-(3-sulfamoylphenyl)-5-(trifluoromethyl)nicotinamide To a mixture of 2-((3H-[1,2,3]triazolo[4,5-b]pyridin-3-yl)oxy)-N-(3-sulfamoylphenyl)-5-(tri-fluoromethyl)nicotinamide (11 g, 22 mmol) and 6-azaspiro[2.5]octane hydrochloride (4.9 g, 33 mmol) in dimethylacetamide (110 mL) was added potassium carbonate (9.2 g, 66 mmol). The mixture was heated to 70° C. for 2.5 h, then cooled to ambient temperature, diluted in water and extracted with ethyl acetate. The organic layer was washed with water, brine, dried over magnesium sulfate, filtered and concentrated under reduced pressure to give a residue that was purified by reverse phase chromatography (5-95% MeCN in water with 0.1% TFA, C18 column) to give the title compound. LRMS m/z (M+H): calculated 455.1, observed 455.3. ¹H NMR δ (ppm) (DMSO-d₆): 10.80 (s, 1H), 8.53 (s, 1H), 8.28 (s, 1H), 7.97 (d, J=2.1 Hz, 1H), 7.82-7.75 (m, 1H), 7.57-7.50 (m, 2H), 7.40 (s, 2H), 3.58-3.50 (m, 4H), 1.38-1.31 (m, 4H), 0.29 (s, 4H).

TABLE 3

The compounds of Examples 44-74 were prepared according to the procedure for Example 43 from the appropriate starting materials.

| Example | Compound | Name | Calc'd [M + H]⁺ | Observed [M + H]⁺ | Conditions |
|---|---|---|---|---|---|
| 44 | | 2-(azepan-1-yl)-N-(3-sulfamoylphenyl)-5-(trifluoromethyl)-pyridine-3-carboxamide | 443.1 | 443.1 | |
| 45 | | 2-[rac-3-azabicyclo[3.2.1]octan-3-yl]-N-(3-sulfamoylphenyl)-5-(trifluoromethyl)pyridine-3-carboxamide | 455.1 | 455.0 | |
| 46 | | N-(3-sulfamoylphenyl)-2-(4-azatricyclo[4.3.1.1³,⁸]undecan-4-yl)-5-(trifluoromethyl)-nicotinamide | 495.2 | 495.3 | |

TABLE 3-continued

The compounds of Examples 44-74 were prepared according to the procedure for Example 43 from the appropriate starting materials.

| Example | Compound | Name | Calc'd [M + H]+ | Observed [M + H]+ | Conditions |
|---|---|---|---|---|---|
| 47 | | N-(3-sulfamoylphenyl)-5-(trifluoromethyl)-2-(3,3,5-trimethylazepan-1-yl)pyridine-3-carboxamide | 485.2 | 485.1 | |
| 48 | | methyl 1-[3-[(3-sulfamoylphenyl)-carbamoyl]-5-(trifluoromethyl)-2-pyridyl]azepane-4-carboxylate | 501.1 | 501.0 | |
| 49 | | 2-(4-methoxyazepan-1-yl)-N-(3-sulfamoyl-phenyl)-5-(trifluoro-methyl)pyridine-3-carboxamide | 473.1 | 473.0 | |
| 50 | | 2-[4-(difluoromethyl)-1-piperidyl]-N-(3-sulfamoylphenyl)-5-(trifluoromethyl)-pyridine-3-carboxamide | 479.1 | 478.9 | |
| 51 | | 2-(3,3-difluoro-1-piperidyl)-N-(3-sulfamoylphenyl)-5-(trifluoromethyl)-pyridine-3-carboxamide | 465.1 | 464.9 | |
| 52 | | 2-(8-oxa-3-azabicyclo[3.2.1]octan-3-yl)-N-(3-sulfamoyl-phenyl)-5-(trifluoro-methyl)pyridine-3-carboxamide | 457.1 | 457.0 | |

TABLE 3-continued

The compounds of Examples 44-74 were prepared according to the procedure for Example 43 from the appropriate starting materials.

| Example | Compound | Name | Calc'd [M + H]+ | Observed [M + H]+ | Conditions |
|---|---|---|---|---|---|
| 53 | | 2-(4-hydroxy-4-methyl-azepan-1-yl)-N-(3-sulfamoylphenyl)-5-(trifluoromethyl)-pyridine-3-carboxamide | 473.1 | 473.0 | |
| 54 | | 2-[(3S)-3-fluoroazepan-1-yl]-N-(3-sulfamoyl-phenyl)-5-(trifluoro-methyl)pyridine-3-carboxamide | 461.1 | 461.0 | |
| 55 | | 2-(6,7-dihydro-4H-thiazol[4,5-c]pyridin-5-yl)-N-(3-sulfamoyl-phenyl)-5-(trifluoro-methyl)pyridine-3-carboxamide | 484.1 | 483.9 | |
| 56 | | 2-(1,4-oxazepan-4-yl)-N-(3-sulfamoylphenyl)-5-(trifluoromethyl)-pyridine-3-carboxamide | 445.1 | 445.0 | |
| 57 | | 2-(8-oxa-3-azabicyclo[3.2.1]octan-3-yl)-N-(3-sulfamoyl-phenyl)-5-(trifluoro-methyl)pyridine-3-carboxamide | 457.1 | 457.0 | |
| 58 | | N-(3-sulfamoylphenyl)-5-(trifluoromethyl)-2-[3-(trifluoromethyl)-azetidin-1-yl]pyridine-3-carboxamide | 469.1 | 468.9 | |

TABLE 3-continued

The compounds of Examples 44-74 were prepared according to the procedure for Example 43 from the appropriate starting materials.

| Example | Compound | Name | Calc'd [M + H]⁺ | Observed [M + H]⁺ | Conditions |
|---|---|---|---|---|---|
| 59 | | 2-(6-azabicyclo[3.2.0]heptan-6-yl)-N-(3-sulfamoyl-phenyl)-5-(trifluoro-methyl)pyridine-3-carboxamide | 441.1 | 441.0 | |
| 60 | | 2-(3,3-difluoropyrrolidin-1-yl)-N-(3-sulfamoyl-phenyl)-5-(trifluoromethyl)pyridine-3-carboxamide | 451.1 | 450.9 | |
| 61 | | methyl 1-[3-[(3-sulfamoylphenyl)carbamoyl]-5-(trifluoro-methyl)-2-pyridyl]-piperidine-4-carboxylate | 487.1 | 486.9 | |
| 62 | | 2-(3-fluoropyrrolidin-1-yl)-N-(3-sulfamoyl-phenyl)-5-(trifluoromethyl)pyridine-3-carboxamide | 433.1 | 432.9 | |
| 63 | | 2-pyrrolidin-1-yl-N-(3-sulfamoylphenyl)-5-(trifluoromethyl)pyridine-3-carboxamide | 415.1 | 414.9 | |
| 64 | | 2-(6-oxa-3-azabicyclo[3.2.1]octan-3-yl)-N-(3-sulfamoyl-phenyl)-5-(trifluoro-methyl)pyridine-3-carboxamide | 457.1 | 457.0 | |

TABLE 3-continued

The compounds of Examples 44-74 were prepared according to the procedure for Example 43 from the appropriate starting materials.

| Example | Compound | Name | Calc'd [M + H]⁺ | Observed [M + H]⁺ | Conditions |
|---|---|---|---|---|---|
| 65 | | 2-(4-hydroxyazepan-1-yl)-N-(3-sulfamoyl-phenyl)-5-(trifluoro-methyl)pyridine-3-carboxamide | 459.1 | 459.0 | |
| 66 | | 2-(4-methoxy-1-piperidyl)-N-(3-sulfamoylphenyl)-5-(trifluoromethyl) pyridine-3-carboxamide | 459.1 | 458.9 | |
| 67 | | methyl 1-[3-[(3-sulfamoylphenyl)carbamoyl]-5-(trifluoro-methyl)-2-pyridyl]-azepane-3-carboxylate | 501.1 | 501.0 | |
| 68 | | 2-(2-isobutylazepan-1-yl)-N-(3-sulfamoyl-phenyl)-5-(trifluoro-methyl)pyridine-3-carboxamide | 499.2 | 499.1 | |
| 69 | | 2-morpholino-N-(3-sulfamoylphenyl)-5-(trifluoromethyl) pyridine-3-carboxamide | 431.1 | 430.9 | |
| 70 | | 2-(1,1-dioxo-1,4-thiazinan-4-yl)-N-(3-sulfamoylphenyl)-5-(trifluoromethyl)pyridine-3-carboxamide | 479.1 | 478.9 | |

TABLE 3-continued

The compounds of Examples 44-74 were prepared according to the procedure for Example 43 from the appropriate starting materials.

| Example | Compound | Name | Calc'd [M + H]+ | Observed [M + H]+ | Conditions |
|---------|----------|------|-----------------|-------------------|------------|
| 71 | | 2-[rac-(1S,5R and 1R,5S)-8-methyl-3,8-diazabicyclo[3.2.1]-octan-3-yl]-N-(3-sulfamoylphenyl)-5-(trifluoromethyl)pyridine-3-carboxamide | 470.1 | 470.0 | |
| 72 | | 2-(1-oxa-8-azaspiro[4.5]decan-8-yl)-N-(3-sulfamoyl-phenyl)-5-(trifluoro-methyl)pyridine-3-carboxamide | 485.1 | 485.0 | |
| 73 | | 2-(2-methyl-6,7-dihydro-4H-oxazolo[4,5-c]pyridin-5-yl)-N-(3-sulfamoyl-phenyl)-5-(trifluoro-methyl)pyridine-3-carboxamide | 482.1 | 481.9 | |
| 74 | | methyl 4-[3-[(3-sulfamoylphenyl)carbamoyl]-5-(trifluoro-methyl)-2-pyridyl]-piperazine-1-carboxylate | 488.1 | 487.9 | |

Example 75

N-(3-carbamoylphenyl)-2-(4,4-difluoroazepan-1-yl)-6-methylnicotinamide

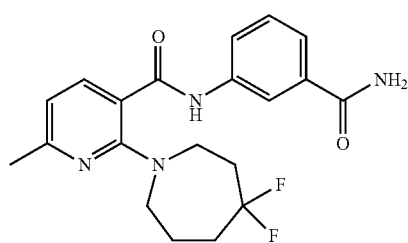 [SMILES: Cc1ccc(C(=O)Nc2cccc(C(N)=O)c2)c(N2CCCC(F)(F)CC2)n1]

Step 1: N-(3-carbamoylphenyl)-2-chloro-6-methylnicotinamide To a solution of 2-chloro-6-methylnicotinic acid (0.50 g, 2.9 mmol) in pyridine (6 mL) were added EDC (0.73 g, 3.8 mmol) and 3-aminobenzamide (0.52 g, 3.8 mmol). The mixture was stirred at ambient temperature for 17 h, then diluted in saturated NaHCO$_3$ and extracted with EtOAc. The organic layer was washed with brine, dried over Na$_2$SO$_4$, filtered and concentrated under reduced pressure. The resulting residue was purified by silica gel chromatography (5-100% (3:1 EtOAc/EtOH)/hexane) to give the title compound.

Step 2: N-(3-carbamoylphenyl)-2-(4,4-difluoroazepan-1-yl)-6-methylnicotinamide To a microwave vial containing a solution of N-(3-carbamoylphenyl)-2-chloro-6-methylnicotinamide (0.93 g, 3.2 mmol), 4,4-difluoroazepine hydrochloride (0.83 g, 4.8 mmol), and DIPEA (1.1 mL, 6.4 mmol) in anhydrous NMP (12 mL) was added K$_2$CO$_3$ (1.3 g, 9.7 mmol). The mixture was heated to 70° C. for 23 h, then at 140° C. for 40 min under microwave irradiation. Then the mixture was partitioned between EtOAc and saturated NH₄Cl. The organic layer was separated, washed with brine, dried over Na₂SO₄, filtered and concentrated under reduced pressure. The resulting residue was purified by silica gel chromatography ((0-100% (3:1 EtOAc/EtOH)/hexane), followed by reverse phase chromatography (5-95% MeCN in water with 0.1% TFA, C18 column). The resulting solid was suspended in ether and DCM, sonicated for 5 minutes to give a fine suspension, which was treated with hexane and filtered to give the title compound. LRMS m/z (M+H): calculated 389.2, observed 389.0. ¹H NMR δ (ppm) (500 MHz, CD₃OD): 8.16 (s, 1H), 7.94 (d, J=7.6 Hz, 1H), 7.88 (d, J=8.0 Hz, 1H), 7.66 (d, J=7.8 Hz, 1H), 7.49 (t, J=7.9 Hz, 1H), 6.85 (d, J=7.6 Hz, 1H), 3.90-3.74 (m, 2H), 3.65 (t, J=5.7 Hz, 2H), 3.37 (s, 3H), 2.53-2.30 (m, 2H), 2.30-2.03 (m, 2H), 1.99 (dt, J=14.8, 7.8 Hz, 2H).

TABLE 4

The compounds of Examples 76-83 were prepared according to the procedure of Example 75 starting from the appropriate starting materials.

| Example | Compound | Name | Calc'd [M + H]⁺ | Observed [M + H]⁺ |
|---|---|---|---|---|
| 76 | | 2-(6-azaspiro[2.5]-octan-6-yl)-5-chloro-4,6-dimethyl-N-(3-sulfamoylphenyl)pyridine-3-carboxamide | 449.1 | 449.2 |
| 77 | | 2-(1-piperidyl)-N-(3-sulfamoylphenyl)-6-(trifluoromethyl)pyridine-3-carboxamide | 429.1 | 429.1 |
| 78 | | 2-(4,4-difluoroazepan-1-yl)-N-(3-sulfamoyl-phenyl)-5-(trifluoromethyl)nicotinamide | 479.4 | 479.3 |
| 79 | | 2-(6-azaspiro[2.6]nonan-6-yl)-N-(3-sulfamoyl-phenyl)-5-(trifluoromethyl)nicotinamide | 469.5 | 469.2 |
| 80 | | 2-(4,4-dimethylazepan-1-yl)-N-(3-sulfamoyl-phenyl)-5-(trifluoromethyl)nicotinamide | 471.5 | 471.3 |

TABLE 4-continued

The compounds of Examples 76-83 were prepared according to the procedure of Example 75 starting from the appropriate starting materials.

| Example | Compound | Name | Calc'd [M + H]+ | Observed [M + H]+ |
|---|---|---|---|---|
| 81 | | 2-(7-oxa-2-azaspiro[3.5]nonan-2-yl)-N-(3-sulfamoyl-phenyl)-5-(trifluoro-methyl)nicotinamide | 471.5 | 471.2 |
| 82 | | 2-(azepan-1-yl)-N-(3-(methylsulfonyl)phenyl)-6-(trifluoro-methyl)nicotinamide | 442.5 | 442.3 |
| 83 | | N-(3-carbamoyl-phenyl)-2-(6-azaspiro[2.5]octan-6-yl)-6-(trifluoro-methyl)-nicotinamide | 419.4 | 419.3 |

Example 84

2-(piperidin-1-yl)-N-(3-sulfamoylphenyl)-6-(trifluoromethoxy)nicotinamide

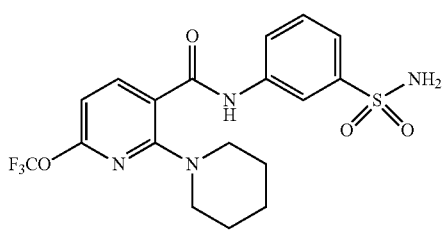 [SMILES: NS(=O)(=O)c1cccc(NC(=O)c2ccc(OC(F)(F)F)nc2N2CCCCC2)c1]

Step 1: 2-chloro-6-(trifluoromethoxy)nicotinic acid To a solution of 2-chloro-6-(trifluoromethoxy)-5-(trimethylsilyl)nicotinic acid (Intermediate 13, 0.12 g, 0.38 mmol) in THF (5 mL) was added dropwise TBAF (0.57 mL in THF, 0.57 mmol). The mixture was stirred at 20° C. for 12 hours, and then concentrated under reduce pressure. The resulting residue was purified by reverse phase chromatography (5-95% MeCN in water with 0.1% TFA, C18 column) to give the title compound.

Step 2: 2-chloro-N-(3-sulfamoylphenyl)-6-(trifluoromethoxy)nicotinamide To a solution of 2-chloro-6-(trifluoromethoxy)nicotinic acid (35 mg, 0.14 mmol), 3-aminobenzenesulfonamide (27 mg, 0.160 mmol) in pyridine (3 mL) was added EDC (36 mg, 0.19 mmol). The mixture was stirred at 20° C. for 1 hour, then concentrated under reduced pressure. The resulting residue was purified by reverse phase chromatography (5-95% MeCN in water with 0.1% TFA, C18 column) to give the title compound.

Step 3: 2-(piperidin-1-yl)-N-(3-sulfamoylphenyl)-6-(trifluoromethoxy)nicotinamide To a solution of 2-chloro-N-(3-sulfamoylphenyl)-6-(trifluoromethoxy)nicotinamide (35 mg, 0.088 mmol) in DMF (3 mL) was added piperidine (15 mg, 0.18 mmol). The mixture was stirred at 80° C. for 2 hour. Then the mixture was purified by reverse phase chromatography (5-95% MeCN in water with 0.1% TFA, C18 column) to give the title compound. LRMS m/z (M+H): calculated 445.1, observed 445.2. $^1$H NMR δ (ppm) (400 MHz, CDCl$_3$): 11.33 (s, 1H), 8.47-8.52 (m, 2H), 7.70-7.73 (m, 2H), 7.52 (t, J=8.0 Hz, 1H), 6.86 (d, J=8.4 Hz, 1H), 5.02 (br, 2H), 3.24-3.26 (m, 4H), 1.81 (br s, 4H), 1.68-1.71 (m, 2H).

Example 85

2-(azepan-1-yl)-N-(3-sulfamoylphenyl)-6-(trifluoromethoxy)-5-(trimethylsilyl)nicotinamide

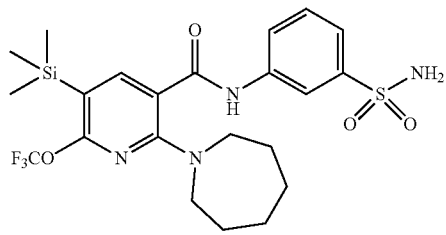 [SMILES: C[Si](C)(C)c1cc(C(=O)Nc2cccc(S(N)(=O)=O)c2)c(N2CCCCCC2)nc1OC(F)(F)F]

Step 1: 2-chloro-N-(3-sulfamoylphenyl)-6-(trifluoromethoxy)-5-(trimethylsilyl)nicotinamide The title compound was prepared from 2-chloro-6-(trifluoromethoxy)-5-(trimethylsilyl)nicotinic acid according to the procedure of Example 84, Step 2.

Step 2: 2-(azepan-1-yl)-N-(3-sulfamoylphenyl)-6-(trifluoromethoxy)-5-(trimethylsilyl)-nicotinamide To a solution of 2-chloro-N-(3-sulfamoylphenyl)-6-(trifluoromethoxy)-5-(trimethylsilyl)nicotinamide (50 mg, 0.11 mmol) in DMF (3 mL) was added azepane (53 mg, 0.53 mmol). The mixture was stirred at 70° C. for 1 hour. Then the mixture was purified by reverse phase chromatography (5-95% MeCN in water with 0.1% NH$_4$OH, C18 column) to give the title compound. LRMS m/z (M+H): calculated 531.2, observed 531.2. $^1$H NMR δ (ppm) (400 MHz, CDCl$_3$): 8.31 (s, 1H), 8.25 (s, 1H), 7.90 (s, 1H), 7.81-7.85 (m, 1H), 7.68-7.70 (m, 1H), 7.52 (t, J=8.0 Hz, 1H), 5.06 (s, 2H), 3.48-3.51 (m, 4H), 1.81 (br s, 4H), 1.54-1.55 (m, 4H), 0.28 (s, 9H).

Example 86

2-(azepan-1-yl)-N-(3-sulfamoylphenyl)-5-(trimethylsilyl)nicotinamide

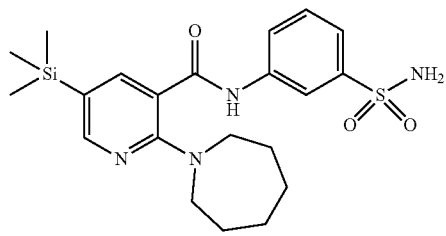 [SMILES: C[Si](C)(C)c1cnc(N2CCCCCC2)c(C(=O)Nc2cccc(S(N)(=O)=O)c2)c1]

Step 1: 2-chloro-5-(trimethylsilyl)pyridine To a solution of 5-bromo-2-chloropyridine (1.0 g, 5.2 mmol) in diethylether (20 mL) was added BuLi (2.1 mL, 5.2 mmol) at −78° C. The mixture was stirred at −78° C. for 1 h, then TMS-Cl (0.66 mL, 5.2 mmol) was added slowly. The mixture was stirred at −78° C. for 2 h, then slowly warmed to 19° C. for 12 h, quenched with water and extracted with EtOAc. The organic layer was washed with brine, dried over anhydrous Na$_2$SO$_4$, filtered and concentrated under reduced pressure to give a residue that was purified by silica gel chromatography (0-3% ethyl acetate/petroleum ether) to give the title compound.

Step 2: 2-chloro-5-(trimethylsilyl)nicotinic acid A lithium tetramethylpiperidine solution was prepared from butyllithium (1.4 mL, 3.4 mmol) in hexane and 2,2,6,6-tetramethylpiperidine (0.53 g, 3.8 mmol) in THF (20 mL) at −78° C. To the lithium tetramethylpiperidine solution at −78° C. was added dropwise over 10 minutes a solution of 2-chloro-5-(trimethylsilyl)pyridine (0.35 g, 1.9 mmol) in THF (4 mL). The resulting mixture was stirred at −78° C. for 2 hours, then carbon dioxide (0.83 g, 19 mmol) was added. Then the mixture was warmed to rt for 1 hour, quenched with water and extracted with EtOAc. The organic layer was dried over sodium sulfate, filtered and concentrated under reduced pressure to give the title compound.

Step 3: 2-(azepan-1-yl)-N-(3-sulfamoylphenyl)-5-(trimethylsilyl)nicotinamide To a solution of 2-chloro-5-(trimethylsilyl)nicotinic acid (0.15 g, 0.65 mmol), and 3-aminobenzenesulfonamide (0.13 g, 0.78 mmol) in pyridine (8 mL) was added EDC (0.16 g, 0.85 mmol). The mixture was stirred at 25° C. for 1 hour. Then the mixture was concentrated to give a residue that was purified by reverse phase chromatography (5-95% MeCN in water with 0.1% TFA, C18 column) to give the title compound.

Step 4: 2-(azepan-1-yl)-N-(3-sulfamoylphenyl)-5-(trimethylsilyl)nicotinamide To a solution of 2-chloro-N-(3-sulfamoylphenyl)-5-(trimethylsilyl)nicotinamide (30 mg, 0.078 mmol) in NMP (3 mL) was added azepane (39 mg, 0.39 mmol). The mixture was stirred at 130° C. for 5 hours, then purified by reverse phase chromatography (5-95% MeCN in water with 0.1% TFA, C18 column) to give the title compound. LRMS m/z (M+H): calculated 447.2, observed 447.0. $^1$H NMR δ (ppm) (400 MHz, CDCl$_3$): 10.07 (s, 1H), 8.32 (d, J=8.4 Hz, 1H), 8.04 (s, 1H), 7.93 (s, 2H), 7.59 (d, J=8.0 Hz, 1H), 7.47 (t, J=8.4 Hz, 1H), 5.98 (br, 2H), 3.70 (br, 4H), 1.83 (br, 4H), 1.57 (br, 4H), 0.28 (s, 9H).

TABLE 5

The compounds of Examples 87-121 were prepared according to the procedure of Example 86 starting with the appropriate starting aterials.

| Example | Compound | Name | Calc'd [M + H]⁺ | Observed [M + H]⁺ |
|---|---|---|---|---|
| 87 | | 2-(2-oxa-7-azaspiro[3.5]nonan-7-yl)-N-(3-sulfamoylphenyl)-5-(trimethylsilyl)-nicotinamide | 475.2 | 475.2 |

TABLE 5-continued

The compounds of Examples 87-121 were prepared according to the procedure of Example 86 starting with the appropriate starting aterials.

| Example | Compound | Name | Calc'd [M + H]⁺ | Observed [M + H]⁺ |
|---------|----------|------|-----------------|-------------------|
| 88 | | 2-(azocan-1-yl)-N-(3-sulfamoylphenyl)-5-(trifluoromethyl)-pyridine-3-carboxamide | 457.1 | 457.2 |
| 89 | | 2-(azepan-1-yl)-6-chloro-N-(3-sulfamoyl-phenyl)pyridine-3-carboxamide | 409.1 | 409.2 |
| 90 | | 2-(azepan-1-yl)-6-methyl-N-(3-sulfamoyl-phenyl)pyridine-3-carboxamide | 389.2 | 389.2 |
| 91 | | 2-(azepan-1-yl)-6-methoxy-N-(3-sulfamoyl-phenyl)pyridine-3-carboxamide | 405.2 | 405.2 |
| 92 | | 2-(azepan-1-yl)-6-chloro-5-fluoro-N-(3-sulfamoylphenyl)-pyridine-3-carboxamide | 427.1 | 427.1 |

TABLE 5-continued

The compounds of Examples 87-121 were prepared according to the procedure of Example 86 starting with the appropriate starting aterials.

| Example | Compound | Name | Calc'd [M + H]⁺ | Observed [M + H]⁺ |
|---|---|---|---|---|
| 93 | | 2-(azepan-1-yl)-6-fluoro-N-(3-sulfamoyl-phenyl)pyridine-3-carboxamide | 393.1 | 393.2 |
| 94 | | 2-(4,4-difluoroazepan-1-yl)-N-(3-methylsulfonylphenyl)-5-(trifluoromethyl)-pyridine-3-carboxamide | 478.1 | 478.2 |
| 95 | | 2-(azocan-1-yl)-N-(3-methylsulfonylphenyl)-5-(trifluoromethyl)-pyridine-3-carboxamide | 456.1 | 456.2 |
| 96 | | 2-(4,4-difluoro-1,3,3a,5,6,6a-hexahydrocyclopenta[c]pyrrol-2-yl)-N-(3-methylsulfonylphenyl)-5-(trifluoromethyl)-pyridine-3-carboxamide | 490.1 | 490.2 |
| 97 | | 2-[(3aS,7aR)-1,3,3a,4,5,6,7,7a-octahydroisoindol-2-yl]-N-(3-methyl-sulfonylphenyl)-5-(trifluoromethyl)pyridine-3-carboxamide | 468.1 | 468.1 |

TABLE 5-continued

The compounds of Examples 87-121 were prepared according to the procedure of Example 86 starting with the appropriate starting aterials.

| Example | Compound | Name | Calc'd [M + H]⁺ | Observed [M + H]⁺ |
|---|---|---|---|---|
| 98 | 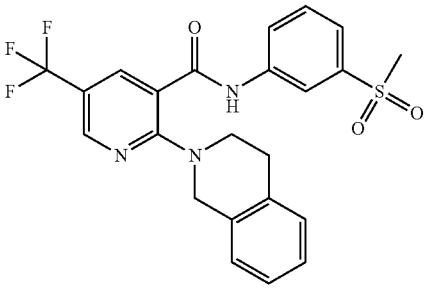 [SMILES: CS(=O)(=O)c1cccc(NC(=O)c2cc(C(F)(F)F)cnc2N2CCc3ccccc3C2)c1] | 2-(3,4-dihydro-1H-isoquinolin-2-yl)-N-(3-methylsulfonylphenyl)-5-(trifluoromethyl)-pyridine-3-carboxamide | 476.1 | 476.1 |
| 99 | 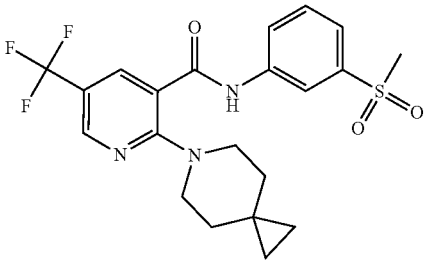 [SMILES: CS(=O)(=O)c1cccc(NC(=O)c2cc(C(F)(F)F)cnc2N2CCC3(CC2)CC3)c1] | 2-(6-azaspiro[2.5]octan-6-yl)-N-(3-methylsulfonylphenyl)-5-(trifluoromethyl)-pyridine-3-carboxamide | 454.1 | 454.1 |
| 100 | 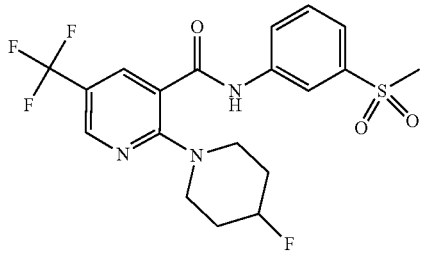 [SMILES: CS(=O)(=O)c1cccc(NC(=O)c2cc(C(F)(F)F)cnc2N2CCC(F)CC2)c1] | 2-(4-fluoro-1-piperidyl)-N-(3-methylsulfonylphenyl)-5-(trifluoromethyl)-pyridine-3-carboxamide | 446.1 | 446.2 |
| 101 | 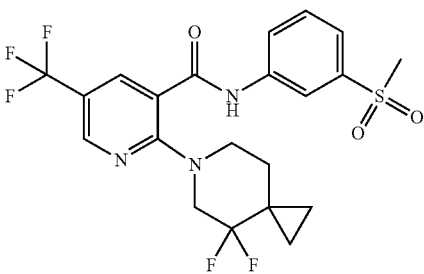 [SMILES: CS(=O)(=O)c1cccc(NC(=O)c2cc(C(F)(F)F)cnc2N2CCC3(CC3)C(F)(F)C2)c1] | 2-(8,8-difluoro-6-azaspiro[2.5]octan-6-yl)-N-(3-methyl-sulfonylphenyl)-5-(trifluoromethyl)pyridine-3-carboxamide | 490.1 | 490.1 |
| 102 | 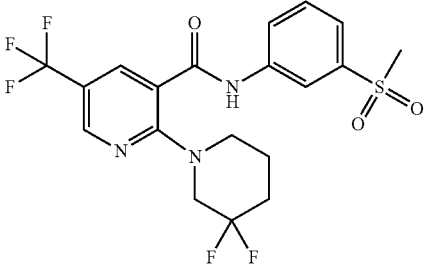 [SMILES: CS(=O)(=O)c1cccc(NC(=O)c2cc(C(F)(F)F)cnc2N2CCCC(F)(F)C2)c1] | 2-(3,3-difluoro-1-piperidyl)-N-(3-methylsulfonylphenyl)-5-(trifluoromethyl)-pyridine-3-carboxamide | 464.1 | 464.1 |

TABLE 5-continued

The compounds of Examples 87-121 were prepared according to the procedure of Example 86 starting with the appropriate starting aterials.

| Example | Compound | Name | Calc'd [M + H]+ | Observed [M + H]+ |
|---|---|---|---|---|
| 103 | | 2-isoindolin-2-yl-N-(3-methylsulfonylphenyl)-5-(trifluoromethyl)-pyridine-3-carboxamide | 462.1 | 462.1 |
| 104 | | 2-(2,3,3a,5,6,6a-hexahydrofuro[3,2-b]pyrrol-4-yl)-N-(3-methylsulfonylphenyl)-5-(trifluoromethyl)pyridine-3-carboxamide | 456.1 | 456.1 |
| 105 | | N-(3-methylsulfonylphenyl)-2-(4-phenyl-1-piperidyl)-5-(trifluoromethyl)pyridine-3-carboxamide | 504.1 | 504.1 |
| 106 | | N-(3-carbamoylphenyl)-2-(4,4-difluoroazepan-1-yl)-5-(trifluoromethyl)pyridine-3-carboxamide | 443.1 | 443.2 |
| 107 | | 2-(azocan-1-yl)-N-(3-carbamoylphenyl)-5-(trifluoromethyl)-pyridine-3-carboxamide | 421.2 | 421.1 |

TABLE 5-continued

The compounds of Examples 87-121 were prepared according to the procedure of Example 86 starting with the appropriate starting aterials.

| Example | Compound | Name | Calc'd [M + H]⁺ | Observed [M + H]⁺ |
|---|---|---|---|---|
| 108 | | N-(3-carbamoylphenyl)-2-(4,4-difluoro-1,3,3a,-5,6,6a-hexahydrocyclopenta[c]pyrrol-2-yl)-5-(trifluoromethyl)-pyridine-3-carboxamide | 455.1 | 455.2 |
| 109 | | N-(3-carbamoylphenyl)-2-(8,8-difluoro-6-azaspiro[2.5]octan-6-yl)-5-(trifluoro-methyl)-pyridine-3-carboxamide | 455.1 | 455.1 |
| 110 | | N-(3-carbamoylphenyl)-2-(3,3-difluoro-1-piperidyl)-5-(trifluoromethyl)pyridine-3-carboxamide | 429.1 | 429.1 |
| 111 | | 2-[(3S,5R)-4,4-difluoro-3,5-dimethyl-1-piperidyl]-N-(1,1-dioxo-2,3-dihydro-1,2-benzothiazol-6-yl)-5-(trifluoromethyl)pyridine-3-carboxamide | 505.1 | 505.2 |
| 112 | | 2-[(3R or 3S)-4,4-difluoro-3-methyl-1-piperidyl]-N-(1,1-dioxo-2,3-dihydro-1,2-benzothiazol-6-yl)-5-(trifluoromethyl)pyridine-3-carboxamide | 491.1 | 491.1 |

TABLE 5-continued

The compounds of Examples 87-121 were prepared according to the procedure of Example 86 starting with the appropriate starting aterials.

| Example | Compound | Name | Calc'd [M + H]+ | Observed [M + H]+ |
|---|---|---|---|---|
| 113 | | 2-[(3S or 3R)-4,4-difluoro-3-methyl-1-piperidyl]-N-(1,1-dioxo-2,3-dihydro-1,2-benzothiazol-6-yl)-5-(trifluoromethyl)pyridine-3-carboxamide | 491.1 | 491.1 |
| 114 | | N-(3-fluoro-5-sulfamoyl-phenyl)-2-(1-piperidyl)-5-(trifluoromethyl)-pyridine-3-carboxamide | 447.1 | 447.0 |
| 115 | | N-(4-fluoro-3-sulfamoyl-phenyl)-2-(1-piperidyl)-5-(trifluoromethyl)pyridine-3-carboxamide | 447.1 | 447.0 |
| 116 | | N-(2-fluoro-5-sulfamoyl-phenyl)-2-(1-piperidyl)-5-(trifluoromethyl)pyridine-3-carboxamide | 447.1 | 447.0 |
| 117 | | 2-(azepan-1-yl)-N-(3-isopropylsulfonylphenyl)-5-(trifluoromethyl)-pyridine-3-carboxamide | 470.2 | 470.3 |

TABLE 5-continued

The compounds of Examples 87-121 were prepared according to the procedure of Example 86 starting with the appropriate starting aterials.

| Example | Compound | Name | Calc'd [M + H]+ | Observed [M + H]+ |
|---|---|---|---|---|
| 118 | | 2-(azepan-1-yl)-N-(1,1-dioxobenzothiophen-6-yl)-5-(trifluoromethyl)-pyridine-3-carboxamide | 452.1 | 452.2 |
| 119 | | 2-(azepan-1-yl)-N-(3-isobutylsulfonylphenyl)-5-(trifluoromethyl)-pyridine-3-carboxamide | 484.2 | 484.3 |
| 120 | | 2-(azepan-1-yl)-N-(3-cyclopentylsulfonylphenyl)-5-(trifluoro-methyl)-pyridine-3-carboxamide | 496.2 | 496.3 |
| 121 | | 2-(azepan-1-yl)-N-(1,1-dioxo-2,3-dihydro-1,2-benzothiazol-6-yl)-5-(trifluoromethyl)-pyridine-3-carboxamide | 455.1 | 455.3 |

Example 122

2-(azepan-1-yl)-3-((2-methyl-1,1-dioxido-2,3-dihydrobenzo[d]isothiazol-6-yl)-carbamoyl)-5-(trifluoromethyl)pyridine

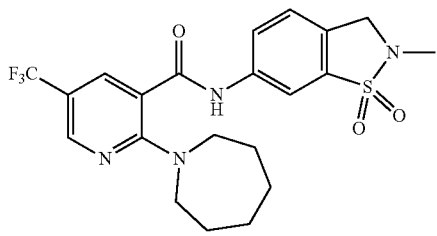 [SMILES: CN1Cc2ccc(NC(=O)c3cc(C(F)(F)F)cnc3N3CCCCCC3)cc2S1(=O)=O]

2-(azepan-1-yl)-3-((2-methyl-1,1-dioxido-2,3-dihydrobenzodisothiazol-6-yl)-carbamoyl)-5-(trifluoromethyl) pyridin-1-ium 2,2,2-trifluoroacetate To a solution of 2-(azepan-1-yl)-N-(1,1-dioxido-2,3-dihydrobenzo[d]isothiazol-6-yl)-5-(trifluoromethyl)nicotinamide (Example 121, 18 mg, 0.041 mmol) in DMF (1 mL) was added DMF-DMA (0.027 mL, 0.20 mmol). The mixture was stirred at 60° C. for 16 h. Then the mixture was purified by reverse phase chromatography (5-95% MeCN in water with 0.1% TFA, C18 column) to give the title compound. LRMS m/z (M+H): calculated 469.1, observed 469.4. $^1$H NMR δ (ppm) (600 MHz, CD$_3$OD): 8.43 (s, 1H), 8.28 (s, 1H), 7.93 (s, 1H), 7.84 (d, J=9.8 Hz, 1H), 7.52 (d, J=8.3 Hz, 1H), 4.36 (s, 2H), 3.66-3.60 (m, 4H), 3.30 (s, 7H), 2.90 (s, 3H), 1.83 (s, 4H), 1.54 (s, 4H).

Examples 123 and 124

(R or S)-2-(4,4-Difluoro-3-methylpiperidin-1-yl)-N-(3-sulfamoylphenyl)-5-(trifluoromethyl)nicotinamide (123) and (S or R)-2-(4,4-difluoro-3-methylpiperidin-1-yl)-N-(3-sulfamoylphenyl)-5-(trifluoromethyl)nicotinamide

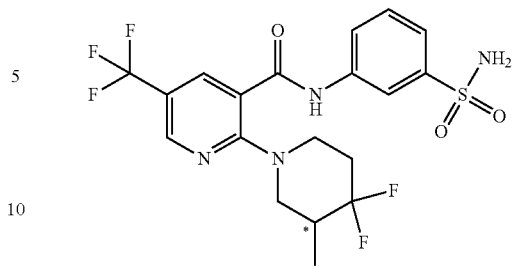

124

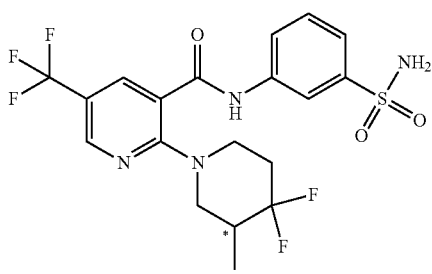

123

A mixture of 2-chloro-N-(3-sulfamoylphenyl)-5-(trifluoromethyl)nicotinamide (Intermediate 14, 0.10 g, 0.26 mmol), 4,4-difluoro-3-methylpiperidine hydrochloride (45 mg, 0.26 mmol), and $K_2CO_3$ (73 mg, 0.53 mmol) in NMP (1.3 mL) was heated at 70° C. for 4 hours. Then the mixture was quenched with aqueous potassium phosphate monobasic (saturated) and extracted with ethyl acetate. The combined organic layers were dried with $MgSO_4$, filtered, and the solvent was evaporated under reduced pressure. The resulting residue was purified by silica gel chromatography (0-100% EtOAc/hexanes) to give a racemic mixture of (R and S)-2-(4,4-difluoro-3-methylpiperidin-1-yl)-N-(3-sulfamoylphenyl)-5-(trifluoromethyl)nicotinamide. Chiral separation (AD-H, 15% ethanol/$CO_2$) gave two enantiomers: enantiomer A (123) and enantiomer B (124): LRMS m/z (M+H): calculated 479.1, observed 479.1. $^1$H NMR δ (ppm) (600 MHz, DMSO-$d_6$): 10.87 (s, 1H), 8.61 (s, 1H), 8.28 (s, 1H), 8.09 (s, 1H), 7.83 (d, J=7.1 Hz, 1H), 7.61-7.55 (m, 2H), 7.42 (s, 2H), 3.98 (d, J=13.0 Hz, 1H), 3.92 (d, J=13.9 Hz, 1H), 3.30-3.23 (m, 1H), 3.08-3.02 (m, 1H), 2.22-2.09 (m, 2H), 2.02-1.88 (m, 1H), 0.90 (d, J=6.8 Hz, 3H).

TABLE 6

The compounds of Examples 125-143 were prepared according to the procedure of Examples 123 and 124 with the appropriate starting materials.

| Example | Compound | Name | Calc'd [M + H]$^+$ | Observed [M + H]$^+$ | Conditions |
|---|---|---|---|---|---|
| 125 | | 2-[(3S,5R)-4,4-difluoro-3,5-dimethyl-1-piperidyl]-N-(3-sulfamoylphenyl)-5-(trifluoromethyl)-pyridine-3-carboxamide | 493.1 | 493.2 | |
| 126 | | 2-[(3S or 3R)-2,2-difluoro-5-azaspiro[2.5]octan-5-yl]-N-(3-sulfamoylphenyl)-5-(trifluoromethyl)-pyridine-3-carboxamide | 491.1 | 491.1 | Chiral Method E, peak 2 |

TABLE 6-continued

The compounds of Examples 125-143 were prepared according to the procedure of Examples 123 and 124 with the appropriate starting materials.

| Example | Compound | Name | Calc'd [M + H]+ | Observed [M + H]+ | Conditions |
|---|---|---|---|---|---|
| 127 | | 2-[(3R or 3S)-2,2-difluoro-5-azaspiro[2.5]octan-5-yl]-N-(3-sulfamoylphenyl)-5-(trifluoromethyl)-pyridine-3-carboxamide | 491.1 | 491.1 | Chiral Method E, peak 1 |
| 128 | | 2-[(1R,6R or 1S,6S)-7,7-difluoro-6-methyl-3-azabicyclo[4.1.0]heptan-3-yl]-N-(3-sulfamoyl-phenyl)-5-(trifluoro-methyl)-pyridine-3-carboxamide | 491.1 | 491.1 | Chiral Method C, peak 2 |
| 129 | | 2-[(1S,6S or 1R,6R)-7,7-difluoro-6-methyl-3-azabicyclo[4.1.0]heptan-3-yl]-N-(3-sulfamoyl-phenyl)-5-(trifluoro-methyl)pyridine-3-carboxamide | 491.1 | 491.1 | Chiral Method C, peak 1 |
| 130 | | N-(3-sulfamoylphenyl)-5-(trifluoromethyl)-2-[(1R,5R or 1S,5S)-1-(trifluoromethyl)-3-azabicyclo[3.2.0]heptan-3-yl]pyridine-3-carboxamide | 509.1 | 509.1 | Chiral Method D, peak 2 |
| 131 | | N-(3-sulfamoylphenyl)-5-(trifluoromethyl)-2-[(1S,5S or 1R,5R)-1-(trifluoromethyl)-3-azabicyclo[3.2.0]heptan-3-yl]pyridine-3-carboxamide | 509.1 | 509.1 | Chiral Method D, peak 1 |

TABLE 6-continued

The compounds of Examples 125-143 were prepared according to the procedure of Examples 123 and 124 with the appropriate starting materials.

| Example | Compound | Name | Calc'd [M + H]+ | Observed [M + H]+ | Conditions |
|---|---|---|---|---|---|
| 132 | | 2-[(1R,5S)-6,6-difluoro-3-azabicyclo[3.1.1]-heptan-3-yl]-N-(3-sulfamoylphenyl)-5-(trifluoromethyl)-pyridine-3-carboxamide | 477.1 | 477.2 | |
| 133 | | N-(3-sulfamoylphenyl)-2-[(1R,5S)-6,6,7,7-tetrafluoro-3-azabicyclo-[3.2.0]heptan-3-yl]-5-(trifluoromethyl)-pyridine-3-carboxamide | 513.1 | 513.2 | |
| 134 | | 2-((1R,5S)-3-azabicyclo[3.2.0]heptan-3-yl]-N-(3-sulfamoyl-phenyl)-5-(trifluoro-methyl)-pyridine-3-carboxamide | 441.1 | 441.2 | |
| 135 | | 2-[(1S,5R or 1R,5S)-6,6-difluoro-3-azabicyclo[3.2.0]heptan-3-yl]-N-(3-sulfamoyl-phenyl)-5-(trifluoro-methyl)pyridine-3-carboxamide | 477.1 | 477.1 | Chiral Method B, peak 1 |
| 136 | | 2-[(1R,5S or 1S,5R)-6,6-difluoro-3-azabicyclo[3.2.0]heptan-3-yl]-N-(3-sulfamoyl-phenyl)-5-(trifluoromethyl)-pyridine-3-carboxamide | 477.1 | 477.1 | Chiral Method B, peak 2 |

TABLE 6-continued

The compounds of Examples 125-143 were prepared according to the procedure of Examples 123 and 124 with the appropriate starting materials.

| Example | Compound | Name | Calc'd [M + H]⁺ | Observed [M + H]⁺ | Conditions |
|---|---|---|---|---|---|
| 137 | | 2-[(1S,4S or 1R,4R)-5,5-difluoro-2-azabicyclo-[2.2.1]heptan-2-yl]-N-(3-sulfamoylphenyl)-5-(trifluoromethyl)-pyridine-3-carboxamide | 477.1 | 477.1 | Chiral Method A, peak 2 |
| 138 | | 2-[(1R,4R or 1S,4S)-5,5-difluoro-2-azabicyclo-[2.2.1]heptan-2-yl]-N-(3-sulfamoylphenyl)-5-(trifluoromethyl)-pyridine-3-carboxamide | 477.1 | 477.1 | Chiral Method A, peak 1 |
| 139 | | 2-(7-azabicyclo[2.2.1]heptan-7-yl)-N-(3-sulfamoyl-phenyl)-5-(trifluoro-methyl)pyridine-3-carboxamide | 441.1 | 441.1 | |
| 140 | | N-(3-sulfamoylphenyl)-5-(trifluoromethyl)-2-[(2S)-2-(trifluoro-methyl)--morpholin-4-yl]pyridine-3-carboxamide | 499.1 | 499.1 | |

TABLE 6-continued

The compounds of Examples 125-143 were prepared according to the procedure of Examples 123 and 124 with the appropriate starting materials.

| Example | Compound | Name | Calc'd [M + H]+ | Observed [M + H]+ | Conditions |
|---|---|---|---|---|---|
| 141 | | N-(3-sulfamoylphenyl)-5-(trifluoromethyl)-2-[(2R)-2-(trifluoromethyl)morpholin-4-yl]pyridine-3-carboxamide | 499.1 | 499.1 | |
| 142 | | 2-[(2R,6R)-2-methyl-6-(trifluoromethyl)morpholin-4-yl]-N-(3-sulfamoylphenyl)-5-(trifluoromethyl)-pyridine-3-carboxamide | 513.1 | 513.2 | |
| 143 | | N-(3-sulfamoylphenyl)-5-(trifluoromethyl)-2-[3-(trifluoromethyl)-piperazin-1-yl]pyridine-3-carboxamide | 498.1 | 499.2 | |

Example 144

(R)—N-(3-sulfamoylphenyl)-5-(trifluoromethyl)-2-(2-(trifluoromethyl)-1,4-oxazepan-4-yl) nicotinamide

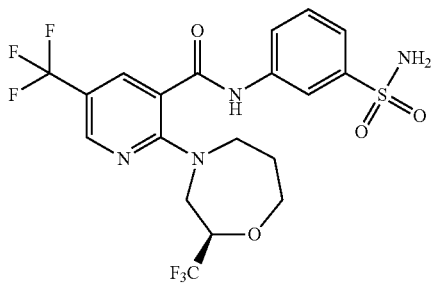 [SMILES: NS(=O)(=O)c1cccc(NC(=O)c2cc(C(F)(F)F)cnc2N2CCCO[C@@H](C(F)(F)F)C2)c1]

To a solution of 2-chloro-N-(3-sulfamoylphenyl)-5-(trifluoromethyl)nicotinamide (Intermediate 14, 40 mg, 0.10 mmol) in NMP (0.5 mL) was added (R)-2-(trifluoromethyl)-1,4-oxazepane hydrobromide (33 mg, 0.13 mmol) and DIPEA (55 µl, 0.32 mmol). The mixture was heated at 70° C. for 4 hours. Then the mixture was quenched with aqueous potassium phosphate monobasic (saturated) and extracted with DCM. The organic layer was dried over $MgSO_4$, filtered and concentrated under reduced pressure to give a residue that was purified by silica gel chromatography (EtOAc/hexane) to give the title compound. LRMS m/z (M+H): calculated 513.1, observed 513.2. $^1$H NMR δ (ppm) (600 MHz, DMSO-$d_6$): 10.90 (s, 1H), 8.56 (s, 1H), 8.20 (s, 1H), 8.05 (s, 1H), 7.79 (d, J=7.2 Hz, 1H), 7.67-7.44 (m, 2H), 7.38 (s, 2H), 4.45 (m, 1H), 4.33 (d, J=14.1 Hz, 1H), 4.20-3.92 (m, 2H), 3.82-3.66 (m, 1H), 3.66-3.56 (m, 1H), 3.57-3.44 (m, 2H), 1.13 (t, J=7.1 Hz, 1H).

TABLE 7

The compounds of Examples 145-150 were prepared according to the procedure of Example 144 starting from the appropriate starting materials.

| Example | Compound | Name | Calc'd [M + H]+ | Observed [M + H]+ |
|---|---|---|---|---|
| 145 | | 2-[(2S,6R)-2-methyl-6-(trifluoromethyl)morpholin-4-yl]-N-(3-sulfamoylphenyl)-5-(trifluoromethyl)pyridine-3-carboxamide | 513.1 | 513.1 |
| 146 | | 2-[(2R,6S)-2-methyl-6-(trifluoromethyl)morpholin-4-yl]-N-(3-sulfamoylphenyl)-5-(trifluoromethyl)pyridine-3-carboxamide | 513.1 | 513.1 |
| 147 | | N-(3-sulfamoylphenyl)-5-(trifluoromethyl)-2-[(2S)-2-(trifluoromethyl)-1,4-oxazepan-4-yl]pyridine-3-carboxamide | 513.1 | 513.1 |
| 148 | | 2-[(2S,6S)-2-methyl-6-(trifluoromethyl)-morpholin-4-yl]-N-(3-sulfamoylphenyl)-5-(trifluoromethyl)pyridine-3-carboxamide | 513.1 | 513.1 |

TABLE 7-continued

The compounds of Examples 145-150 were prepared according to the procedure of Example 144 starting from the appropriate starting materials.

| Example | Compound | Name | Calc'd [M + H]+ | Observed [M + H]+ |
|---|---|---|---|---|
| 149 | | 2-[(2R,6S or 2S,6R)-2,6-dimethylmorpholin-4-yl]-N-(3-sulfamoylphenyl)-5-(trifluoromethyl)pyridine-3-carboxamide | 459.1 | 459.1 |
| 150 | | 2-[(2S,6S or 2R,6R)-2,6-dimethylmorpholin-4-yl]-N-(3-sulfamoylphenyl)-5-(trifluoromethyl)pyridine-3-carboxamide | 459.1 | 459.1 |

Example 151

2-(azepan-1-yl)-3-((3-(N-(pyrimidin-4-yl)sulfamoyl)phenyl)carbamoyl)-5-(trifluoromethyl)pyridin-1-ium

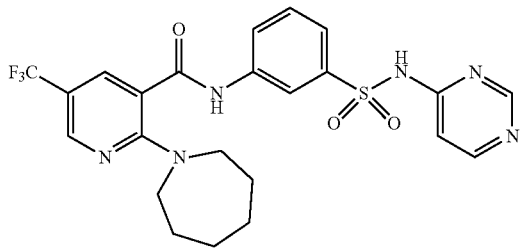 [SMILES: O=C(Nc1cccc(S(=O)(=O)Nc2ccncn2)c1)c1cc(C(F)(F)F)cnc1N1CCCCCC1]

Step 1: 2-(azepan-1-yl)-N-(3-bromophenyl)-5-(trifluoromethyl)nicotinamide The title compound was prepared from 2-chloro-5-(trifluoromethyl)nicotinic acid according to the procedure of Example 86.

Step 2: 2-(azepan-1-yl)-N-(3-(benzylthio)phenyl)-5-(trifluoromethyl)nicotinamide A mixture of 2-(azepan-1-yl)-N-(3-bromophenyl)-5-(trifluoromethyl)nicotinamide (1.0 g, 2.3 mmol), Xantphos (0.065 g, 0.11 mmol), and Pd$_2$(dba)$_3$ (0.052 g, 0.057 mmol) was flushed with nitrogen, then dioxane (10 mL) and DIPEA (0.79 mL, 4.5 mmol) were added. The mixture was heated to 120° C. for 10 min, and then benzyl mercaptan (0.28 mL, 2.4 mmol) was added dropwise over 3 min. The resulting mixture was heated at 120° C. for 2 h. Then the mixture was cooled to rt and stirred for 16 h. The mixture was then concentrated and purified by silica gel chromatography (0-25% ethyl acetate/hexanes) to give the title compound.

Step 3: perfluorophenyl 3-(2-(azepan-1-yl)-5-(trifluoromethyl)nicotinamido)benzenesulfonate To a mixture of 2-(azepan-1-yl)-N-(3-(benzylthio)phenyl)-5-(trifluoromethyl)nicotinamide (0.60 g, 1.2 mmol), acetonitrile (12 mL), acetic acid (0.44 mL) and water (0.29 mL) at 0° C. was added 1,3-dichloro-5,5-dimethylhydantoin (0.51 g, 2.6 mmol). The mixture was stirred at 0° C. for 30 min, then pentafluorophenol (0.48 g, 2.6 mmol) and TEA (0.43 mL, 3.1 mmol) were added. The mixture was stirred at rt for 1 h. Then the mixture was diluted with EtOAc, washed with water, brine, dried over Na$_2$SO$_4$, filtered, and concentrated under reduced pressure. The resulting residue was purified by silica gel chromatography (0-50% EtOAc/hexanes) to give the title compound.

Step 4: 2-(azepan-1-yl)-3-((3-(N-(pyrimidin-4-yl)sulfamoyl)phenyl)carbamoyl)-5-(trifluoro-methyl)pyridin-1-ium 2,2,2-trifluoroacetate To a mixture of perfluorophenyl 3-(2-(azepan-1-yl)-5-(trifluoromethyl)nicotinamido)benzenesulfonate (20 mg, 0.033 mmol), pyrimidin-4-amine (3.4 mg, 0.036 mmol) and THF (2 mL) at 0° C. was added LHMDS [1M in THF] (0.069 mL, 0.069 mmol) dropwise over 1 min. The mixture was stirred for 20 min, then TFA (7.6 μl, 0.098 mmol) was added dropwise and the mixture was diluted with DCM. Then the mixture was stirred for 10 min at rt, and concentrated under reduced pressure. The resulting residue was purified by reverse phase chromatography (5-95% MeCN in water with 0.1% TFA, C18 column) to give the title compound. LRMS m/z (M+H): calculated 521.2, observed 521.4. $^1$H NMR δ (ppm) (600 MHz, CD$_3$OD): 8.70 (s, 1H), 8.55 (s, 1H), 8.43 (s, 1H), 8.39 (d, J=6.6 Hz, 1H), 7.90 (d, J=2.2 Hz, 1H), 7.83-7.77 (m, 2H), 7.55 (t, J=8.0 Hz, 1H), 7.20 (d, J=5.6 Hz, 1H), 3.64-3.59 (m, 4H), 1.81 (s, 4H), 1.53 (s, 4H).

Example 152

2-(4,4-difluoropiperidin-1-yl)-N-(3-(methylsulfonyl)phenyl)-5-(trifluoromethyl)nicotinamide

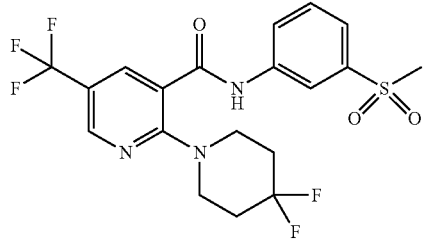 [SMILES: CS(=O)(=O)c1cccc(NC(=O)c2cc(C(F)(F)F)cnc2N2CCC(F)(F)CC2)c1]

Step 1: 2-chloro-N-(3-(methylsulfonyl)phenyl)-5-(trifluoromethyl)nicotinamide To a solution of 2-chloro-5-(trifluoromethyl)nicotinic acid (1.0 g, 4.4 mmol) and 3-(methylsulfonyl)aniline (0.83 g, 4.9 mmol) at 0° C. in pyridine (22 mL) was added $POCl_3$ (0.45 mL, 4.9 mmol) via syringe dropwise. The mixture was stirred at 0° C. for 1 h, then quenched with brine and extracted with EtOAc. The organic layer was washed with brine, dried over $MgSO_4$, filtered and concentrated under reduced pressure to give a residue that was purified by silica gel chromatography (0-30% ethyl acetate:ethanol (3:1)/hexanes) to give the title compound.

Step 2: 2-(4,4-difluoropiperidin-1-yl)-N-(3-(methylsulfonyl)phenyl)-5-(trifluoromethyl)-nicotinamide To a suspension of 2-chloro-N-(3-(methylsulfonyl)phenyl)-5-(trifluoromethyl)-nicotinamide (1.1 g, 2.9 mmol) and $K_2CO_3$ (0.49 g, 3.5 mmol) in NMP (15 mL) was added 4, 4-difluoropiperidine (0.36 mL, 3.2 mmol). The mixture was stirred at 65° C. for 1.5 h. Then the mixture was cooled to rt, diluted with water and extracted with EtOAc. The organic layer was washed with water, dried over $MgSO_4$, filtered and concentrated under reduced pressure. The resulting residue was purified by silica gel chromatography (0-25% ethyl acetate: ethanol (3:1)/hexanes) to give the title compound. LRMS m/z (M+H): calculated 464.1, observed 464.1. $^1$H NMR δ (ppm) (500 MHz, $CDCl_3$): 9.65 (s, 1H), 8.64 (s, 1H), 8.46 (d, J=2.2 Hz, 1H), 8.25 (s, 1H), 7.93 (d, J=8.0 Hz, 1H), 7.79-7.73 (d, 1H), 7.62 (t, J=8.0 Hz, 1H), 3.64-3.57 (m, 4H), 3.10 (s, 3H), 2.15 (tt, J=13.3, 5.7 Hz, 4H).

Example 153

5-isobutyl-2-(piperidin-1-yl)-N-(3-sulfamoylphenyl)nicotinamide

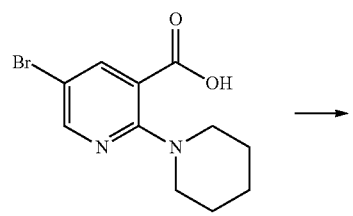

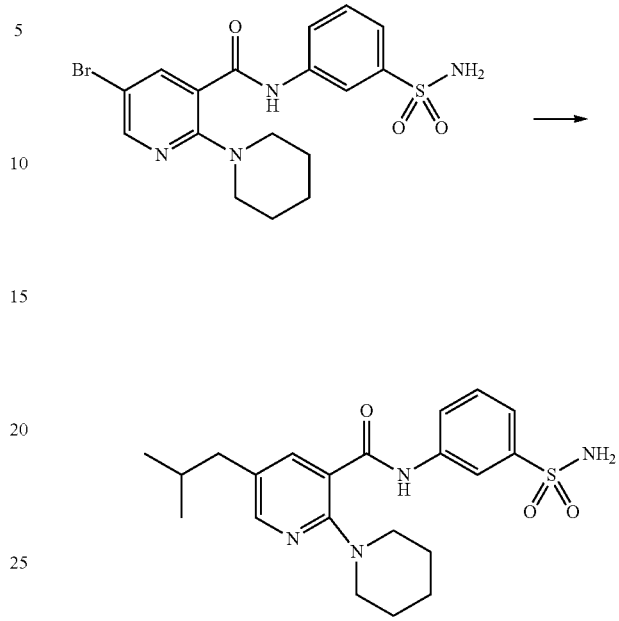

Step 1: 5-bromo-2-(piperidin-1-yl)-N-(3-sulfamoylphenyl)nicotinamide A mixture of 5-bromo-2-(piperidin-1-yl)nicotinic acid (Intermediate 7, 0.50 g, 1.8 mmol) in $SOCl_2$ (3.0 mL, 1.8 mmol) was stirred at 80° C. for 2 h, then concentrated under reduced pressure. The resulting residue was dissolved in pyridine (15 mL) and treated with 3-aminobenzenesulfonamide (0.31 g, 1.8 mmol). The mixture was stirred at 20° C. for 2 h, then concentrated under reduced pressure. The resulting residue was purified by silica gel chromatography (PE:ethyl acetate=1:1) to give the title compound.

Step 2: 5-isobutyl-2-(piperidin-1-yl)-N-(3-sulfamoylphenyl)nicotinamide A mixture of nickel(II) iodide (7.1 mg, 0.023 mmol), nicotinimidamide hydrochloride (3.6 mg, 0.023 mmol) and zinc (30 mg, 0.45 mmol) in a vial was evacuated and backfilled with nitrogen. DMA (1 mL) was added and the mixture was stirred for 5 minutes at rt. To the mixture was added a solution of 5-bromo-2-(piperidin-1-yl)-N-(3-sulfamoylphenyl)nicotinamide (50 mg, 0.11 mmol), 1-bromo-2-methylpropane (31 mg, 0.23 mmol) and sodium iodide (34 mg, 0.23 mmol) in DMA (2 mL). The mixture was heated to 100° C. for 5 h. Then the mixture was diluted with DMF and purified by reverse phase chromatography (21-100% MeCN in water with 0.1% TFA, C18 column) to give the title compound. LRMS m/z (M+H): calculated 417.2, observed 417.0. $^1$H NMR δ (ppm) (400 MHz, $CD_3OD$): 8.38 (s, 1H), 8.09-8.12 (m, 2H), 7.85 (d, J=7.6 Hz, 1H), 7.70 (d, J=7.6 Hz, 1H), 7.53-7.61 (m, 1H), 3.39 (br s, 4H), 2.54 (d, J=7.2 Hz, 2H), 1.91 (dt, J=14.0, 6.8 Hz, 1H), 1.63-1.80 (m, 6H), 0.95 (d, J=6.8 Hz, 6H).

TABLE 8

The compound of Example 154 was prepared according to the procedure of Example 153 starting from the appropriate starting materials.

| Example | Compound | Name | Calc'd [M + H]+ | Observed [M + H]+ |
|---|---|---|---|---|
| 154 | | 5-cyclopentyl-2-(piperidin-1-yl)-N-(3-sulfamoylphenyl)-nicotinamide | 429.5 | 429.0 |

Example 155

2-(azepan-1-yl)-6-methoxy-5-methyl-N-(3-sulfamoylphenyl)nicotinamide

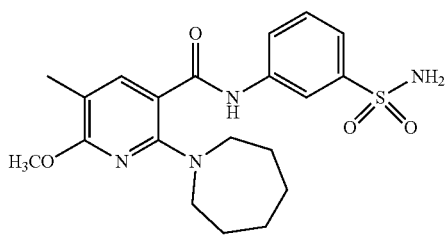 [SMILES: COc1nc(N2CCCCCC2)c(C(=O)Nc2cccc(S(N)(=O)=O)c2)cc1C]

Step 1: methyl 2-(azepan-1-yl)-6-methoxy-5-methylnicotinate To a solution of methyl 2-(azepan-1-yl)-5-bromo-6-methoxynicotinate (Intermediate 9, 0.20 g, 0.58 mmol) in dioxane (5 mL) and water (1 mL) were added potassium trifluoro(methyl)borate (0.11 g, 0.87 mmol), $K_2CO_3$ (0.16 g, 1.2 mmol) and $PdCl_2(dppf)$ (43 mg, 0.058 mmol). The mixture was stirred at 100° C. for 6 hours, then diluted with water and extracted with EtOAc. The organic layer was washed with brine, dried over $Na_2SO_4$, filtered and concentrated to give a residue that was purified by silica gel chromatography (PE/EtOAc=5:1) to give the title compound.

Step 2: 2-(azepan-1-yl)-6-methoxy-5-methylnicotinic acid To a solution of methyl 2-(azepan-1-yl)-6-methoxy-5-methylnicotinate (0.13 g, 0.47 mmol) in MeOH (3 mL) and water (1 mL) was added lithium hydroxide hydrate (59 mg, 1.4 mmol). The mixture was stirred at 40° C. for 12 hours, then at 65° C. for 3 hours. Then the mixture was diluted with water and washed with 1:1 PE/EtOAc. The aqueous layer was separated, acidified by citric acid and extracted with EtOAc. The organic layer was washed with brine, dried over $Na_2SO_4$, filtered and concentrated to give the title compound.

Step 3: 2-(azepan-1-yl)-6-methoxy-5-methyl-N-(3-sulfamoylphenyl)nicotinamide To a solution of 2-(azepan-1-yl)-6-methoxy-5-methylnicotinic acid (30 mg crude) in pyridine (1.5 mL) were added EDC (43 mg, 0.23 mmol) and 3-aminobenzenesulfonamide (20 mg, 0.11 mmol). The mixture was stirred at 50° C. for 6 hours. Then the mixture was concentrated under reduced pressure to give a residue that was purified by reverse phase chromatography (40-100% MeCN in water with 0.1% TFA, C18 column) to give the title compound. LRMS m/z (M+H): calculated 419.2, observed 419.0. $^1$H NMR δ (ppm) (400 MHz, $CD_3OD$): 8.33 (s, 1H), 7.83 (d, J=7.2 Hz, 2H), 7.68 (d, J=8.4 Hz, 1H), 7.49-7.57 (m, 1H), 3.99 (s, 3H), 3.62 (br s, 4H), 2.16 (s, 3H), 1.94 (br s, 4H), 1.66 (br s, 4H).

Example 156

2-(azepan-1-yl)-5-bromo-6-methoxy-N-(3-sulfamoylphenyl)nicotinamide

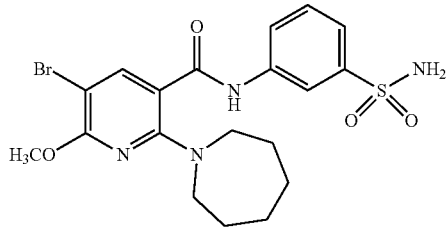 [SMILES: COc1nc(N2CCCCCC2)c(C(=O)Nc2cccc(S(N)(=O)=O)c2)cc1Br]

Step 1: 2-(azepan-1-yl)-5-bromo-6-methoxynicotinic acid To a solution of methyl 2-(azepan-1-yl)-5-bromo-6-methoxynicotinate (Intermediate 9, 0.10 g, 0.29 mmol) in MeOH (5 mL) and water (1 mL) was added lithium hydroxide hydrate (37 mg, 0.87 mmol). The mixture was stirred at 65° C. for 12 hours. Then the mixture was dissolved in water and washed with 1:1 PE/EtOAc. The aqueous layer was separated, acidified with citric acid and extracted with EtOAc. The organic layer was washed with brine, dried over $Na_2SO_4$, filtered and concentrated to give the title compound.

Step 2: 2-(azepan-1-yl)-5-bromo-6-methoxy-N-(3-sulfamoylphenyl)nicotinamide To a solution of 2-(azepan-1-yl)-5-bromo-6-methoxynicotinic acid (60 mg, 0.13 mmol) in pyridine (1.5 mL) were added EDC (50 mg, 0.26 mmol) and 3-aminobenzenesulfonamide (23 mg, 0.13 mmol). The mixture was stirred at 24° C. for 60 minutes, then concentrated to give a residue that was purified by reverse phase chromatography (40-100% MeCN in water with 0.1% TFA, C18 column) to give the title compound. LRMS m/z (M+H): calculated 483.1, observed 483.0. $^1$H NMR δ (ppm) (400 MHz, $CD_3OD$): 8.31 (s, 1H), 7.76-7.83 (m, 2H), 7.65 (d, J=8.0 Hz, 1H), 7.48-7.56 (m, 1H), 3.96 (s, 3H), 3.54-3.57 (m, 4H), 1.85 (br s, 4H), 1.55 (br s, 4H).

TABLE 9

The compounds of Examples 157 and 158 were prepared according to the procedure of Example 156 starting with the appropriate starting materials.

| Example | Compound | Name | Calc'd [M + H]⁺ | Observed [M + H]⁺ |
|---|---|---|---|---|
| 157 | | 2-(azepan-1-yl)-5-cyano-6-methyl-N-(3-sulfamoylphenyl)-pyridine-3-carboxamide | 414.2 | 414.1 |
| 158 | | 2-(azepan-1-yl)-4-chloro-6-methyl-N-(3-sulfamoylphenyl)-pyridine-3-carboxamide | 423.1 | 423.2 |

Example 159

5-cyclobutyl-2-(4,4-difluoroazepan-1-yl)-N-(3-sulfamoylphenyl)nicotinamide

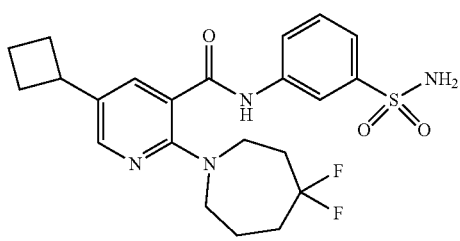 [SMILES: NS(=O)(=O)c1cccc(NC(=O)c2cc(C3CCC3)cnc2N2CCCC(F)(F)CC2)c1]

A vial containing NiI$_2$ (3.8 mg, 0.012 mmol), picolinimidamide hydrochloride (1.9 mg, 0.012 mmol) and zinc (16 mg, 0.24 mmol) was evacuated and backfilled with nitrogen, then DMA (1 mL) was added. The mixture was stirred for 5 minutes at 25° C., then a solution of 5-bromo-2-(4,4-difluoroazepan-1-yl)-N-(3-sulfamoylphenyl)nicotinamide (Intermediate 10, 30 mg, 0.061 mmol), bromocyclobutane (16 mg, 0.12 mmol) and sodium iodide (18 mg, 0.12 mmol) in DMA (1 mL) was added. The resulting mixture was heated to 100° C. for 15 h, then filtered and purified by reverse phase chromatography (27-100% MeCN in water with 0.1% TFA, C18 column) to give the title compound. LRMS m/z (M+H): calculated 465.2, observed 465.0. ¹H NMR δ (ppm) (400 MHz, CD$_3$OD): 8.34 (s, 1H), 8.04 (d, J=2.0 Hz, 1H), 7.98 (d, J=1.6 Hz, 1H), 7.84 (d, J=8.0 Hz, 1H), 7.70 (d, J=8.0 Hz, 1H), 7.52-7.59 (m, 1H), 3.67-3.78 (m, 2H), 3.52-3.65 (m, 3H), 2.28-2.44 (m, 4H), 2.16-2.26 (m, 2H), 2.02-2.15 (m, 3H), 1.86-2.01 (m, 3H).

Example 160

2-(4,4-difluoroazepan-1-yl)-5-(oxetan-3-yl)-N-(3-sulfamoylphenyl)nicotinamide

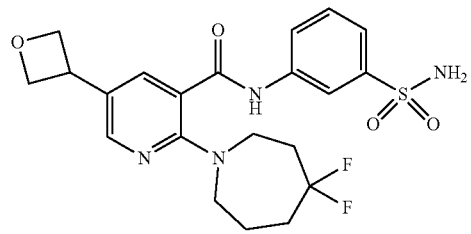 [SMILES: NS(=O)(=O)c1cccc(NC(=O)c2cc(C3COC3)cnc2N2CCCC(F)(F)CC2)c1]

The title compound was prepared from 5-bromo-2-(4,4-difluoroazepan-1-yl)-N-(3-sulfamoylphenyl)nicotinamide (Intermediate 10) using the procedure of Example 159 using the appropriate starting materials. LRMS m/z (M+H): calculated 467.2, observed 466.9. ¹H NMR δ (ppm) (400 MHz, CD$_3$OD): 8.34 (s, 1H), 8.22 (s, 1H), 7.95 (d, J=2.8 Hz, 1H), 7.85 (d, J=8.0 Hz, 1H), 7.68 (d, J=7.6 Hz, 1H), 7.50-7.57 (m, 1H), 5.08 (dd, J=6.0, 8.4 Hz, 2H), 4.74 (t, J=6.4 Hz, 2H), 4.27 (d, J=6.0 Hz, 1H), 3.71 (br s, 2H), 3.47-3.55 (m, 2H), 2.34 (br s, 2H), 1.90-2.10 (m, 4H).

Example 161

5-(but-3-en-1-yl)-2-(4,4-difluoroazepan-1-yl)-N-(3-sulfamoylphenyl)nicotinamide

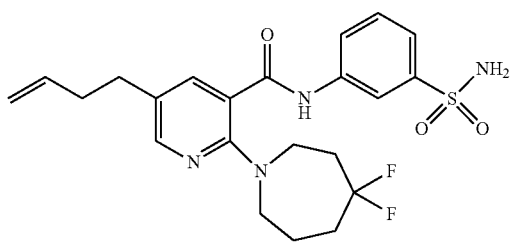 [SMILES: C=CCCc1cnc(N2CCCC(F)(F)CC2)c(C(=O)Nc2cccc(S(N)(=O)=O)c2)c1]

The title compound was prepared from 5-bromo-2-(4,4-difluoroazepan-1-yl)-N-(3-sulfamoyl-phenyl)nicotinamide (Intermediate 10) using the procedure of Example 159 using the appropriate starting materials. LRMS m/z (M+H): calculated 465.2, observed 465.2. $^1$H NMR δ (ppm) (400 MHz, CD$_3$OD): 8.33 (br s, 1H), 7.90-8.06 (m, 2H), 7.82 (d, J=6.8 Hz, 1H), 7.69 (br d, J=8.4 Hz, 1H), 7.50-7.59 (m, 1H), 5.80-5.92 (m, 1H), 4.92-5.09 (m, 2H), 3.50-3.77 (m, 4H), 2.72 (t, J=7.6 Hz, 2H), 2.27-2.44 (m, 3H), 1.85-2.14 (m, 5H).

Example 162

2-(4,4-difluoroazepan-1-yl)-5-isopropyl-N-(3-sulfamoylphenyl)nicotinamide

Step 1: 2-(4,4-difluoroazepan-1-yl)-5-(prop-1-en-2-yl)-N-(3-sulfamoylphenyl)nicotinamide A mixture of 5-bromo-2-(4,4-difluoroazepan-1-yl)-N-(3-sulfamoylphenyl)nicotinamide (Intermediate 10, 0.10 g, 0.20 mmol), PdCl$_2$(dppf) (15 mg, 0.020 mmol), trifluoro(prop-1-en-2-yl)-14-borane, potassium salt (45 mg, 0.31 mmol) and K$_2$CO$_3$ (57 mg, 0.41 mmol) in dioxane (1 mL) and water (0.2 mL) was degassed and backfilled with nitrogen three times. The mixture was heated to 100° C. for 2 h, filtered and concentrated. The resulting residue was dissolved in ethyl acetate. The combined organic layers were washed with saturated brine, dried over Na$_2$SO$_4$, filtered and concentrated to give a residue that was purified by silica gel chromatography (PE/EtOAc=1:1) to give the title compound.

Step 2: 2-(4,4-difluoroazepan-1-yl)-5-isopropyl-N-(3-sulfamoylphenyl)nicotinamide A suspension of 2-(4,4-difluoroazepan-1-yl)-5-(prop-1-en-2-yl)-N-(3-sulfamoylphenyl)nicotinamide (90 mg, 0.20 mmol) and Pd/C (21 mg, 0.020 mmol) in MeOH (10 mL) was degassed and backfilled with hydrogen three times. The mixture was stirred at 20° C. under 15 psi of hydrogen pressure for 10 h. Then the mixture was filtered and concentrated to give a residue that was purified by reverse phase chromatography (20-100% MeCN in water with 0.1% TFA, C18 column) to give the title compound. LRMS m/z (M+H): calculated 453.2, observed 453.2. $^1$H NMR δ (ppm) (400 MHz, CD$_3$OD): 8.35 (s, 1H), 8.11 (br s, 1H), 8.00 (s, 1H), 7.84 (d, J=8.0 Hz, 1H), 7.68-7.73 (m, 1H), 7.52-7.59 (m, 1H), 3.70-3.78 (m, 2H), 3.63 (br t, J=5.6 Hz, 2H), 2.94-3.04 (m, 1H), 2.30-2.44 (m, 2H), 2.05-2.18 (m, 2H), 2.00 (br d, J=5.8 Hz, 2H), 1.31 (d, J=5.6 Hz, 6H).

TABLE 10

The compound of Example 163 was prepared according to the procedure of Example 162 using the appropriate starting materials.

| Example | Compound | Name | Calc'd [M + H]$^+$ | Observed [M + H]$^+$ |
|---|---|---|---|---|
| 163 | 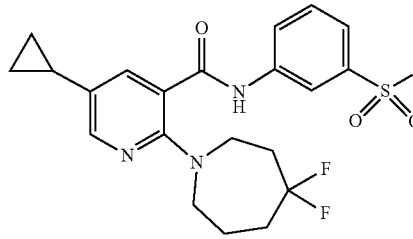 | 5-cyclopropyl-2-(4,4-difluoroazepan-1-yl)-N-(3-sulfamoylphenyl)nicotinamide | 451.5 | 451.1 |

Example 163

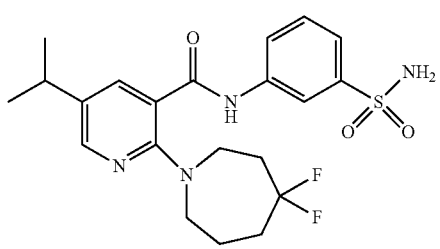 [SMILES: CC(C)c1cnc(N2CCCC(F)(F)CC2)c(C(=O)Nc2cccc(S(N)(=O)=O)c2)c1]

Example 164

2-(azepan-1-yl)-5-(perfluoroethyl)-N-(3-sulfamoylphenyl)nicotinamide

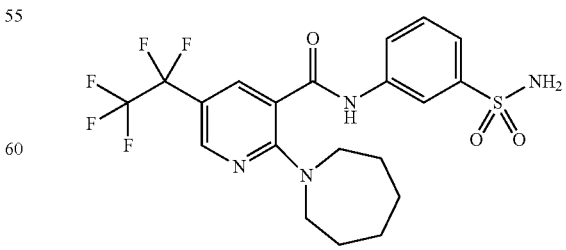

Step 1: methyl 5-bromo-2-fluoronicotinate To a mixture of 5-bromo-2-fluoronicotinic acid (2.9 g, 13 mmol) in DCM (20 mL) and methanol (6.7 mL) at 0° C. was added trimethylsilyldiazomethane (2.0 molar in hexanes, 7.4 mL, 15 mmol). The mixture was warmed from 0° C. over 2 h, and then concentrated to give the title compound.

Step 2: methyl 2-(azepan-1-yl)-5-bromonicotinate A vial containing methyl 5-bromo-2-fluoronicotinate (0.50 g, 2.1 mmol) and sodium bicarbonate (0.36 g, 4.3 mmol) was purged with nitrogen, then a solution of azapane (0.21 g, 2.1 mmol) in DMF (2.8 mL) was added. The mixture was heated to 80° C. for 2 h. Then the mixture was cooled to ambient temperature, filtered and purified by reverse phase chromatography (5-95% MeCN in water with 0.1% TFA, C18 column) to give the title compound.

Step 3: methyl 2-(azepan-1-yl)-5-(perfluoroethyl)nicotinate To a solution of potassium tert-butoxide (2.2 g, 20 mmol) in DMF (11 mL) was added copper(I) chloride (0.98 g, 9.9 mmol) in a glove box under an atmosphere of nitrogen. The mixture was stirred 30 min, then the mixture was purged and charged with 1,1,1,2,2-pentafluoroethane three times using a balloon. The mixture was stirred at ambient temperature for 1 h, then the balloon was removed. Triethylamine trihydrofluoride (0.26 mL, 1.6 mmol) was added, and the mixture stirred at ambient temperature for 10 min. Then the mixture was added to methyl 2-(azepan-1-yl)-5-bromonicotinate (0.49 g, 1.6 mmol). The resulting mixture was heated to 80° C. for 16 h, then at 125° C. for 24 h. Then the mixture was cooled to ambient temperature, diluted with a 50/50 mixture of saturated aqueous sodium bicarbonate solution and ammonium hydroxide, and extracted with ethyl acetate. The organic layer was washed with saturated brine, dried over $MgSO_4$, filtered, and concentrated under reduced pressure. The resulting residue was purified by reverse phase chromatography (5-75% MeCN in water with 0.1% TFA, C18 column) to give the title compound.

Step 4: 2-(azepan-1-yl)-5-(perfluoroethyl)nicotinic acid To a solution of methyl 2-(azepan-1-yl)-5-(perfluoroethyl) nicotinate (63 mg, 0.18 mmol) in MeOH (0.9 mL) and THF (0.9 mL) was added aqueous 1 M sodium hydroxide (0.36 mL, 0.36 mmol). The mixture was stirred at ambient temperature for 16 hours, then at 75° C. for 24 hours. Then the mixture was cooled to rt, quenched with 1 M HCl and concentrated under a stream of nitrogen to give the title compound.

Step 5: 2-(azepan-1-yl)-5-(perfluoroethyl)-N-(3-sulfamoylphenyl)nicotinamide To a mixture methyl 2-(azepan-1-yl)-5-(perfluoroethyl)nicotinic acid (15 mg, 0.044 mmol) in DMF (0.44 m) was added 3-aminobenzenesulfonamide (23 mg, 0.13 mmol), DIPEA (39 m, 0.22 mmol) and HATU (21 mg, 0.055 mmol). The mixture was stirred at ambient temperature for 16 h, and heated to 60° C. for 8 h. Then the mixture was cooled to ambient temperature and purified by reverse phase chromatography (5-90% MeCN in water with 0.100 TFA, C18 column) to give the title compound. LRMS m/z (M+H): calculated 493.1, observed 493.3 (M+1). $^1$H NMR δ (ppm) ($CD_3OD$): 8.38 (s, 1H), 8.32 (s, 1H), 7.81 (d, J=8.1 Hz, 2H), 7.67 (d, J=8.0 Hz, 1H), 7.53 (t, J=8.0 Hz, 1H), 3.69-3.60 (m, 4H), 1.83 (s, 4H), 1.54 (s, 4H).

TABLE 11

The compounds of Examples 165-167 were prepared according to the procedure of Example 164 from the appropriate starting materials.

| Example | Compound | Name | Calc'd [M + H]$^+$ | Observed [M + H]$^+$ |
|---|---|---|---|---|
| 165 | | 6-(1,1,2,2,2-pentafluoroethyl)-2-(1-piperidyl)-N-(3-sulfamoylphenyl)pyridine-3-carboxamide | 479.1 | 479.3 |
| 166 | | 2-(azepan-1-yl)-N-(3-methylsulfonylphenyl)-5-(1,1,2,2,2-pentafluoroethyl)pyridine-3-carboxamide | 492.1 | 492.3 |
| 167 | | 2-(azepan-1-yl)-N-(3-carbamoylphenyl)-5-(1,1,2,2,2-pentafluoroethyl)pyridine-3-carboxamide | 457.2 | 457.3 |

Example 168

2-(azepan-1-yl)-6-methyl-N-(3-sulfamoylphenyl)-5-(trifluoromethyl)nicotinamide

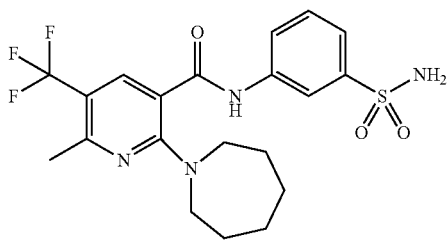 [SMILES: Cc1nc(N2CCCCCC2)c(C(=O)Nc2cccc(S(N)(=O)=O)c2)cc1C(F)(F)F]

Step 1: 1-(6-methyl-5-(trifluoromethyl)pyridin-2-yl)azepane A mixture of 1-(6-chloro-5-(trifluoromethyl)pyridin-2-yl)azepane (Intermediate 11, 0.70 g, 2.5 mmol), potassium carbonate (0.35 g, 2.5 mmol), PdCl$_2$(dppf) (1.8 g, 2.5 mmol) and potassium trifluoro(methyl)borate (0.31 g, 2.5 mmol) in dioxane (4 mL) and water (2 mL) was degassed and backfilled with nitrogen three times. The mixture was heated to 120° C. for 10 h, then diluted with water and extracted with EtOAc. The organic layers were washed with brine, dried over anhydrous Na$_2$SO$_4$, filtered and concentrated to give a residue that was purified by silica gel chromatography (5% ethyl acetate/PE) to give the title compound.

Step 2: 1-(3-bromo-6-methyl-5-(trifluoromethyl)pyridin-2-yl)azepane To a solution of 1-(6-methyl-5-(trifluoromethyl)pyridin-2-yl)azepane (0.55 g, 2.1 mmol) in DMF (10 mL) was added 1,3-dibromo-5,5-dimethylimidazolidine-2,4-dione (0.36 g, 1.3 mmol). The mixture was stirred at 25° C. for 0.5 h, then diluted with water and extracted with EtOAc. The combined organic layers were washed with brine, dried over anhydrous Na$_2$SO$_4$, filtered and concentrated to give a residue that was purified by silica gel chromatography (100% PE) to give the title compound.

Step 3: methyl 2-(azepan-1-yl)-6-methyl-5-(trifluoromethyl)nicotinate A mixture of 1-(3-bromo-6-methyl-5-(trifluoromethyl)pyridin-2-yl)azepane (0.13 g, 0.39 mmol), PdCl$_2$(dppf) (28 mg, 0.039 mmol) and triethylamine (78 mg, 0.77 mmol) in MeOH (5 mL) was degassed and backfilled with CO (50 psi). The mixture was heated to 70° C. for 10 h, then concentrated under reduced pressure to give a residue that was purified by silica gel chromatography (5% EtOAc/PE) to give the title compound.

Step 4: 2-(azepan-1-yl)-6-methyl-5-(trifluoromethyl)nicotinic acid To a solution of methyl 2-(azepan-1-yl)-6-methyl-5-(trifluoromethyl)nicotinate (0.34 g, 1.1 mmol) in MeOH (5 mL) was added a solution of lithium hydroxide hydrate (0.23 g, 5.4 mmol) in water (2 mL). The mixture was stirred at 50° C. for 48 h. Then the mixture was acidified with 2 M HCl to pH~2, and the mixture was extracted with EtOAc. The combined organic layers were dried over anhydrous Na$_2$SO$_4$, filtered and concentrated under reduced pressure to the title compound.

Step 5: 2-(azepan-1-yl)-6-methyl-N-(3-sulfamoylphenyl)-5-(trifluoromethyl)nicotinamide A solution of 2-(azepan-1-yl)-6-methyl-5-(trifluoromethyl)nicotinic acid (40 mg crude) in sulfurous dichloride (2.0 mL, 0.13 mmol) was stirred at 80° C. for 2 hours. Then the mixture was concentrated under reduced pressure to give a residue, which was dissolved in pyridine (2 mL) and treated with 3-aminobenzene-sulfonamide (43 mg, 0.25 mmol). The resulting mixture was stirred at 30° C. for 2 h, diluted in DMF and purified by reverse phase chromatography (52-100% CH$_3$CN in water with 0.1% TFA, C18 column) to give the title compound. LRMS m/z (M+H): calculated 457.1, observed 457.1. $^1$H NMR δ (ppm) (400 MHz, CD$_3$OD): 8.31 (s, 1H), 7.79-7.84 (m, 2H), 7.67 (dd, J=7.6, 1.6 Hz, 1H), 7.50-7.55 (m, 1H), 3.61-3.64 (m, 4H), 2.52 (d, J=0.8 Hz, 3H), 1.82 (br s, 4H), 1.49-1.57 (m, 4H).

Example 169

2-(azepan-1-yl)-6-methoxy-N-(3-sulfamoylphenyl)-5-(trifluoromethyl)nicotinamide

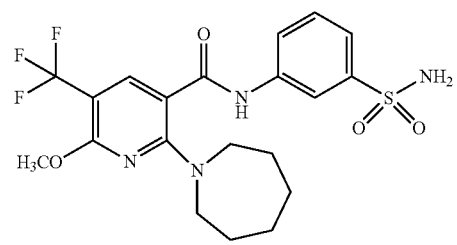 [SMILES: COc1nc(N2CCCCCC2)c(C(=O)Nc2cccc(S(N)(=O)=O)c2)cc1C(F)(F)F]

Step 1: 1-(6-methoxy-5-(trifluoromethyl)pyridin-2-yl)azepane A mixture of 1-(6-chloro-5-(trifluoromethyl)pyridin-2-yl)azepane (Intermediate 11, 0.75 g, 2.7 mmol) and sodium methanolate (0.22 g, 4.0 mmol) in DMF (5 mL) was stirred at 100° C. for 10 h, then diluted with water and extracted with EtOAc. The combined organic layers were washed with brine, dried over anhydrous Na$_2$SO$_4$, filtered and concentrated to give a residue that was purified by silica gel chromatography (0-15% ethyl acetate/PE) to give the title compound.

Step 2: 1-(3-bromo-6-methoxy-5-(trifluoromethyl)pyridin-2-yl)azepane To a solution of 1-(6-methoxy-5-(trifluoromethyl)pyridin-2-yl)azepane (0.50 g, 1.8 mmol) in DMF (10 mL) was added 1,3-dibromo-5,5-dimethylimidazolidine-2,4-dione (0.31 g, 1.1 mmol). The mixture was stirred at 25° C. for 0.5 h, then diluted with water and extracted with EtOAc. The combined organic layers were washed with brine, dried over anhydrous Na$_2$SO$_4$, filtered and concentrated to give a residue that was purified by silica gel chromatography (100% PE) to give the title compound.

Step 3: 2-(azepan-1-yl)-6-methoxy-5-(trifluoromethyl)nicotinonitrile To a solution of 1-(3-bromo-6-methoxy-5-(trifluoromethyl)pyridin-2-yl)azepane (0.10 g, 0.28 mmol) in DMF (3 mL) were added dicyanozinc (66 mg, 0.57 mmol) and PdCl$_2$(dppf) (21 mg, 0.028 mmol). The mixture was stirred at 140° C. for 3 hours under a nitrogen atmosphere, then diluted with water and extracted with EtOAc. The organic layer was washed with brine, dried over Na$_2$SO$_4$, filtered and concentrated to give a residue that was purified by silica gel chromatography (5% EtOAc/PE) to give the title compound.

Step 4: 2-(azepan-1-yl)-6-methoxy-5-(trifluoromethyl)nicotinamide To a solution of 2-(azepan-1-yl)-6-methoxy-5-(trifluoromethyl)nicotinonitrile (80 mg, 0.24 mmol) in DMSO (2 mL) was added K₂CO₃ (67 mg, 0.48 mmol) at 60° C. The mixture was stirred for 5 minutes, then hydrogen peroxide (2.0 mL, 0.24 mmol) was added. The resulting mixture was stirred at 60° C. for 2 h, then diluted with water and extracted with EtOAc. The organic layers were dried over anhydrous Na₂SO₄, filtered and concentrated to give a residue that was purified by silica gel chromatography (25% EtOAc/PE) to give the title compound.

Step 5: 2-(azepan-1-yl)-N-(3-(N,N-bis(2,4-dimethoxybenzyl)sulfamoyl)phenyl)-6-methoxy-5-(trifluoromethyl)nicotinamide To a solution of 2-(azepan-1-yl)-6-methoxy-5-(trifluoro-methyl)nicotinamide (40 mg, 0.13 mmol) in dioxane (5 mL) was added Cs₂CO₃ (82 mg, 0.25 mmol), Brettphos-Pd-G3 (11 mg, 0.013 mmol) and 3-amino-N,N-bis(2,4-dimethoxybenzyl)-benzenesulfonamide (0.10 g, 0.19 mmol). The mixture was stirred at 100° C. for 10 hours under a nitrogen atmosphere. Then the mixture was diluted with water and extracted with EtOAc. The organic layer was washed with brine, dried over Na₂SO₄, filtered and concentrated to give a residue that was purified by silica gel chromatography (50% EtOAc: PE) to give the title compound.

Step 6: 2-(azepan-1-yl)-6-methoxy-N-(3-sulfamoylphenyl)-5-(trifluoromethyl)nicotinamide A solution of 2-(azepan-1-yl)-N-(3-(N,N-bis(2,4-dimethoxybenzyl)sulfamoyl)phenyl)-6-methoxy-5-(trifluoro-methyl)nicotinamide (40 mg, 0.052 mmol) in DCM (1 mL) and TFA (0.5 mL) was stirred at 30° C. for 4 h. Then the mixture was concentrated under reduced pressure to give a residue that was purified by reverse phase chromatography (35-100% MeCN in water with 0.1% TFA, C18 column) to give the title compound. LRMS m/z (M+H): calculated 473.1, observed 472.9. ¹H NMR δ (ppm) (400 MHz, CD₃OD): 8.30 (s, 1H), 7.85 (s, 1H), 7.80 (d, J=8.4 Hz, 1H), 7.65 (d, J=8.0 Hz, 1H), 7.49-7.54 (m, 1H), 3.99 (s, 3H), 3.60-3.63 (m, 4H), 1.86 (br s, 4H), 1.55 (br s, 4H).

Example 170

2-(4,4-difluoropiperidin-1-yl)-N-(2-fluoro-3-sulfamoylphenyl)-5-(trifluoromethyl)nicotinamide

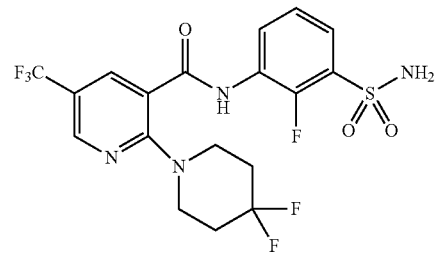 [SMILES: NS(=O)(=O)c1cccc(NC(=O)c2cc(C(F)(F)F)cnc2N2CCC(F)(F)CC2)c1F]

Step 1: N-(3-(N,N-bis(2,4-dimethoxybenzyl)sulfamoyl)-2-fluorophenyl)-2-(4,4-difluoro-piperidin-1-yl)-5-(trifluoromethyl)nicotinamide To a solution of 3-bromo-N,N-bis(2,4-dimethoxybenzyl)-2-fluorobenzenesulfonamide (Intermediate 2, 36 mg, 0.065 mmol) in dioxane (2 mL) were added 2-(4, 4-difluoropiperidin-1-yl)-5-(trifluoromethyl)nicotinamide (Intermediate 15, 20 mg, 0.065 mmol), Brettphos-Pd-G3 (5.9 mg, 6.5 μmol) and Cs₂CO₃ (42 mg, 0.13 mmol). The mixture was stirred at 100° C. under nitrogen for 10 h. Then the mixture was cooled to rt, diluted with water and extracted with EtOAc. The combined organic layers were dried over Na₂SO₄, filtered and concentrated under reduced pressure to give a residue that was purified by silica gel chromatography (25% EtOAc/PE) to give the title compound.

Step 2: 2-(4,4-difluoropiperidin-1-yl)-N-(2-fluoro-3-sulfamoylphenyl)-5-(trifluoromethyl)-nicotinamide To a stirred mixture of N-(3-(N,N-bis(2,4-dimethoxybenzyl)sulfamoyl)-2-fluorophenyl)-2-(4,4-difluoropiperidin-1-yl)-5-(trifluoromethyl)nicotinamide (20 mg, 0.026 mmol) in DCM (2 mL) at 20° C. was added TFA (2.0 mL, 0.026 mmol). The mixture was stirred at 20° C. for 30 minutes, and then concentrated under reduced pressure. The resulting residue was purified by by reverse phase chromatography (5-95% MeCN in water with 0.1% TFA, C18 column) to give the title compound. LRMS m/z (M+H): calculated 483.1, observed 482.9 483.1. ¹H NMR δ (ppm) (400 MHz, CD₃OD): 8.57 (s, 1H), 8.18 (t, J=7.2 Hz, 1H), 8.13 (d, J=4.0 Hz, 1H), 7.70-7.74 (m, 1H), 7.35 (t, J=8.0 Hz, 1H), 3.68-3.71 (m, 4H), 2.00-2.13 (m, 4H).

TABLE 12

The compound of Example 171 was prepared according to the procedure of Example 170 starting with the appropriate starting materials.

| Example | Compound | Name | Calc'd [M + H]⁺ | Observed [M + H]⁺ |
|---|---|---|---|---|
| 171 | | N-(3,4-difluoro-5-sulfamoylphenyl)-2-(4,4-difluoropiperidin-1-yl)-5-(trifluoromethyl)nicotinamide | 501.4 | 501.2 |

Example 172

2-(4,4-difluoroazepan-1-yl)-5-(difluoromethoxy)-N-(3-sulfamoylphenyl)nicotinamide

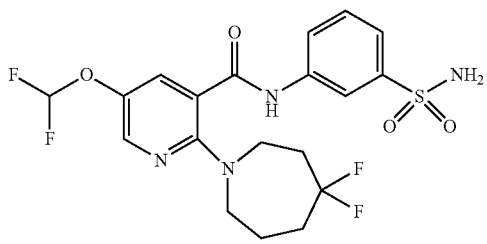 [SMILES: NS(=O)(=O)c1cccc(NC(=O)c2cc(OC(F)F)cnc2N2CCCC(F)(F)CC2)c1]

Step 1: 5-bromo-2-(4,4-difluoroazepan-1-yl)nicotinonitrile To a solution of 5-bromo-2-chloronicotinonitrile (3.0 g, 14 mmol) in NMP (20 mL) was added 4,4-difluoroazepane (2.8 g, 21 mmol) and DIPEA (5.5 mL, 41 mmol). The mixture was stirred at 50° C. for 10 hours, then diluted with water and extracted with EtOAc. The organic layers were washed with brine, dried over anhydrous $Na_2SO_4$, filtered and concentrated to give a residue that was purified by silica gel chromatography (15% EtOAc/hexane) to give the title compound.

Step 2: (5-cyano-6-(4,4-difluoroazepan-1-yl)pyridin-3-yl)boronic acid A mixture of 5-bromo-2-(4,4-difluoroazepan-1-yl)nicotinonitrile (1.5 g, 4.7 mmol), $PdCl_2(dppf)$ (0.35 g, 0.47 mmol), bis(pinacolato)-diboron (2.4 g, 9.5 mmol) and potassium acetate (0.93 g, 9.5 mmol) in dioxane (20 mL) was degassed and backfilled with nitrogen three times. The mixture was heated to 80° C. for 2 h. Then the mixture was cooled to rt, filtered and concentrated under reduce pressure to give the title compound.

Step 3: 2-(4,4-difluoroazepan-1-yl)-5-hydroxynicotinonitrile To a mixture of (5-cyano-6-(4,4-difluoroazepan-1-yl)pyridin-3-yl)boronic acid (1.7 g, 4.6 mmol) in THF (10 mL) and water (10 mL) was added aqueous KOH (0.26 g, 4.6 mmol) at 0° C., followed by $H_2O_2$ (0.40 mL, 4.6 mmol). The reaction mixture was warmed to 20° C. for 2 hours, then quenched with aqueous sodium thiosulfate solution, acidified to pH~6 with aqueous hydrochloric acid (1.2 N), diluted with water and extracted with EtOAc. The combined organic layers were washed with brine, dried over anhydrous $Na_2SO_4$, filtered and concentrated under reduced pressure to give a residue that was purified by silica gel chromatography (0-26% ethyl acetate/PE) to give the title compound.

Step 4: 2-(4,4-difluoroazepan-1-yl)-5-(difluoromethoxy)nicotinonitrile A mixture of 2-(4,4-difluoroazepan-1-yl)-5-hydroxynicotinonitrile (1.0 g, 4.0 mmol), $K_2CO_3$ (1.1 g, 7.9 mmol) and sodium chlorodifluoroacetate (1.2 g, 7.9 mmol) in DMF (10 mL) and water (2 mL) was stirred at 110° C. for 10 h, then diluted with water and extracted with EtOAc. The organic layers were washed with brine, dried over anhydrous $Na_2SO_4$, filtered and concentrated to give a residue that was purified by silica gel chromatography (0-25% ethyl acetate/PE) to give the title compound.

Step 5: 2-(4,4-difluoroazepan-1-yl)-5-(difluoromethoxy)nicotinamide To a mixture of 2-(4,4-difluoroazepan-1-yl)-5-(difluoromethoxy)nicotinonitrile (0.25 g, 0.82 mmol) in DMSO (5 mL) was added $K_2CO_3$ (0.23 g, 1.6 mmol), followed by $H_2O_2$ (3.0 mL, 34 mmol). The mixture was warmed to 35° C. for 1 hour, then diluted with water and extracted with EtOAc. The organic layers were washed with brine, dried over anhydrous $Na_2SO_4$, filtered and concentrated to give a residue that was purified by silica gel chromatography (50% EtOAc/PE) to give the title compound.

Step 6: N-(3-(N,N-bis(2,4-dimethoxybenzyl)sulfamoyl)phenyl)-2-(4,4-difluoroazepan-1-yl)-5-(difluoromethoxy)nicotinamide A mixture of BrettPhos-Pd-G3 (14 mg, 0.016 mmol), 2-(4,4-difluoroazepan-1-yl)-5-(difluoromethoxy)nicotinamide (50 mg, 0.16 mmol), 3-bromo-N,N-bis(2,4-dimethoxybenzyl)benzenesulfonamide (0.12 g, 0.23 mmol) and $Cs_2CO_3$ (0.10 g, 0.31 mmol) in dioxane (5 mL) was degassed and backfilled with nitrogen three times. The mixture was heated to 100° C. for 4 h, then cooled to rt, filtered and concentrated. The resulting residue that was purified by silica gel chromatography (50% EtOAc/PE) to give the title compound.

Step 7: 2-(4,4-difluoroazepan-1-yl)-5-(difluoromethoxy)-N-(3-sulfamoylphenyl)nicotinamide A solution of N-(3-(N,N-bis(2,4-dimethoxybenzyl)sulfamoyl)phenyl)-2-(4,4-difluoroazepan-1-yl)-5-(difluoromethoxy)nicotinamide (0.11 g, 0.13 mmol) in TFA (1 mL) and DCM (1 mL) was stirred at 20° C. for 10 hours. Then the mixture was concentrated under reduced pressure to give a residue that was purified by reverse phase chromatography (35-100% MeCN in water with 0.1% TFA, C18 column) to give the title compound. LRMS m/z (M+H): calculated 477.1, observed 477.1. $^1$H NMR δ (ppm) (400 MHz, $CD_3OD$): 8.33 (t, J=2.0 Hz, 1H), 8.14 (d, J=2.4 Hz, 1H), 7.82 (d, J=8.0 Hz, 1H), 7.64-7.71 (m, 2H), 7.50-7.57 (m, 1H), 6.54-6.97 (m, 1H), 3.66-3.75 (m, 2H), 3.50 (t, J=6.0 Hz, 2H), 2.25-2.41 (m, 2H), 1.86-2.07 (m, 4H).

Example 173

5-chloro-2-(4,4-difluoroazepan-1-yl)-N-(3-(methylsulfonyl)phenyl)nicotinamide

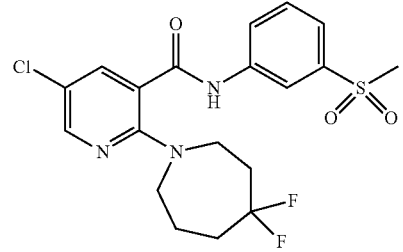 [SMILES: CS(=O)(=O)c1cccc(NC(=O)c2cc(Cl)cnc2N2CCCC(F)(F)CC2)c1]

Step 1: methyl 5-chloro-2-(4,4-difluoroazepan-1-yl)nicotinate To a mixture of 4,4-difluoroazepane hydrochloride (0.35 g, 2.0 mmol) in DMSO (10 mL) was added DIPEA (0.59 mL, 3.4 mmol). The mixture was sonicated, then methyl 2,5-dichloro-nicotinate (0.35 g, 1.7 mmol) and $K_2CO_3$ (0.70 g, 5.1 mmol) was added. The mixture was heated at 50° C. for 16 hours in a sealed vial. Then the mixture was cooled to rt and diluted with EtOAc. The organic layer was washed with 5% aqueous AcOH, water and brine, dried over $MgSO_4$ and concentrated under reduced pressure. The resulting residue was purified by silica gel chromatography (EtOAc/hexanes) to give the title compound.

Step 2: 5-chloro-2-(4,4-difluoroazepan-1-yl)nicotinic acid To a solution of methyl 5-chloro-2-(4,4-difluoroazepan-1-yl)nicotinate (0.42 g, 1.4 mmol) in a 4:4:1 mixture of $THF/MeOH/H_2O$ was added NaOH (4.8 mL, 4.8 mmol, 1M). The mixture was stirred at ambient temperature for 3 days, then concentrated to remove organic solvents, acidified with AcOH and diluted with EtOAc. The organic layer was washed with water and brine, dried over MgSO$_4$, filtered and concentrated to the title compound.

Step 3: 5-chloro-2-(4,4-difluoroazepan-1-yl)-N-(3-(methylsulfonyl)phenyl)nicotinamide To a solution of 5-chloro-2-(4,4-difluoroazepan-1-yl)nicotinic acid (50 mg, 0.17 mmol) in pyridine (1 mL) was added 3-(methylsulfonyl)aniline (35 mg, 0.21 mmol) and EDC (50 mg, 0.26 mmol). The mixture was sonicated and stirred at ambient temperature for 16 h. Then the mixture was concentrated and purified by silica gel chromatography (EtOAc/hexanes) to give the title compound. LRMS m/z (M+H): calculated 444.1, observed 444.1. $^1$H NMR δ (ppm) (500 MHz, CDCl$_3$) □ 9.65 (s, 1H), 8.30 (s, 1H), 8.20 (s, 1H), 8.10 (s, 1H), 7.98 (d, 1H), 7.73 (d, 1H), 7.60 (t, 1H), 3.61 (m, 2H), 3.42 (t, 2H), 3.09 (s, 3H), 2.40 (m, 2H), 2.13 (m, 2H), 1.93 (m, 2H).

TABLE 13

The compounds of Examples 174-178 were prepared according to the procedure of Example 173 starting with the appropriate starting materials.

| Example | Compound | Name | Calc'd [M + H]$^+$ | Observed [M + H]$^+$ |
|---|---|---|---|---|
| 174 | | 2-(azepan-1-yl)-6-chloro-4,5-dimethyl-N-(3-sulfamoylphenyl)-pyridine-3-carboxamide | 437.1 | 437.1 |
| 175 | | 2-(azepan-1-yl)-4-methyl-N-(3-sulfamoyl-phenyl)pyridine-3-carboxamide | 389.2 | 389.2 |
| 176 | | 5-cyano-2-(4,4-difluoroazepan-1-yl)-6-methyl-N-(3-methyl-sulfonylphenyl)pyridine-3-carboxamide | 449.1 | 449.1 |
| 177 | | N-(3-carbamoylphenyl)-5-cyano-2-(4,4-difluoroazepan-1-yl)-6-methyl-pyridine-3-carboxamide | 414.2 | 414.2 |
| 178 | | 2-(azepan-1-yl)-N-(3-carbamoylphenyl)-5-cyano-6-methyl-pyridine-3-carboxamide | 378.2 | 378.2 |

Example 179

5-chloro-2-(4,4-difluoroazepan-1-yl)-N,4,6-trimethyl-N-(3-sulfamoylphenyl)nicotinamide

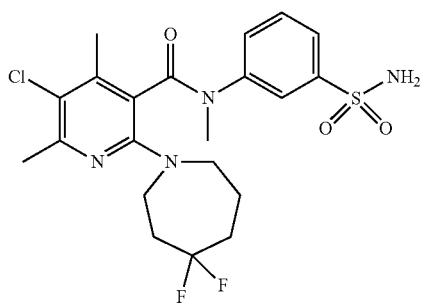 [SMILES: Cc1nc(N2CCCC(F)(F)CC2)c(C(=O)N(C)c2cccc(S(N)(=O)=O)c2)c(C)c1Cl]

Step 1: 5-chloro-2-(4,4-difluoroazepan-1-yl)-4,6-dimethylnicotinonitrile To a mixture of 2,5-dichloro-4,6-dimethylnicotinonitrile (2.0 g, 9.9 mmol) and 4,4-difluoroazepane hydrochloride (2.0 g, 12 mmol) in NMP (15 mL) was added DIPEA (5.2 mL, 30 mmol) at 25° C. The resulting mixture was stirred at 100° C. for 18 h, then additional 4,4-difluoroazepane hydrochloride (0.20 g, 1.2 mmol) was added, and the reaction mixture was stirred at 120° C. for 2 h. The mixture was cooled to room temperature, treated with water and extracted with ethyl acetate. The combined organic layers were washed with brine, dried over Na$_2$SO$_4$, filtered and concentrated under reduced pressure to give a residue that was purified by silica gel chromatography (20% petroleum ether/ethyl acetate) to give the title compound.

Step 2: 5-chloro-2-(4,4-difluoroazepan-1-yl)-4,6-dimethylnicotinamide To a mixture of 5-chloro-2-(4,4-difluoroazepan-1-yl)-4,6-dimethylnicotinonitrile (1.0 g, 3.3 mmol) and KOH (0.56 g, 10 mmol) in DMSO (8 mL) was added H$_2$O$_2$ (2.0 mL, 23 mmol) slowly. The resulting mixture was stirred at 25° C. for 30 minutes. Then the mixture was quenched with saturated Na$_2$SO$_3$ aqueous solution, diluted in water and extracted with ethyl acetate. The combined organic layers were washed with brine, dried over Na$_2$SO$_4$, filtered and concentrated under reduced pressure to give a residue that was purified by silica gel chromatography (45% petroleum ether/ethyl acetate) to give the title compound.

Step 3: N-(3-(N,N-bis(2,4-dimethoxybenzyl)sulfamoyl)phenyl)-5-chloro-2-(4,4-difluoroazepan-1-yl)-4,6-dimethylnicotinamide To a mixture of 5-chloro-2-(4,4-difluoroazepan-1-yl)-4,6-dimethylnicotinamide (0.20 g, 0.63 mmol), 3-bromo-N,N-bis(2,4-dimethoxybenzyl)benzene-sulfonamide (Intermediate 3, 0.34 g, 0.63 mmol) and Cs$_2$CO$_3$ (0.62 g, 1.9 mmol) in dioxane (5 mL) was added Xantphos-G2 (56 mg, 0.063 mmol). The reaction mixture was stirred at 100° C. for 18 h under an atmosphere of nitrogen. Then the mixture was cooled to room temperature, treated with water and extracted with EtOAc. The combined organic layers were washed with brine, dried over Na$_2$SO$_4$, filtered and concentrated under reduced pressure to give a residue that was purified by silica gel chromatography (19% petroleum ether/ethyl acetate 1:1) to give the title compound.

Step 4: N-(3-(N,N-bis(2,4-dimethoxybenzyl)sulfamoyl)phenyl)-5-chloro-2-(4,4-difluoroazepan-1-yl)-N,4,6-trimethylnicotinamide To a mixture of N-(3-(N,N-bis(2,4-dimethoxybenzyl)-sulfamoyl)phenyl)-5-chloro-2-(4,4-difluoroazepan-1-yl)-4,6-dimethylnicotinamide (0.10 g, 0.13 mmol) in THF (3 mL) was added NaH (26 mg, 0.65 mmol) at 25° C. The mixture was stirred at 25° C. for 10 min under an atmosphere of nitrogen, then iodomethane (0.049 mL, 0.78 mmol) was added. The reaction mixture was stirred at 25° C. for 2 hours. Then the mixture was treated with water and extracted with EtOAc. The combined organic layers were washed with brine, dried over Na$_2$SO$_4$, filtered and concentrated under reduced pressure to give the title compound.

Step 5: 5-chloro-2-(4,4-difluoroazepan-1-yl)-N,4,6-trimethyl-N-(3-sulfamoylphenyl)-nicotinamide To a mixture of N-(3-(N,N-bis(2,4-dimethoxybenzyl)sulfamoyl)phenyl)-5-chloro-2-(4,4-difluoroazepan-1-yl)-N,4,6-trimethylnicotinamide (0.12 g crude) in DCM (3 mL) was added TFA (2 mL). The reaction mixture was stirred at 25° C. for 3 hours. Then the mixture was concentrated under reduced pressure and purified by reverse phase chromatography (45-75% MeCN in water with 0.1% TFA, C18 column) to give the title compound. LRMS m/z (M+H): calculated 487.1, observed 487.2. $^1$H NMR δ (400 MHz, CD$_3$OD) 7.66 (d, J=6.8 Hz, 1H), 7.49 (s, 1H), 7.32 (t, J=8.0 Hz, 1H), 7.11 (d, J=8.0 Hz, 1H), 3.51 (td, J=4.8, 12.8 Hz, 1H), 3.45 (s, 3H), 3.32-3.38 (m, 1H), 3.14-3.27 (m, 2H), 2.39 (s, 3H), 2.28 (s, 3H), 1.70-2.15 (m, 6H).

Example 180

2-cyclopropyl-4-(4,4-difluoroazepan-1-yl)-N-(3-sulfamoylphenyl)pyrimidine-5-carboxamide

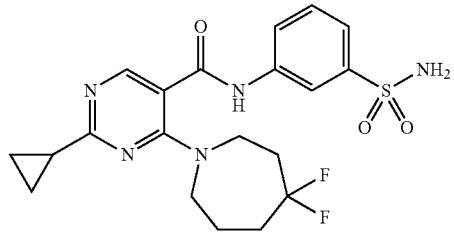 [SMILES: NS(=O)(=O)c1cccc(NC(=O)c2cnc(C3CC3)nc2N2CCCC(F)(F)CC2)c1]

Step 1: ethyl 2-cyclopropyl-4-(4,4-difluoroazepan-1-yl)pyrimidine-5-carboxylate To a solution of ethyl 4-chloro-2-cyclopropylpyrimidine-5-carboxylate (0.20 g, 0.88 mmol) in THF (10 mL) was added DIPEA (0.46 mL, 2.6 mmol) and 4,4-difluoroazepane hydrochloride (0.30 g, 1.8 mmol). The reaction mixture was stirred at 40° C. for 2 hours. The residue was diluted with water and extracted with ethyl acetate. The combined organic layers were washed with brine, dried over Na$_2$SO$_4$, filtered and concentrated under reduced pressure to give a residue that was purified by silica gel chromatography (petroleum ether:ethyl acetate 5:1) to give the title compound.

Step 2: 2-cyclopropyl-4-(4,4-difluoroazepan-1-yl)pyrimidine-5-carboxylic acid To a mixture of ethyl 2-cyclopropyl-4-(4,4-difluoroazepan-1-yl)pyrimidine-5-carboxylate (0.26 g, 0.80 mmol) in EtOH (5 mL) was added a solution of LiOH (38 mg, 1.6 mmol) in water (3 mL) at 25° C. The reaction mixture was stirred at 25° C. for 1 hour and then stirred at 60° C. for 18 hours. The mixture was partitioned between ethyl acetate and water, then the aqueous layer was acidified with 2N HCl to pH 3-4 and extracted with ethyl acetate. The combined organic layers were washed with brine, dried over anhydrous Na$_2$SO$_4$, filtered and concentrated under reduced pressure to give the title compound.

Step 3: 2-cyclopropyl-4-(4,4-difluoroazepan-1-yl)-N-(3-sulfamoylphenyl)pyrimidine-5-carboxamide To a mixture of 2-cyclopropyl-4-(4,4-difluoroazepan-1-yl)pyrimidine-5-carboxylic acid (60 mg, 0.20 mmol) and 3-aminobenzenesulfonamide (42 mg, 0.24 mmol) in pyridine (1.5 mL) was added POCl$_3$ (0.038 mL, 0.40 mmol) at 0° C. The reaction mixture was stirred at 50° C. for 2 hours. Then the mixture was purified by reverse phase chromatography (32-62% (45-75% MeCN in water with 0.1% TFA, C18 column) to give the title compound. LRMS m/z (M+H): calculated 452.2, observed 452.2. $^1$H NMR δ (500 MHz, CD$_3$OD) 8.34 (s, 1H), 8.30 (s, 1H), 7.84 (d, J=8.0 Hz, 1H), 7.70 (d, J=8.0 Hz, 1H), 7.52-7.59 (m, 1H), 3.79-3.81 (m, 2H), 3.56 (t, J=6.0 Hz, 2H), 2.31-2.33 (m, 2H), 2.07-2.14 (m, 1H), 1.98-2.01 (m, 4H), 1.04-1.15 (m, 4H).

Example 181

3-(4,4-difluoroazepan-1-yl)-N-(3-sulfamoylphenyl)-6-(trifluoromethyl)pyridazine-4-carboxamide

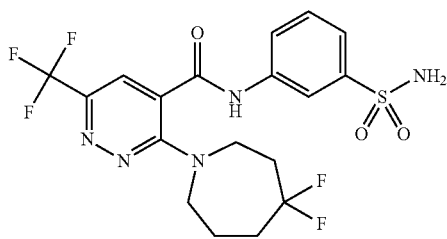 [SMILES: NS(=O)(=O)c1cccc(NC(=O)c2cc(C(F)(F)F)nnc2N2CCCC(F)(F)CC2)c1]

Step 1: 4,4-difluoro-1-(6-(trifluoromethyl)pyridazin-3-yl)azepane To a solution of 3-chloro-6-(trifluoromethyl)pyridazine (0.30 g, 1.6 mmol) in NMP (5 mL) was added 4,4-difluoroazepane hydrochloride (0.34 g, 2.0 mmol) and DIPEA (0.86 mL, 4.9 mmol). The reaction mixture was heated to 150° C. for 10 min under microwave irradiation. Then the mixture was cooled to 20° C., diluted in water and extracted with ethyl acetate. The combined organic layers were dried over Na$_2$SO$_4$, filtered and concentrated under reduced pressure to give a residue that was purified by silica gel chromatography (0-30% petroleum ether/ethyl acetate) to give the title compound.

Step 2: 1-(4-bromo-6-(trifluoromethyl)pyridazin-3-yl)-4,4-difluoroazepane A mixture of 4,4-difluoro-1-(6-(trifluoromethyl)pyridazin-3-yl)azepane (0.30 g, 1.1 mmol) and 1,3-dibromo-5,5-dimethylimidazolidine-2,4-dione (0.92 g, 3.2 mmol) in acetic acid (5 mL) was stirred at 40° C. for 18 h. The mixture was cooled to 20° C., diluted in water and extracted with ethyl acetate. The combined organic layers were dried over Na$_2$SO$_4$, filtered and concentrated under reduced pressure to give a residue that was purified by silica gel chromatography (0-10% petroleum ether/ethyl acetate) to give the title compound.

Step 3: 3-(4,4-difluoroazepan-1-yl)-6-(trifluoromethyl)pyridazine-4-carbonitrile To a solution of 1-(4-bromo-6-(trifluoromethyl)pyridazin-3-yl)-4,4-difluoroazepane (0.15 g, 0.42 mmol) in DMA (2 mL) was added dicyanozinc (0.25 g, 2.1 mmol), dppf (46 mg, 0.083 mmol) and Pd$_2$(dba)$_3$ (38 mg, 0.042 mmol). The reaction mixture was degassed and backfilled with nitrogen three times, then stirred at 160° C. for 1 hour. The mixture was cooled to 20° C., diluted in water and extracted with ethyl acetate. The combined organic layers were washed with brine, dried over Na$_2$SO$_4$, filtered and concentrated under reduced pressure to give a residue that was purified by silica gel chromatography (25% ethyl acetate in petroleum ether) to give the title compound.

Step 4: 3-(4,4-difluoroazepan-1-yl)-6-(trifluoromethyl)pyridazine-4-carboxamide To a solution of 3-(4,4-difluoroazepan-1-yl)-6-(trifluoromethyl)pyridazine-4-carbonitrile (0.11 g, 0.36 mmol) in DMSO (2 mL) was added K$_2$CO$_3$ (0.25 g, 1.8 mmol) and hydrogen peroxide (0.12 g, 3.6 mmol) at 20° C. The reaction mixture was stirred at 20° C. for 1 hour. Then the mixture was diluted in water and extracted with ethyl acetate. The combined organic layers were washed with brine, dried over Na$_2$SO$_4$, filtered and concentrated under reduced pressure to give a residue that was purified by silica gel chromatography (50% ethyl acetate in petroleum ether) to give the title compound.

Step 5: N-(3-(N,N-bis(2,4-dimethoxybenzyl)sulfamoyl)phenyl)-3-(4,4-difluoroazepan-1-yl)-6-(trifluoromethyl)pyridazine-4-carboxamide To a stirred mixture of 3-(4,4-difluoroazepan-1-yl)-6-(trifluoromethyl)pyridazine-4-carboxamide (40 mg, 0.12 mmol), 3-bromo-N,N-bis(2,4-dimethoxybenzyl)benzenesulfonamide (Intermediate 3, 99 mg, 0.18 mmol) and Cs$_2$CO$_3$ (0.12 g, 0.37 mmol) in 1,4-dioxane (2 mL) was added Brettphos Pd G3 (11 mg, 0.012 mmol). The reaction mixture was stirred at 100° C. for 18 h. Then the mixture was cooled to room temperature, diluted with water and extracted with ethyl acetate. The combined organic layers were washed with brine, dried over Na$_2$SO$_4$, filtered and concentrated under reduced pressure to give the title compound.

Step 6: 3-(4,4-difluoroazepan-1-yl)-N-(3-sulfamoylphenyl)-6-(trifluoromethyl)pyridazine-4-carboxamide To a mixture of N-(3-(N,N-bis(2,4-dimethoxybenzyl)sulfamoyl)phenyl)-3-(4,4-difluoroazepan-1-yl)-6-(trifluoromethyl)pyridazine-4-carboxamide (80 mg, 0.10 mmol) in DCM (2 mL) was added TFA (2 mL). The reaction mixture was stirred at 20° C. for 1 hour. Then the mixture was concentrated under reduced pressure to give a residue that was purified by reverse phase chromatography (37-57% MeCN in water with 0.1% TFA, C18 column) to give the title compound. LRMS m/z (M+H): calculated 480.1 observed 480.0. $^1$H NMR δ (500 MHz, CD$_3$OD) 8.36 (t, J=2.0 Hz, 1H), 7.95 (s, 1H), 7.83-7.88 (m, 1H), 7.74 (dd, J=1.0, 8.0 Hz, 1H), 7.52-7.63 (m, 1H), 3.98 (td, J=2.5, 5.5 Hz, 2H), 3.68 (t, J=5.5 Hz, 2H), 2.34-2.49 (m, 2H), 2.00-2.15 (m, 4H).

Example of a Pharmaceutical Composition

As a specific embodiment of an oral pharmaceutical composition, a 100 mg potency tablet is composed of 100 mg of any one of the Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

Biological Assays

Qube® Assay Experimental Procedure

Compounds were tested on human Nav1.8 and Nav1.5 channels stably expressed in human embryo kidney (HEK) 293 cells. Sodium current measurements on Qube® were conducted as follows: automated 384-well patch-clamp assays on the Qube® platform (Sophion Biosciences) were used to measure the inhibition of sodium flow through human Nav1.8 and Nav1.5 channels. Whole-cell voltage-clamp recordings were performed in QChips® (Sophion Biosciences) at room temperature. Nav1.8 current measurements on Qube® were obtained as follows: Nav1.8 currents were elicited with a 10 second 1 Hertz (Hz) pulse train from a holding potential of −90 millivolts (mV), delivered to the cells once per minute in the control condition (DMSO only) and after compound addition. The 1 hertz pulse train stimulation consisted of ten test pulses to 10 millivolt (mV) for 20 milliseconds (ms), each of which was followed by a 980 millisecond repolarization to −67 millivolts. At the end of the 10 second pulse train stimulation, a 5 second hyperpolarization step to −100 millivolt (mV) was used to recover Nav1.8 from fast inactivation. The peak currents elicited by the $1^{st}$ and $10^{th}$ test pulses were used to determine $IC_{50}$ values for resting inhibition and inactivated state inhibition. Nav1.5 current measurements on Qube® were obtained as follows: Nav1.5 currents were elicited with a 20 second 3 Hertz pulse train in the control condition (DMSO only) and after compound addition. The pulse train consisted of sixty 20 millisecond test pulses to 0 millivolt from a holding potential of −80 millivolt (mV). The average peak currents elicited by the last 3 test pulses were used to determine $IC_{50}$ values for Nav1.5 inhibition.

The following buffers were used for the Qube® recordings: External buffer for Nav1.8 Qube® recording: 150 NaCl, 2 $CaCl_2$, 5 KCl, 1 Mg $Cl_2$, 10 HEPES, 12 Dextrose; External buffer for Qube® Nav1.5 recording: 120 N-Methyl-D-Glucamine, 40 NaCl, 1 KCl, 2.7 $CaCl_2$, 5 HEPES, 0.5 $MgCl_2$; and Internal buffer for Qube® recording: 120 CsF, 30 CsCl, 10 EGTA, 5 HEPES, 5 NaF, 2 $MgCl_2$.

For all Qube® experiments offline analysis was used to determine percent inhibition as a function of drug concentration. $IC_{50}$ values were determined by fitting to the Hill equation.

The compounds of the present invention have Nav 1.8 $IC_{50}$ values in the Qube® Assay of less than 10 micromolar. Specific $IC_{50}$ values of the compounds of Examples 1-181 in the Qube® Assay are listed in Table 1.

TABLE I

| Example | $IC_{50}$ (nM) |
|---|---|
| 1 | 47 |
| 2 | 0.7 |
| 3 | 7.6 |
| 4 | 14 |
| 5 | 49 |
| 6 | 8325 |
| 7 | 3.5 |
| 8 | 5.8 |
| 9 | 7.0 |
| 10 | 9.2 |
| 11 | 31 |
| 12 | 54 |
| 13 | 13 |
| 14 | 18 |
| 15 | 19 |
| 16 | 24 |
| 17 | 29 |
| 18 | 52 |
| 19 | 295 |
| 20 | 74 |
| 21 | 254 |
| 22 | 470 |
| 23 | 112 |
| 24 | 4433 |
| 25 | 337 |
| 26 | 2.1 |
| 27 | 4427 |
| 28 | 211 |
| 29 | 10 |
| 30 | 12 |
| 31 | 22 |
| 32 | 24 |
| 33 | 44 |
| 34 | 603 |
| 35 | 29 |
| 36 | 31 |
| 37 | 106 |
| 38 | 279 |
| 39 | 2.5 |
| 40 | 1179 |
| 41 | 4629 |
| 42 | 2685 |
| 43 | 57 |
| 44 | 9.5 |
| 45 | 12 |
| 46 | 12 |
| 47 | 29 |
| 48 | 161 |
| 49 | 186 |
| 50 | 239 |
| 51 | 244 |
| 52 | 301 |
| 53 | 304 |
| 54 | 338 |
| 55 | 405 |
| 56 | 448 |
| 57 | 575 |
| 58 | 616 |
| 59 | 698 |
| 60 | 737 |
| 61 | 1615 |
| 62 | 1831 |
| 63 | 2003 |
| 64 | 2155 |
| 65 | 2210 |
| 66 | 2612 |
| 67 | 2984 |
| 68 | 3650 |
| 69 | 4056 |
| 70 | 5476 |
| 71 | 5545 |
| 72 | 6612 |
| 73 | 8387 |
| 74 | 9973 |
| 75 | 16 |
| 76 | 2.2 |
| 77 | 286 |
| 78 | 6.1 |
| 79 | 10 |
| 80 | 11 |
| 81 | 4244 |
| 82 | 60 |
| 83 | 180 |
| 84 | 248 |
| 85 | 1218 |
| 86 | 77 |
| 87 | 7876 |
| 88 | 6.0 |
| 89 | 16 |
| 90 | 17 |
| 91 | 29 |
| 92 | 31 |
| 93 | 59 |
| 94 | 8.4 |
| 95 | 20 |
| 96 | 40 |
| 97 | 49 |
| 98 | 93 |
| 99 | 131 |
| 100 | 227 |
| 101 | 260 |
| 102 | 706 |
| 103 | 2329 |
| 104 | 7329 |

TABLE I-continued

IC$_{50}$ values (nM) for Examples in the Na$_v$1.8 Qube ® Assay

| Example | IC$_{50}$ (nM) |
|---|---|
| 105 | 8724 |
| 106 | 32 |
| 107 | 73 |
| 108 | 148 |
| 109 | 860 |
| 110 | 3772 |
| 111 | 63 |
| 112 | 72 |
| 113 | 73 |
| 114 | 242 |
| 115 | 567 |
| 116 | 3004 |
| 117 | 778 |
| 118 | 2284 |
| 119 | 2403 |
| 120 | 3020 |
| 121 | 189 |
| 122 | 9137 |
| 123 | 3.0 |
| 124 | 15 |
| 125 | 2.4 |
| 126 | 14 |
| 127 | 110 |
| 128 | 14 |
| 129 | 63 |
| 130 | 16 |
| 131 | 113 |
| 132 | 170 |
| 133 | 21 |
| 134 | 25 |
| 135 | 37 |
| 136 | 87 |
| 137 | 82 |
| 138 | 881 |
| 139 | 3464 |
| 140 | 83 |
| 141 | 553 |
| 142 | 1149 |
| 143 | 2175 |
| 144 | 502 |
| 145 | 15 |
| 146 | 26 |
| 147 | 32 |
| 148 | 113 |
| 149 | 351 |
| 150 | 414 |
| 151 | 687 |
| 152 | 67 |
| 153 | 2235 |
| 154 | 1792 |
| 155 | 32 |
| 156 | 19 |
| 157 | 10 |
| 158 | 910 |
| 159 | 2.5 |
| 160 | 681 |
| 161 | 3.2 |
| 162 | 7.1 |
| 163 | 7.3 |
| 164 | 15 |
| 165 | 342 |
| 166 | 30 |
| 167 | 85 |
| 168 | 3.2 |
| 169 | 42 |
| 170 | 119 |
| 171 | 137 |
| 172 | 7.5 |
| 173 | 7.8 |
| 174 | 6.0 |
| 175 | 290 |
| 176 | 7.3 |
| 177 | 28 |
| 178 | 54 |
| 179 | 873 |
| 180 | 24 |
| 181 | 70 |

The scope of the claims should not be limited by the preferred embodiments set forth in the examples, but should be given the broadest interpretation consistent with the description as a whole.

While the invention has been described and illustrated with reference to certain particular embodiments thereof, those skilled in the art will appreciate that various adaptations, changes, modifications, substitutions, deletions, or additions of procedures and protocols may be made without departing from the scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention.

What is claimed is:

1. A compound of structural formula I:

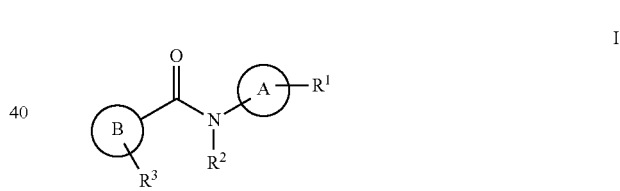

or a pharmaceutically acceptable salt thereof, wherein
A is phenyl or phenyl fused to a saturated or unsaturated 5- or 6-membered ring containing 0-3 heteroatoms independently selected from O, S and N(R$^b$)$_q$, wherein each phenyl, 5-membered ring and 6-membered ring is unsubstituted;
B is selected from the group consisting of:
 (1) pyridine;
 (2) pyrimidine; and
 (3) pyridazine;
wherein pyridine, pyrimidine and pyridazine is unsubstituted or substituted with one to three substituents selected from R$^b$:
R$^1$ is selected from the group consisting of:
 (1) —SO$_2$NH$_2$,
 (2) —SO$_2$NH-heteroaryl,
 (3) —SO$_2$C$_{1-6}$alkyl,
 (4) —SO$_2$C$_{3-6}$cycloalkyl,
 (5) —SO$_2$C$_{3-6}$cycloheteroalkyl,
 (6) —C(O)NH$_2$, and
 (7) —CN,
wherein each alkyl, cycloalkyl, cycloheteroalkyl and heteroaryl is unsubstituted or substituted with one to four substituents selected from R$^d$;

R² is selected from the group consisting of:
(1) hydrogen, and
(2) —C$_{1-6}$alkyl;

R³ is selected from the group consisting of:
(1) pyrrolidine,
(2) azetidine,
(3) piperidine,
(4) piperazine,
(5) azepane,
(6) azocane,
(7) thiomorpholine,
(8) oxazepane,
(9) 1,4-oxazepane,
(10) isoindoline,
(11) 2-isoindoline,
(12) dihydroisoquinoline,
(13) octahydroisoindole,
(14) azabicyclo[2.2.1]heptane,
(15) azabicyclo[3.1.1]heptane,
(16) azabicyclo[4.1.0]heptane,
(17) azabicyclo[3.2.1]octane,
(18) diazabicyclo[3.2.1]octane,
(19) azabicyclo[3.2.0]heptane,
(20) oxa-azabicyclo[3.2.1]octane,
(21) azaspiro[2.5]octane,
(22) azaspiro[2.6]nonane,
(23) azaspiro[3.5]nonane,
(24) oxa-azaspiro[3.5}nonane,
(25) oxa-oazaspiro[4.5]decane,
(26) dihydrothieno[3,2-c]pyridine,
(27) dihydrothiazolo[4,5-c]pyridine,
(28) dihydrooxazolo[4,5-c]pyridine,
(29) dihydroimidazo[1,2-a]pyrazine,
(30) hexahydrofuro[3,2-b]pyrrole,
(31) hexahydrocyclopenta[c]pyrrole, and
(32) azatricyclo[4.3.1.13,8]undecane,
wherein R³ is unsubstituted or substituted with one to eight substituents selected from R$^c$;
each R$^a$ is selected from the group consisting of:
(1) —C$_{1-6}$alkyl,
(2) —OC$_{1-6}$alkyl,
(3) halogen,
(4) —OH,
(5) oxo,
(6) —CN,
(7) —C$_{3-6}$cycloalkyl, and
(8) —C$_{2-5}$cycloheteroalkyl,
wherein each alkyl, cycloalkyl and cycloheteroalkyl is unsubstituted or substituted with one to six substituents selected from halogen, OH, NH$_2$, NH(C$_{1-6}$alkyl) and N(C$_{1-6}$alkyl)$_2$;
each R$^b$ is independently selected from the group consisting of:
(1) —CF$_3$,
(2) —CF$_2$CF$_3$,
(3) —CHF$_2$,
(4) —OCHF$_2$,
(5) —OCH$_2$CF$_3$,
(6) —OCF$_3$,
(7) CN,
(8) halogen,
(9) —Si(C$_{1-6}$alkyl)$_3$,
(10) —C$_{1-6}$alkyl-O—R$^k$,
(11) —C$_{1-6}$alkyl,
(12) —C$_{2-6}$alkenyl,
(13) —C$_{2-6}$alkynyl,
(14) —C$_{3-6}$cycloalkyl,
(15) —C$_{2-6}$cycloheteroalkyl,
(16) aryl,
(17) heteroaryl,
(18) —C$_{1-6}$alkyl-C$_{3-6}$cycloalkyl,
(19) —C$_{1-6}$alkyl-C$_{2-6}$cycloheteroalkyl,
(20) —C$_{1-6}$alkyl-aryl,
(21) —C$_{1-6}$alkyl-heteroaryl,
(22) —C$_{2-6}$alkenyl-C$_{3-6}$cycloalkyl,
(23) —C$_{2-6}$alkenyl-C$_{2-6}$cycloheteroalkyl,
(24) —C$_{2-6}$alkenyl-aryl,
(25) —C$_{2-6}$alkenyl-heteroaryl,
(26) —C$_{2-6}$alkynyl-C$_{3-6}$cycloalkyl,
(27) —C$_{2-6}$alkynyl cycloheteroalkyl,
(28) —C$_{2-6}$alkynyl-aryl,
(29) —C$_{2-6}$alkynyl-heteroaryl,
(30) NO$_2$,
(31) —OH,
(32) —(CH$_2$)$_p$-OC$_{1-6}$alkyl,
(33) —(CH$_2$)$_p$-OC$_{2-6}$alkenyl,
(34) —(CH$_2$)$_p$-OC$_{2-6}$alkynyl,
(35) —(CH$_2$)$_p$-OC$_{3-6}$cycloalkyl,
(36) —(CH$_2$)$_p$-OC$_{2-6}$hetetocycloalkyl,
(37) —(CH$_2$)$_p$-O-aryl,
(38) —(CH$_2$)$_p$-O-heteroaryl,
(39) —OC$_{1-6}$alkyl-C$_{3-6}$cycloalkyl,
(40) —OC$_{1-6}$alkyl-C$_{2-6}$heterocycloalkyl,
(41) —OC$_{1-6}$alkyl-aryl,
(42) —OC$_{1-6}$alkyl-heteroaryl,
(43) —S(O)$_m$R$^k$,
(44) —C$_{1-6}$alkyl-S(O)$_m$R$^k$,
(45) —C(O)R$^k$,
(46) —N(R$^i$)$_2$, and
(47) —NR$^i$R$^k$,
wherein each R$^b$ is unsubstituted or substituted with one to five substituents selected from R$_f$;
each R$^C$ is independently selected from the group consisting of:
(1) —CF$_3$,
(2) —CH$_2$CF$_3$,
(3) —CHF$_2$,
(4) —OCHF$_2$,
(5) —OCF$_3$,
(6) CN,
(7) oxo,
(8) —OH,
(9) halogen,
(10) —C$_{1-6}$alkyl,
(11) —C$_{2-6}$alkenyl,
(12) —C$_{2-6}$alkynyl,
(13) —C$_{3-6}$cycloalkyl,
(14) —C$_{2-6}$cycloheteroalkyl,
(15) —C$_{1-6}$alkyl-C$_{3-6}$cycloalkyl,
(16) —C$_{1-6}$alkyl-C$_{2-6}$cycloheteroalkyl,
(17) —C$_{1-6}$alkyl-aryl,
(18) —C$_{1-6}$alkyl-heteroaryl,
(19) —C$_{1-6}$alkenyl-C$_{3-6}$cycloalkyl,
(20) —C$_{1-6}$alkenyl-aryl,
(21) —C$_{1-6}$alkenyl heteroaryl,
(22) —C$_{1-6}$alkenyl-C$_{2-6}$cycloheteroalkyl,
(23) —C$_{2-6}$alkynyl-C$_{3-6}$cycloalkyl,
(24) —C$_{2-6}$alkynyl-C$_{2-6}$cycloheteroalkyl,
(25) —C$_{2-6}$alkynyl-aryl,
(26) —C$_{2-6}$alkynyl heteroaryl,
(27) —OC$_{1-6}$alkyl,
(28) —OC$_{2-6}$alkenyl,
(29) —OC$_{2-6}$alkynyl,
(30) —OC$_{3-6}$cycloalkyl,

(31) —OC$_{2-6}$heterocycloalkyl,
(32) —O-aryl,
(33) —O-heteroaryl,
(34) —OC$_{1-6}$alkyl-cycloalkyl,
(35) —OC$_{1-6}$alkyl-cycloheteroalkyl,
(36) —OC$_{1-6}$alkyl-aryl,
(37) —OC$_{1-6}$alkyl-heteroaryl,
(38) —S(O)$_m$R$^L$,
(39) —S(O)R$^L$,
(40) —S—R$^L$,
(41) —C$_{1-6}$alkyl-S(O)$_m$R$^L$,
(42) —C(O)R$^L$,
(43) —C(O)C$_{1-6}$alkyl-R$^L$,
(44) —OC(O)R$^L$,
(45) —CO$_2$R$^L$,
(46) aryl, and
(47) heteroaryl,
wherein each R$^C$ is unsubstituted or substituted with one to five substituents selected from R$^g$:
R$^d$ is independently selected from the group consisting of:
(1) hydrogen,
(2) halogen,
(3) OH,
(4) oxo,
(5) —C$_{1-6}$alkyl,
(6) —OC$_{1-6}$alkyl,
(7) NH$_2$,
(8) NH(C$_{1-6}$alkyl), and
(9) N(C$_{1-6}$alkyl)$_2$;
each R$^e$ is independently selected from the group consisting of:
(1) hydrogen,
(2) —C$_{1-6}$alkyl, and
(3) C$_{2-6}$alkenyl;
each R$_f$ is selected from the group consisting of:
(1) halogen,
(2) —C$_{1-6}$alkyl,
(3) —OH,
(4) —OC$_{1-6}$alkyl,
(5) —OC$_{3-6}$cycloalkyl,
(6) —OC$_{2-6}$cycloheteroalkyl,
(7) CN,
(8) —NH$_2$,
(9) —NH(C$_{1-6}$alkyl),
(10) —NH(C$_{3-6}$cycloalkyl),
(11) —NH(C$_{2-6}$cycloheteroalkyl),
(12) —N(C$_{1-6}$alkyl)$_2$,
(13) —N(C$_{3-6}$cycloalkyl)$_2$, and
(14) —N(C$_{2-6}$cycloheteroalkyl)$_2$,
wherein each alkyl, cycloalkyl, and cycloheteroalkyl is unsubstituted or substituted with one to three substituents independently selected from: —OH, halogen, cyano, and —S(O)$_2$CH$_3$;
each R$^g$ is selected from the group consisting of:
(1) halogen,
(2) C$_{1-6}$alkyl,
(3) —OH,
(4) —OC$_{1-6}$alkyl,
(5) —S(O)$_m$-C$_{1-6}$alkyl,
(6) —CN,
(7) —CF$_3$,
(8) —OCHF$_2$, and
(9) —OCF$_3$,
wherein each alkyl is unsubstituted or substituted with one to three substituents independently selected from: —OH, halogen, cyano, and —S(O)$_2$CH$_3$;

each R$^h$ is independently selected from the group consisting of:
(1) hydrogen, and
(2) —C$_{1-6}$alkyl;
each R$^i$ is independently selected from the group consisting of:
(1) hydrogen, and
(2) —C$_{1-6}$alkyl;
each R$^j$ is selected from the group consisting of:
(1) —C$_{1-6}$alkyl,
(2) —C$_{2-6}$alkenyl,
(3) —C$_{3-6}$cycloalkyl,
(4) —C$_{2-6}$cycloheteroalkyl,
(5) aryl, and
(6) heteroaryl,
wherein each alkyl, alkenyl, cycloalkyl, cycloheteroalkyl, aryl and heteroaryl is unsubstituted or substituted with one to three substituents independently selected from: —C$_{1-6}$alkyl, —C$_{3-6}$cycloalkyl, —OH, —OC$_{1-6}$alkyl, —OC$_{3-6}$cycloalkyl, halogen, cyano, and —S(O)$_2$CH$_3$;
each R$^k$ is selected from the group consisting of:
(1) —C$_{1-6}$alkyl,
(2) —C$_{2-6}$alkenyl,
(3) —C$_{3-6}$cycloalkyl,
(4) —C$_{3-6}$cycloalkyl,
(5) —C$_{2-6}$cycloheteroalkyl,
(6) aryl, and
(7) heteroaryl,
wherein each alkyl, alkenyl, cycloalkyl, cycloheteroalkyl, aryl and heteroaryl is unsubstituted or substituted with one to three substituents independently selected from: —C$_{1-6}$alkyl, —C$_{3-6}$cycloalkyl, —OH, —OC$_{1-6}$alkyl, —OC$_{3-6}$cycloalkyl, halogen, cyano, and —S(O)$_2$CH$_3$;
each R$^L$ is selected from the group consisting of:
(1) —C$_{1-6}$alkyl,
(2) —C$_{2-6}$alkenyl,
(3) —C$_{3-6}$cycloalkyl,
(4) —C$_{2-6}$cycloheteroalkyl,
(5) aryl, and
(6) heteroaryl,
wherein each alkyl, alkenyl, cycloalkyl, cycloheteroalkyl, aryl and heteroaryl is unsubstituted or substituted with one to three substituents independently selected from: —C$_{1-6}$alkyl, —C$_{3-6}$cycloalkyl, —OH, —OC$_{1-6}$alkyl, —OC$_{3-6}$cycloalkyl, halogen, cyano, and —S(O)$_2$CH$_3$;
each R$^m$ is independently selected from the group consisting of:
(1) hydrogen, and
(2) —C$_{1-6}$alkyl;
each n is independently 0, 1, 2, 3 or 4;
each m is independently 0, 1 or 2;
each p is independently 0, 1, 2, 3 or 4;
each q is independently 0 or 1; and
each r is independently 0 or 1.

2. The compound according to claim 1 wherein R$^2$ is hydrogen; or a pharmaceutically acceptable salt thereof.

3. The compound according to claim 1 wherein A is selected from the group consisting of:
(1) phenyl,
(2) dihydrobenzothiazole,
(3) dihydrobenzoisothiazole, and
(4) benzothiophene,
wherein A is unsubstituted;
or a pharmaceutically acceptable salt thereof.

4. The compound according to claim 1 wherein A is phenyl, wherein phenyl is unsubstituted; or a pharmaceutically acceptable salt thereof.

5. The compound according to claim 1 wherein B is pyridine, wherein pyridine is unsubstituted or substituted with one to three substituents selected from $R^b$; or a pharmaceutically acceptable salt thereof.

6. The compound according to claim 1 wherein $R^1$ is selected from the group consisting of:
(1) —$SO_2NH_2$,
(2) —$SO_2C_{1-6}$alkyl, and
(3) —$C(O)NH_2$,
wherein each alkyl is unsubstituted or substituted with one to four substituents selected from $R^d$,
or a pharmaceutically acceptable salt thereof.

7. The compound according to claim 1 wherein $R^3$ is selected from the group consisting of:
(1) piperidine,
(2) azepane, and
(3) azaspiro[2.5]octane,
wherein $R^3$ is unsubstituted or substituted with one to eight substituents selected from $R^c$;
or a pharmaceutically acceptable salt thereof.

8. The compound according to claim 1 wherein
A is selected from the group consisting of:
(1) phenyl,
(2) dihydrobenzothiazole,
(3) dihydrobenzoisothiazole, and
(4) benzothiophene,
wherein A is unsubstituted;
B is pyridine, wherein pyridine is unsubstituted or substituted with one to three substituents selected from $R^b$;
$R^1$ is selected from the group consisting of:
(1) —$SO_2NH_2$,
(2) —$SO_2NH$-heteroaryl,
(3) —$SO_2C_{1-6}$alkyl,
(4) —$SO_2C_{3-6}$cycloalkyl,
(5) —$SO_2C_{3-6}$cycloheteroalkyl,
(6) —$C(O)NH_2$, and
(7) —CN,
wherein each alkyl, cycloalkyl, cycloheteroalkyl and heteroaryl is unsubstituted or substituted with one to four substituents selected from $R^d$;
$R^2$ is hydrogen;
$R^3$ is selected from the group consisting of:
(1) pyrrolidine,
(2) azetidine,
(3) piperidine,
(4) piperazine,
(5) azepane,
(6) azocane,
(7) thiomorpholine,
(8) oxazepane,
(9) isoindoline,
(10) dihydroisoquinoline,
(11) octahydroisoindole,
(12) azabicyclo[2.2.1]heptane,
(13) azabicyclo[3.1.1]heptane,
(14) azabicyclo[4.1.0]heptane,
(15) azabicyclo[3.2.1]octane,
(16) diazabicyclo[3.2.1]octane,
(17) azabicyclo[3.2.0]heptane,
(18) oxa-azabicyclo[3.2.1]octane,
(19) azaspiro[2.5]octane,
(20) azaspiro[2.6]nonane,
(21) oxa-azaspiro[3.5]nonane,
(22) oxa-oazaspiro[4.5]decane,
(23) dihydrothiazolo[4,5-c]pyridine,
(24) dihydrooxazolo[4,5-c]pyridine,
(25) hexahydrofuro[3,2-b]pyrrole,
(26) hexahydrocyclopenta[c]pyrrole, and
(27) azatricyclo[4.3.1.13,8]undecane,
wherein $R^3$ is unsubstituted or substituted with one to eight substituents selected from $R^C$;
or a pharmaceutically acceptable salt thereof.

9. The compound according to claim 1 wherein $R^2$ is hydrogen;
A is phenyl, wherein phenyl is unsubstituted or substituted with one to three substituents selected from $R^a$;
B is pyridine, wherein pyridine is unsubstituted or substituted with one to three substituents selected from $R^b$;
$R^1$ is selected from the group consisting of:
(1) —$SO_2NH_2$,
(2) —$SO_2C_{1-6}$alkyl, and
(3) —$C(O)NH_2$,
wherein each alkyl is unsubstituted or substituted with one to four substituents selected from $R^d$:
$R^2$ is hydrogen;
$R^3$ is selected from the group consisting of:
(1) piperidine,
(2) azepane, and
(3) azaspiro[2.5]octane,
wherein $R^3$ is unsubstituted or substituted with one to eight substituents selected from $R^c$;
or a pharmaceutically acceptable salt thereof.

10. A compound selected from:
(1) 2-(4,4-difluoropiperidin-1-yl)-N-(3-sulfamoylphenyl)-5-(trifluoromethyl)-nicotinamide;
(2) 2-(azepan-1-yl)-5-chloro-4,6-dimethyl-N-(3-sulfamoylphenyl)nicotinamide;
(3) 2-(azepan-1-yl)-6-chloro-5-fluoro-4-methyl-N-(3-sulfamoylphenyl)pyridine-3-carboxamide;
(4) 2-(azepan-1-yl)-4,6-dimethyl-N-(3-sulfamoylphenyl)pyridine-3-carboxamide;
(5) 5-chloro-2-(3,3-difluoropyrrolidin-1-yl)-4,6-dimethyl-N-(3-sulfamoylphenyl)pyridine-3-carboxamide;
(6) 5-fluoro-2-(1-piperidyl)-N-(3-sulfamoylphenyl)pyridine-3-carboxamide;
(7) 2-(azepan-1-yl)-5-chloro-4,6-dimethyl-N-(3 -methylsulfonylphenyl)pyridine-3-carboxamide;
(8) 6-chloro-2-(4,4-difluoroazepan-1-yl)-4-methyl-N-(3-methylsulfonylphenyl)pyridine-3-carboxamide;
(9) 6-chloro-2-(4,4-difluoroazepan-1-yl)-N-(3-methylsulfonylphenyl)pyridine-3-carboxamide;
(10) 2-(4,4-difluoroazepan-1-yl)-6-methyl-N-(3-methylsulfonylphenyl)pyridine-3-carboxamide;
(11) 2-(4,4-difluoroazepan-1-yl)-6-methoxy-N-(3-methylsulfonylphenyl)pyridine-3-carboxamide;
(12) 5-chloro-4,6-dimethyl-N-(3-methylsulfonylphenyl)-2-(1-piperidyl)pyridine-3-carboxamide;
(13) 2-(6-azaspiro [2.5]octan-6-yl)-N-(3-carbamoylphenyl)-5-chloro-4,6-dimethyl-pyridine-3-carboxamide;
(14) N-(3-carbamoylphenyl)-6-chloro-2-(4,4-difluoroazepan-1-yl)pyridine-3-carboxamide;
(15) N-(3-carbamoylphenyl)-5-chloro-2-(4,4-difluoroazepan-1-yl)pyridine-3-carboxamide;
(16) N-(3-carbamoylphenyl)-5-chloro-2-(4,4-difluoro-1-piperidyl)-4,6-dimethyl-pyridine-3-carboxamide;
(17) N-(3-carbamoylphenyl)-6-chloro-2-(4,4-difluoroazepan-1-yl)-4-methyl-pyridine-3-carboxamide;
(18) N-(3-carbamoylphenyl)-2-(4,4-difluoroazepan-1-yl)-6-methoxy-pyridine-3-carboxamide;
(19) N-(3-carbamoylphenyl)-5-chloro-4,6-dimethyl-2-(1-piperidyl)pyridine-3-carboxamide;
(20) 5-chloro-N-(3-cyanophenyl)-2-(4,4-difluoro-1-piperidyl)-4,6-dimethyl-pyridine-3-carboxamide;

(21) 2-(azepan-1-yl)-N-(3-cyanophenyl)-5-(trifluoromethyl)pyridine-3-carboxamide;
(22) 2-(azepan-1-yl)-N-(4-cyanophenyl)-5-(trifluoromethyl)pyridine-3-carboxamide;
(23) 2-(azepan-1-yl)-5-methyl-N-(3-sulfamoylphenyl) nicotinamide;
(24) 2-(azepan-1-yl)-N-(3-pyrrolidin-1-ylsulfonylphenyl)-5-(trifluoromethyl)pyridine-3-carboxamide;
(25) 2-(azepan-1-yl)-N-(2-hydroxy-5-sulfamoyl-phenyl)-5-(trifluoromethyl)pyridine-3-carboxamide;
(26) 2-(azepan-1-yl)-5-chloro-6-methyl-N-(3-sulfamoylphenyl)nicotinamide;
(27) 2-(piperidin-1-yl)-N-(3-sulfamoylphenyl)-5-(p-tolyl)nicotinamide;
(28) N-(2,4-difluoro-3-sulfamoylphenyl)-2-(4,4-difluoropiperidin-1-yl)-5-(trifluoromethyl)nicotinamide;
(29) 2-(azepan-1-yl)-6-chloro-4-methyl-N-(3-sulfamoylphenyl)nicotinamide;
(30) 2-(azepan-1-yl)-5,6-dimethyl-N-(3-sulfamoylphenyl)pyridine-3-carboxamide;
(31) 2-(azepan-1-yl)-5-chloro-N-(3-sulfamoylphenyl)pyridine-3-carboxamide;
(32) 2-(azepan-1-yl)-5-bromo-N-(3-sulfamoylphenyl)pyridine-3-carboxamide;
(33) 2-(azepan-1-yl)-4-bromo-N-(3-sulfamoylphenyl)pyridine-3-carboxamide;
(34) 2-(azepan-1-yl)-5-(3-pyridyl)-N-(3-sulfamoylphenyl)pyridine-3-carboxamide;
(35) 2-(azepan-1-yl)-5-bromo-N-(3-methylsulfonylphenyl)pyridine-3-carboxamide;
(36) 2-(azepan-1-yl)-5,6-dimethyl-N-(3-methylsulfonylphenyl)pyridine-3-carboxamide;
(37) 2-(azepan-1-yl)-N-(3-carbamoylphenyl)-5,6-dimethyl-pyridine-3-carboxamide;
(38) 2-(azepan-1-yl)-5-bromo-N-(3-carbamoylphenyl) pyridine-3-carboxamide;
(39) 2-(4,4-difluoroazepan-1-yl)-N-(3-sulfamoylphenyl)-5-(trifluoromethoxy)nicotinamide;
(40) 6-(tert-butyl)-5-chloro-2-(piperidin-1-yl)-N-(3-sulfamoylphenyl)nicotinamide;
(41) 6-tert-butyl-N-(3-methylsulfonylphenyl)-2-(1-piperidyl)pyridine-3-carboxamide;
(42) 6-(tert-butyl)-2-(piperidin-1-yl)-N-(3-sulfamoylphenyl)nicotinamide;
(43) 2-(6-azaspiro [2.5]octan-6-yl)-N-(3 -sulfamoylphenyl)-5-(trifluoromethyl)nicotinamide;
(44) 2-(azepan-1-yl)-N-(3-sulfamoylphenyl)-5-(trifluoromethyl)pyridine-3-carboxamide;
(45) 2-[rac-3-azabicyclo[3.2.1]octan-3-yl]-N-(3-sulfamoylphenyl)-5-(trifluoromethyl)pyridine-3-carboxamide;
(46) N-(3-sulfamoylphenyl)-2-(4-azatricyclo-[4.3.1.13,8] undecan-4-yl)-5-(trifluoromethyl)-nicotinamide;
(47) N-(3-sulfamoylphenyl)-5-(trifluoromethyl)-2-(3,3,5-trimethylazepan-1-yl)pyridine-3-carboxamide;
(48) methyl 1-[3-[(3 -sulfamoylphenyl)carbamoyl]-5-(trifluoromethyl)-2-pyridyl]azepane-4-carboxylate;
(49) 2-(4-methoxyazepan-1-yl)-N-(3-sulfamoylphenyl)-5-(trifluoromethyl)pyridine-3-carboxamide;
(50) 2-[4-(difluoromethyl)-1-piperidyl]-N-(3-sulfamoylphenyl)-5-(trifluoromethyl)pyridine-3-carboxamide;
(51) 2-(3,3-difluoro-1-piperidyl)-N-(3 -sulfamoylphenyl)-5-(trifluoromethyl)pyridine-3-carboxamide;
(52) 2-(8-oxa-3-azabicyclo[3.2.1]octan-3-yl)-N-(3-sulfamoylphenyl)-5-(trifluoromethyl)pyridine-3-carboxamide;
(53) 2-(4-hydroxy-4-methyl-azepan-1-yl)-N-(3-sulfamoylphenyl)-5-(trifluoromethyl)pyridine-3-carboxamide;
(54) 2-[(3S)-3-fluoroazepan-1-yl]-N-(3-sulfamoylphenyl)-5-(trifluoromethyl)pyridine-3-carboxamide;
(55) 2-(6,7-dihydro-4H-thiazolo[4,5-c]pyridin-5-yl)-N-(3-sulfamoylphenyl)-5-(trifluoromethyl)-pyridine-3-carboxamide;
(56) 2-(1,4-oxazepan-4-yl)-N-(3-sulfamoylphenyl)-5-(trifluoromethyl)pyridine-3-carboxamide;
(57) 2-(8-oxa-3-azabicyclo[3.2.1]octan-3-yl)-N-(3-sulfamoylphenyl)-5-(trifluoromethyl)pyridine-3-carboxamide;
(58) N-(3-sulfamoylphenyl)5-(trifluoromethyl)-2-[3-(trifluoromethyl)azetidin-1-yl]pyridine-3-carboxamide;
(59) 2-(6-azabicyclo[3.2.0]heptan-6-yl)-N-(3-sulfamoylphenyl)-5-(trifluoromethyl)pyridine-3-carboxamide;
(60) 2-(3,3-difluoropyrrolidin-1-yl)-N-(3-sulfamoylphenyl)-5 -(trifluoromethyl)pyridine-3-carboxamide;
(61) methyl 1-[3-[(3-sulfamoylphenyl)carbamoyl]-5-(trifluoromethyl)-2-pyridyl]piperidine-4-carboxylate;
(62) 2-(3 -fluoropyrrolidin-1-yl)-N-(3-sulfamoylphenyl)-5 -(trifluoromethyl)pyridine-3-carboxamide;
(63) 2-pyrrolidin-1-yl-N-(3-sulfamoylphenyl)-5-(trifluoromethyl)pyridine-3-carboxamide;
(64) 2-(6-oxa-3-azabicyclo[3.2.1]octan-3-yl)-N-(3-sulfamoylphenyl)-5-(trifluoromethyl)pyridine-3-carboxamide;
(65) 2-(4-hydroxyazepan-1-yl)-N-(3 -sulfamoylphenyl)-5-(trifluoromethyl)pyridine-3-carboxamide;
(66) 2-(4-methoxy-1-piperidyl)-N-(3-sulfamoylphenyl)-5-(trifluoromethyl)pyridine-3-carboxamide;
(67) methyl 1-[3-[(3-sulfamoylphenyl)carbamoyl]-5-(trifluoromethyl)-2-pyridyl]azepane-3-carboxylate;
(68) 2-(2-isobutylazepan-1-yl)-N-(3 -sulfamoylphenyl)-5 -(trifluoromethyl)pyridine-3-carboxamide;
(69) 2-morpholino-N-(3 -sulfamoylphenyl)-5-(trifluoromethyl)pyridine-3-carboxamide;
(70) 2-(1,1-dioxo-1,4-thiazinan-4-yl)-N-(3-sulfamoylphenyl)-5-(trifluoromethyl)pyridine-3-carboxamide;
(71) 2-[rac-(1S,5R and 1R,5S)-8-methyl-3,8-diazabicyclo[3.2.1]octan-3-yl]-N-(3-sulfamoylphenyl)-5-(trifluoromethyl)pyridine-3 -carboxamide;
(72) 2-(1-oxa-8-azaspiro [4.5]decan-8-yl)-N-(3-sulfamoylphenyl)-5 -(trifluoromethyl)pyridine-3-carboxamide;
(73) 2-(2-methyl-6,7-dihydro-4H-oxazolo[4,5-c]pyridin-5-yl)-N-(3-sulfamoylphenyl)-5-(trifluoromethyl)pyridine-3-carboxamide;
(74) methyl 4-[3-[(3-sulfamoylphenyl)carbamoyl]-5-(trifluoromethyl)-2-pyridyl]piperazine-1-carboxylate;
(75) N-(3-carbamoylphenyl)-2-(4,4-difluoroazepan-1-yl)-6-methylnicotinamide;
(76) 2-(6-azaspiro[2.5]octan-6-yl)-5-chloro-4,6-dimethyl-N-(3-sulfamoylphenyl)pyridine-3-carboxamide;
(77) 2-(1-piperidyl)-N-(3 -sulfamoylphenyl)-6-(trifluoromethyl)pyridine-3-carboxamide;
(78) 2-(4,4-difluoroazepan-1-yl)-N-(3-sulfamoylphenyl)-5-(trifluoromethyl)nicotinamide;
(79) 2-(6-azaspiro [2.6]nonan-6-yl)-N-(3 -sulfamoylphenyl)-5-(trifluoromethyl)nicotinamide;
(80) 2-(4,4-dimethylazepan-1-yl)-N-(3-sulfamoylphenyl)-5-(trifluoromethyl)nicotinamide;
(81) 2-(7-oxa-2-azaspiro[3.5]nonan-2-yl)-N-(3-sulfamoylphenyl)-5-(trifluoromethyl)nicotinamide;

(82) 2-(azepan-1-yl)-N-(3-(methylsulfonyl)phenyl)-6-(trifluoromethyl)nicotinamide;
(83) N-(3-carbamoylphenyl)-2-(6-azaspiro[2.5]octan-6-yl)-6-(trifluoromethyl)nicotinamide;
(84) 2-(piperidin-1-yl)-N-(3-sulfamoylphenyl)-6-(trifluoromethoxy)nicotinamide;
(85) 2-(azepan-1-yl)-N-(3-sulfamoylphenyl)-6-(trifluoromethoxy)-5-(trimethylsilyl)nicotinamide;
(86) 2-(azepan-1-yl)-N-(3-sulfamoylphenyl)-5-(trimethylsilyl)nicotinamide;
(87) 2-(2-oxa-7-azaspiro[3.5]nonan-7-yl)-N-(3-sulfamoylphenyl)-5-(trimethylsilyl)nicotinamide;
(88) 2-(azocan-1-yl)-N-(3-sulfamoylphenyl)-5-(trifluoromethyl)pyridine-3-carboxamide;
(89) 2-(azepan-1-yl)-6-chloro-N-(3-sulfamoylphenyl)pyridine-3-carboxamide;
(90) 2-(azepan-1-yl)-6-methyl-N-(3-sulfamoylphenyl)pyridine-3-carboxamide;
(91) 2-(azepan-1-yl)-6-methoxy-N-(3-sulfamoylphenyl)pyridine-3-carboxamide;
(92) 2-(azepan-1-yl)-6-chloro-5-fluoro-N-(3-sulfamoylphenyl)pyridine-3-carboxamide;
(93) 2-(azepan-1-yl)-6-fluoro-N-(3-sulfamoylphenyl)pyridine-3-carboxamide;
(94) 2-(4,4-difluoroazepan-1-yl)-N-(3-methylsulfonylphenyl)-5-(trifluoromethyl)pyridine-3-carboxamide;
(95) 2-(azocan-1-yl)-N-(3-methylsulfonylphenyl)-5-(trifluoromethyl)pyridine-3-carboxamide;
(96) 2-(4,4-difluoro-1,3,3a,5,6,6a-hexahydrocyclopenta[c]pyrrol-2-yl)-N-(3-methylsulfonylphenyl)-5-(trifluoromethyl)pyridine-3-carboxamide;
(97) 2-[(3aS,7aR)-1,3,3a,4,5,6,7,7a-octahydroisoindol-2-yl]-N-(3-methylsulfonylphenyl)-5-(trifluoromethyl)pyridine-3-carboxamide;
(98) 2-(3,4-dihydro-1H-isoquinolin-2-yl)-N-(3-methylsulfonylphenyl)-5-(trifluoromethyl)pyridine-3-carboxamide;
(99) 2-(6-azaspiro[2.5]octan-6-yl)-N-(3-methylsulfonylphenyl)-5-(trifluoromethyl)pyridine-3-carboxamide;
(100) 2-(4-fluoro-1-piperidyl)-N-(3-methylsulfonylphenyl)-5-(trifluoromethyl)pyridine-3-carboxamide;
(101) 2-(8,8-difluoro-6-azaspiro[2.5]octan-6-yl)-N-(3-methylsulfonylphenyl)-5-(trifluoromethyl)pyridine-3-carboxamide;
(102) 2-(3,3-difluoro-1-piperidyl)-N-(3-methylsulfonylphenyl)-5-(trifluoromethyl)pyridine-3-carboxamide;
(103) 2-isoindolin-2-yl-N-(3-methylsulfonylphenyl)-5-(trifluoromethyl)pyridine-3-carboxamide;
(104) 2-(2,3,3a,5,6,6a-hexahydrofuro[3,2-b]pyrrol-4-yl)-N-(3-methylsulfonylphenyl)-5-(trifluoromethyl)pyridine-3-carboxamide;
(105) N-(3-methylsulfonylphenyl)-2-(4-phenyl-1-piperidyl)-5-(trifluoromethyl)pyridine-3-carboxamide;
(106) N-(3-carbamoylphenyl)-2-(4,4-difluoroazepan-1-yl)-5-(trifluoromethyl)pyridine-3-carboxamide;
(107) 2-(azocan-1-yl)-N-(3-carbamoylphenyl)-5-(trifluoromethyl)pyridine-3-carboxamide;
(108) N-(3-carbamoylphenyl)-2-(4,4-difluoro-1,3,3a,5,6,6a-hexahydrocyclopenta[c]pyrrol-2-yl)-5-(trifluoromethyl)pyridine-3-carboxamide;
(109) N-(3-carbamoylphenyl)-2-(8,8-difluoro-6-azaspiro[2.5]octan-6-yl)-5-(trifluoromethyl)pyridine-3-carboxamide;
(110) N-(3-carbamoylphenyl)-2-(3,3-difluoro-1-piperidyl)-5-(trifluoromethyl)pyridine-3-carboxamide;
(111) 2-[(3S,5R)-4,4-difluoro-3,5-dimethyl-1-piperidyl]-N-(1,1-dioxo-2,3-dihydro-1,2-benzothiazol-6-yl)-5-(trifluoromethyl)pyridine-3-carboxamide;
(112) 2-[(3R)-4,4-difluoro-3-methyl-1-piperidyl]-N-(1,1-dioxo-2,3-dihydro-1,2-benzothiazol-6-yl)-5-(trifluoromethyl)pyridine-3-carboxamide;
(113) 2-[(3S)-4,4-difluoro-3-methyl-1-piperidyl]-N-(1,1-dioxo-2,3-dihydro-1,2-benzothiazol-6-yl)-5-(trifluoromethyl)pyridine-3-carboxamide;
(114) N-(3-fluoro-5-sulfamoyl-phenyl)-2-(1-piperidyl)-5-(trifluoromethyl)pyridine-3-carboxamide;
(115) N-(4-fluoro-3-sulfamoyl-phenyl)-2-(1-piperidyl)-5-(trifluoromethyl)pyridine-3-carboxamide;
(116) N-(2-fluoro-5-sulfamoyl-phenyl)-2-(1-piperidyl)-5-(trifluoromethyl)pyridine-3-carboxamide;
(117) 2-(azepan-1-yl)-N-(3-isopropylsulfonylphenyl)-5-(trifluoromethyl)pyridine-3-carboxamide;
(118) 2-(azepan-1-yl)-N-(1,1-dioxobenzothiophen-6-yl)-5-(trifluoromethyl)pyridine-3-carboxamide;
(119) 2-(azepan-1-yl)-N-(3-isobutylsulfonylphenyl)-5-(trifluoromethyl)pyridine-3-carboxamide;
(120) 2-(azepan-1-yl)-N-(3-cyclopentylsulfonylphenyl)-5-(trifluoromethyl)pyridine-3-carboxamide;
(121) 2-(azepan-1-yl)-N-(1,1-dioxo-2,3-dihydro-1,2-benzothiazol-6-yl)-5-(trifluoromethyl)pyridine-3-carboxamide;
(122) 2-(azepan-1-yl)-3-((2-methyl-1,1-dioxido-2,3-dihydrobenzo[d]isothiazol-6-yl)carbamoyl)-5-(trifluoromethyl)pyridine;
(123) (R)-2-(4,4-Difluoro-3-methylpiperidin-1-yl)-N-(3-sulfamoylphenyl)-5-(trifluoromethyl)nicotinamide;
(124) (S)-2-(4,4-difluoro-3-methylpiperidin-1-yl)-N-(3-sulfamoylphenyl)-5-(trifluoromethyl)nicotinamide;
(125) 2-[(3S,5R)-4,4-difluoro-3,5-dimethyl-1-piperidyl]-N-(3-sulfamoylphenyl)-5-(trifluoro-methyl)pyridine-3-carboxamide;
(126) 2-[(3S)-2,2-difluoro-5-azaspiro[2.5]octan-5-yl]-N-(3-sulfamoylphenyl)-5-(trifluoromethyl)pyridine-3-carboxamide;
(127) 2-[(3R)-2,2-difluoro-5-azaspiro[2.5]octan-5-yl]-N-(3-sulfamoylphenyl)-5-(trifluoromethyl)pyridine-3-carboxamide;
(128) 2-[(1R,6R)-7,7-difluoro-6-methyl-3-azabicyclo[4.1.0]heptan-3-yl]-N-(3-sulfamoylphenyl)-5-(trifluoromethyl)pyridine-3-carboxamide;
(129) 2-[(1S,6S)-7,7-difluoro-6-methyl-3-azabicyclo[[4.1.0]heptan-3-yl]-N-(3-sulfamoylphenyl)-5-(trifluoromethyl)pyridine-3-carboxamide;
(130) N-(3-sulfamoylphenyl)-5-(trifluoromethyl)-2-[(1R,5R)-1-(trifluoromethyl)-3-azabicyclo-[3.2.0]heptan-3-yl]pyridine-3-carboxamide;
(131) N-(3-sulfamoylphenyl)-5-(trifluoromethyl)-2-[(1 8,5 S)-1-(trifluoromethyl)-3-azabicyclo-[3.2.0]heptan-3-yl]pyridine-3-carboxamide;
(132) 2-[(1R,5S)-6,6-difluoro-3-azabicyclo[3.1.1]heptan-3-yl]-N-(3-sulfamoylphenyl)-5-(trifluoromethyl)pyridine-3-carboxamide;
(133) N-(3-sulfamoylphenyl)-2-[(1R,5S)-6,6,7,7-tetrafluoro-3-azabicyclo[3.2.0]heptan-3-yl]-5-(trifluoromethyl)pyridine-3-carboxamide;
(134) 2-[(1R,5S)-3-azabicyclo[3.2.0]heptan-3-yl]-N-(3-sulfamoylphenyl)-5-(trifluoromethyl)pyridine-3-carboxamide;

(135) 2-[(1S,5R)-6,6-difluoro-3-azabicyclo[3.2.0]heptan-3-yl]-N-(3-sulfamoylphenyl)-5-(trifluoromethyl)pyridine-3-carboxamide;
(136) 2-[(1R,5S)-6,6-difluoro-3-azabicyclo[3.2.0]heptan-3-yl]-N-(3-sulfamoylphenyl)-5-(trifluoromethyl)pyridine-3-carboxamide;
(137) 2-[(1S,4S)-5,5-difluoro-2-azabicyclo[2.2.1]heptan-2-yl]-N-(3-sulfamoylphenyl)-5-(trifluoromethyl)pyridine-3-carboxamide;
(138) 2-[(1R,4R)-5,5-difluoro-2-azabicyclo[2.2.1]heptan-2-yl]-N-(3-sulfamoylphenyl)-5-(trifluoromethyl)pyridine-3-carboxamide;
(139) 2-(7-azabicyclo[2.2.1]heptan-7-yl)-N-(3-sulfamoylphenyl)-5-(trifluoromethyl)pyridine-3-carboxamide;
(140) N-(3-sulfamoylphenyl)-5 -(trifluoromethyl)-2-[(2S)-2-(trifluoromethyl)morpholin-4-yl]pyridine-3-carboxamide;
(141) N-(3-sulfamoylphenyl)-5-(trifluoromethyl)-2-[(2R)-2-(trifluoromethyl)morpholin-4-yl]pyridine-3-carboxamide;
(142) 2-[(2R,6R)-2-methyl-6-(trifluoromethyl)morpholin-4-yl]-N-(3-sulfamoylphenyl)-5-(trifluoromethyl)pyridine-3-carboxamide;
(143) N-(3-sulfamoylphenyl)-5-(trifluoromethyl)-2-[3-(trifluoromethyl)piperazin-1-yl]pyridine-3-carboxamide;
(144) (R)-N-(3-sulfamoylphenyl)-5-(trifluoromethyl)-2-(2-(trifluoromethyl)-1,4-oxazepan-4-yl)-nicotinamide;
(145) 2-[(2S,6R)-2-methyl-6-(trifluoromethyl)morpholin-4-yl]-N-(3-sulfamoylphenyl)-5-(trifluoromethyl)pyridine-3-carboxamide;
(146) 2-[(2R,6S)-2-methyl-6-(trifluoromethyl)morpholin-4-yl]-N-(3-sulfamoylphenyl)-5-(trifluoromethyl)pyridine-3-carboxamide;
(147) N-(3-sulfamoylphenyl)-5-(trifluoromethyl)-2-[(2S)-2-(trifluoromethyl)-1,4-oxazepan-4-yl]pyridine-3-carboxamide;
(148) 2-[(2S,6S)-2-methyl-6-(trifluoromethyl)morpholin-4-yl]-N-(3-sulfamoylphenyl)-5-(trifluoromethyl)pyridine-3-carboxamide;
(149) 2-[(2R,6S or 2S,6R)-2,6-dimethylmorpholin-4-yl]-N-(3-sulfamoylphenyl)-5-(trifluoromethyl)pyridine-3-carboxamide;
(150) 2-[(2S,6S or 2R,6R)-2,6-dimethylmorpholin-4-yl]-N-(3-sulfamoylphenyl)-5-(trifluoromethyl)pyridine-3-carboxamide;
(151) 2-(azepan-1-yl)-3-((3-(N-(pyrimidin-4-yl)sulfamoyl)phenyl)carbamoyl)-5-(trifluoromethyl)pyridin-1-ium;
(152) 2-(4,4-difluoropiperidin-1-yl)-N-(3-(methylsulfonyl)phenyl)-5-(trifluoromethyl)nicotinamide;
(153) 5-isobutyl-2-(piperidin-1-yl)-N-(3-sulfamoylphenyl)nicotinamide;
(154) 5-cyclopentyl-2-(piperidin-1-yl)-N-(3-sulfamoylphenyl)nicotinamide;
(155) 2-(azepan-1-yl)-6-methoxy-5-methyl-N-(3-sulfamoylphenyl)nicotinamide;
(156) 2-(azepan-1-yl)-5-bromo-6-methoxy-N-(3-sulfamoylphenyl)nicotinamide;
(157) 2-(azepan-1-yl)-5-cyano-6-methyl-N-(3-sulfamoylphenyl)pyridine-3-carboxamide;
(158) 2-(azepan-1-yl)-4-chloro-6-methyl-N-(3-sulfamoylphenyl)pyridine-3-carboxamide;
(159) 5-cyclobutyl-2-(4,4-difluoroazepan-1-yl)-N-(3-sulfamoylphenyl)nicotinamide;
(160) 2-(4,4-difluoroazepan-1-yl)-5-(oxetan-3-yl)-N-(3-sulfamoylphenyl)nicotinamide;
(161) 5-(but-3-en-1-yl)-2-(4,4-difluoroazepan-1-yl)-N-(3-sulfamoylphenyl)nicotinamide;
(162) 2-(4,4-difluoroazepan-1-yl)-5-isoropyl-N-(3-sulfamoylphenyl)nicotinamide;
(163) 5-cyclopropyl-2-(4,4-difluoroazepan-1-yl)-N-(3-sulfamoylphenyl)nicotinamide;
(164) 2-(azepan-1-yl)-5-(perfluoroethyl)-N-(3-sulfamoylphenyl)nicotinamide
(165) 6-(1,1,2,2,2-pentafluoroethyl)-2-(1-piperidyl)-N-(3-sulfamoylphenyl)pyridine-3-carboxamide;
(166) 2-(azepan-1-yl)-N-(3-methylsulfonylphenyl)-5-(1,1,2,2,2-pentafluoroethyl)pyridine-3-carboxamide;
(167) 2-(azepan-1-yl)-N-(3-carbamoylphenyl)-5-(1,1,2,2,2-pentafluoroethyl)pyridine-3-carboxamide;
(168) 2-(azepan-1-yl)-6-methyl-N-(3-sulfamoylphenyl)-5-(trifluoromethyl)nicotinamide;
(169) 2-(azepan-1-yl)-6-methoxy-N-(3-sulfamoylphenyl)-5-(trifluoromethyl)nicotinamide;
(170) 2-(4,4-difluoropiperidin-1-yl)-N-(2-fluoro-3-sulfamoylphenyl)-5-(trifluoromethyl)nicotinamide;
(171) N-(3,4-difluoro-5-sulfamoylphenyl)-2-(4,4-difluoropiperidin-1-yl)-5-(trifluoromethyl)nicotinamide;
(172) 2-(4,4-difluoroazepan-1-yl)-5-(difluoromethoxy)-N-(3-sulfamoylphenyl)nicotinamide;
(173) 5-chloro-2-(4,4-difluoroazepan-1-yl)-N-(3-(methylsulfonyl)phenyl)nicotinamide;
(174) 2-(azepan-1-yl)-6-chloro-4,5-dimethyl-N-(3-sulfamoylphenyl)pyridine-3-carboxamide;
(175) 2-(azepan-1-yl)-4-methyl-N-(3-sulfamoylphenyl)pyridine-3-carboxamide;
(176) 5-cyano-2-(4,4-difluoroazepan-1-yl)-6-methyl-N-(3-methylsulfonylphenyl)pyridine-3-carboxamide;
(177) N-(3-carbamoylphenyl)-5-cyano-2-(4,4-difluoroazepan-1-yl)-6-methyl-pyridine-3-carboxamide; and
(178) 2-(azepan-1-yl)-N-(3-carbamoylphenyl)-5-cyano-6-methyl-pyridine-3-carboxamide;
or a pharmaceutically acceptable salt thereof.

11. The compound according to claim 1 selected from:
(1) 5-chloro-2-(4,4-difluoroazepan-1-yl)-N,4,6-trimethyl-N-(3-sulfamoylphenyl)nicotinamide;
(2) 2-cyclopropyl-4-(4,4-difluoroazepan-1-yl)-N-(3-sulfamoylphenyl)pyrimidine-5-carboxamide; and
(3) 3-(4,4-difluoroazepan-1-yl)-N-(3-sulfamoylphenyl)-6-(trifluoromethyl)pyridazine-4-carboxamide;
or a pharmaceutically acceptable salt thereof.

12. A pharmaceutical composition comprising a compound of claim 1, or a pharmaceutically acceptable salt thereof, and a pharmaceutically acceptable carrier.

13. A method of treating or preventing a pain disorder that is responsive to the inhibition of Nav1.8 channel activity in a patient in need thereof comprising administration of a therapeutically effective amount of a compound according to claim 1, or a pharmaceutically acceptable salt thereof.

14. The method of claim 13 wherein the pain disorder is selected from: acute pain, inflammatory pain, or neuropathic pain.

15. A method of treating a disorder that is responsive to the inhibition of Nav1.8 channel activity in a patient in need thereof comprising administration of a therapeutically effective amount of a compound according to claim 1, or a pharmaceutically acceptable salt thereof, wherein the disorder is selected from: a cough disorder, an acute itch disorder and a chronic itch disorder.

* * * * *